(12) United States Patent
Kuwata

(10) Patent No.: US 12,177,601 B2
(45) Date of Patent: Dec. 24, 2024

(54) CONTROL APPARATUS, RADIOGRAPHIC IMAGING SYSTEM, CONTROL METHOD, AND RECORDING MEDIUM

(71) Applicant: Konica Minolta, Inc., Tokyo (JP)

(72) Inventor: Masahiro Kuwata, Machida (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 18/539,763

(22) Filed: Dec. 14, 2023

(65) Prior Publication Data

US 2024/0129428 A1 Apr. 18, 2024

Related U.S. Application Data

(63) Continuation of application No. 17/407,792, filed on Aug. 20, 2021, now Pat. No. 11,895,428, which is a
(Continued)

(30) Foreign Application Priority Data

Jun. 12, 2019 (JP) .................. 2019-109144

(51) Int. Cl.
*H04N 5/32* (2023.01)
*A61B 6/46* (2024.01)
*H04N 25/75* (2023.01)

(52) U.S. Cl.
CPC .............. *H04N 5/32* (2013.01); *A61B 6/465* (2013.01); *H04N 25/75* (2023.01)

(58) Field of Classification Search
None
See application file for complete search history.

(56) References Cited

U.S. PATENT DOCUMENTS

| 2002/0060302 A1 | 5/2002 | Aonuma |
| 2006/0135764 A1 | 6/2006 | Fatheree et al. |

(Continued)

FOREIGN PATENT DOCUMENTS

| JP | 2010-081960 A | 4/2010 |
| JP | 2011-224337 A | 11/2011 |

(Continued)

OTHER PUBLICATIONS

Office Action dated Aug. 22, 2023 for the corresponding Japanese patent application No. 2019-109144, with English translation.
(Continued)

*Primary Examiner* — Edwin C Gunberg
(74) *Attorney, Agent, or Firm* — LUCAS & MERCANTI, LLP

(57) ABSTRACT

A control apparatus connected to a plurality of radiographic imaging apparatuses, includes a receiver that receives state information indicating whether a state is a first state in which the radiographic imaging apparatus is not connected to or synchronized with a specific synchronization source or a second state in which the radiographic imaging apparatus is connected to and synchronized with the specific synchronization source, from each of the plurality of radiographic imaging apparatuses, a hardware processor that makes a first determination that at least one of the plurality of radiographic imaging apparatuses is in the first state or a second determination that all of the plurality of radiographic imaging apparatuses are in the second state, based on the state information received from each of the plurality of radiographic imaging apparatuses, and an outputter that outputs whether a determination result by the hardware processor is the first determination or the second determination.

12 Claims, 46 Drawing Sheets

Related U.S. Application Data continuation of application No. 16/894,168, filed on Jun. 5, 2020, now Pat. No. 11,134,205.

(56) References Cited

U.S. PATENT DOCUMENTS

2012/0300904 A1  11/2012  Shimada et al.
2020/0110044 A1* 4/2020  Fukazu .................. G06F 3/14

FOREIGN PATENT DOCUMENTS

| | | |
|---|---|---|
| JP | 2016-140513 A | 8/2016 |
| JP | 2019-017625 A | 2/2019 |
| WO | 2006030592 A1 | 3/2006 |

OTHER PUBLICATIONS

Office Action dated Apr. 4, 2023 for the corresponding Japanese patent application No. 2019-109144, with English translation.
Japanese Patent Office, "Decision of Refusal" mailed Apr. 2, 2024, which was issued for the corresponding Japanese Patent Application No. 2019-109144, with English translation, 3 pages.
Japanese Patent Office, "Decision of Dismissal of Amendment" mailed Apr. 2, 2024, which was issued for the corresponding Japanese Patent Application No. 2019-109144, with English translation, 12 pages.

* cited by examiner

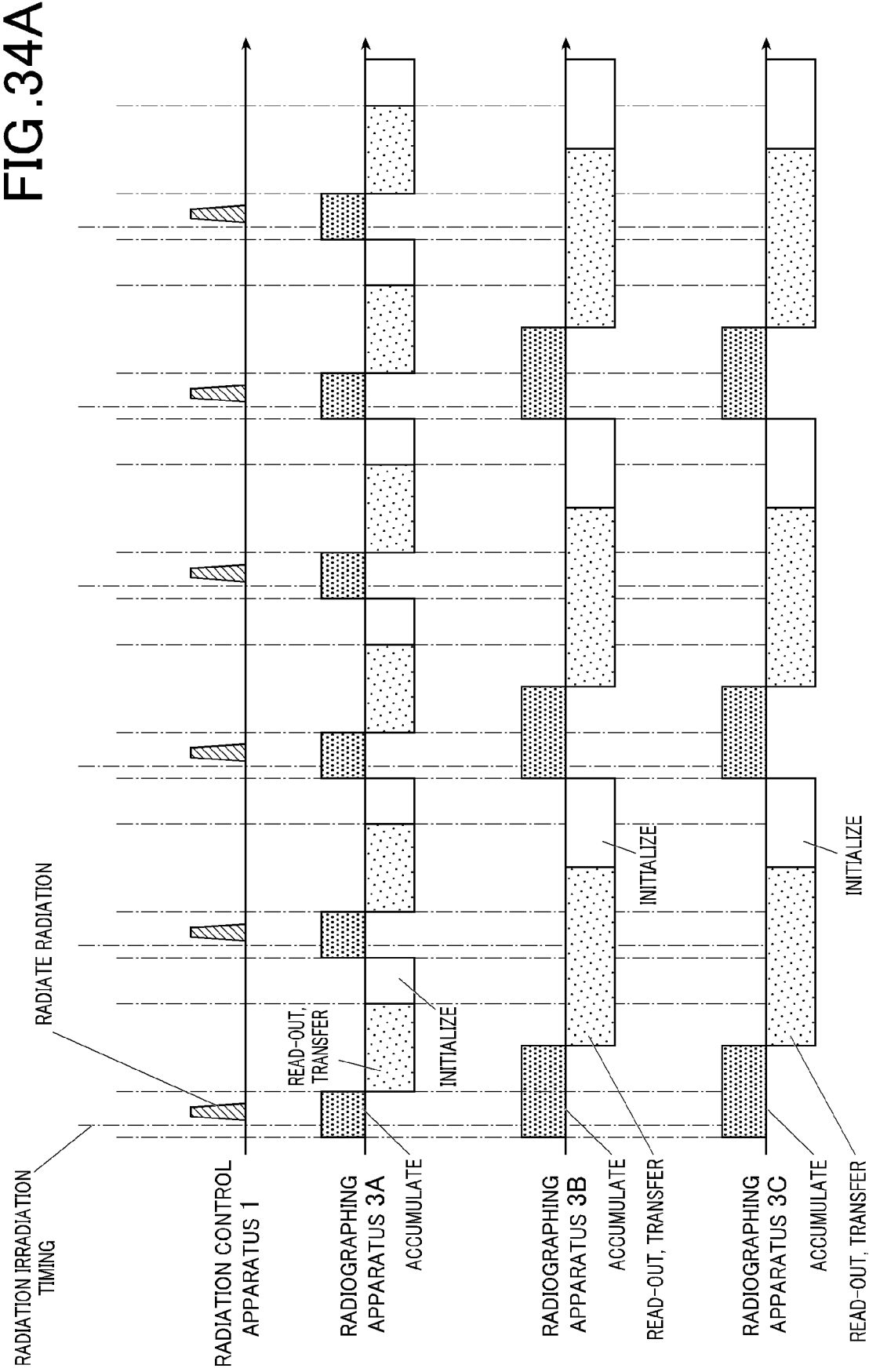

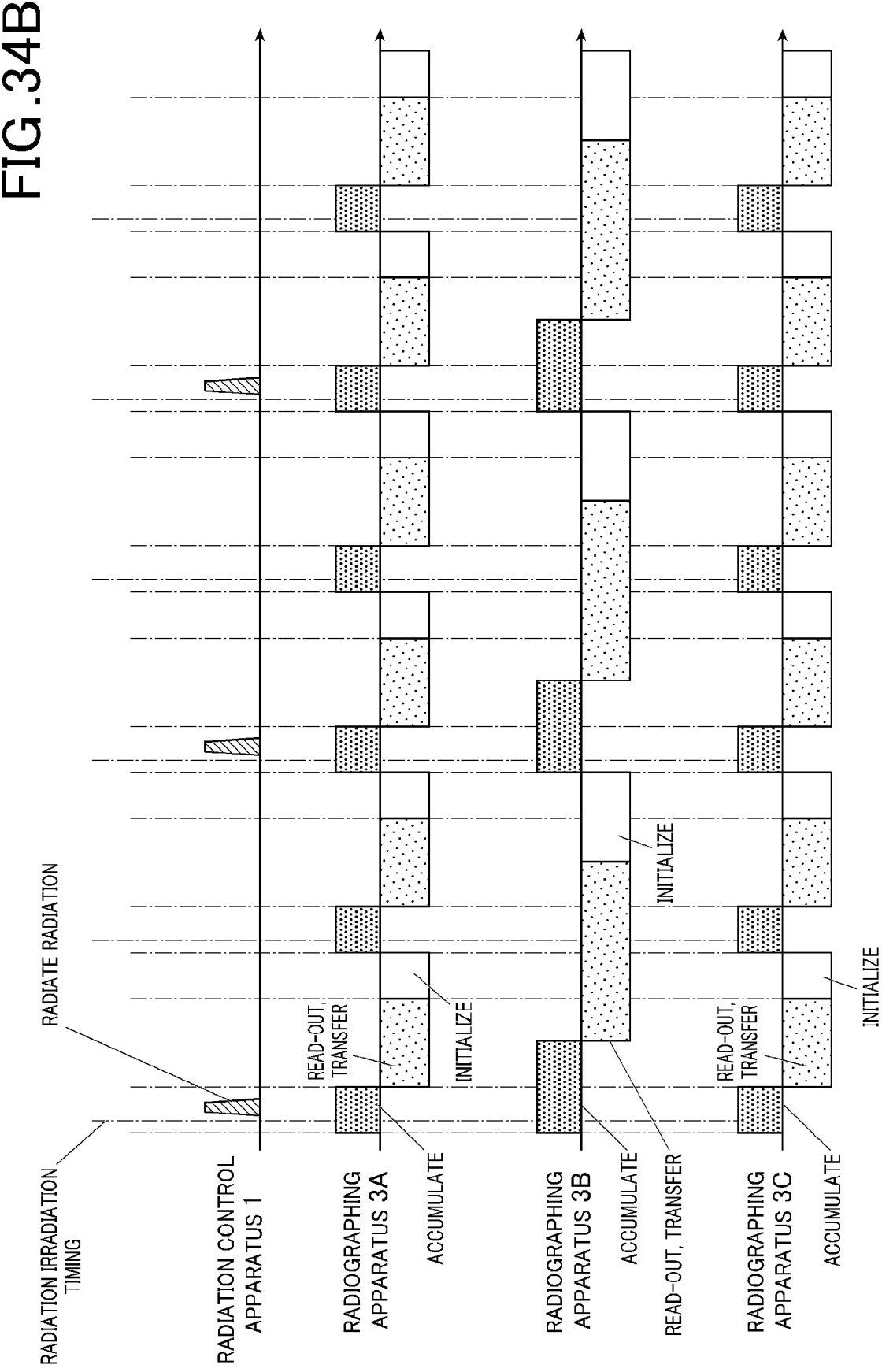

FIG.44
SEARCH RANGE OF
FIRST IMAGE
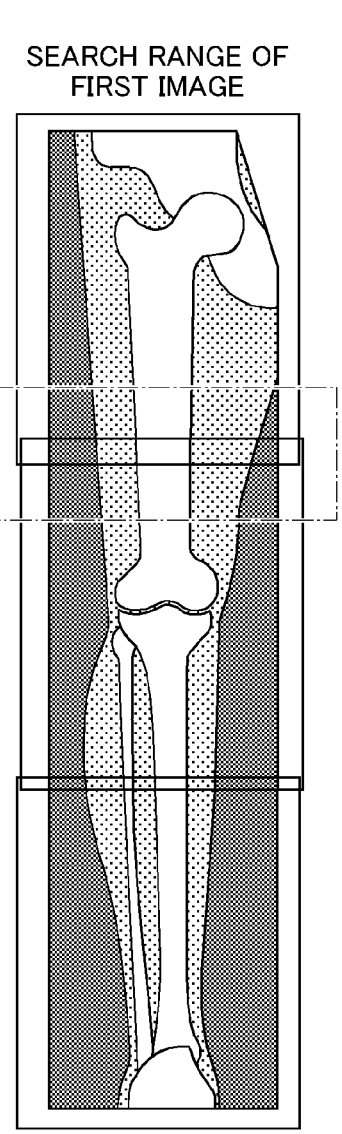
SEARCH RANGE OF
SECOND AND
SUBSEQUENT IMAGES
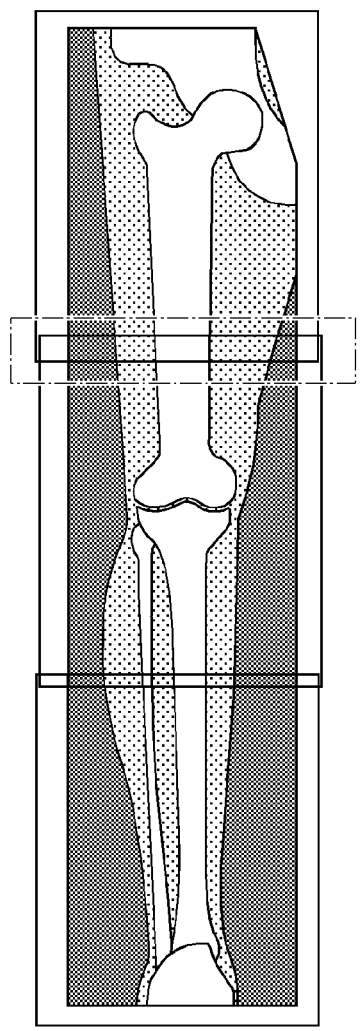

CONTROL APPARATUS, RADIOGRAPHIC IMAGING SYSTEM, CONTROL METHOD, AND RECORDING MEDIUM

CROSS-REFERENCE TO RELATED APPLICATIONS

This application is a continuation of U.S. patent application Ser. No. 17/407,792 filed on Aug. 20, 2021, which is a continuation of U.S. patent application Ser. No. 16/894,168 filed on Jun. 5, 2020, now U.S. Pat. No. 11,134,205 issued on Sep. 28, 2021, which in turn claims priority of Japanese Patent Application No. 2019-109144 filed on Jun. 12, 2019, all applications are incorporated herein by reference in their entirety.

BACKGROUND

Technological Field

The present invention relates to a control apparatus, a radiographic imaging system, a control method, and a recording medium.

Description of the Related Art

In recent years, following a radiography film and a CR cassette, various kinds of radiographic imaging apparatuses (FPD: Flat Panel Detector) in which radiation detection elements are arranged in two dimensions, and which acquire image data by accumulating and reading out electric charges generated within the radiation detection elements in accordance with radiation which is radiated from radiation irradiation apparatuses and which penetrates through a subject, have been developed. Further, because image reading speed and image transfer speed of the radiographic imaging apparatuses have been improved, it has become possible to successively acquire a plurality of radiographs using these.

For example, JP 2010-81960A discloses a technique of providing timers which count time respectively at a console and an electronic cassette (radiographic imaging apparatus), and performing radiographing while adjusting a timing of the radiographing so as to match a timing of irradiation of radiation by achieving time synchronization of these. Further, J P 2010-81960A discloses that time synchronization is achieved using an atomic clock, radio waves of a GPS satellite, radio waves of a mobile phone, radio waves of a television and a radio, or the like.

By the way, in recent years, it has been proposed to radiograph a subject with a plurality of radiographic imaging apparatuses which are arranged, and generate a long-length image by connecting the obtained radiographs. Further, it has also been proposed to successively irradiate a subject with radiation at predetermined time intervals with a plurality of radiographic imaging apparatuses which are arranged, to acquire a plurality of long-length images indicating a dynamic state of the subject. In such radiographing, it is necessary to accumulate and read out radiation while timings of a plurality of radiographic imaging apparatuses are adjusted to match each other.

However, because, in a medical facility, radiographing is performed with equipment which is disposed indoors, there are cases where radio waves cannot always be sufficiently received from outside. Particularly, in a radiographing room in which radiographing is performed using radiation, because the radiographing room has a structure which is covered with lead for radiation protection, there are cases where the strength of radio waves from outside is weak. Further, because there are cases where equipment which may be affected by radio waves, such as a pace maker, is used in a medical institution, it may be difficult to increase the strength of radio waves. Therefore, as described in JP 2010-81960A, in a case where time synchronization is achieved using an atomic clock, radio waves of a GPS satellite, radio waves of a mobile phone, radio waves of a television and a radio, or the like, there is a risk of a defect in synchronization in association with a failure in adjustment of time due to insufficient strength of radio waves.

To solve such a problem, it can be considered that a plurality of radiographic imaging apparatuses perform radiographing while adjusting operation timings and time to match each other using a signal from a synchronization source locally provided for each system (an apparatus which outputs a timing signal and time information which become a reference to be used for a plurality of pieces of equipment to adjust operation timings to match each other). However, in this case, there is a possibility that a plurality of synchronization sources may locally exist, and there are cases where a plurality of radiographic imaging apparatuses cannot appropriately perform radiographing as a result of operating in coordination with different synchronization sources.

SUMMARY

A problem to be solved by the present invention is to, in a case where radiographing is successively performed using a plurality of radiographic imaging apparatuses, suppress a risk that the radiographic imaging apparatuses perform radiographing in coordination with different synchronization sources.

To achieve at least one of the abovementioned objects, according to an aspect of the present invention, there is provided a control apparatus connected to a plurality of radiographic imaging apparatuses, including a receiver that receives state information indicating whether a state is a first state in which the radiographic imaging apparatus is not connected to a specific synchronization source or a second state in which the radiographic imaging apparatus is connected to the specific synchronization source, from each of the plurality of radiographic imaging apparatuses, a hardware processor that makes a first determination that at least one of the plurality of radiographic imaging apparatuses is in the first state or a second determination that all of the plurality of radiographic imaging apparatuses are in the second state, based on the state information received from each of the plurality of radiographic imaging apparatuses, and an outputter that outputs whether a determination result by the hardware processor is the first determination or the second determination.

According to another aspect of the present invention, there is provided a control apparatus connected to a plurality of radiographic imaging apparatuses, including a receiver that receives state information indicating whether a state is a first state in which the radiographic imaging apparatus does not coordinate with a specific synchronization source or a second state in which the radiographic imaging apparatus coordinates with the specific synchronization source, from each of the plurality of radiographic imaging apparatuses, a hardware processor that makes a first determination that at least one of the plurality of radiographic imaging apparatuses is in the first state or a second determination that all of the plurality of radiographic imaging apparatuses are in the second state, based on the state information received from each of the plurality of radiographic imaging apparatuses, and an outputter that outputs whether a determination result by the hardware processor is the first determination or the second determination.

According to another aspect of the present invention, there is provided a radiographic imaging system that successively performs long-length radiography using a plurality of radiographic imaging apparatuses, each of the plurality of radiographic imaging apparatuses outputting state information indicating whether a state is a first state in which the radiographic imaging apparatus is not connected to a specific synchronization source or a second state in which the radiographic imaging apparatus is connected to the specific synchronization source, the radiographic imaging system including a hardware processor that makes a first determination that at least one of the plurality of radiographic imaging apparatuses is in the first state or a second determination that all of the plurality of radiographic imaging systems are in the second state, based on the state information output from each of the plurality of radiographic imaging apparatuses, and performs control to cause whether or not it is possible to perform long-length radiography to be displayed at a display in an identifiable form, based on whether a determination result is the first determination or the second determination.

According to another aspect of the present invention, there is provided a radiographic imaging system that successively performs long-length radiography using a plurality of radiographic imaging apparatuses, each of the plurality of radiographic imaging apparatuses outputting state information indicating whether a state is a first state in which the radiographic imaging apparatus does not coordinate with a specific synchronization source or a second state in which the radiographic imaging apparatus is connected to the specific synchronization source, the radiographic imaging system including a hardware processor that makes a first determination that at least one of the plurality of radiographic imaging apparatuses is in the first state or a second determination that all of the plurality of radiographic imaging apparatuses are in the second state, based on the state information output from each of the plurality of radiographic imaging apparatuses, and performs control to cause whether or not it is possible to perform long-length radiography to be displayed at a display in an identifiable form, based on whether a determination result is the first determination or the second determination.

According to another aspect of the present invention, there is provided a control method at a control apparatus connected to a plurality of radiographic imaging apparatuses, including receiving state information indicating whether a state is a first state in which the radiographic imaging apparatus is not connected to a specific synchronization source or a second state in which the radiographic imaging apparatus is connected to the specific synchronization source, from each of the plurality of radiographic imaging apparatuses, making a first determination that at least one of the plurality of radiographic imaging apparatuses is in the first state or a second determination that all of the plurality of radiographic imaging apparatuses are in the second state, based on the state information received from each of the plurality of radiographic imaging apparatuses, and performing control to cause whether or not it is possible to perform long-length radiography to be displayed at a display in an identifiable form based on whether a determination result in the determination is the first determination or the second determination.

According to another aspect of the present invention, there is provided a control method at a control apparatus connected to a plurality of radiographic imaging apparatuses, including receiving state information indicating whether a state is a first state in which the radiographic imaging apparatus does not coordinate with a specific synchronization source or a second state in which the radiographic imaging apparatus is connected to the specific synchronization source, from each of the plurality of radiographic imaging apparatuses, making a first determination that at least one of the plurality of radiographic imaging apparatuses is in the first state or a second determination that all of the plurality of radiographic imaging apparatuses are in the second state, based on the state information received from each of the plurality of radiographic imaging apparatuses, and performing control to cause whether or not it is possible to perform long-length radiography to be displayed at a display in an identifiable form, based on whether a determination result in the determination is the first determination or the second determination.

According to another aspect of the present invention, there is provided a computer-readable non-transitory recording medium storing a program causing a computer to be used as a control apparatus to execute the control method according to the present invention.

BRIEF DESCRIPTION OF THE DRAWINGS

The advantages and features provided by one or more embodiments of the invention will become more fully understood from the detailed description given hereinafter and the appended drawings which are given by way of illustration only, and thus are not intended as a definition of the limits of the present invention, and wherein:

FIG. 34A is a timing chart of radiation irradiation, and accumulation/read-out in a case where a radiation irradiation timing is adjusted to match a high frame rate;

FIG. 34B is a timing chart of radiation irradiation, and accumulation/read-out in a case where the radiation irradiation timing is adjusted to match a low frame rate;

FIG. 44 is a view illustrating a search range of a connection position;

DETAILED DESCRIPTION OF THE EMBODIMENTS

Embodiments of the present invention will be described below with reference to the drawings. However, a technical scope of the present invention is not limited to that illustrated in the following description of the embodiments and the drawings.

Note that, here, description will be provided in order of related art 1-A which is a basis of a first-A embodiment of the present invention, the first-A embodiment, related art 1-B which is a basis of a first-B embodiment, the first-B embodiment and a second embodiment.

<Related Art 1-A>

First, the related art 1-A which is a basis of a system 100 (which will be described in detail later) according to a first-A embodiment of the present invention will be described with reference to FIG. 1.

[System Configuration]

First, a schematic configuration of a radiographic imaging system according to the related art 1-A (hereinafter, referred to as a conventional system 100A) will be described. FIG. 1 is a block diagram illustrating the conventional system 100A.

Figure 1:
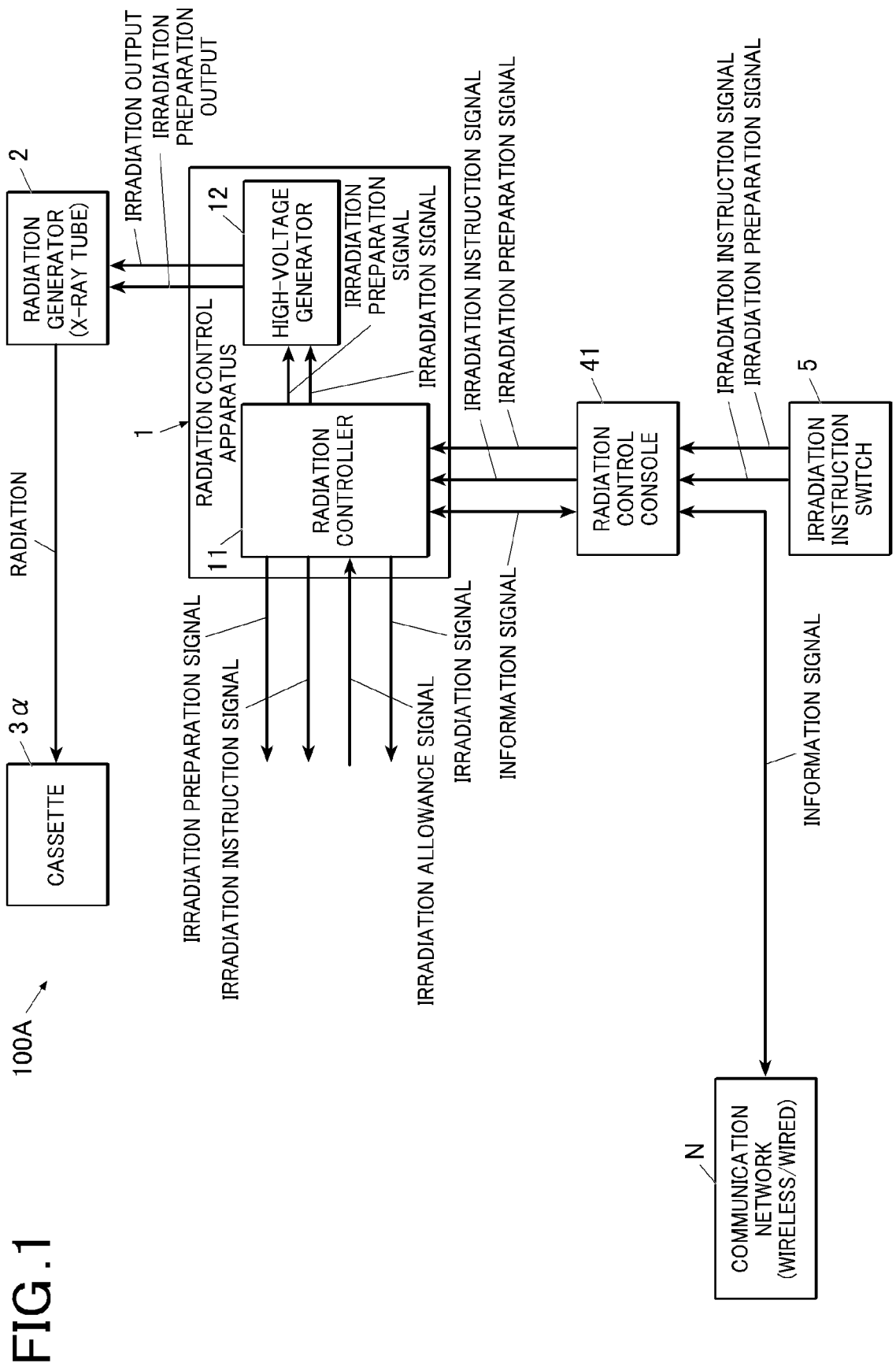
FIG. 1 is a block diagram illustrating a radiographic imaging system according to related art 1-A.

For example, as illustrated in FIG. 1, the conventional system 100A includes a radiation controller 11, a high-voltage generator 12, a radiation generator 2, a cassette 30c, a radiation control console 41, and an irradiation instruction switch 5, and is configured to be able to capture a still image with a radiographic imaging film, a CR, or the like, while a radiation irradiation timing does not coordinate with a radiographing timing.

Note that, while FIG. 1 illustrates a case where the radiation controller 11 and the high-voltage generator 12 constitute a radiation control apparatus 1 together (for example, are stored in one chassis), the radiation controller 11 and the high-voltage generator 12 can be independently configured, for example, can be disposed in different chassis.

The radiation controller 11, which controls radiation irradiation, is configured with, for example, a computer, or the like, including a central processing unit (CPU), a read only memory (ROM) in which programs for causing the radiation controller 11 to operate are stored, a random access memory (RAM), an input/output interface, or the like, which are connected to a bus, an field programmable gate array (FPGA), or the like, which are not illustrated. Note that the radiation controller 11 may be configured with a dedicated control circuit.

Specifically, based on that it is detected that an irradiation preparation signal from the radiation control console 41 is put into an ON state, the radiation controller 11 can put the irradiation preparation signal to be output to the high-voltage generator 12 into an ON state or can put the irradiation preparation signal into a state where the irradiation preparation signal can be output to other external equipment.

Further, based on that it is detected that an irradiation instruction signal for giving an instruction to radiate radiation from the radiation control console 41 is put into an ON state, the radiation controller 11 can put this irradiation instruction signal into a state where the radiation instruction signal can be output to external equipment and can transmit an irradiation signal in accordance with radiographing conditions set by the radiation control console 41 to the high-voltage generator 12.

These irradiation preparation signal and irradiation instruction signal which can be output from the radiation controller 11 to external equipment are used, for example, in a case where the external equipment is connected to the radiation controller 11.

With these irradiation preparation signal and irradiation instruction signal, the external equipment can prepare radiographing based on the irradiation preparation signal and the irradiation instruction signal output from the radiation controller 11 in radiographing which requires preparation of the external equipment other than the cassette 3α upon irradiation of radiation.

Examples of such external equipment can include a grid rocking apparatus, or the like, which are provided on a radiation incidence plane of the cassette 3α and which are used to rock a grid upon radiographing.

Note that the above-described external equipment includes external equipment having a configuration where, after radiographing preparation is completed, an irradiation allowance signal is transmitted to the radiation controller 11. Therefore, it is also possible to employ a configuration where the radiation controller 11 includes a connector for receiving input of the irradiation allowance signal from the external equipment, and transmits an irradiation signal to the high-voltage generator 12 only in a case where both the irradiation instruction signal from the radiation control console 41 and the irradiation allowance signal from the external equipment are put into an ON state.

With such a configuration, because the irradiation allowance signal is not input to the radiation controller 11 until radiographing preparation of the external equipment is completed, it is possible to prevent radiation from being radiated before radiographing preparation of the external equipment is completed.

For example, in a case where the external equipment is the grid rocking apparatus described above, it is also possible to employ a configuration where the grid rocking apparatus starts rocking and, after rocking speed reaches designated rocking speed, an irradiation allowance signal is input from the grid rocking apparatus to the radiation controller 11. With such a configuration, because the radiation controller 11 outputs an irradiation signal only after both the irradiation instruction signal from the irradiation instruction switch 5 based on an operation by a radiographer and the irradiation allowance signal from the external equipment are input, it is possible to prevent radiation from being radiated before preparation of the external equipment is completed.

Meanwhile, in a case where it is not desired to use an irradiation allowance signal from the external equipment at the radiation controller 11, it is necessary to, for example, disable the irradiation allowance signal or keep a state of the irradiation allowance signal always in an ON or OFF state.

For example, in a case where the radiation controller 11 is configured to be able to switch whether or not to use the irradiation allowance signal from the external equipment in judgment as to whether or not to output the irradiation signal, it is possible to disable the irradiation allowance signal by switching a state so as not to use the irradiation allowance signal in the judgement.

Meanwhile, in a case where such switching cannot be performed, and, in a case where, for example, the irradiation allowance signal is configured to be controlled by two signal lines being open or closed, by keeping two signal lines always open or closed, the irradiation allowance signal is kept always in an ON or OFF state.

Further, it is also possible to employ a configuration where the radiation controller 11 does not transmit the irradiation signal until a predetermined waiting period has elapsed since it had been detected that the irradiation preparation signal had been put into an ON state, even if it is detected that the irradiation instruction signal is put into an ON state.

With such a configuration, in a case where the high-voltage generator 12 and the radiation generator 2 require some period for preparation after detecting that the irradiation preparation signal is put into an ON state, it is possible to prevent radiation from being radiated although irradiation preparation is not completed.

The high-voltage generator 12 is configured to be able to output an irradiation preparation output to the radiation generator 2 based on that it is detected that the irradiation preparation signal from the radiation controller 11 is put into an ON state.

Further, the high-voltage generator 12 is configured to be able to apply a high voltage (in accordance with the input irradiation signal) required for the radiation generator 2 to generate radiation, to the radiation generator 2 as irradiation output, based on that the irradiation signal is received from the radiation controller 11.

Note that, while FIG. 1 illustrates a configuration where, if the high-voltage generator 12 detects that the irradiation preparation signal from the radiation controller 11 is put into an ON state, the high-voltage generator 12 outputs the irradiation preparation output to the radiation generator 2, it is also possible to employ a configuration where the radiation controller 11 directly outputs the irradiation preparation signal to the radiation generator 2, and the radiation generator 2 converts the irradiation preparation signal into the irradiation preparation output and prepares irradiation.

The radiation generator 2 (radiation tube) includes, for example, an electron gun and an anode, and is configured to be able to generate radiation (for example, an X ray) in accordance with the high voltage applied from the high-voltage generator 12.

Specifically, when a high voltage is applied, the electron gun radiates an electron beam to the anode, and the anode generates radiation by receiving the electron beam.

Note that, because when the anode generates radiation, a portion of the anode where the electron beam is received produces heat, and the temperature of the portion becomes high, to stably radiate radiation, it is necessary to constantly change a position irradiated with the electron beam at the anode. Therefore, there is a case where a rotating anode which radiates an electron beam while rotating the anode is used.

The above-described irradiation preparation output from the high-voltage generator 12 can be used as, for example, an instruction to start rotation of the rotating anode.

The cassette 30c stores a radiography film or a fluorescent plate, and, when radiation which penetrates through an object under examination is incident, it is possible to form a radiograph of the object under examination.

The radiation control console 41 is configured to be able to set information regarding the object under examination and radiographing conditions (such as a tube voltage, a tube current and an irradiation period) at the radiation controller 11 using connection of an information signal.

Figure 4:
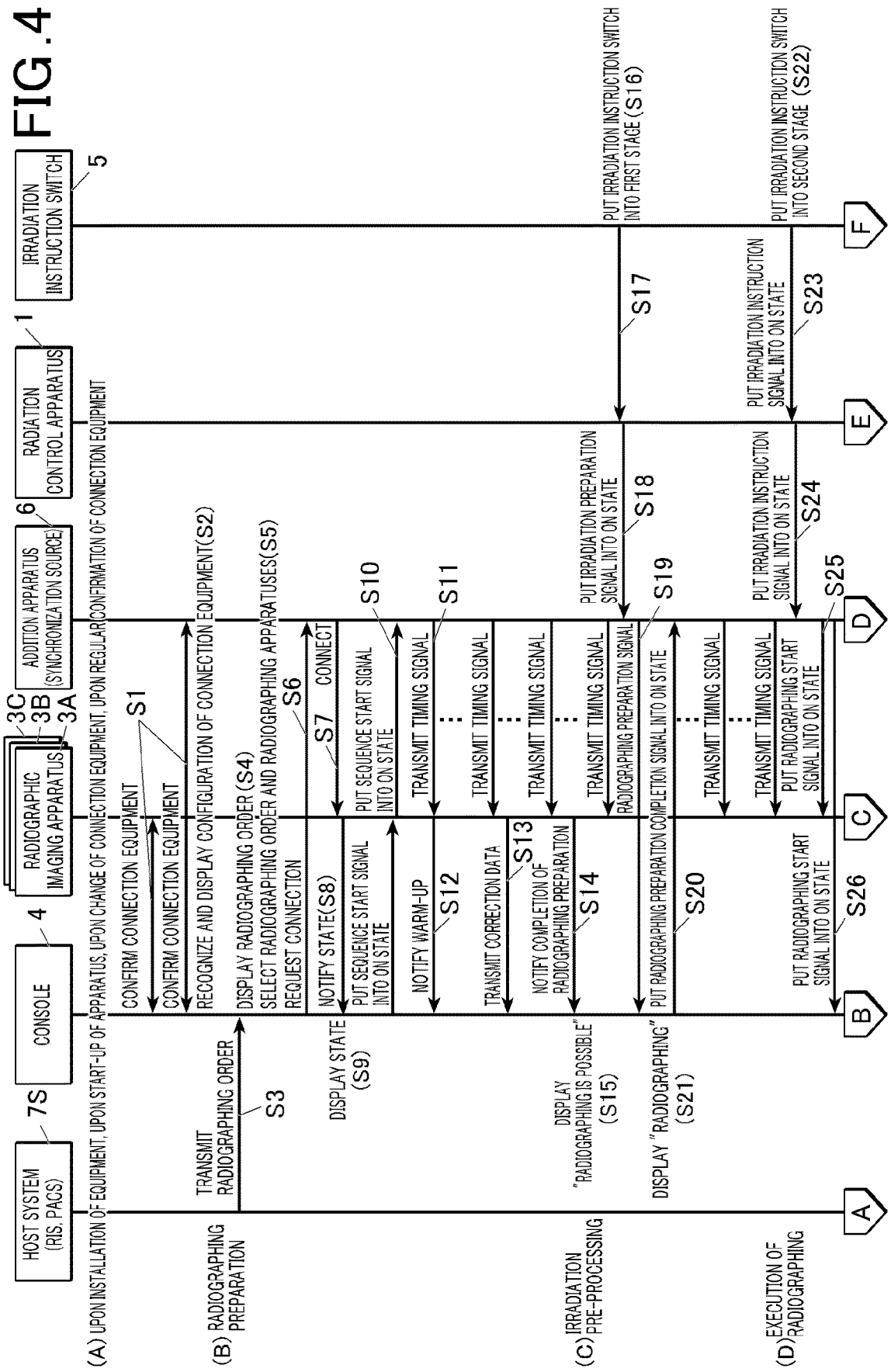
FIG. 4 is a ladder chart illustrating a first half of an operation of the radiographic imaging system in FIG. 2.
Figure 11:
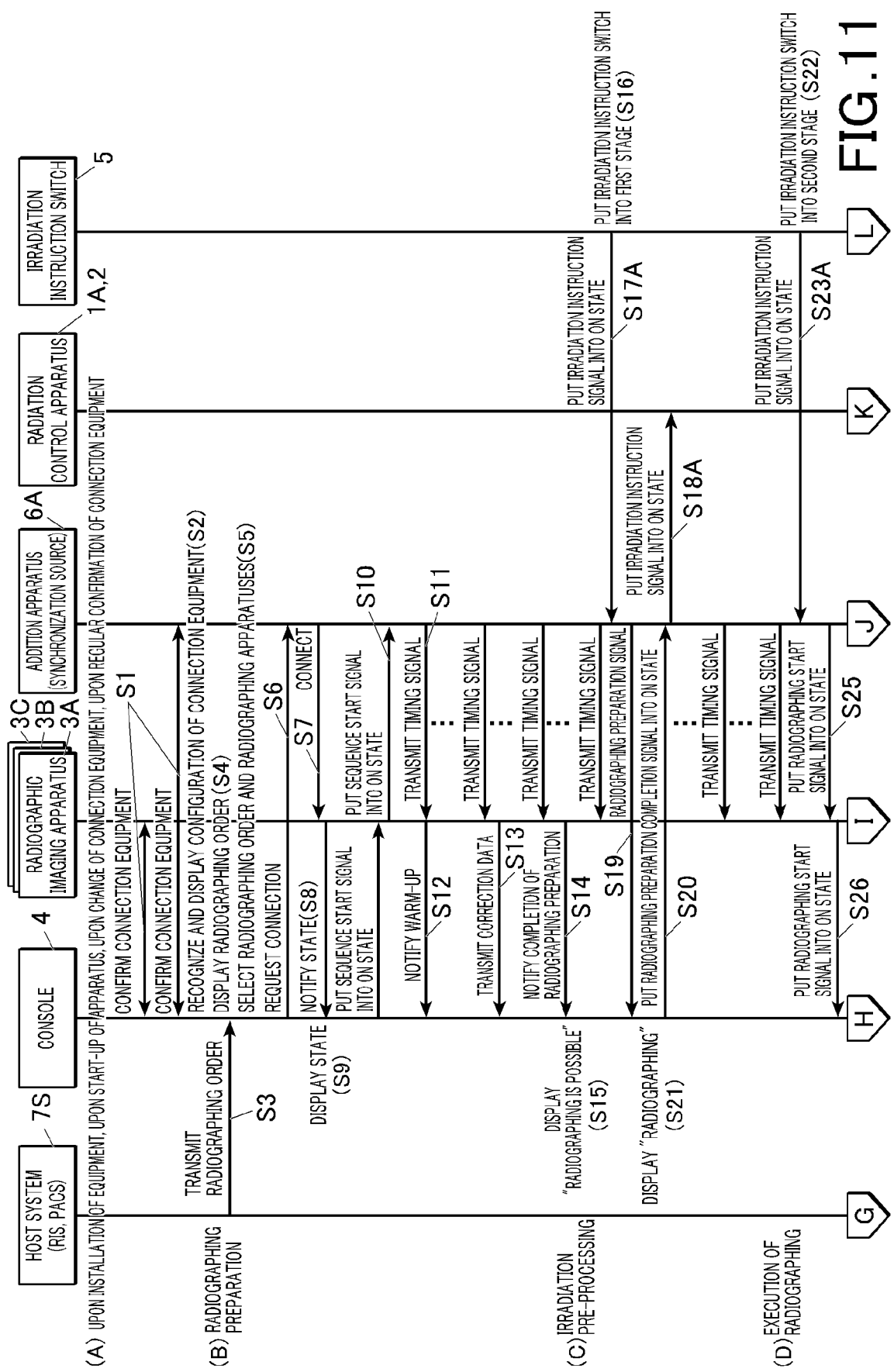
FIG. 11 is a ladder chart illustrating a first half of an operation of the radiographic imaging system in FIG. 10.

Note that the radiation control console 41 may be able to perform communication with a host system 7S (such as a radiology information system (RIS), and a picture archiving and communication system (PACS), see FIG. 4 and FIG. 11) via a communication network N such as an in-hospital LAN. The communication network N includes a plurality of communication networks configured centering around a plurality of pieces of communication network equipment (base units).

The irradiation instruction switch 5 is used by a radiographer to give an instruction to radiate radiation.

The irradiation instruction switch 5 in the present embodiment is configured to be able to perform an operation in two stages. Specifically, it is possible to put the irradiation preparation signal to be output to the radiation control console 41 into an ON state by putting the irradiation instruction switch 5 into a first stage, and it is possible to put the irradiation instruction signal to be output to the radiation control console 41 into an ON state by putting the irradiation instruction switch 5 into a second stage.

Note that, while FIG. 1 illustrates a configuration where the irradiation instruction switch 5 is connected to the radiation control console 41, and the irradiation preparation signal and the irradiation instruction signal output from the irradiation instruction switch 5 are input to the radiation controller 11 via the radiation control console 41, the irradiation instruction switch 5 may be connected to the radiation controller 11, and the irradiation preparation signal and the irradiation instruction signal may be directly input to the radiation controller 11.

[Operation]

An operation of the above-described conventional system 100A will be described next.

(Irradiation Preparation Operation)

If the irradiation instruction switch 5 is put into the first stage by the radiographer, the irradiation instruction switch 5 puts the irradiation preparation signal to be output to the radiation controller 11 via the radiation control console 41 into an ON state.

If the radiation controller 11 detects that the irradiation preparation signal is put into an ON state, the radiation controller 11 puts the irradiation preparation signal to be output to the high-voltage generator 12 into an ON state, and puts the irradiation preparation signal into a state where the irradiation preparation signal can be output to the external equipment.

If the high-voltage generator 12 detects that the irradiation preparation signal is put into an ON state, the high-voltage generator 12 outputs the irradiation preparation output to the radiation generator 2.

If the irradiation preparation output is input, the radiation generator 2 starts preparation for generating radiation.

This preparation for generating radiation indicates an operation of, for example, rotating a rotating anode, or the like, in a case where the anode is a rotating anode.

(Irradiation Operation)

Subsequently, if the irradiation instruction switch is put into the second stage by the radiographer, the irradiation instruction switch 5 puts the irradiation instruction signal to be output to the radiation controller 11 via the radiation control console 41 into an ON state.

If the radiation controller 11 detects that the irradiation instruction signal is put into an ON state, the radiation controller 11 puts this irradiation instruction signal into a state where the irradiation instruction signal can be output to the external equipment and transmits an irradiation signal to the high-voltage generator 12.

Note that, in a case where the radiation controller 11 is configured to judge whether or not to radiate radiation based on the irradiation allowance signal from the external equipment, in a case where the irradiation instruction signal from the irradiation instruction switch 5 or the radiation control console 41 is in an ON state, and the irradiation allowance signal is received from the external equipment, the radiation controller 11 transmits the irradiation signal to the high-voltage generator 12.

If the high-voltage generator 12 receives the irradiation signal, the high-voltage generator 12 applies a high voltage required for irradiation of radiation at the radiation generator 2, to the radiation generator 2 (performs an irradiation output).

If a high voltage is applied from the high-voltage generator 12, the radiation generator 2 generates radiation in accordance with the applied voltage.

A direction, an area, radiation quality, or the like, of irradiation, of the generated radiation are adjusted by a controller such as a collimator which is not illustrated, and the radiation is radiated to the object under examination and the cassette 3α behind the object under examination. Part of the radiation penetrates through the object under examination and is incident on the cassette 3α.

If the radiation is incident on the cassette 3α, a radiograph is formed on a stored film or fluorescent plate.

Here, if a timing at which the above-described irradiation preparation signal is put into an ON state is close to a timing at which the above-described irradiation instruction signal is put into an ON state, because, for example, irradiation is performed before speed of rotation of the rotating anode of the radiation generator 2 reaches sufficient speed, there is a case where, as a result of a local portion of the rotating anode excessively producing heat, the rotating anode may be damaged, or a radiated amount of radiation may become unstable (may become insufficient or excessive for irradiation intensity of an electron beam).

However, by configuring the radiation controller 11 as described above so that the irradiation signal is not transmitted until a predetermined waiting period has elapsed since it had been detected that the irradiation preparation signal had been put into an ON state, even if it is detected that the irradiation instruction signal is put into an ON state, it is possible to prevent occurrence of such a problem.

In this manner, in radiographing using the conventional system 100A, only one radiograph (still image) of the object under examination is captured based on a radiographing operation of one time.

First-A Embodiment

A first-A embodiment of the present invention will be described next with reference to FIG. 2 to FIG. 8. Note that the same reference numerals will be assigned to components equivalent to those in the above-described related art 1-A, and description thereof will be omitted.

[System Configuration]

Figure 2:
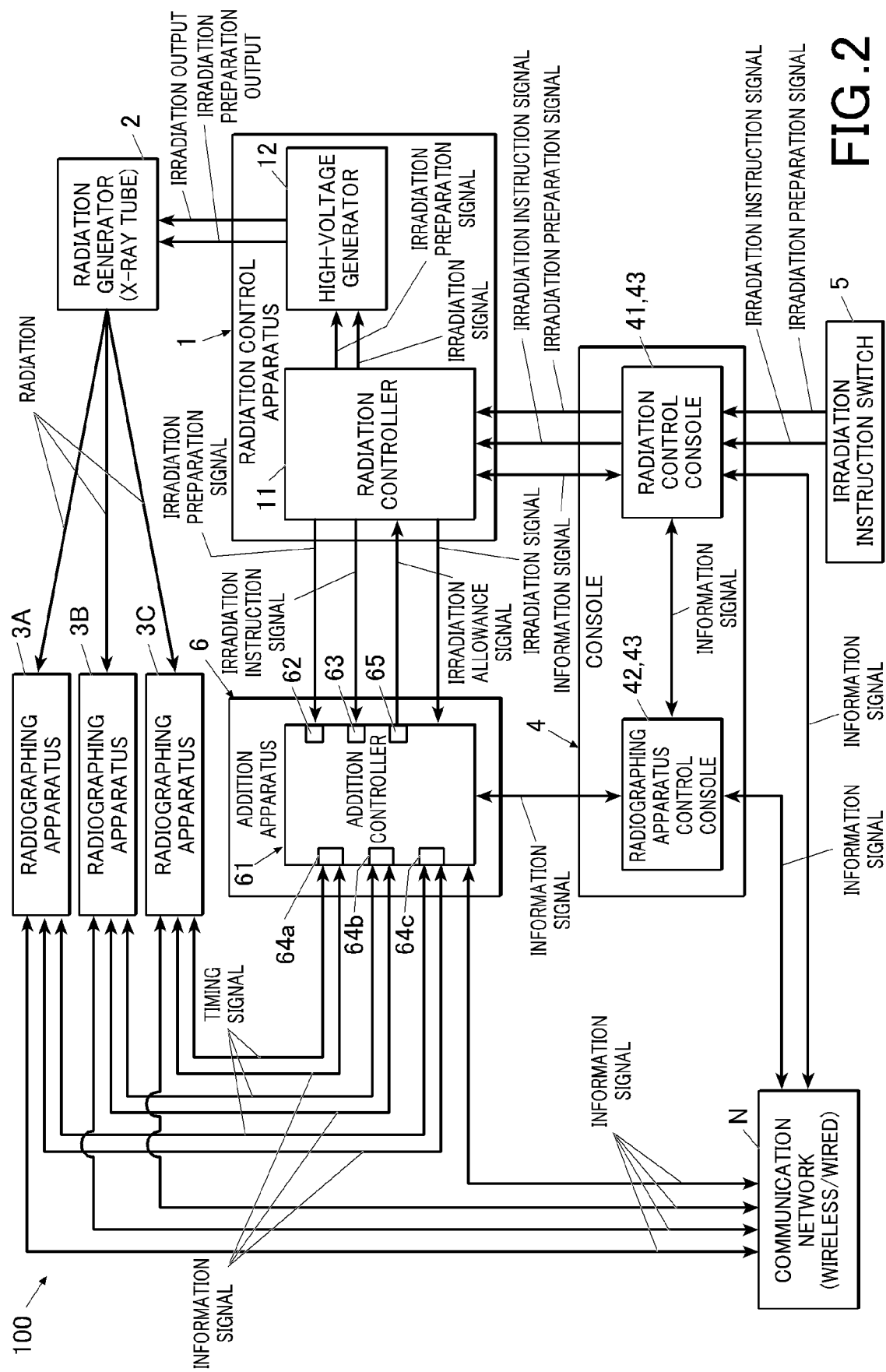
FIG. 2 is a block diagram illustrating a radiographic imaging system according to a first-A embodiment of the present invention.
Figure 3:
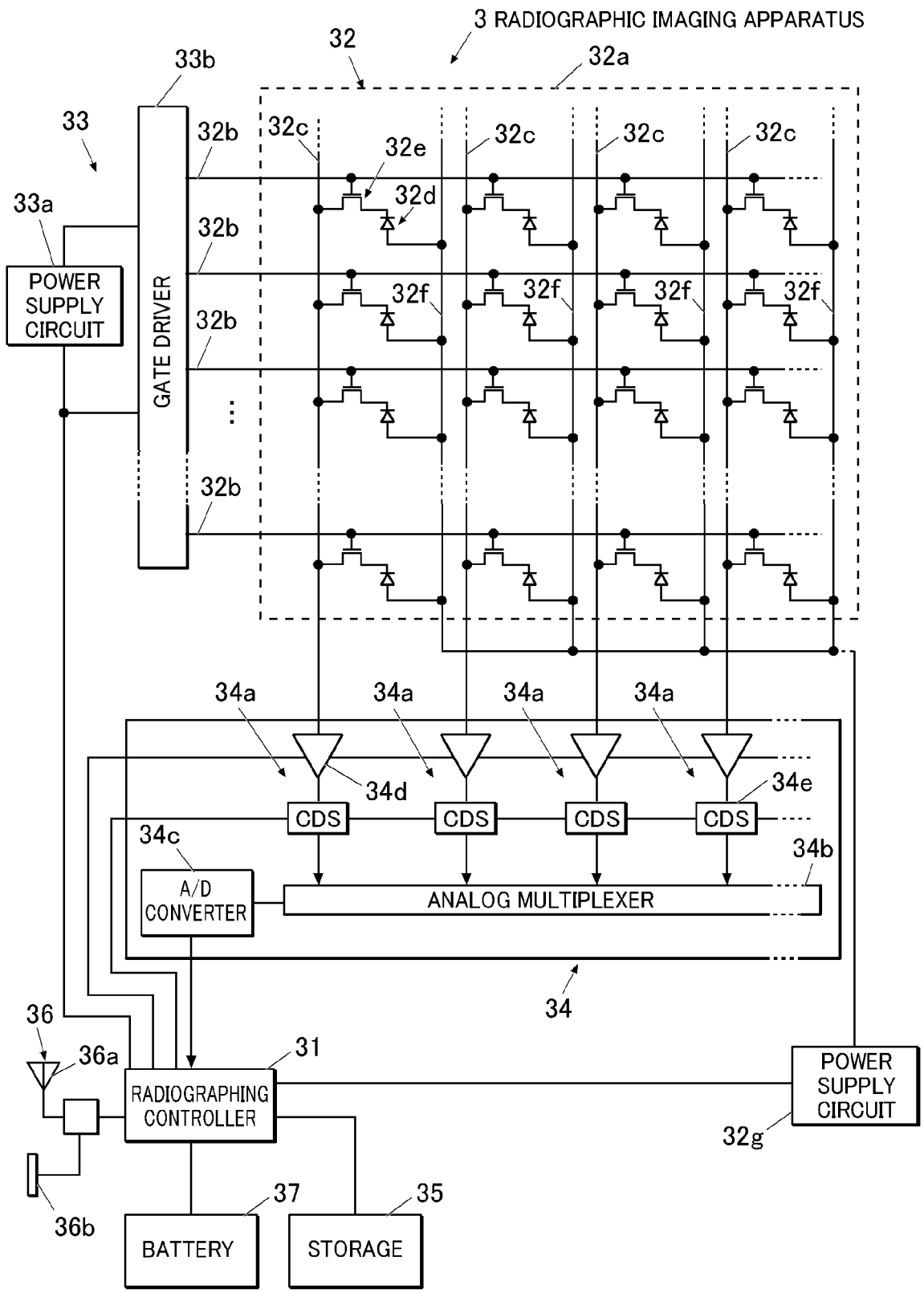
FIG. 3 is a block diagram illustrating a radiographic imaging apparatus provided in the radiographic imaging system in FIG. 2.

First, a system configuration of a radiographic imaging system (hereinafter, a system 100) according to the present embodiment will be described. FIG. 2 is a block diagram illustrating the system 100, and FIG. 3 is a block diagram of a radiographic imaging apparatus 3.

For example, as illustrated in FIG. 2, the system 100 according to the present embodiment is a system in which the cassette 3α in the conventional system 100A is replaced with a plurality of radiographic imaging apparatuses 3 (hereinafter, radiographing apparatuses 3), and, further, a radiographing apparatus control console 42 and an addition apparatus 6 are added. As will be described later, this system 100 is a system which successively performs long-length radiographing a plurality of times at predetermined intervals using the plurality of radiographing apparatuses 3, and can acquire a plurality of long-length images indicating a dynamic state of the subject. The plurality of radiographing apparatuses 3 preferably performs radiographing in a state where overlapping and positions thereof are adjusted, and there is a case where radiographing is performed using a holder or a radiographing platform which is not illustrated, and which includes a storage for storing the plurality of radiographing apparatuses 3. Note that, while, in the following embodiment, a case will be described as an example where radiographing is performed using three radiographing apparatuses 3, the number of radiographing apparatuses to be used is not particularly limited. Further, description will be provided assuming that the radiographing apparatuses 3 to be used for radiographing are radiographing apparatuses 3A to 3C.

In the present embodiment, the radiation generator 2 successively radiates radiation if a voltage is continuously applied from the radiation control apparatus 1, and if a pulsed voltage is applied, the radiation generator 2 can radiate pulsed radiation. In other words, the radiation generator 2 supports still radiography and serial radiography.

The still radiography is radiography in which radiation of a duration set in radiographing conditions is radiated only once in an irradiation start operation of one time, and one radiograph of the object under examination is generated.

Serial radiography is a radiographing mode in which a plurality of radiographs indicating a dynamic state of the object under examination are generated by successively radiating pulsed radiation of a duration set in the radiographing conditions in an irradiation start operation of one time, and successively performing radiographing a plurality of times in accordance with the irradiation.

Hereinafter, radiographing in which long-length radiography of successively performing radiographing a plurality of times using a plurality of radiographing apparatuses 3A to 3C is performed in a serial radiography mode will be referred to as long-length serial radiography. Further, a series of long-length images obtained by long-length serial radiography will be referred to as a long-length dynamic image, and individual radiographs (including radiographs before and after connection processing) which constitute the long-length dynamic image will be referred to as a frame image or a radiograph.

The radiographing apparatus 3 includes a radiographing controller 31, a radiation detector 32, a scanning driver 33, a read-out unit 34, a storage 35, a communicator 36, or the like, as illustrated in FIG. 3 other than a chassis and a scintillator which are not illustrated. Further, respective components 31 to 36 receive power supply from a battery 37.

At the chassis, a power supply switch, a switch, an indicator, which are not illustrated, a connector 36b of the communicator 36 which will be described later, or the like, are provided.

The scintillator emits an electromagnetic wave such as visible light, whose wavelength is longer than that of radiation, when receiving radiation.

The radiographing controller 31 is configured with a computer, or the like, including a central processing unit (CPU), a read only memory (ROM) in which programs for causing the radiographing apparatus 3 to operate are stored, a random access memory (RAM), an input/output interface, or the like, which are connected to a bus, an field programmable gate array (FPGA), or the like, which are not illustrated. Note that the radiographing controller 31 may be configured with a dedicated control circuit.

The radiation detector 32, which generates electric charges by receiving radiation, is configured with a substrate 32a, a plurality of scanning lines 32b, a plurality of signal lines 32c, a plurality of radiation detection elements 32d, a plurality of switch elements 32e, a plurality of bias lines 32f, a power supply circuit 32g, or the like.

The substrate 32a is formed in a plate shape and is disposed so as to face the scintillator in parallel.

The plurality of scanning lines 32b are provided at predetermined intervals so as to extend in parallel to each other.

The plurality of signal lines 32c are provided at predetermined intervals so as to extend in parallel to each other, are provided so as to extend in orthogonal to the scanning lines 32b, and are provided so as not to be in conduction with respective scanning lines.

In other words, the plurality of scanning lines 32b and signal lines 32c are provided to form a grid.

The radiation detection elements 32d, which respectively generate electrical signals (currents, electric charges) in accordance with amounts of radiation (light amounts of electromagnetic waves converted by the scintillator) radiated on the radiation detection elements, are configured with, for example, photodiodes, phototransistors, or the like.

The plurality of radiation detection elements 32d are respectively provided on a surface of the substrate 32a within a plurality of regions segmented with the plurality of scanning lines 32b and signal lines 32c. In other words, the plurality of radiation detection elements 32d are arranged in a matrix. Therefore, each of the radiation detection elements 32d faces the scintillator.

A drain terminal of the switch element 32e which is a switch element is connected to one terminal of each radiation detection element 32d, and a bias line is connected to the other terminal.

A plurality of switch elements 32e are respectively provided within a plurality of regions segmented with the plurality of scanning lines 32b and signal lines 32c in a similar manner to the radiation detection elements 32d.

A gate electrode of each switch element 32e is connected to the adjacent scanning line 32b, a source electrode is connected to the adjacent signal line 32c, and a drain electrode is connected to one terminal of the radiation detection element 32d in the same region.

A plurality of bias lines 32f are connected to other terminals of the respective radiation detection elements 32d.

The power supply circuit 32g generates a reverse bias voltage and applies the reverse bias voltage to the respective radiation detection elements via the bias lines 32f.

The scanning driver 33 is configured with a power supply circuit 33a, a gate driver 33b, or the like.

The power supply circuit 33a generates an ON voltage and an OFF voltage which are different voltages, and supplies the voltages to the gate driver 33b.

The gate driver 33b switches a voltage to be applied to each scanning line 32b between an ON voltage and an OFF voltage.

The read-out unit 34 includes a plurality of read-out circuits 34a, an analog multiplexer 34b, an A/D converter 34c, or the like.

The plurality of read-out circuits 34a are respectively connected to the respective signal lines 32c of the radiation detector 32, and apply a reference voltage to the respective signal lines 32c.

Further, each read-out circuit 34a is configured with an integration circuit 34d, a correlated double sampling circuit (hereinafter, a CDS circuit) 34e, or the like.

The integration circuit 34d integrates electric charges discharged to the signal lines 32c, and outputs a voltage value in accordance with the integrated electric charge amount to the CDS circuit 34e.

The CDS circuit 34e samples and holds the output voltage of the integration circuit 34d before an ON voltage is applied to the scanning line 32b to which the radiation detection element 32d from which a signal is to be read out is connected (during an OFF voltage is applied), applies an ON voltage to the corresponding scanning line 32b to read out signal charges of the radiation detection element, and outputs a difference from an output voltage of the integration circuit 34d after an OFF voltage is applied to the corresponding scanning line 32b.

The analog multiplexer 34b outputs a plurality of differential signals output from the CDS circuit 34e to the A/D converter 34c one by one.

The A/D converter 34c sequentially converts image data of input analog voltage values into image data of digital values.

The storage 35 is configured with static RAM (SRAM), synchronous DRAM (SDRAM), a NAND flash memory, an hard disk drive (HDD), or the like.

The communicator 36 includes an antenna 36a for performing communication with outside and a connector 36b.

Further, the communicator 36 can select either wireless communication or wired communication based on a control signal from outside. In other words, in a case where wireless communication is selected, the communicator 36 can perform wireless communication using the antenna 36a, and, in a case where wired communication is selected, the communicator 36 can transmit/receive information by using a wired LAN, a dedicated signal line, or the like. Further, in a case where it is desired to achieve synchronization using wired communication, it is possible to achieve synchronization by using protocol such as, for example, network time protocol (NTP) and a method specified in international standards IEEE 1588.

The radiographing apparatus 3 configured in this manner is put into one of an "initialization state", an "accumulation state" and a "read-out/transfer state" when the radiographing apparatus 3 is powered on. A timing for switching the state will be described later.

The "initialization state" is a state in which an ON voltage is applied to each switch element 32e, and electric charges generated by the radiation detection elements 32d are not accumulated in respective pixels (the electric charges are discharged to the signal lines 32c).

The "accumulation state" is a state in which an OFF voltage is applied to each switch element 32e, and the electric charges generated by the radiation detection elements 32d can be accumulated in the pixels (the electric charges are not discharged to the signal lines 32c).

The "read-out/transfer state" is a state in which an ON voltage is applied to each switch element 32e, the read-out unit 34 is driven to read out image data based on the electric charges which have been flowing in, and transmit the image data to other apparatuses.

Note that, depending on configurations of elements and apparatuses, because the accumulated electric charges are cleared by read-out, there is a case where "read-out" and "initialization" are performed at the same time as the same operation instead of "read-out" and "initialization" being distinguished as different kinds of operation.

Note that, while, here, an example of a so-called indirect-type radiographing apparatus will be described which obtains an electrical signal by converting radiated radiation into an electromagnetic wave of other wavelengths, such as visible light, the present invention may be a so-called direct-type radiographing apparatus which directly converts radiation into an electrical signal at the detection elements.

Further, if image data of a radiograph can be generated, other configurations of the radiographing apparatus 3 are not limited to that illustrated in FIG. 3.

As illustrated in FIG. 2, the radiographing apparatus control console 42 is configured to be able to transmit/receive an information signal to/from the radiation control console 41 and set information regarding the object under examination, the radiographing conditions, or the like, at the radiographing apparatuses 3A to 3C.

Note that, while the radiation control console 41 performs setting of the radiation controller 11, and the radiographing apparatus control console 42 performs setting of the radiographing apparatuses 3A to 3C, because these perform setting regarding the same radiographing, in the following description, there is a case where these will be collectively and broadly referred to as a console 4.

For example, the console 4 is configured with a computer, or the like, including a central processing unit (CPU, a hardware processor), a read only memory (ROM) in which programs for causing the console 4 to operate are stored, a random access memory (RAM), an operator (such as a keyboard and a mouse), a display 43 (display means such as a liquid crystal display), an input/output interface, a communicator (receiver, outputter), or the like, which are not illustrated, and which are connected to a bus. Functions of the radiation control console 41 and the radiographing apparatus control console 42 are respectively executed through cooperation between radiation control programs stored in the ROM and the RAM, and the CPU, and through cooperation between radiographing control programs and the CPU. Alternatively, the radiation control console 41 and the radiographing apparatus control console 42 may be configured with a computer, or the like, including a CPU, a read only memory (ROM), RAM, an operator, the display 43, an input/output interface, a communicator, or the like, which are not illustrated, and which are connected to a bus.

Here, the input/output interface includes a connector, or the like, for connecting the console 4 to each of the radiation control apparatus 1 and the addition apparatus 6 in a wired manner. The communicator includes a connector for connecting the console 4 to a communication network such as an in-hospital LAN, an antenna, or the like.

Note that there is a case where the consoles 4 are associated with the radiation control apparatuses 1 on a one-to-one basis, or there is a case where one console 4 is connected to a plurality of radiation control apparatuses 1, and a radiation control apparatus 1 to which the console 4 is to be connected is selected and controlled for each time of radiographing. Alternatively, there is a case where one radiation control apparatus 1 is connected to a plurality of consoles 4, and a radiographer selects and operates a console 4 to be used.

While FIG. 2 illustrates a configuration where, in a case where the radiographing apparatus control console 42 performs setting of the radiographing conditions, or the like, setting of the radiation controller 11 is performed via the radiation control console 41 (by an information signal being transmitted and received between the radiation control console 41 and the radiographing apparatus control console 42), it is also possible to employ a configuration where the radiographing apparatus control console 42 directly performs setting of the radiation controller 11.

Further, it is also possible to employ a configuration where the radiation control console 41 performs setting of the radiographing apparatuses 3A to 3C.

Further, while FIG. 2 illustrates a configuration where the console 4 is connected to the radiographing apparatuses 3A to 3C via the addition apparatus 6, the console 4 can be directly connected to the radiographing apparatuses 3A to 3C, and for example, as illustrated in FIG. 2, can be connected to the radiographing apparatuses 3A to 3C via the communication network.

Further, the console 4 can set an operation of the addition apparatus 6.

Specifically, it is possible to set the number of times of output of the irradiation allowance signal (maximum number of radiographs to be captured) or an output period during which output of the irradiation allowance signal is repeated, at the addition apparatus 6 before the addition apparatus 6 outputs the irradiation allowance signal.

Note that the console 4 may display the number of times of output or the output period set at the addition apparatus 6, at the display 43.

Further, when a radiographing start signal to be input to the addition apparatus 6 is put into an ON state, the console 4 may display information indicating that it is possible to perform irradiation at the display 43.

Further, while the addition apparatus 6 outputs the irradiation allowance signal, the console 4 may display information indicating that radiation is being radiated, at the display 43.

In the present embodiment, the console 4 functions as a control apparatus.

The addition apparatus 6 includes an addition controller 61 including a first acquirer 62, a second acquirer 63, a first connector 64, and a second connector 65. In long-length serial radiography, it is necessary to adjust a radiographing timing of all the radiographing apparatuses 3 to be used for radiographing and a radiation irradiation timing by the radiation control apparatus 1 so as to match each other. The addition apparatus 6 is a synchronization source which generates and outputs a timing signal and the irradiation allowance signal for adjusting the radiographing timing and the radiation irradiation timing so as to match each other.

The addition controller 61 can be configured to comprehensively control operations of respective components of the addition apparatus 6 with the CPU, the RAM, or the like.

In this case, various kinds of processing programs stored in the storage which is not illustrated are read out and deployed to the RAM, and various kinds of processing are executed in accordance with the processing programs.

The first acquirer 62, which has a contact (for example, a connector) with the radiation controller 11, acquires the irradiation preparation signal output by the irradiation instruction switch 5 via the radiation controller 11 in the present embodiment.

The second acquirer 63, which has a contact (for example, a connector) with the radiation controller 11, acquires the irradiation instruction signal output by the irradiation instruction switch 5 via the radiation controller 11 in the present embodiment.

Here, in the examples illustrated in FIG. 1 and FIG. 2, description has been provided using an example where the irradiation preparation signal and the irradiation instruction signal from the irradiation instruction switch 5 are input to the radiation controller 11 via the console 4. However, the signals from the irradiation instruction switch 5 are not required to be input to the radiation controller 11 via the console 4, and may be configured to be directly input to the radiation controller 11 from the irradiation instruction switch 5 without involving the console 4 depending on equipment configurations.

In a case where the signals from the irradiation instruction switch 5 are input to the radiation controller 11 via the console 4, the console 4 can recognize that irradiation preparation and irradiation instruction are issued from the radiographer in a similar manner to the radiation controller 11, and the console 4 can make a notification of an operation, display, or the like, in accordance with the irradiation preparation and the irradiation instruction in accordance with these input signals.

Meanwhile, in a case where the signals from the irradiation instruction switch 5 are input to the radiation controller 11 without involving the console 4, the radiation controller 11 can receive signals of irradiation preparation and irradiation instruction without being affected by other equipment, so that the radiation controller 11 can perform a more stable and secure operation.

The first connectors 64 (64a to 64c) have contacts (for example, connectors) with the radiographing apparatuses 3A to 3C, and can input an irradiation start allowance signal.

Note that, because the irradiation start allowance signal is a signal which is put into an ON state when the radiographing apparatuses 3A to 3C are put into a state where radiographing is possible, and which is put into an OFF state when the radiographing apparatuses 3A to 3C are put into a state where radiographing is not possible, the irradiation start allowance signal is a signal indicating drive states of the radiographing apparatuses 3A to 3C in the present invention.

The second connector 65, which is a connector in the present embodiment, can be connected to the radiation controller 11 by one end of a cable whose other end is connected to the radiation controller 11 being inserted.

Further, the second connector 65 can output the irradiation allowance signal to the radiation controller 11.

Note that, while FIG. 2 illustrates a configuration where the first acquirer 62, the second acquirer 63, the first connector 64, the second connector 65 directly transmit/receive information and signals to/from other apparatuses (the first and the second acquirers 63 and the second connector 65 transmit/receive information and signals to/from the radiation control apparatus 1, and the first connector 64 transmits/receives information and signals to/from the radiographing apparatuses 3A to 3C), at least one of the first acquirer 62, the second acquirer 63, the first connector 64, and the second connector 65 may be able to be connected to other apparatuses via a relay which can relay signals and which is not illustrated.

Further, while FIG. 2 illustrates a case where the first acquirer 62, the second acquirer 63, the first connector 64, and the second connector 65 are separately provided, at least two of the first acquirer 62, the second acquirer 63, the first connector 64 and the second connector 65 may be integrally configured (respective components 62 to 65 may be combined).

The addition controller 61 of the addition apparatus 6 configured in this manner can repeatedly output pulsed irradiation allowance signals which give an instruction to radiate radiation from the second connector 65 to the radiation controller 11 with a predetermined period based on the irradiation instruction signal acquired from the radiation controller 11 via the second acquirer 63 and the irradiation start allowance signals input from the radiographing apparatuses 3A to 3C via the first connector 64.

Note that the addition controller 61 may be configured not to output the irradiation allowance signal until a predetermined waiting period has elapsed since it had been detected that the irradiation start allowance signal had been put into an ON state even if it is detected that the radiographing start signal is put into an ON state.

Further, the addition controller 61 outputs the timing signal which gives an instruction of a radiographing timing for capturing a radiograph from the first connector 64 to the radiographing apparatuses 3A to 3C based on a timing at which the irradiation allowance signal is output.

The radiographing timing is, for example, set at a timing at which an operation of accumulating electric charges of the radiograph is started. In other words, the radiographing apparatuses 3A to 3C according to the present embodiment start accumulation of electric charges in accordance with the timing signal and sequentially perform operations of finishing accumulation, reading out electric charges in the respective pixels, forming images of the electric charges in the respective pixels, storing and transferring the images using respective timers of the radiographing apparatuses 3A to 3C.

By such control being performed, the addition controller 61 can control both the radiation irradiation timing by the irradiation allowance signal and the accumulation timing for accumulating electric charges upon radiation irradiation by the timing signal. As a result, it is possible to reliably accumulate electric charges by radiation irradiation, so that it is possible to reliably acquire a radiograph by radiation irradiation.

Note that, in a case where the electric charge accumulation operation is started at the above-described radiographing timing in this manner, the radiographing apparatuses 3A to 3C may wait in a state where a timing transitions to the accumulation timing at which radiographing operation is performed by radiation irradiation, and may start an accumulation operation in accordance with the timing signal.

By such control being performed, the addition controller 61 can reliably acquire a radiograph by radiation irradiation in a similar manner to the above-described case.

Further, as the radiographing timing which is triggered by input of this timing signal, a timing at which one of various kinds of operation which are to be repeatedly performed by the radiographing apparatuses 3A to 3C is started can be set other than the above-described electric charge accumulation operation.

For example, in a case where it is necessary to reset the electric charges accumulated in the respective pixels before the accumulation operation, a timing at which reset is started may be set as the above-described radiographing timing.

In this case, the operation of the radiographing apparatuses 3A to 3C may sequentially transition to the accumulation operation after reset is completed.

By such control being performed, it is possible to start the accumulation operation of accumulating electric charges by radiation irradiation in a state where dark electric charges which are noise components accumulated over time before electric charges by radiation irradiation are accumulated in the respective pixels are discharged by reset, so that it is possible to acquire a radiograph with less noise.

Alternatively, a timing at which the accumulation operation is finished may be set as the above-described radiographing timing. Alternatively, a timing at which read-out of the accumulated electric charges is started by the timing signal may be set as the above-described radiographing timing.

By such control being performed, the addition controller 61 can control both the radiation irradiation timing by the irradiation allowance signal and the timing at which accumulation of the electric charges by radiation irradiation is finished by the timing signal or the timing at which the electric charges accumulated by radiation irradiation are read out. As a result, it is possible to reliably accumulate the electric charges by radiation irradiation, so that it is possible to reliably acquire a radiograph by radiation irradiation.

Note that the timing signal may be used for finishing each operation instead of being used for starting each operation. For example, the accumulation operation may be started in accordance with a timing at which the timing signal changes from an OFF state to an ON state, and the accumulation operation may be finished in accordance with a timing at which the timing signal changes from an ON state to an OFF state.

By such control being performed, the addition controller 61 can reliably acquire a radiograph by radiation irradiation in a similar manner to the above-described each case.

Further, in the present embodiment, the timing signal is repeatedly output with the same period as that of the irradiation allowance signal.

Further, in the present embodiment, the addition controller 61 repeatedly outputs the irradiation allowance signal until the number of times of output reaches a predetermined number of times of output or until a predetermined output period has elapsed since the irradiation allowance signal had been output first.

Note that the timing signal may be output delayed or ahead by a predetermined period since the irradiation allowance signal has been output.

Further, the addition controller 61 can be configured to include a timer for controlling a timing to repeatedly transmit the timing signal and the irradiation allowance signal with a predetermined period.

Further, the addition controller 61 can be configured to include a counter which counts the number of times of output to repeatedly output the timing signal and the irradiation allowance signal until the number of times of output reaches the predetermined number of times of output. Alternatively, the addition controller 61 can be configured to include a timer to repeatedly output the timing signal and the irradiation allowance signal until a predetermined output period has elapsed since the timing signal and the irradiation allowance signal had been output first.

Further, it is also possible to employ a configuration where the timing signal is output before the irradiation instruction switch 5 is put into the second stage (the irradiation instruction signal is acquired).

Specifically, it is also possible to employ a configuration where the timing signal is output, for example, also from when a sequence start signal is acquired (it is detected that the sequence start signal is put into an ON state) until when the irradiation instruction signal is acquired, or from when the irradiation preparation signal is acquired (it is detected that the irradiation preparation signal is put into an ON state) until when the irradiation instruction signal is acquired.

Here, there is a case where the radiographing apparatus 3 is connected to the communication network, and there is a case where the radiographing apparatus 3 is not connected to the communication network. For example, a plurality of radiographing apparatuses 3 are not always stored in a holder or a radiographing platform for capturing a plurality of radiographs (for long-length radiography), and there is a case where the radiographing apparatus 3 is stored in a radiographing platform for performing radiographing with one radiographing apparatus, a moving radiographing apparatus for rounding, or the like. Also in such a state, to display which radiographing apparatus 3 can be used at the console 4, the console 4 needs to continue transmission/reception of the information signal from/to the respective radiographing apparatuses 3. In such a case, it is possible to utilize connection of the information signal between the communication network and the respective radiographing apparatuses 3. As such connection, for example, it is possible to use a wireless access point as the communication network, and it is possible to use wireless communication between the communication network and the respective radiographing apparatuses 3. Meanwhile, as will be described later, in order that the plurality of radiographing apparatuses 3A to 3C perform long-length serial radiography, the plurality of radiographing apparatuses 3A to 3C need to connect the timing signal with the addition controller 61. In such a case, there is a case where the respective radiographing apparatuses 3A to 3C connect not only the timing signal but also the information signal with the addition controller 61. In such a case, it is possible to perform an operation such that (1) connection between the communication network and the respective radiographing apparatuses 3A to 3C is not performed, (2) even if the communication network is connected to the respective radiographing apparatuses 3A to 3C, the radiographing apparatuses 3A to 3C perform connection with the addition apparatus 6 while priority is given to connection between the addition apparatus 6 and the radiographing apparatuses 3A to 3C, (3) while connection between the communication network and the respective radiographing apparatuses 3A to 3C is continued, priority is given to connection between the addition apparatus 6 and the respective radiographing apparatuses 3A to 3C, and a communication session between the communication network and the radiographing apparatuses 3A to 3C is finished, or is not started, and a communication session between the addition apparatus 6 and the radiographing apparatuses 3A to 3C is started, or (4) while the communication session between the communication network and the radiographing apparatuses 3A to 3C is continued, priority is given to communication between the addition apparatus 6 and the respective radiographing apparatuses 3A to 3C.

[Operation]

Figure 5:
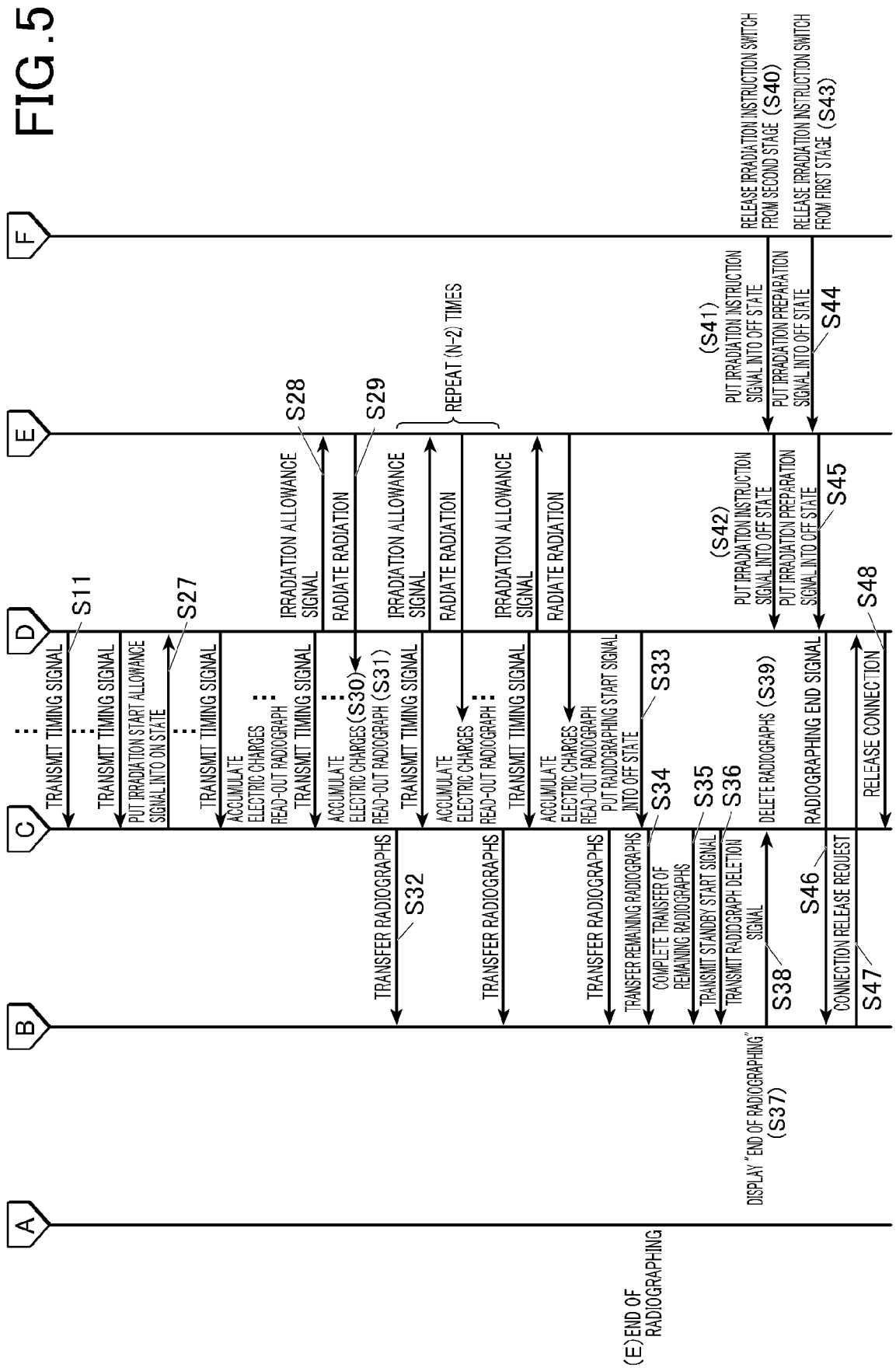
FIG. 5 is a ladder chart illustrating a last half of the operation of the radiographic imaging system in FIG. 2.

An operation of the above-described system 100 will be described next. FIG. 4 and FIG. 5 are ladder charts illustrating the operation of the system 100 according to the present embodiment. Here, a vertical direction of the ladder charts in FIG. 4 and FIG. 5 illustrate an example of an operation order and does not illustrate an actual time interval. Therefore, there is a case where it takes longer time at a portion where an interval is larger than other portions where an interval is smaller, or there is a case where it takes equal time or shorter time. Further, while the radiographing apparatuses 3A to 3C are collectively illustrated due to space limitations, the radiographing apparatuses 3A to 3C respectively transmit/receive signals illustrated in FIG. 4 and FIG. 5. Further, while the radiographing apparatuses 3A to 3C transmit/receive signals at the same timing, the timing may be shifted in accordance with performance and property of the respective radiographing apparatuses 3A to 3C. Here, the performance and the property are, for example, performance of the radiographing apparatus such as the number of pixels with which the radiographing apparatus can perform radiographing, a pixel size, a radiographing frame rate, start-up time, pixel sensitivity, pixel response speed, and a radiographing size, and, a difference in property due to variation provided for each radiographing apparatus even between the radiographing apparatuses having the same performance, and it is possible to set a setting value indicating the property in accordance with individual radiographing apparatuses upon shipment from the factory or upon maintenance, and change the performance and the property by performing processing in accordance with the setting value.

The operation of the radiation control apparatus 1 in the ladder charts illustrated in FIG. 4 and FIG. 5 is executed by control by the radiation controller 11. The operation of the radiographing apparatuses 3A to 3C is executed by control by the radiographing controller 31. Operation of the addition apparatus 6 is executed by control by the addition controller 61. The operation of the console 4 is executed through cooperation between the CPU of the console 4 and the programs stored in the ROM and the RAM.

(A: Upon Installation of Equipment, Upon Start-Up of Apparatus, Upon Change of Connection Equipment, and Upon Regular Confirmation of Connection Equipment)

First, as illustrated in FIG. 4, the console 4, particularly, the radiographing apparatus control console 42 confirms equipment connected to a radiographing environment controlled by the console 4 (such as the radiation control apparatus 1, the radiographing apparatus 3, the addition apparatus 6, a cradle and a radiographing platform) and the communication network upon installation of the equipment, upon start-up of the radiographing system, upon change of connection equipment, and upon other regular confirmation of connection equipment (step S1), and displays a configuration of equipment and a connection configuration at the display 43 of the console 4 (step S2).

Figure 6:
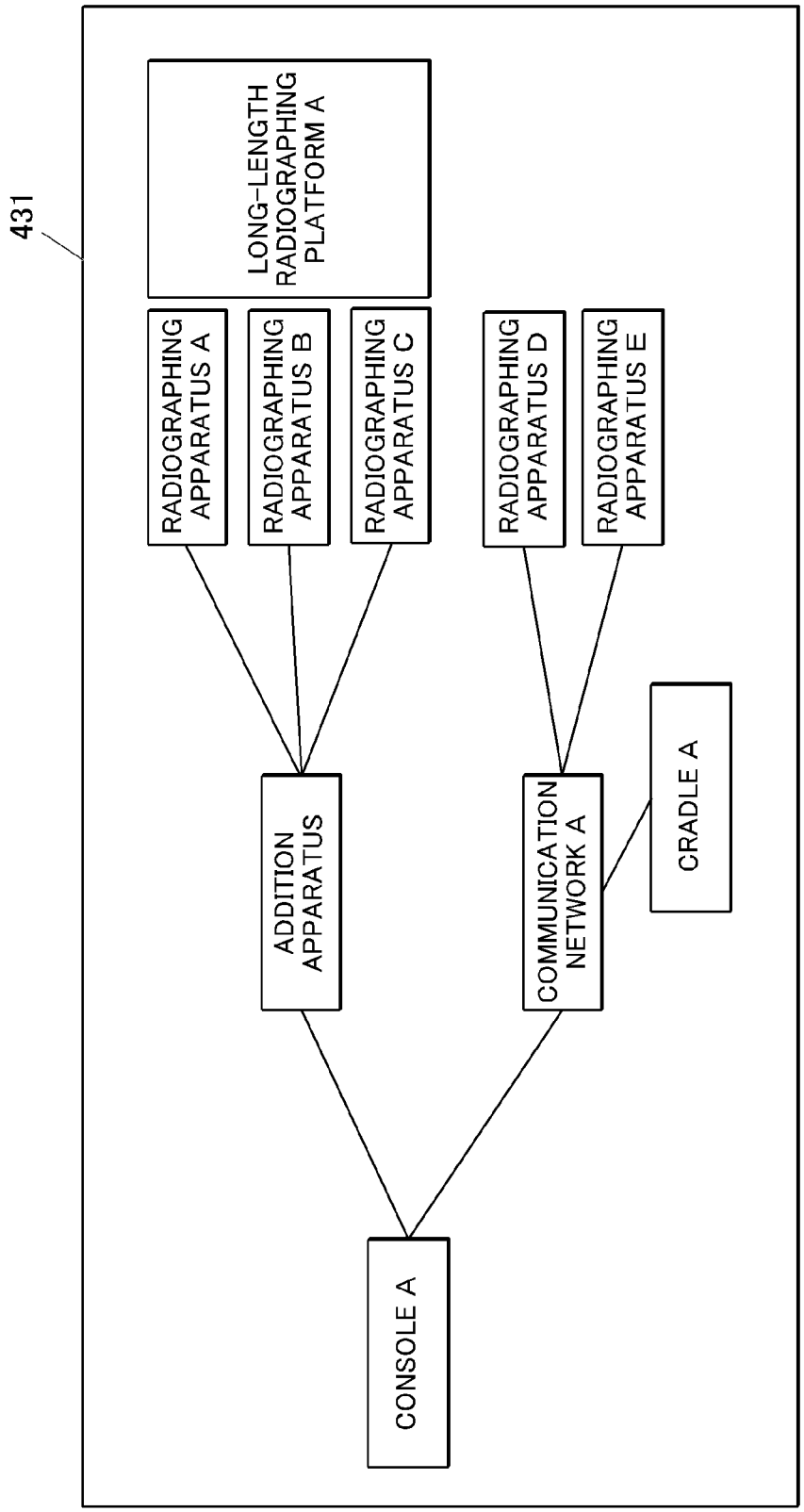
FIG. 6 is a view illustrating an example of a system state display screen.

Here, because there is a case where a plurality of radiation control apparatuses 1, radiographing apparatuses 3, addition apparatuses 6, cradles, radiographing platforms, communication networks (base units) or the like, are provided in a hospital, the radiographer needs to confirm equipment connected to the radiographing environment controlled by the console 4 and a connection configuration. For example, by a system state display screen 431 as illustrated in FIG. 6 being displayed at the display 43, the user can confirm a configuration of equipment connected to the radiographing environment controlled by the console 4, and a connection configuration.

It is possible to confirm equipment connected to the radiographing environment controlled by the console 4 and the connection configuration by, for example, combination of communication identification information (ID) and address information of equipment which becomes components within the system 100 being stored in the console 4, and the console 4 requesting whether or not there is connection to each piece of equipment, and an ID, and each piece of equipment returning whether or not there is connection and the ID. Here, in a case where other pieces of equipment are further connected to each piece of equipment (for example, in a case where the radiographing apparatus 3 is connected to the addition apparatus 6), the equipment to which other pieces of equipment are connected acquires IDs of the other pieces of equipment and transmits the information to the console 4. By this means, the console 4 can grasp whether each piece of equipment is directly connected, or is connected via other pieces of equipment or the communication network.

As the ID, for example, an ID specific to each piece of equipment such as a MAC address set specific to equipment, a BSSID specific to equipment, and a serial number set specific to the apparatus can be used, or an ID set later such as a set IP address and a set ESSID can be used.

Note that it is also possible to employ a configuration where the base unit of the communication network sets the radiographing apparatus 3 connected to a wired connector with which the base unit performs communication as equipment (an extension unit) to which the communication network base unit is to be wirelessly connected, and acquires an ID. For example, in the configuration illustrated in FIG. 6, the communication network A (base unit) can be connected to the radiographing apparatus 3 through wireless connection, the communication network A is also connected to a cradle A which can be connected to the radiographing apparatus 3 in a wired manner. If the radiographing apparatus 3 is connected to the cradle A which can be connected in a wired manner, the connected radiographing apparatus 3 is set so as to be connected to a communication network A or preferentially connected. Further, the cradle A reads an ID of the radiographing apparatus 3 and transmits the ID of the connected radiographing apparatus 3 to the communication network A and the console 4 as information read at the cradle A. To indicate that the information is read at the cradle A, for example, it is also possible to transmit the ID of the radiographing apparatus 3 to the console 4 along with the ID of the cradle A or the communication network A. The console 4 can grasp which radiographing apparatus 3 is wirelessly connected via which communication network from a relationship between IDs stored in advance and equipment, and, for example, can display the information at the display 43 as the system state display screen 431 illustrated in FIG. 6.

(B: Radiographing Preparation)

Thereafter, when the console 4 receives a radiographing order from the host system 7S such as an RIS and an HIS (step S3), the console 4 displays the received radiographing order at the display 43 of the console 4 (step S4).

At this time, it is also possible to employ a configuration where a worker is notified that a new radiographing order is received using light and sound.

The radiographer performs an operation of changing a radiographing order, or the like, in response to the displayed radiographing order and selects the radiographing order to be processed next and the radiographing apparatuses 3A to 3C, or the like, to be used (step S5).

At this time, the operator may select the radiographing apparatuses 3A to 3C to be used among a plurality of connected radiographing apparatuses 3. For example, the operator can select the radiographing apparatuses 3A to 3C to be used from the system state display screen 431 as illustrated in FIG. 6 displayed at the console 4.

Further, it is also possible to employ a configuration where the radiographing apparatuses 3A to 3C which are recommended are automatically selected from a plurality of the connected radiographing apparatuses 3 in accordance with radiographing manipulation of the radiographer using the console 4.

Further, in a case where there is no particular change, it is also possible to employ a configuration where the radiographing apparatuses 3A to 3C which have been used in previous radiographing are automatically and continuously selected.

Alternatively, for example, in a case of long-length radiography, holders for radiography or long-length radiographing platforms are used to fix relative positions of the plurality of radiographing apparatuses 3A to 3C. Therefore, in a case where long-length radiography is selected, the radiographing apparatuses 3 which are provided on these holders for radiography or the long-length radiographing platforms may be selected as the radiographing apparatuses 3A to 3C.

Alternatively, for example, in a case of long-length serial radiography, the radiographing apparatuses 3A to 3C to be used need to be connected to the same synchronization source so that radiographing is performed while adjusting the radiographing timings to match each other. Therefore, in a case where a radiographing order of long-length serial radiography is selected, the radiographing apparatuses 3A to 3C connected to a specific addition apparatus 6 which becomes the synchronization source or a base unit of a specific communication network may be automatically selected. As the specific addition apparatus 6 which becomes the synchronization source, the addition apparatus 6 connected to the radiation control apparatus 1 may be automatically selected, or may be selected by the radiographer from the system state display screen 431. In the present embodiment, it is assumed that the addition apparatus 6 which is connected to the radiation control apparatus 1 in a wired manner is automatically selected.

Here, it is necessary to change a state of equipment to be connected to a connection state which is required for performing radiographing of the radiographing order depending on the selected radiographing order. Particularly, because a plurality of radiographing apparatuses 3 are required in long-length radiography in which a plurality of radiographing apparatuses 3 are arranged and the plurality of radiographing apparatuses 3 capture transparent radiographs at the same time by radiation being radiated with radiation, there is a case where the radiographing apparatus 3 is temporarily brought from another radiographing platform to perform radiographing.

Confirmation after the connection state of the equipment is changed can be performed through the following mechanism.

First, IDs of respective pieces of equipment are stored in advance in the RAM of the console 4 upon installation of the equipment. In a case where there are a plurality of consoles 4, the IDs may be stored in the RAMs of the respective consoles 4, or information stored in a RAM of one console 4 may be deployed (transmitted) to other consoles 4.

As in the present embodiment, in a case where the radiographing apparatuses 3A to 3C are connected in a wired manner, by establishing communication connection with the radiographing apparatuses 3A to 3C and acquiring the IDs of the radiographing apparatuses 3A to 3C, it is possible to grasp to which equipment the radiographing apparatuses 3A to 3C are connected at the console 4. For example, by the radiographing apparatus 3A being connected to a wired cable connected to the addition apparatus 6, communication connection between the addition apparatus 6 and the radiographing apparatus 3A is established. Thereafter, the addition apparatus 6 acquires an ID of the radiographing apparatus 3A using the established communication connection and transmits the information to the console 4. At this time, an ID of the addition apparatus 6 itself may be transmitted together. The console 4 which acquires the information can recognize that the radiographing apparatus 3A is connected via the addition apparatus 6, and can display that the radiographing apparatus 3A is connected at the display 43 of the console 4 as the system state display screen 431, for example, as in FIG. 6. The radiographer can confirm that the radiographing apparatus 3A is surely connected to the specific addition apparatus 6 which becomes the synchronization source from such a system state display screen 431, and can perform radiographing.

If the radiographing apparatuses 3A to 3C to be used are selected, the console 4 respectively transmits a communication connection request to the radiographing apparatuses 3A to 3C and the addition apparatus 6 (step S6).

If the radiographing apparatuses 3A to 3C and the addition apparatus 6 receive the connection request, the radiographing apparatuses 3A to 3C and the addition apparatus 6 are respectively connected to the console 4 (step S7).

Note that, as illustrated in FIG. 4, it is possible to employ a configuration where the connection request is transmitted from the console 4 to the addition apparatus 6, and further, transmitted from the addition apparatus 6 to the radiographing apparatuses 3A to 3C.

While the radiographing apparatuses 3A to 3C can be connected to the console 4 via the communication network as illustrated in FIG. 2 or can be directly connected to the console 4, if the console 4 is directly connected to the radiographing apparatuses 3A to 3C, there is a possibility that the radiographing apparatus 3 which is not connected to the addition apparatus 6 may be connected to the console 4 as the radiographing apparatuses 3A to 3C to be used for radiographing, and a connection configuration in a state where the addition apparatus 6 coordinates with the radiographing apparatuses 3A to 3C cannot be established. However, as described above, by giving priority to connection between the addition apparatus 6 and the radiographing apparatuses 3A to 3C over connection between the communication network and the radiographing apparatuses 3A to 3C, and connecting the radiographing apparatuses 3A to 3C to the console 4 via the addition apparatus 6, it is possible to reliably achieve connection with the radiographing apparatuses 3A to 3C connected to the addition apparatus 6.

Alternatively, while not illustrated, it is also possible to employ a configuration where the connection request is transmitted to respective radiographing apparatuses 3A to 3C using the console 4, and, thereafter, the connection request is transmitted from the respective radiographing apparatuses 3A to 3C to the addition apparatus 6.

Because setting of the radiographing apparatuses 3A to 3C to be used for radiographing is made at the console 4, with such a configuration, it is possible to reliably select the radiographing apparatuses 3A to 3C to be used and connect the radiographing apparatuses 3A to 3C to the addition apparatus 6, and it is possible to establish a state where the addition apparatus 6 and the radiographing apparatuses 3A to 3C to be used coordinate with each other without selecting a wrong radiographing apparatus 3.

Further, with such a configuration, it is possible to select and connect the radiographing apparatuses 3A to 3C from the whole radiographing apparatuses 3 which can be used not only from the radiographing apparatuses 3 connected to the addition apparatus 6 as described above.

Further, here, it is also possible to employ a configuration where, when the radiographing apparatuses 3A to 3C start connection, a mode of the radiographing apparatuses 3A to 3C automatically transitions from the above-described mode with a lower power consumption for radiographing preparation or in which radiographing is possible to a mode with a higher power consumption than that in the mode with a lower power consumption.

If connection with the console 4 is started, the radiographing apparatuses 3A to 3C notify the console 4 of a state of the own apparatus using the communicator 36 (step S8).

For example, the radiographing apparatuses 3A to 3C notify the console 4 that the mode of the radiographing apparatuses 3A to 3C transitions to a mode for radiographing preparation or in which radiographing is possible, or whether or not the state is a state where subsequent radiographing preparation can be started.

Further, the radiographing apparatuses 3A to 3C may notify the console 4 of a remaining battery level (remaining power level), remaining memory capacity, communication stability, communication speed, or the like of the own apparatus, of the own apparatus.

Further, in a case where the radiographing apparatuses 3A to 3C are connected to the addition apparatus 6, the radiographing apparatuses 3A to 3C may notify the console 4 of the IDs of the own apparatuses by way of the addition apparatus 6 to which the apparatuses are connected, so that it is possible to confirm at the console 4 whether or not all of the radiographing apparatuses 3A to 3C are connected to the specific addition apparatus 6 which becomes the synchronization source. Alternatively, the radiographing apparatuses 3A to 3C may notify the console 4 of the IDs of the own apparatuses and the ID of the addition apparatus 6 to which the apparatuses are connected, so that it is possible to confirm at the console 4 whether or not the respective radiographing apparatuses 3A to 3C are connected to the specific addition apparatus 6 which becomes the synchronization source from a relationship between the IDs and the equipment stored in advance.

The IDs of the own apparatuses transmitted to the console 4 by the radiographing apparatuses 3A to 3C by way of the addition apparatus 6, and the ID of the addition apparatus 6 described above become state information indicating whether a state is a first state in which the respective radiographing apparatuses 3A to 3C are not connected to the specific synchronization source or a second state in which the radiographing apparatuses 3A to 3C are connected to the specific synchronization source.

When the console 4 receives notifications of the states transmitted from the radiographing apparatuses 3A to 3C at the communicator, the console 4 displays whether or not the states of the respective radiographing apparatuses 3A to 3C are states where subsequent radiographing preparation can be started (that is, a state where radiographing is possible) at the display 43 in an identifiable form based on the received notifications of the states (step S9).

Further, the console 4 may be configured to receive notifications of remaining battery levels, remaining memory capacity, communication stability, communication speed, or the like, from the radiographing apparatuses 3A to 3C, determine whether or not the states of the radiographing apparatuses 3A to 3C are sufficient for performing radiographing of the selected radiographing order, and display whether or not it is possible to perform radiographing at the display 43 in an identifiable form based on the determination result. Whether or not the states are sufficient for performing radiographing of the radiographing order can be determined by, for example, setting thresholds in advance for the remaining battery level, the remaining memory capacity, the communication stability, the communication speed, or the like, and determining whether or not values notified from the radiographing apparatuses 3A to 3C are equal to or greater than the thresholds. The above-described thresholds may be able to be individually set because states required for radiographing are different for each radiographing order, portion to be radiographed and each radiographing apparatus 3 to be used.

Further, the console 4 may have a function of determining and outputting whether or not the state is a first state in which at least one of the radiographing apparatuses 3A to 3C is not connected to the specific addition apparatus 6 which becomes the synchronization source, or a second state in which all of the radiographing apparatuses 3A to 3C are connected to the specific addition apparatus 6 which becomes the synchronization source based on the IDs notified from the radiographing apparatuses 3A to 3C and a communication path, or the IDs notified from the radiographing apparatuses 3A to 3C and the ID of the addition apparatus 6, and may be configured to display whether or not it is possible to continue radiographing using the radiographing apparatuses 3A to 3C at the display 43 in an identifiable form based on the output of the determination result. Alternatively, the console 4 may have a function of determining and outputting whether the state is a first state in which at least one of the radiographing apparatuses 3A to 3C is not connected to the specific addition apparatus 6 which becomes the synchronization source, or a second state in which all of the radiographing apparatuses 3A to 3C are connected to the specific addition apparatus 6 using the above-described method described in [Upon installation of equipment, upon start-up of apparatus, upon change of connection equipment, upon regular confirmation of connection equipment], and may be configured to display whether or not it is possible to continue radiographing (long-length radiographing) using the radiographing apparatuses 3A to 3C at the display 43 in an identifiable form based on the output of the determination result. Specifically, in a case where it is determined that the state is the first state in which at least one of the radiographing apparatuses 3A to 3C is not connected to the specific addition apparatus 6 (first determination), display is performed in a form indicating that radiographing is not possible, while, in a case where it is determined that the state is the second state in which all of the radiographing apparatuses 3A to 3C are connected to the specific addition apparatus 6 (second determination), display is performed in a form indicating that radiographing is possible.

Further, at this timing, the console 4 may be configured to determine whether all of the radiographing apparatuses 3A to 3C to be used for radiographing support serial radiography (support serial processing), or can perform radiographing at a frame rate common to all the radiographing apparatuses 3A to 3C to be used for radiographing, or support resolution and binning required for the selected radiographing order. For example, it is possible to perform determination by storing characteristic information (such as, for example, whether it is possible to perform serial radiography or it is only possible to capture a still image, frame rates, resolution and binning factors) of the apparatuses in the RAM of the console 4 in advance in association with the IDs of the respective radiographing apparatuses 3, acquiring the characteristic information of the radiographing apparatuses 3A to 3C based on the respective IDs transmitted from the radiographing apparatuses 3A to 3C, and checking the characteristic information against conditions required for radiographing of the radiographing order. Further, the console 4 may be configured to display whether or not it is possible to perform radiographing at the display 43 in an identifiable form based on the determination result.

Only one of the above-described determination methods may be performed, or a plurality of the above-described determination methods may be performed in combination.

Figure 7:
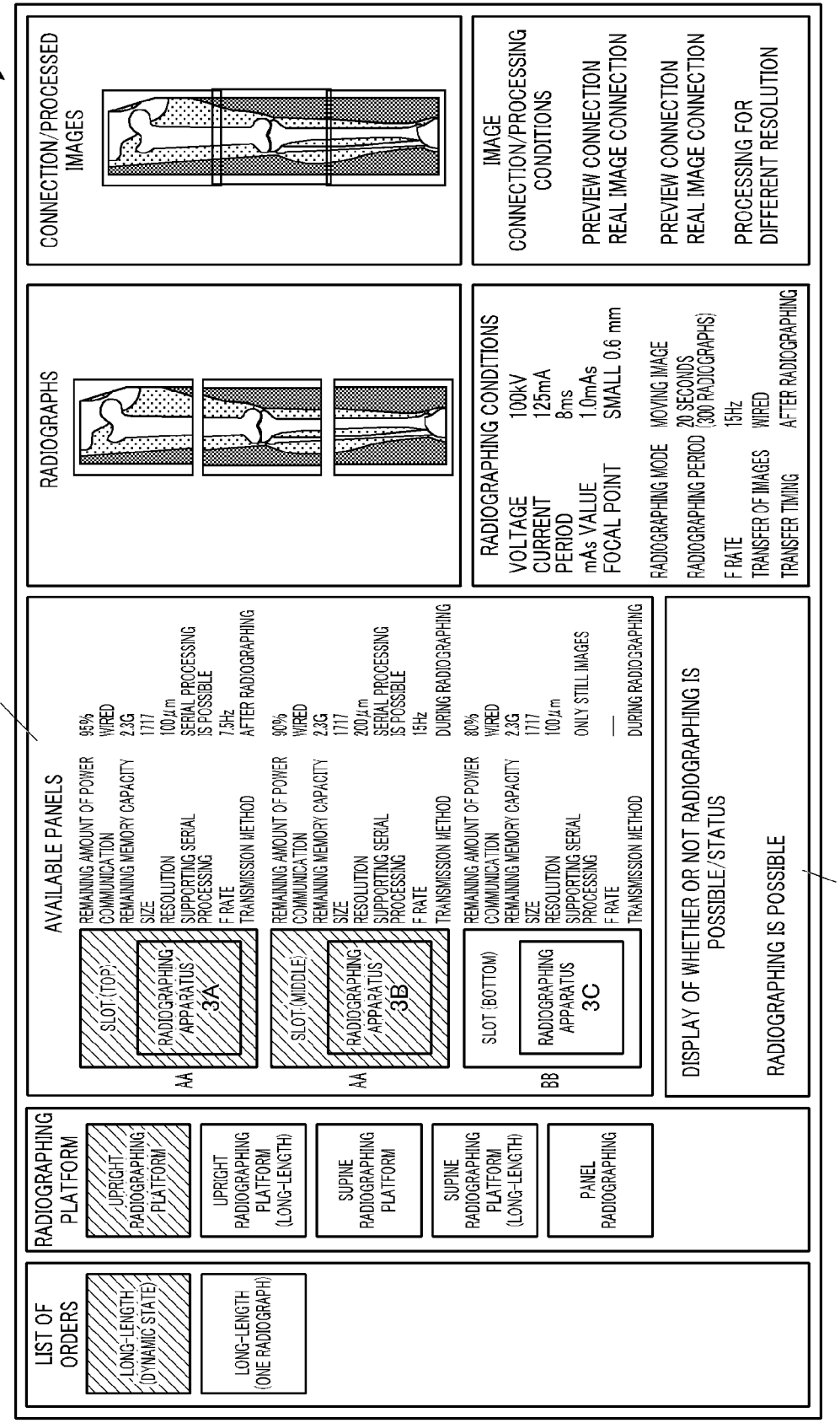
FIG. 7 is a view illustrating an example of a radiographing screen.

Further, for example, in a case where there is the radiographing apparatus 3 which cannot perform radiographing as a result of the above-described determination, the console 4 displays the radiographing apparatus 3 at the display 43 in an identifiable form. For example, by displaying a radiographing screen 432 as illustrated in FIG. 7 at the display 43, and displaying "AA" if the apparatus can perform radiographing, and "BB" if the apparatus cannot perform radiographing, in association with information of the respective radiographing apparatuses 3A to 3C at a use panel field 432a in which information regarding the respective radiographing apparatuses 3A to 3C to be used is displayed, it is possible to clearly display the radiographing apparatus 3 which cannot perform radiographing. Further, it is also possible to display reasons why the apparatus cannot perform radiographing using a symbol, characters, or the like. Further, it is also possible to display that the apparatus cannot perform radiographing and reasons why the apparatus cannot perform radiographing using color. Note that, in the radiographing screen 432, regions for displaying information (including whether or not the apparatus can perform radiographing) of the respective radiographing apparatuses 3A to 3C are provided so as to correspond to an arrangement relationship of the radiographing apparatuses 3A to 3C determined by storages (holders or radiographing platforms) which store the radiographing apparatuses 3A to 3C upon radiographing. For example, in a case where the radiographing apparatus 3A is stored in an upper stage of the holder, the radiographing apparatus 3B is stored in a middle stage, and the radiographing apparatus 3C is stored in a lower stage, as illustrated in FIG. 7, in the radiographing screen 432, a region for displaying information regarding the radiographing apparatus 3A is disposed in an upper part, a region for displaying information regarding the radiographing apparatus 3B is disposed in a middle part, and a region for displaying information regarding the radiographing apparatus 3C is disposed in a lower part.

Alternatively, the console 4 may display a specific region of the radiographing screen 432, for example, a color of a display field 432b indicating whether or not radiographing is possible/a status in a first color if it is possible to perform radiographing, and in a second color different from the first color if it is impossible to perform radiographing as a result of the above-described determination.

Further, while, in the above description, a configuration has been employed where the radiographing apparatuses 3A to 3C transmit information indicating states of the own apparatuses to the console 4, and whether or not the states of the respective radiographing apparatuses 3A to 3C are a state in which it is possible to start subsequent radiographing preparation is determined at the console 4, it is also possible to employ a configuration where the above-described determination is performed at the respective radiographing apparatuses 3A to 3C, and the determination results are transmitted to the console 4. Further, while, in FIG. 4, these notifications are transmitted from the radiographing apparatuses 3A to 3C to the console 4, these notifications may be transmitted to the console 4 via the addition apparatus 6.

Further, here, it is also possible to employ a configuration where the console 4 transmits a control signal of giving an instruction to emit light only to the radiographing apparatus 3 connected to the specific addition apparatus 6 which becomes the synchronization source, and causes only a light emitter disposed at the radiographing apparatus 3 connected to the specific addition apparatus 6 to emit light.

Alternatively, the console 4 may transmit a control signal of giving an instruction to emit light to the respective connected radiographing apparatuses 3 so that only the respective radiographing apparatuses 3 connected to the specific addition apparatus 6 which becomes the synchronization source emit light in a light emission pattern different from those of the others. Examples of the light emission pattern different from those of the others can include, for example, color, a light emission timing, a light emission mode (such as lighting and blinking), or the like.

By causing only the radiographing apparatus 3 connected to the specific addition apparatus 6 which becomes the synchronization source to emit light, or causing the radiographing apparatus 3 connected to the specific addition apparatus 6 which becomes the synchronization source to emit light in a light emission pattern different from those of others, the radiographer can easily identify the radiographing apparatus 3 connected to the specific addition apparatus 6 which becomes the synchronization source, so that it is possible to reliably prevent radiographing from being performed using an unintended radiographing apparatus 3.

Further, the console 4 may be configured to transmit a control signal of giving an instruction to emit light only to the radiographing apparatus 3 designated as an apparatus to be used for radiographing among the radiographing apparatuses 3 connected to the specific addition apparatus 6, and cause only a light emitter disposed at the corresponding radiographing apparatus 3 to emit light. Alternatively, the console 4 may transmit a control signal of giving an instruction to emit light to the respective connected radiographing apparatuses 3 so that only the radiographing apparatus 3 designated as an apparatus to be used for radiographing among the radiographing apparatuses 3 connected to the specific addition apparatus 6 which becomes the synchronization source in the above description to emit light in a light emission pattern different from those of the others.

For example, while, typically, three radiographing apparatuses 3 are loaded in a long-length radiographing platform or a long-length radiographing holder (also in the present embodiment, description is provided assuming that the radiographing apparatuses 3A to 3C are used for radiographing), there is a case where only two among them are used for radiographing depending on a size (physical size) of the object under examination and a portion to be radiographed. In such a case, because the radiographer cannot directly understand which two radiographing apparatuses among three radiographing apparatuses loaded in the long-length radiographing platform or the long-length radiographing holder are actually two radiographing apparatuses 3 (for example, 3A and 3B) designated at the console 4, there is a case where the radiographer performs radiographing while misidentifying the radiographing apparatuses 3 different from the radiographing apparatuses 3A and 3B designated at the console 4 as targets which are to perform radiographing, and correct radiographing is not performed. For example, if the radiographing apparatuses 3A and 3B among the radiographing apparatuses 3 which can perform radiographing and which are connected to the addition apparatus 6 which becomes the synchronization source are designated as the radiographing apparatuses 3 to be used at the radiographing screen 432 illustrated in FIG. 7, by only the designated radiographing apparatuses 3A and 3B being caused to emit light or being caused to emit light in a light emission pattern different from those of the others, the radiographer can easily recognize the designated radiographing apparatuses 3A and 3B.

Further, it is also possible to employ a configuration where display at the console 4 and the light emission patterns of the light emitters disposed at the radiographing apparatuses 3A to 3C are displayed in association with each other so as to make the positional relationship of the respective radiographing apparatuses 3A to 3C stored in the long-length radiographing platform or holder clear, that is, vertical order. For example, in a case where the radiographing apparatus 3A is disposed at an upper stage, the radiographing apparatus 3B is disposed at a middle stage, and the radiographing apparatus 3C is disposed at a lower stage, by displaying the radiographing apparatuses 3A to 3C at the console 4 (for example, on the radiographing screen 432) in different types of color, and transmitting information of display color along with an instruction to emit light to the radiographing apparatuses 3A to 3C from the console 4, it is possible to realize a configuration of causing also the light emitters disposed at the radiographing apparatuses 3A to 3C to emit light in different types of color. Alternatively, it is also possible to employ a configuration where display of the console 4 is associated with light emission timings or light emission intervals of the light emitters of the radiographing apparatuses 3A to 3C.

Note that whether or not to perform display control in step S9 by the console 4 may be switched in accordance with whether or not a radiographing order of long-length radiography (including long-length serial radiography) is designated. In other words, only in a case where a radiographing order of long-length radiography is designated, the above-described display control may be performed.

Subsequently, if the radiographer sets the radiographing conditions, or the like, at the console 4 and instructs the console 4 to start radiographing, the console 4 sets the radiographing conditions at the radiation control apparatus 1 and the radiographing apparatuses 3A to 3C to put a sequence start signal of giving an instruction to start radiographing sequence into an ON state for the radiographing apparatuses 3A to 3C and the addition apparatus 6. Then, the sequence start signal is transmitted to the radiographing apparatuses 3A to 3C and the addition apparatus (step S10). The sequence start signal can be transmitted using, for example, information signals transmitted and received between the console 4 and the addition apparatus 6, and information signals transmitted and received between the addition apparatus 6 and the radiographing apparatuses 3A to 3C.

While, in the sequence illustrated in FIG. 4, an example has been described where the sequence start signal is transmitted from the console 4 to the radiographing apparatuses 3A to 3C, and the sequence start signal is transmitted from the radiographing apparatuses 3A to 3C to the addition apparatus 6, it is also possible to employ a configuration where the sequence start signal is directly transmitted from the console 4 to the addition apparatus 6 and the radiographing apparatuses 3A to 3C. Alternatively, it is also possible to employ a configuration where the console 4 establishes connection with the addition apparatus 6, and the sequence start signal is transmitted from the addition apparatus 6 to the radiographing apparatuses 3A to 3C.

When the radiographing apparatuses 3A to 3C and the addition apparatus 6 detect that the sequence start signal is put into an ON state, the radiographing apparatuses 3A to 3C and the addition apparatus 6 start radiographing preparation.

When the addition apparatus 6 receives the sequence start signal, the addition apparatus 6 puts a read-out instruction signal (see FIG. 14) into an ON state to transmit the read-out instruction signal to the radiographing apparatuses 3A to 3C and repeatedly output a timing signal at predetermined time intervals (step S11).

The radiographing apparatuses 3A to 3C perform a read-out operation every time the radiographing apparatuses 3A to 3C receive the timing signal output from the addition apparatus 6.

Here, because the radiographing apparatus 3 consumes power when performing the read-out operation, a temperature inside circuits within the radiographing apparatus 3 increases. Further, due to this increase in a temperature, sensitivity of the radiographing apparatus 3, particularly, the radiation detection element 32*d* changes, and an image (signal value) with respect to the same radiation transmission amount changes. While this change of the image due to increase in a temperature is not problematic in a case where one image is captured, in a case where serial radiography in which a plurality of still images are successively captured is performed as in the system 100 according to the present invention, change of the image due to increase in a temperature during radiographing becomes problematic. Therefore, at the radiographing apparatus 3, by the read-out operation being repeatedly performed before serial radiography is performed, it is possible to reduce change of the image due to increase in a temperature upon subsequent serial radiography. In this manner, the read-out operation before radiographing serves as warm-up of the radiographing apparatus 3.

The radiographing apparatuses 3A to 3C notify the console 4 that warm-up is started using the communicator 36 in an initial stage in which the read-out operation is repeated (step S12).

Note that notification of warm-up in step S12 may be omitted.

Further, the radiographing apparatuses 3A to 3C transmit images read in a last half of the read-out operation for warm-up to the console 4 as correction data (step S13).

A plurality of pixels of the radiographing apparatuses 3A to 3C have different characteristics, and levels of electric charges corresponding to brightness of the images are different for each pixel even in a state where radiation is not radiated. Therefore, by acquiring the images read out in the last half of warm-up as the correction data and, for example, subtracting respective signal values of the correction data from respective signal values of the captured radiographs obtained later, it is possible to obtain a captured radiograph from which variation for each pixel is removed.

Note that, while a case has been described as an example where the correction data is simply subtracted from the captured radiograph as a method for using the correction data, it is also possible to remove noise components using various kinds of operations.

Here, in a case where an image such as the correction data is required, the read-out electric charges are converted into an image, in a case where an image is not required, it is also possible to perform a reset operation of discarding the read-out electric charges without converting the read-out electric charges into an image.

Alternatively, it is also possible to perform a reset operation of converting the read-out electric charges into an image and discarding the image.

Here, a case has been described in the description of FIG. 4 where the correction data is transmitted to the console 4, and correction is performed at the console 4. However, in recent years, because processing performance of the radiographing apparatus 3 and storage capacity of a storage of the radiographing apparatus 3 have been improved, it is also possible to store the correction data in a memory of the radiographing apparatus 3 without transmitting the correction data to the console 4 and perform all or part of correction processing within the radiographing apparatus 3. Further, in a case where all or part of the correction processing is performed also at the console 4, it is also possible to employ a configuration where the correction data is stored in the memory within the radiographing apparatus 3 while the correction data is transmitted to the console 4.

When the warm-up is completed, the radiographing apparatuses 3A to 3C notify the console 4 that radiographing preparation is completed (step S14). Here, the console 4 can judge that the warm-up is completed in a case where, for example, the warm-up of the number of times of read-out set in advance is finished, or in a case where a read-out operation period set in advance has elapsed. The console 4 can judge that the warm-up of all the radiographing apparatuses to be used for radiographing is completed by receiving notifications of completion of the warm-up from all of the radiographing apparatuses 3A to 3C.

Here, the notifications of completion of the warm-up may be directly transmitted from the respective radiographing apparatuses 3A to 3C to the console 4, or may be transmitted from the respective radiographing apparatuses 3A to 3C to the addition apparatus 6, and may be transmitted from the addition apparatus 6 to the console 4. The addition apparatus 6 may judge that the warm-up of all the radiographing apparatuses to be used for radiographing is completed by receiving the notifications of completion of the warm-up from all of the respective radiographing apparatuses 3A to 3C, and may transmit a judgement result to the console 4.

Alternatively, a notification of completion of the warm-up of the respective radiographing apparatuses 3A to 3C may be transmitted from the addition apparatus 6 to the console 4, and the console 4 may judge that the warm-up of all the radiographing apparatuses to be used for radiographing is completed.

When the console 4 receives a notification of completion of radiographing preparation, the console 4 displays that "radiographing is possible" at the display 43 of the console 4 (step S15).

Note that it is also possible to employ a configuration where radiographing is performed without the warm-up being performed (for example, processing from step S12 to S13 is omitted, and the processing transitions to notification of completion of radiographing preparation). Alternatively, it is also possible to employ a configuration where the radiographer selects whether or not to perform the warm-up. For example, in a case where it is necessary to quickly perform radiographing as in an emergency medical site, or the like, it is also possible to employ a control configuration where radiographing can be performed without the warm-up being performed by an instruction not to perform the warm-up being input at the console 4. Alternatively, in a case where radiographing is continuously performed in response to a plurality of similar radiographing orders, because, in second and subsequent radiographing, the states of the radiographing apparatuses 3A to 3C are close to states where the warm-up is completed, it is possible to perform radiographing without performing the warm-up again.

Whether or not to perform the warm-up in this manner may be switched by the radiographer through an operation input to the operator of the console 4. Alternatively, it is also possible to employ a configuration where a temperature gauge which measures a temperature is provided at the radiographing apparatus 3, and the radiographing controller 31 of the radiographing apparatus 3 switches whether or not to perform the warm-up in accordance with the temperature measured at the temperature gauge or a state of temperature change. Alternatively, it is also possible to employ a configuration where the console 4 judges whether or not to perform the warm-up in accordance with the number of radiographs captured in a past specific period, a radiographing mode, an interval of past radiographing, or the like. Alternatively, it is also possible to employ a configuration where whether or not to perform the warm-up is judged in combination of these. In a case where the console 4 switches whether or not to perform the warm-up, for example, the console 4 transmits a control signal indicating whether or not to perform the warm-up to the radiographing apparatuses 3A to 3C to cause the radiographing apparatuses 3A to 3C to switch whether or not to perform the warm-up.

Further, it is also possible to employ a configuration where the number of times of the read-out operation for the warm-up or time at which the read-out operation for the warm-up is performed is changed as well as whether or not to perform the warm-up being simply judged.

Further, whether or not to perform the warm-up may be judged with different conditions for the radiographing apparatuses 3A to 3C to be used for radiographing, or may be judged for all of the radiographing apparatuses 3A to 3C with a condition for an apparatus which requires the read-out operation for the warm-up most among the radiographing apparatuses 3A to 3C to be used for radiographing.

(C: Irradiation Pre-Processing)

The addition apparatus 6 continuously repeatedly transmits a timing signal to the radiographing apparatuses 3A to 3C, and the radiographing apparatuses 3A to 3C repeat the read-out operation of the radiographing apparatuses 3A to 3C every time the radiographing apparatuses 3A to 3C receive this timing signal. Here, while the radiographing apparatuses 3A to 3C converts the read-out electric charges into an image in a case where an image such as the correction data is required, the radiographing apparatuses 3A to 3C may perform the reset operation of discarding the read-out electric charges without converting the read-out electric charges into an image in a case where an image is not required. Alternatively, the radiographing apparatuses 3A to 3C may perform the reset operation of converting the read-out electric charges into an image and discarding the image.

If the radiographer finishes positioning of the object under examination and puts the irradiation instruction switch 5 into a first stage (step S16), the irradiation instruction switch 5 puts the irradiation preparation signal to be output to the radiation controller 11 via the console 4 into an ON state (step S17).

When the radiation controller 11 of the radiation control apparatus 1 detects that this irradiation preparation signal is put into an ON state, the radiation controller 11 puts the irradiation preparation signal to be output to the high-voltage generator 12 and the addition apparatus 6 into an ON state (step S18). By this means, the first acquirer 62 of the addition apparatus 6 acquires the irradiation preparation signal (to be output before the irradiation instruction signal and after the sequence start signal is put into an ON state).

In this manner, the radiation control apparatus 1 including the radiation controller 11 starts irradiation preparation of radiation in accordance with the irradiation preparation signal.

When the addition controller 61 of the addition apparatus 6 detects that the irradiation preparation signal from the radiation controller 11 is put into an ON state, the addition controller 61 transmits a radiographing preparation signal to the console 4 (step S19).

When the console 4 receives the radiographing preparation signal, the console 4 starts radiographing preparation. The radiographing preparation at the console 4 is operations of, for example, confirming that setting of the radiographing apparatus control console 42 which constitutes the console 4 is the same as setting of the radiation control console 41 which controls radiation irradiation, and confirming that the designated radiographing conditions, or the like, are set at the radiation control apparatus 1 and the radiographing apparatuses 3A to 3C.

Further, the console 4 may request notification of states of the radiographing apparatuses 3A to 3C as described above in this stage, and may confirm at least one of states of the radiographing apparatuses 3A to 3C described above again as final confirmation.

Here, for example, if it is unclear whether or not the radiographing apparatuses 3A to 3C are connected to the specific addition apparatus 6 which becomes the synchronization source, or it is unclear whether or not other preparation is completed, the radiographer cannot know a timing for transmitting an instruction to radiate radiation, which becomes problematic. Therefore, the console 4, for example, may request notification of states to the radiographing apparatuses 3A to 3C as described above in response to the irradiation instruction switch 5 (which is put into the first stage), may determine whether or not the radiographing apparatuses 3A to 3C are connected to the specific addition apparatus 6 which becomes the synchronization source, and may display whether or not the state is a state where radiographing is possible at the display 43 in an identifiable form based on the determination result.

By this means, the radiographer can perform radiographing after confirming whether or not the radiographing apparatuses 3A to 3C coordinate with the specific synchronization source.

When the console 4 completes the radiographing preparation, the console 4 puts a radiographing preparation completion signal to be output to the addition apparatus 6 into an ON state and outputs the radiographing preparation completion signal (step S20).

Then, "radiographing" is displayed at the display 43 of the console 4 (step S21).

Here, while a case has been described above where the radiographing preparation is started in response to the irradiation preparation signal from the addition apparatus 6, the radiographing preparation may be started in response to the irradiation preparation signal from the irradiation instruction switch 5. Alternatively, the radiographing preparation may be started in response to irradiation preparation information through a communication signal with the radiation controller 11.

Further, the console 4 may be configured to lock an input of change, or the like, of the radiographing conditions to the console 4 so that the radiographing conditions, or the like, cannot be changed in a stage in which the radiographing preparation is completed.

While, in a case of still radiography, because radiographing is finished in a short period, there is a low risk of the radiographing conditions, or the like, being changed during radiographing, and it is less necessary to employ such a configuration, in a case of serial radiography, because a radiographing period is long, there is a higher risk of the radiographer or the third party other than the radiographer intentionally or unconsciously changing the radiographing conditions, or the like, by operating a console screen.

Therefore, by locking the input of change of the radiographing conditions, or the like, to the console 4 until radiographing sequence is finished from this stage, it is possible to reliably prevent such change of the radiographing conditions.

Note that, while FIG. 4 illustrates a case where the radiographing preparation signal is output from the addition apparatus 6 to the console 4, there is also a case where the radiographing preparation signal is not output to the console 4 but output to the radiographing apparatuses 3A to 3C, so as to cause the radiographing apparatuses 3A to 3C to perform radiographing preparation, and, when radiographing preparation of the radiographing apparatuses 3A to 3C is completed, the radiographing preparation completion signal is output from the radiographing apparatuses 3A to 3C to the addition apparatus 6.

Further, there is also a case where the radiographing preparation signal is output to both the console 4 and the radiographing apparatuses 3A to 3C so as to cause both to respectively perform radiographing preparation, and, when radiographing preparation of the both is completed, the radiographing preparation completion signal is transmitted from the console 4 and the radiographing apparatuses 3A to 3C to the addition apparatus 6, and the addition apparatus 6 judges that all the radiographing preparation is completed in a stage in which the addition apparatus 6 receives the radiographing preparation completion signal from the both.

Further, while not illustrated, it is also possible to employ a configuration where, in a case where the radiation controller 11 of the radiation control apparatus 1 includes a connector which inputs the radiographing preparation completion signal indicating that radiographing preparation of external equipment is completed, the addition apparatus 6 outputs the radiographing preparation completion signal to the radiation controller 11.

The radiation controller 11 can detect that the states of the radiographing apparatuses 3A to 3C are states in which radiographing is possible by detecting that the radiographing preparation completion signal from the addition apparatus 6 is put into an ON state. Here, as a result of the radiation control apparatus 1 performing control so that radiation is radiated after it is detected that the radiographing preparation completion signal is put into an ON state, it is possible to reliably exclude a risk of the object under examination being uselessly exposed to radiation due to radiation being radiated in a state where the radiographing apparatuses 3A to 3C cannot perform radiographing. Further, in this case, it is also possible to employ a configuration where the console 4 judges that radiographing preparation is completed by receiving information indicating that the radiation control apparatus 1 has received the radiographing preparation completion signal through a communication path such as an information signal, or the like, which connects the radiation control apparatus 1 and the console 4.

Further, while not illustrated, in a case where the console 4, the radiographing apparatuses 3A to 3C, the addition controller 61 or at least part of them includes a connector to which a radiographing preparation completion signal is input, which can be input by external equipment to indicate that radiographing preparation has been completed, it is also possible to employ a configuration where the console 4, the radiographing apparatuses 3A to 3C or both of them transmits the radiographing preparation completion signal in a case where a signal indicating that radiographing preparation has been completed is input from the external equipment.

With such a configuration, the addition apparatus 6 can know that the console 4, the radiographing apparatuses 3A to 3C and the external equipment are put into a state where radiographing preparation has been completed by detecting that the radiographing preparation completion signal is put into an ON state, and by control being performed so that radiation is radiated after the radiographing preparation completion signal is received, it is possible to reliably exclude a risk that the object under examination is uselessly exposed to radiation due to radiation being radiated in a state where at least one of the console 4, the radiographing apparatuses 3A to 3C and the external equipment cannot perform radiographing.

(D: Execution of Radiographing)

Subsequently, when the radiographer puts the irradiation instruction switch 5 into a second stage (step S22), the irradiation instruction switch 5 puts the irradiation instruction signal to be transmitted to the radiation control apparatus 1 via the console 4 into an ON state and outputs the irradiation instruction signal (step S23).

At this time, the addition apparatus 6 continuously repeatedly transmits the timing signal to the radiographing apparatuses 3A to 3C, and the radiographing apparatuses 3A to 3C repeat the read-out operation every time this timing signal is received. Here, while the read-out electric charges are converted into an image in a case where an image such as the correction data is required, it is also possible to perform the reset operation of discarding the read-out electric charges without converting the electric charges into an image in a case where an image is not required. Alternatively, it is also possible to perform the reset operation of converting the electric charges into an image and discarding the image.

The radiation controller 11 of the radiation control apparatus 1 does not transmit the irradiation signal to the high-voltage generator 12 because the irradiation allowance signal from the addition apparatus 6 is in an OFF state at this time point even if the irradiation instruction signal is input from the irradiation instruction switch 5.

Meanwhile, the radiation controller 11 puts the irradiation instruction signal to be transmitted to the addition controller 61 into an ON state (step S24).

When the addition apparatus 6 receives the irradiation instruction signal, the addition apparatus 6 puts the radiographing start signal which is to be output to the radiographing apparatuses 3A to 3C and the console 4, and which makes a notification as to whether or not to allow start of radiographing, into an ON state (step S25 and S26).

When the radiographing apparatuses 3A to 3C detect that the radiographing start signal is put into an ON state, for example, as illustrated in FIG. 5, the radiographing apparatuses 3A to 3C put the irradiation start allowance signal to be output to the addition apparatus 6 into an ON state by being triggered by the read-out operation which is being performed by the apparatuses at that time point being finished (step S27). This is because, in the read-out operation of the radiographing apparatuses 3A to 3C, images of the whole light receiving surface are acquired by the electric charges accumulated in the pixels arranged in two dimensions, being sequentially read out, and if the irradiation start allowance signal is put into an ON state and radiation is radiated during read-out, a difference occurs in a signal value between the pixels for which read-out has been completed and the pixels for which read-out has not been completed, which significantly degrades image quality.

Meanwhile, in the present embodiment, because radiation irradiation and image read-out of the radiographing apparatuses 3A to 3C are performed based on the irradiation allowance signal and the timing signal from the addition apparatus 6 as will be described later, radiation is not radiated during the read-out operation in normal routine. Therefore, it is also possible to put the irradiation start allowance signal into an ON state without taking into account a read-out timing of the radiographing apparatuses 3A to 3C described above.

The radiographing apparatuses 3A to 3C repeat the read-out operation in accordance with the timing signal from the addition apparatus 6 also after the irradiation start allowance signal is put into an ON state. The image read out after the irradiation start allowance signal is put into an ON state may be stored in memories of the radiographing apparatuses 3A to 3C as the radiograph or may be transferred to the console 4. Alternatively, it is also possible to store part or all of the image in the memories as the image obtained by reading out the electric charges of the respective radiation detection elements 32d and transmit part or all of the image to the console 4.

As will be described later, because radiographing is repeated at relatively short time intervals in serial radiography, there is a case where the radiographs are not transmitted to the console 4 in time for radiographing intervals. Particularly, in a case where the radiographing apparatuses 3A to 3C are connected to the addition controller 61, or the radiographing apparatuses 3A to 3C are connected to the console 4 through wireless communication, because communication speed is affected by a wireless situation, by storing the captured image data in the memories within the radiographing apparatuses 3A to 3C as described above and transmitting part or all of the image data to the console 4, it is possible to continue radiographing without causing a radiographing error due to loss of image data or a transfer delay.

Further, the console 4 may request information and notifications of states to the radiographing apparatuses 3A to 3C in this stage and may confirm at least one of information and a state of the above-described radiographing apparatuses 3A to 3C again as final confirmation. Further, as a result of confirmation being performed again, in a case where it is determined that all of the radiographing apparatuses 3A to 3C are radiographing apparatuses designated by the radiographer, and are put into a state where it is possible to continue radiographing, the console 4 may transmit a control signal to the radiographing apparatuses 3A to 3C so that the radiographing apparatuses 3A to 3C output irradiation start allowance signal to the addition apparatus 6.

Further, examples of information to be confirmed can include an own apparatus ID, characteristic information (such as, for example, whether or not serial radiography can be performed/only still radiography can be performed, a frame rate, resolution, and a binning factor), or the like. By confirming the information, it is possible to confirm that all of the radiographing apparatuses 3A to 3C to be used for radiographing are radiographing apparatuses designated by the radiographer.

By this means, in a case where radiographing apparatuses different from the radiographing apparatuses designated by the radiographer are recognized as the radiographing apparatuses to be used for radiographing due to noise, a failure of wireless communication, and, in a case where the addition apparatus 6 is connected to the radiographing apparatuses 3A to 3C in a wired manner, disconnection, attachment and detachment, or the like, of a line, which is not intended by the radiographer, it is possible to reliably prevent radiographing from being continued without the radiographer noticing that.

Particularly, when positioning is performed, because adjustment is performed while positions of the radiographing apparatuses 3A to 3C and the object under examination are changed, there is a case where problems as described above may occur.

Examples of states to be confirmed can include, a remaining battery level (remaining power level), remaining memory capacity, communication stability, communication speed, a control state (whether the state transitions to a state where radiographing is possible among a plurality of states of the radiographing apparatus), or the like, of the radiographing apparatus. By confirming the state, it is possible to confirm that all of the radiographing apparatuses 3A to 3C to be used for radiographing are put into a state where radiographing is possible.

By this means, in a case where, although radiographing is possible upon start of the radiographing sequence, radiographing becomes impossible as a result of the state transitioning immediately before radiographing, it is possible to reliably prevent radiographing from being continued while the radiographer does not recognize that radiographing becomes impossible. Particularly, while it is necessary to position the object under examination at a position and in a state appropriate for radiographing until radiographing is started, there is a case where it takes time for this positioning depending on the object under examination, and the states of the radiographing apparatuses may change during this time.

These are judged at the console 4, and, in a case where it is impossible to continue radiographing, control may be performed so that the radiographer is notified through a display screen of the console 4, sound, or the like. Alternatively, judgement may be performed at the addition apparatus 6, and the console 4 may be notified of the judgement result. It is also possible to perform control so that the console 4 receives a notification from the addition apparatus 6 and notifies the radiographer through the display screen of the console 4, sound, or the like, in a case where it is impossible to continue radiographing.

The addition apparatus 6 can detect that the respective radiographing apparatuses 3A to 3C are put into a state where radiographing is possible by receiving the irradiation start allowance signal from the radiographing apparatuses 3A to 3C. Therefore, the addition apparatus 6 may be configured to release an interlock so as to be able to output the irradiation allowance signal for allowing irradiation of radiation to the radiation controller 11 when receiving the irradiation start allowance signal from all of the radiographing apparatuses 3A to 3C to be used for radiographing. This may be implemented as part of transition of state transition control as will be described later.

By employing a configuration where irradiation of radiation is allowed after the irradiation start allowance signal from all of the radiographing apparatuses 3A to 3C is received in this manner, it is possible to prevent the object under examination from being uselessly exposed to radiation due to radiation being radiated at a timing at which preparation of part of the radiographing apparatuses 3 to be used for radiographing is not completed or in a state where part of the radiographing apparatuses 3A to 3C cannot perform radiographing due to an error, or the like.

When the addition apparatus 6 receives the irradiation start allowance signals from all of the radiographing apparatuses 3A to 3C, the addition apparatus 6 detects that the radiographing apparatuses 3A to 3C are put into a state where radiographing is possible, releases an interlock so as to be able to output the irradiation allowance signal which allows irradiation of radiation to the radiation controller 11, and repeatedly transmits the irradiation allowance signal to the radiation controller 11 in accordance with a timing at which the timing signal is transmitted to the radiographing apparatuses 3A to 3C (step S28). The addition controller 61 includes a timing generator for outputting the timing signal and the irradiation allowance signal at fixed intervals, and the addition controller 61 repeatedly continues output of the timing signal and the irradiation allowance signal in accordance with the timing generated by this timing generator.

Here, it is also possible to employ a configuration where the timing signal and the irradiation allowance signal are output to the radiographing apparatuses 3A to 3C at the same time, or it is also possible to employ a configuration where the timing signal and the irradiation allowance signal are respectively output in accordance with the radiographing timing of the radiographing apparatuses 3A to 3C and the radiation irradiation timing of the radiation control apparatus 1.

In a case where the timing signal and the irradiation allowance signal are output to the radiographing apparatuses 3A to 3C at the same time, it is possible to reduce a risk that the timing fluctuates due to an output delay upon output of signals. Further, it is also possible to branch the same signal output and use the branched signal output for the timing signal and the irradiation allowance signal.

Meanwhile, it is also possible to employ a configuration where the timing signal and the irradiation allowance signal are respectively output at required timings while the radiographing timing on the radiographing apparatus 3 side and the radiation irradiation timing of the radiation control apparatus 1 being taken into account at the addition apparatus 6. It is assumed that the addition apparatus 6 is used in combination with various types of radiographing apparatuses 3A to 3C and the radiation control apparatus 1, and there is an apparatus which cannot adjust a timing for actually performing part of the radiographing sequence or radiation irradiation since the timing signal and the irradiation allowance signal have been received, depending on the radiographing apparatuses 3A to 3C and the radiation control apparatus 1 to be combined. Therefore, by the addition apparatus 6 outputting the timing signal and the irradiation allowance signal while taking into account an operation timing of the radiographing apparatuses 3A to 3C and the radiation control apparatus 1, it is possible to perform radiographing while combining various kinds of radiographing apparatuses 3A to 3C and the radiation control apparatus 1. The addition apparatus may be configured to be able to individually adjust respective timings of signal output to match characteristics of these various kinds of radiographing apparatuses 3A to 3C and the radiation control apparatus 1.

Further, it is also possible to employ a configuration where the timings can be respectively adjusted so that the timing signal to be output to the respective radiographing apparatuses 3A to 3C is output at a timing in accordance with the respective radiographing apparatuses 3A to 3C with respect to a timing for outputting the irradiation allowance signal.

By enabling the timing signal to be output in accordance with the respective radiographing apparatuses 3A to 3C, it is possible to successively perform radiographing at a stable timing even if the radiographing apparatuses 3A to 3C which perform the different radiographing operation are combined.

Because the irradiation instruction signal and the irradiation allowance signal arrive at the same timing every time the radiation controller 11 of the radiation control apparatus 1 receives the irradiation allowance signal, the radiation controller 11 repeatedly transmits the irradiation signal to the high-voltage generator 12.

Every time the high-voltage generator 12 receives the irradiation signal, the high-voltage generator 12 repeatedly generates a high voltage required for irradiation of radiation and repeatedly outputs the high voltage to the radiation generator 2 as irradiation output.

The radiation generator 2 repeatedly radiates radiation to the radiographing apparatuses 3A to 3C every time irradiation output is input (step S29).

The radiated radiation penetrates through the object under examination which is not illustrated and which is disposed between the radiographing apparatuses 3A to 3C and the radiation generator 2 and is incident on the radiographing apparatuses 3A to 3C.

Meanwhile, the radiographing apparatuses 3A to 3C accumulate electric charges of an amount in accordance with intensity of the incident radiation in accordance with a timing at which the timing signal is received (step S30), and repeats read-out of the electric charges as radiographs (step S31).

The radiographing apparatuses 3A to 3C transfer the read-out radiographs to the console 4 (step S32).

Note that, in a case where a configuration is employed where the radiographs are transferred to the console 4, and the radiographs are not transferred to the console 4 in time due to a data amount and a communication environment, part of the radiographs among a plurality of radiographs or part of one radiograph may be stored in a memory, and the remaining may be transferred to the console 4.

Here, FIG. 5 illustrates a sequence where, after the addition apparatus 6 receives the irradiation start allowance signal from all of the radiographing apparatuses 3A to 3C, and before the addition apparatus 6 outputs the irradiation allowance signal and acquires radiographs as a result of the radiographing apparatuses 3A to 3C being irradiated with radiation, the addition apparatus 6 acquires an image immediately before the radiographing apparatuses 3A to 3C are irradiated with radiation by outputting the timing signal to the radiographing apparatuses 3A to 3C only once.

In this manner, it is also possible to employ a sequence where a timing for outputting the timing signal and the irradiation allowance signal are adjusted at the addition apparatus 6, so that an image in a state where radiation is not radiated is acquired immediately before irradiation of radiation. Such an image can be used as a dark image immediately before radiographing is performed by radiation being radiated, and as an image for performing offset correction on the radiographs which are captured by radiation being radiated thereafter.

Alternatively, unlike with FIG. 5, when the addition apparatus 6 receives the irradiation start allowance signal from the radiographing apparatuses 3A to 3C, the addition apparatus 6 may output the timing signal and the irradiation allowance signal at a timing of outputting the next timing signal and the irradiation allowance signal, and may perform radiographing without acquiring a dark image immediately before radiographing is performed by radiation being radiated. In this case, it is only necessary to perform correction such as offset correction using correction data acquired in advance, and it is possible to promptly perform radiographing after a radiographing instruction being issued by the radiographer.

Alternatively, it is also possible to employ a configuration where, after radiographing is performed by radiation being continuously radiated, a dark image is acquired after only a timing signal for the radiographing timing is output a required number of times without the irradiation allowance signal for the radiation irradiation timing being output, and correction such as offset correction is performed using the image.

An example of operations of the radiation control apparatus 1 and the radiographing apparatuses 3A to 3C based on the timing signal will be described below with reference to FIG. 8. Here, a case will be described where electric charges are accumulated in accordance with the timing signal at the radiographing apparatuses 3A to 3C.

Figure 8:
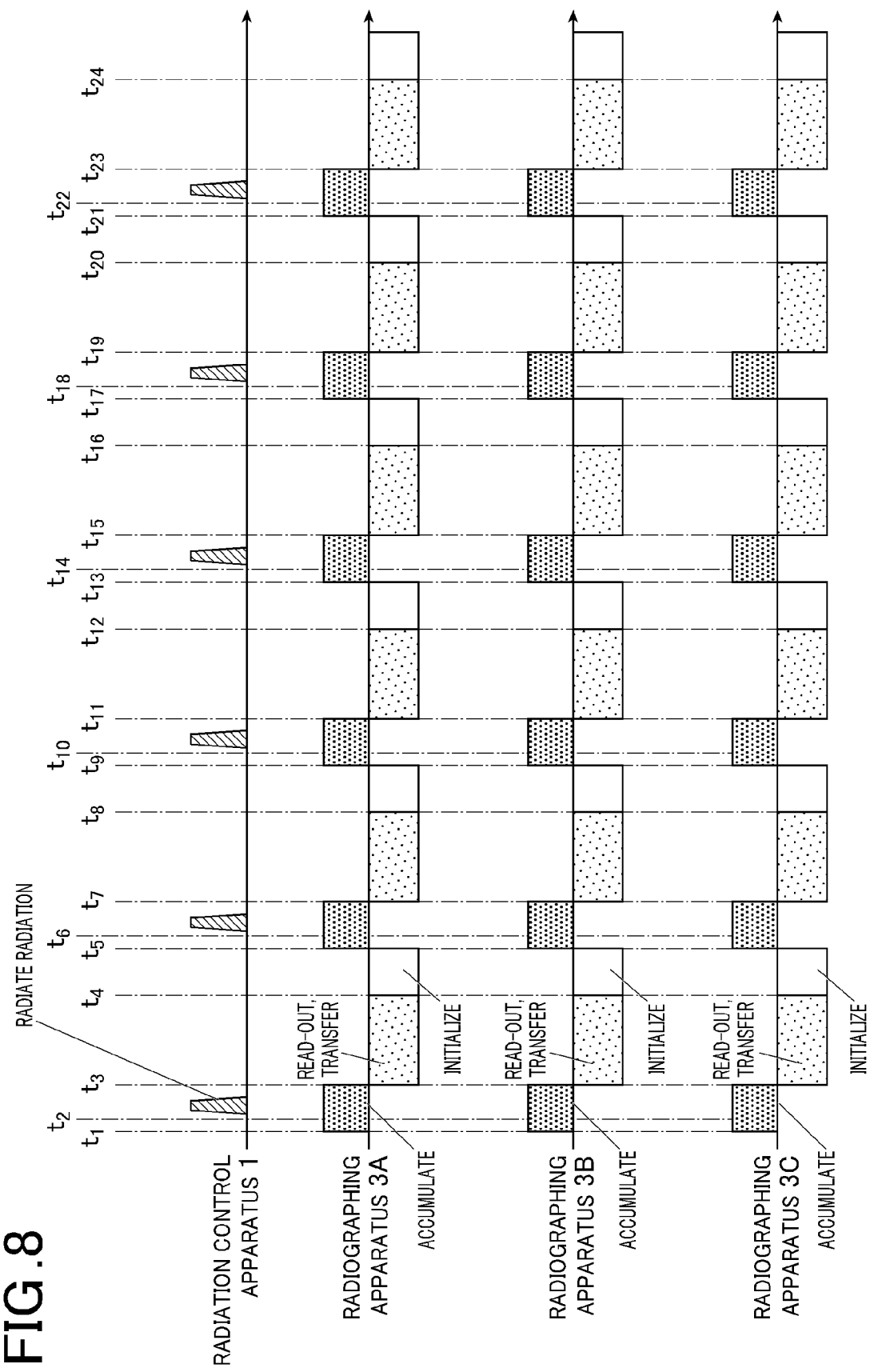
FIG. 8 is a view illustrating timings of a radiation irradiation operation and an accumulation operation of the radiographic imaging system in FIG. 2.

As illustrated in FIG. 8, states of the radiographing apparatuses 3A to 3C transition to states where electric charges generated by radiation detection elements 32d can be accumulated within the pixels by an OFF voltage being applied to the respective scanning lines 32b when the radiographing apparatuses 3A to 3C receive the timing signal from the addition controller 61 (t1, t5, t9, . . . ).

The addition controller 61 outputs the irradiation allowance signal at a timing linked with the timing at which the timing signal is transmitted, and the radiation control apparatus 1 radiates radiation to the radiographing apparatuses 3A to 3C in accordance with the irradiation allowance signal (t2, t6, t10, . . . ).

The radiographing apparatuses 3A to 3C continue a mode in which electric charges are accumulated for a predetermined period with the timers provided at the own apparatuses (t1 to t3, t5 to t7, t9 to t11, . . . ).

When the radiographing apparatuses 3A to 3C receive radiation during the above-described mode in which electric charges are accumulated, the radiographing apparatuses 3A to 3C generate electric charges at the respective radiation detection elements 32d of the radiation detectors 32 and accumulate the electric charges in the respective pixels (step S28).

Thereafter, the radiographing apparatuses 3A to 3C perform the read-out operation of discharging the electric charges accumulated in the respective pixels to the signal lines 32c by applying an ON voltage to the respective switch elements 32e after the predetermined period has elapsed, timed with the timers provided at the own apparatuses. In the read-out operation, the radiographing apparatuses 3A to 3C read out image data based on the electric charges which have flown in at the read-out unit 34 and convert the image data into image data. Further, the converted image data is stored in the memories of the radiographing apparatuses 3A to 3C, and/or at least part of the image data is transferred to the console 4 (t3 to t4, t7 to t8, t11 to t12, . . . ). Then, in a mode in which electric charges are accumulated at the next timing, initialization is performed so that the electric charges accumulated in the respective pixels are discharged so as to prevent influence of the electric charges previously accumulated in a mode in which electric charges are accumulated (t4 to t5, t8 to t9, t12 to t13).

Here, while description of the read-out operation and initialization has been separately provided in FIG. 8, because the read-out operation is performed by the electric charges accumulated in the respective pixels being discharged in the read-out operation, read-out and initialization are performed at the same time. Therefore, it is not necessary to provide an initialization operation stage separately from a read-out operation stage, or it is also possible to further provide an initialization operation stage for causing the electric charges to be discharged again other than the read-out operation stage.

(E: End of Radiographing)

At the addition apparatus 6, for example, the number of radiographs to be captured in accordance with the selected radiographing order is set by the console 4 upon start of radiographing. The addition apparatus 6 counts the number of times of output of the irradiation allowance signal, compares the number of times with the above-described set number of radiographs to be captured, and, when the number of times of output of the irradiation allowance signal reaches the number of radiographs to be captured, judges that long-length serial radiography is completed.

When the addition apparatus 6 judges that long-length serial radiography is completed, the addition apparatus 6 puts the radiographing start signal into an OFF state, and transmits a radiographing start signal OFF signal to at least the radiographing apparatuses 3A to 3C among the console 4, the radiographing apparatuses 3A to 3C and the radiation control apparatus 1 (step S33). Further, when the addition apparatus 6 judges that long-length serial radiography is completed, the addition apparatus 6 stops output of at least the irradiation allowance signal out of the timing signal and the irradiation allowance signal described above or all of the timing signal and the irradiation allowance signal.

Here, in a similar manner to acquisition of the dark image before radiographing is performed by radiation being radiated described above, after long-length serial radiography, the addition apparatus 6 can acquire the dark image by performing radiographing in a state where radiation is not radiated after radiographing is performed by irradiation of radiation, by outputting only a timing signal at a timing at which the timing signal and the irradiation allowance signal are output.

By using the dark images before and after radiographing is performed by irradiation of radiation, it is possible to perform correction while taking into account fluctuation during a radiographing period by inferring the dark image during a serial radiographing period and performing offset correction, or the like, on the radiograph using the inferred dark image.

Alternatively, in a case where the dark image is not acquired before radiographing is performed by irradiation of radiation, it is also possible to correct a radiograph acquired through radiographing by irradiation of radiation using the dark image acquired after the radiographing.

When the radiographing apparatuses 3A to 3C detect an OFF state of the radiographing start signal, the radiographing apparatuses 3A to 3C transfer radiographs (which will be referred to as remaining radiographs) of the radiographing, which are stored in the memories of the own apparatuses and which have not been transferred yet, to the console 4 (step S34). When the radiographing apparatuses 3A to 3C complete transfer of all the remaining radiographs, the radiographing apparatuses 3A to 3C transmit a remaining radiograph transfer completion signal to the console 4 (step S35).

When the console 4 receives the remaining radiograph transfer completion signal from all of the radiographing apparatuses 3A to 3C, the console 4 starts work of confirming the transmitted radiographs.

When the radiographing apparatuses 3A to 3C complete transfer of the remaining radiographs, states of the radiographing apparatuses 3A to 3C transition from a radiographing waiting state to a standby state, and the radiographing apparatuses 3A to 3C transmit a standby start signal to the console 4 (step S36).

When the console 4 receives the standby start signal from all of the radiographing apparatuses 3A to 3C, the console 4 causes "end of radiographing" to be displayed at the display 43 (step S37). Further, the console 4 transmits a radiograph deletion signal which gives an instruction to delete radiographs to the radiographing apparatuses 3A to 3C (step S38).

Note that control may be performed so that the radiograph deletion signal is transmitted after the work for confirming the radiographs is completed and it is confirmed that there is no problem in all the transferred radiographs.

When the radiographing apparatuses 3A to 3C receive the radiograph deletion signal, the radiographing apparatuses 3A to 3C delete radiographs captured through long-length serial radiography, stored in the memories of the own apparatuses (step S39). By this means, it is possible to secure a memory region for the next radiographing.

When the radiographer releases the irradiation instruction switch 5 from the second stage in response to display of "end of radiographing" displayed at the display 43 of the console 4 (step S40), the irradiation instruction switch 5 puts the irradiation instruction signal into an OFF state (step S41), and, further, the radiation controller 11 also puts the irradiation instruction signal into an OFF state (step S42).

Thereafter, when the radiographer releases the irradiation instruction switch 5 from the first stage (step S43), the irradiation instruction switch 5 puts the irradiation preparation signal into an OFF state (step S44), and, further, the radiation controller 11 also puts the irradiation preparation signal into an OFF state (step S45).

When the addition apparatus 6 detects that the irradiation instruction signal and the irradiation preparation signal are put into an OFF state, the addition apparatus 6 transmits a radiographing end signal indicating that radiographing is finished to the console 4 (step S46).

When the console 4 receives the radiographing end signal from the addition apparatus 6, the console 4 transmits a disconnection request to the addition apparatus 6 (step S47).

When the addition apparatus 6 receives the radiographing end signal from the console 4, the addition apparatus 6 disconnects the radiographing apparatuses 3A to 3C (step S48), and puts the sequence start signal into an OFF state to finish the radiographing sequence, and the state transitions to a state where a radiographing instruction is waited.

By the system 100 according to the present embodiment operating as described above, long-length serial radiography in which a plurality of frame images are repeatedly captured in a short period is performed.

Modified Example 1: Count the Number of Captured Radiographs at Radiographing Apparatuses 3A to 3C Note that, while an example has been described in the above-described embodiment where the addition apparatus 6 counts the number of times of transmission of the irradiation allowance signal, and, in a case where the counted number of times of output of the irradiation allowance signal reaches a maximum number of radiographs to be captured, it is judged that the maximum number of radiographs to be captured is reached, it is also possible to configure an apparatus such that the number of times of reception of the timing signal after the radiographing apparatuses 3A to 3C transmit the irradiation start allowance signal, the number of times the radiographing apparatuses 3A to 3C receive the timing signal and read out the electric charges in the respective pixels, or the number of times the radiographing apparatuses 3A to 3C perform read-out and store radiographs, or transfer the radiographs to the console 4, is counted, and judgement is performed in accordance with whether or not the number of times reaches the maximum number of radiographs to be captured set in advance.

It is also possible to employ a configuration where the console 4 or the addition apparatus 6 is notified that the number of radiographs to be captured is reached from the radiographing apparatuses 3A to 3C which are used for radiographing. It is also possible to employ a configuration where the console 4 or the addition apparatus 6 finish radiographing by receiving notifications that the number of radiographs to be captured is reached from all or part of the radiographing apparatuses 3A to 3C which are used for radiographing.

By a radiographing end timing being controlled by the number of radiographs actually captured at the radiographing apparatuses 3A to 3C, it is possible to perform control using the number of radiographs more accurately.

By this means, for example, even in a case where the number of times of irradiation of radiation is different from the number of times of radiographing due to a failure by unintended noise, or the like, it is possible to control radiographing based on the number of radiographs.

Modified Example 2: Operation of Radiation Controller Upon Serial Radiography

In the above-described embodiment, the radiation controller 11 receives the irradiation instruction signal from the irradiation instruction switch 5 and repeatedly receives the irradiation allowance signal from the addition controller 61.

This irradiation allowance signal is, for example, transmitted to the radiation controller 11 as a pulsed signal corresponding to irradiation of radiation for radiographing individual frames of a long-length dynamic image. Further, the radiation controller 11 transmits an irradiation signal to the high-voltage generator 12 on a one-to-one basis in response to the irradiation allowance signal which is repeatedly received, and radiates radiation.

Further, in a case where one still image is captured, it is sufficient if the radiation controller 11 transmits the irradiation allowance signal once in response to reception of the irradiation instruction signal of one time.

Therefore, it is possible to employ a configuration where, to capture a still image, in order to prevent radiation from being erroneously radiated a plurality of times as a result of the irradiation allowance signal being received a plurality of times for the irradiation instruction signal of one time, even if the irradiation allowance signal is received a plurality of times for the irradiation instruction signal of one time, the irradiation signal is transmitted only once for the first input of the irradiation allowance signal. For example, it is possible to employ a configuration where the radiation controller 11 is controlled so as not to output the irradiation signal for input of the irradiation allowance signal until a fixed period has elapsed since the irradiation signal had been output once for input of the irradiation allowance signal of one time.

Meanwhile, if the radiation controller 11 transmits the irradiation signal only once for the irradiation allowance signal of one time as described above, serial radiography in which irradiation of radiation is repeated a plurality of times for the irradiation instruction signal of one time cannot be performed as in the system 100 according to the present embodiment.

Therefore, it is also possible to configure the radiation controller 11 so as to transmit the irradiation signal to the high-voltage generator 12 a plurality of times in accordance with the irradiation allowance signal in a case where the irradiation allowance signal is received a plurality of times during a period while the irradiation instruction signal of one time is input, which is a period during which the radiographer depresses the irradiation instruction switch 5.

By this means, it is possible to perform serial radiography in which irradiation of radiation is repeated a plurality of times for the irradiation instruction signal of one time.

Note that a control mode may be switched between (1) a control mode in which the irradiation signal is transmitted only once for the irradiation allowance signal of one time, and (2) a control mode in which, in a case where the irradiation allowance signal is input a plurality of times during a period while the irradiation instruction signal is input, the irradiation signal is transmitted to the high-voltage generator 12 a plurality of times in accordance with input of the irradiation allowance signal, in accordance with the radiographing type (whether still radiography or serial radiography).

It is also possible to employ a configuration where this switching of the control mode of the radiation controller 11 in accordance with the radiographing type can be performed at the console 4, and the control mode is changed from the console 4 based on receipt of a signal indicating the radiographing type.

With such a configuration, it is possible to reliably prevent a risk that the object under examination is uselessly exposed to radiation as a result of radiation being erroneously radiated a plurality of times when a still image is captured.

Modified Example 3: Timing Limitation of Radiation Controller Upon Serial Radiography Here, the radiation controller 11 can also perform control so that, in a case where, along with the irradiation instruction signal which is continuously input from the irradiation instruction switch 5 during the radiographing period, the irradiation allowance signal is successively transmitted from the addition controller 61 for irradiation of radiation for respective frames of long-length serial radiography, in a case where an interval between the two successive irradiation allowance signals is shorter than a specific interval, the irradiation signal is not transmitted to the high-voltage generator 12.

For example, if electrical noise is mixed into the irradiation allowance signal to be transmitted from the addition controller 61 to the radiation controller 11, and the radiation controller 11 receives a signal similar to the irradiation allowance signal at an unintended timing, the state may become a state similar to a state where the radiation controller 11 repeatedly receives the irradiation allowance signal at an interval which is too short for the high-voltage generator 12 to generate a high voltage required for irradiation of radiation. In such a case, if the radiation controller 11 forcedly transmits the irradiation signal to the high-voltage generator 12, an excessive current may flow through the high-voltage generator 12, and the high-voltage generator 12 may fail.

Therefore, in the above-described embodiment, it is also possible to configure the radiation controller 11 so that, in a case where the irradiation allowance signal is repeatedly received from the addition controller 61 while the irradiation instruction signal input from the irradiation instruction switch 5 is put into an ON state, a length of a reception interval of the two successive irradiation allowance signals is compared with a minimum reception interval set in advance, and in a case where it is determined that the length is shorter than the minimum reception interval, the irradiation signal is not transmitted to the high-voltage generator 12. It is also possible to employ a configuration where an appropriate minimum time interval is set as the minimum time interval from a frame rate of radiographing.

By this means, it is possible to prevent the high-voltage generator 12 from failing due to an excessive current flowing through the high-voltage generator 12.

Modified Example 4: Timing of Start of Coordination with Synchronization Source

While a case has been described in the above-described embodiment where coordination between the radiographing apparatuses 3A to 3C and the synchronization source is started from start of the radiographing sequence (the addition apparatus 6 transmits the timing signal to the radiographing apparatuses 3A to 3C), it is also possible to start coordination between the radiographing apparatuses 3A to 3C and the synchronization source after the irradiation instruction switch 5 is put into the first stage. Alternatively, it is also possible to start coordination between the radiographing apparatus 3A to 3C and the synchronization source after the irradiation instruction switch 5 is put into the second stage. While there is a possibility that coordination with the synchronization source may be off upon actual radiographing if the radiographing apparatuses 3A to 3C coordinate with the synchronization source in an unnecessarily early stage, by starting coordination with the synchronization source in a preparation stage before radiographing, it is possible to prevent coordination with the synchronization source from being off.

Modified Example 5: Timing of Starting Coordination with Synchronization Source

Further, the radiographing apparatus 3 may determine time for starting coordination with the synchronization source based on types of the radiographing apparatuses 3A to 3C to be used for radiographing because a period required for coordinating with the synchronization source is different depending on the type. For example, the radiographing apparatuses 3A to 3C may start coordination with the synchronization source in accordance with a reset start timing required by the radiographing apparatuses 3A to 3C. For example, in a case where it is necessary to reset the electric charges accumulated in the respective pixels before the accumulation operation at the radiographing apparatuses 3A to 3C, coordination with the synchronization source may be started after the reset is completed. Further, in a case where different types of radiographing apparatuses 3A to 3C are combined, coordination with the synchronization source may be started so as to be conformed to the radiographing apparatus which takes longest time. Further, in a case where different types of radiographing apparatuses 3A to 3C are combined, periods required for the respective radiographing apparatuses 3A to 3C to complete coordination with the synchronization source may be different from each other. Therefore, coordination with the synchronization source may be started at a required timing after a period required for the respective radiographing apparatuses 3A to 3C to complete synchronization.

[Effects]

As described above, in the system 100 according to the present embodiment, the radiation control apparatus 1 can output the irradiation signal a plurality of times for acquisition (detection of an ON state) of the irradiation instruction signal of one time, by connecting the addition controller 61 to the radiation control apparatus 1 which can perform irradiation of radiation only once for an instruction of irradiation of radiation of one time in the conventional system 100A illustrated in FIG. 1. Therefore, it is possible to perform radiographing in which still images are repeatedly captured a plurality of times in a short period, that is, serial radiography, using the radiographing apparatuses 3A to 3C.

Further, the conventional system 100A illustrated in FIG. 1 is widespread as a radiographing apparatus which captures a simple still image. Therefore, a medical institution which uses the conventional system 100A can easily convert the conventional system 100A including an existing radiation generation apparatus to a system which supports serial radiography only by adding the radiographing apparatus 3 and the addition apparatus 6 without updating the expensive radiation generation apparatus (the radiation control apparatus 1, the high-voltage generator 12, and the radiation generator 2).

Further, in the system 100, because radiographing is performed after it is confirmed at the console 4 that all of the radiographing apparatuses 3 (3A to 3C) to be used for radiographing are connected to the specific addition apparatus 6 which is the synchronization source, it is possible to minimize a risk that radiographing cannot be correctly performed at all the radiographing apparatuses 3 (3A to 3C) as a result of radiographing being performed in a state where part of the radiographing apparatuses 3 to be used for radiographing is connected to other synchronization sources, and radiographing being performed at a timing different from other radiographing apparatuses 3 to be used for radiographing. By this means, it is possible to minimize a risk that the object under examination is uselessly exposed to radiation as a result of radiographing failing.

<Related Art 1-B>

Related art 1-B which becomes a basis of a system 200 (which will be described in detail later) according to a first-B embodiment of the present invention will be described next with reference to FIG. 9. Note that the same reference numerals will be assigned to components which are the same as those of the above-described related art 1-A, and description thereof will be omitted.

[System Configuration]

A schematic configuration of a radiographic imaging system (hereinafter, referred to as a conventional system 200A) according to the related art 1-B will be described first. FIG. 9 is a block diagram illustrating a schematic configuration of the conventional system 200A.

Figure 9:
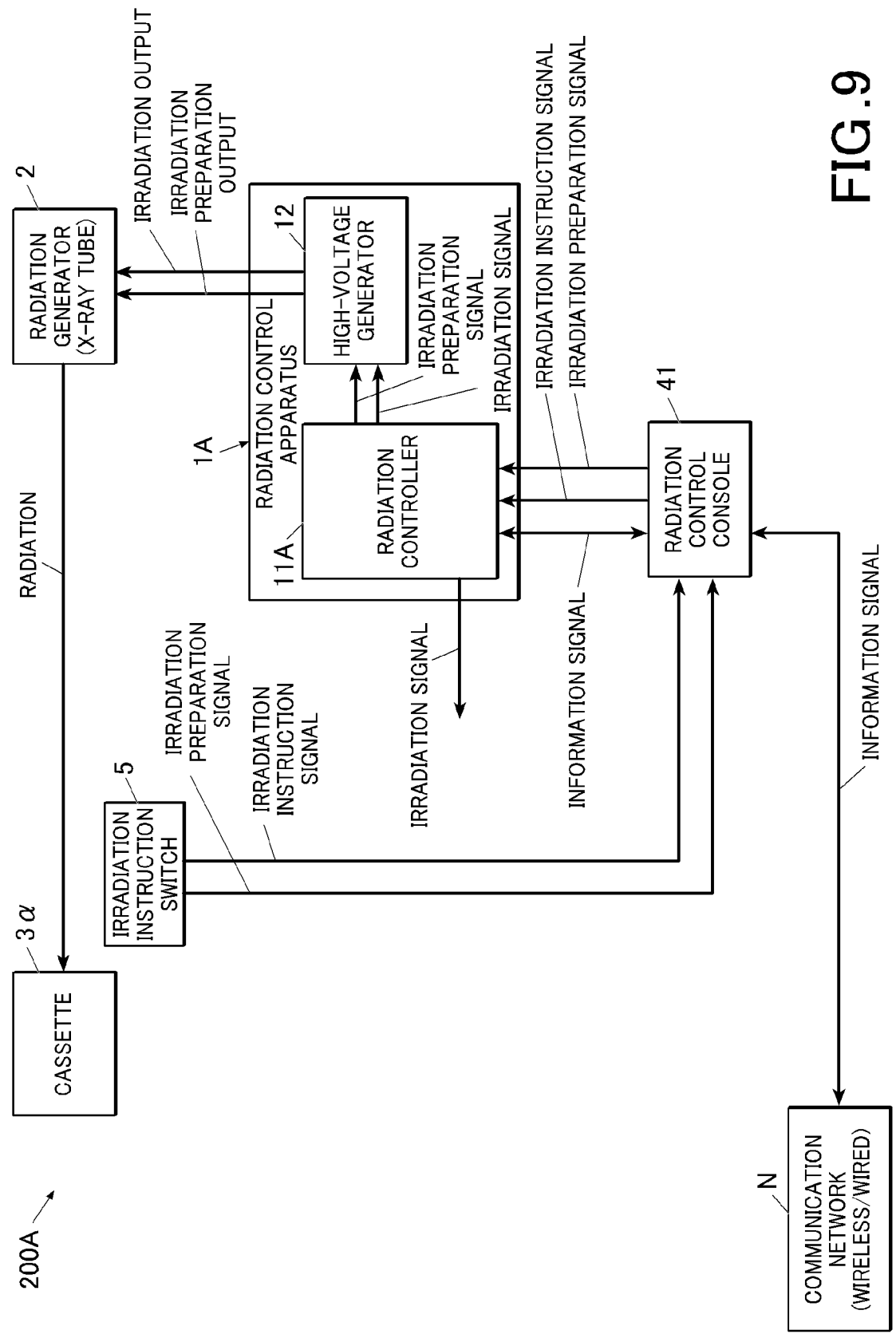
FIG. 9 is a block diagram illustrating a radiographic imaging system according to related art 1-B.

For example, as illustrated in FIG. 9, the conventional system 200A is different from the above-described conventional system 100A in a configuration of the radiation controller 11A provided at the radiation control apparatus 1A.

Specifically, while the radiation controller 11 of the conventional system 100A is configured to be able to output the irradiation preparation signal and the irradiation instruction signal to external equipment based on detecting that the irradiation preparation signal and the irradiation instruction signal from the radiation control console 41 are put into an ON state, the radiation controller 11A of the conventional system 200A does not have such a configuration.

Further, while the radiation controller 11 of the conventional system 100A is configured to be able to receive the irradiation allowance signal from external equipment, the radiation controller 11A of the conventional system 200A does not have such a configuration.

Because other configurations of the respective components of the conventional system 200A and modified examples thereof are similar to those described for the conventional system 100A, the description will be incorporated.

[Operation]

An operation of the above-described conventional system 200A will be described next.

(Irradiation Preparation Operation)

When the irradiation instruction switch 5 is put into the first stage by the radiographer, the irradiation instruction switch 5 puts the irradiation preparation signal to be output to the radiation controller 11A via the radiation control console 41 into an ON state.

When the radiation controller 11A detects that the irradiation preparation signal is put into an ON state, the radiation controller 11A puts the irradiation preparation signal to be output to the high-voltage generator 12 into an ON state.

Note that, while output of the irradiation preparation signal from the radiation controller 11A to external equipment is not illustrated in FIG. 9, in a case where the operation is performed in coordination with the external equipment, the irradiation preparation signal may be output to the external equipment.

When the high-voltage generator 12 detects that the irradiation preparation signal is put into an ON state, the high-voltage generator 12 outputs irradiation preparation output to the radiation generator 2.

The radiation generator 2 starts preparation for generating radiation when the irradiation preparation output is input.

In a case where a rotating anode is used as the anode, for example, an operation of rotating the rotating anode, or the like, is performed.

(Irradiation Operation)

Subsequently, when the irradiation instruction switch is put into the second stage by the radiographer, the irradiation instruction switch 5 puts the irradiation instruction signal to be output to the radiation controller 11A via the radiation control console 41 into an ON state.

Note that, while output of the irradiation instruction signal from the radiation controller 11A to external equipment is not illustrated in FIG. 9, in a case where the operation is performed in coordination with external equipment, the irradiation instruction signal may be output to the external equipment.

Because the related art 1-B does not employ a configuration where the irradiation allowance signal is received from external equipment, control for transmitting the irradiation signal in a case where the irradiation instruction signal and the irradiation allowance signal are input is not performed. Therefore, the radiation controller 11A transmits the irradiation signal to the high-voltage generator 12 only when it is detected that the irradiation instruction signal is put into an ON state.

When the high-voltage generator 12 receives the irradiation signal, the high-voltage generator 12 applies a high voltage required for irradiation of radiation at the radiation generator 2 to the radiation generator 2 as an irradiation output.

When the high voltage is applied from the high-voltage generator 12, the radiation generator 2 generates radiation in accordance with the applied voltage.

The generated radiation is radiated to the object under examination and the cassette 3α behind the object under examination after a direction of irradiation, a region, radiation quality, or the like, of the radiation are adjusted by a controller such as a collimator which is not illustrated. Part of the radiation penetrates through the object under examination and is incident on the cassette 3α.

If the radiation is incident on the cassette 3α, a radiograph is formed on a stored film or fluorescent plate.

Here, to prevent irradiation from being performed before rotation of the rotating anode reaches sufficient speed, in a similar manner to the above-described related art 1-A, the radiation controller 11A may be configured so that the irradiation signal is not transmitted even if it is detected that the irradiation instruction signal is put into an ON state until a predetermined waiting period has elapsed since it had been detected that the irradiation preparation signal had been put into an ON state as described above.

In this manner, in radiographing using the conventional system 200A, in a similar manner to a case where the above-described conventional system 100A is used, only one radiograph (still image) of the object under examination is captured based on the radiographing operation of one time.

First-B Embodiment

A first-B embodiment of the present invention will be described next with reference to FIG. 10 to FIG. 12. Note that the same reference numerals will be assigned to components which are equivalent to those in the above-described first-A embodiment, and description thereof will be omitted. Further, various modified patterns described in the first-A embodiment can also be applied to the present embodiment.

In the radiographic imaging system, while there is a radiation controller 11 which includes an inputter to which the irradiation allowance signal is input from outside, and which transmits the irradiation signal in accordance with the irradiation instruction from the radiographer and irradiation allowance from outside as described above in the related art 1-A, there is also a radiation controller 11A which includes only the inputter to which the irradiation instruction signal is input from outside, and which captures a still image as described above in the related art 1-B.

The radiographic imaging system (hereinafter, the system 200) according to the present embodiment is configured to be able to successively perform radiographing by adding an addition apparatus 6A also to such a radiation controller 11A.

[System Configuration]

A system configuration of the system 200 will be described first. FIG. 10 is a block diagram illustrating a schematic configuration of the system 200 according to the first-B embodiment.

Figure 10:
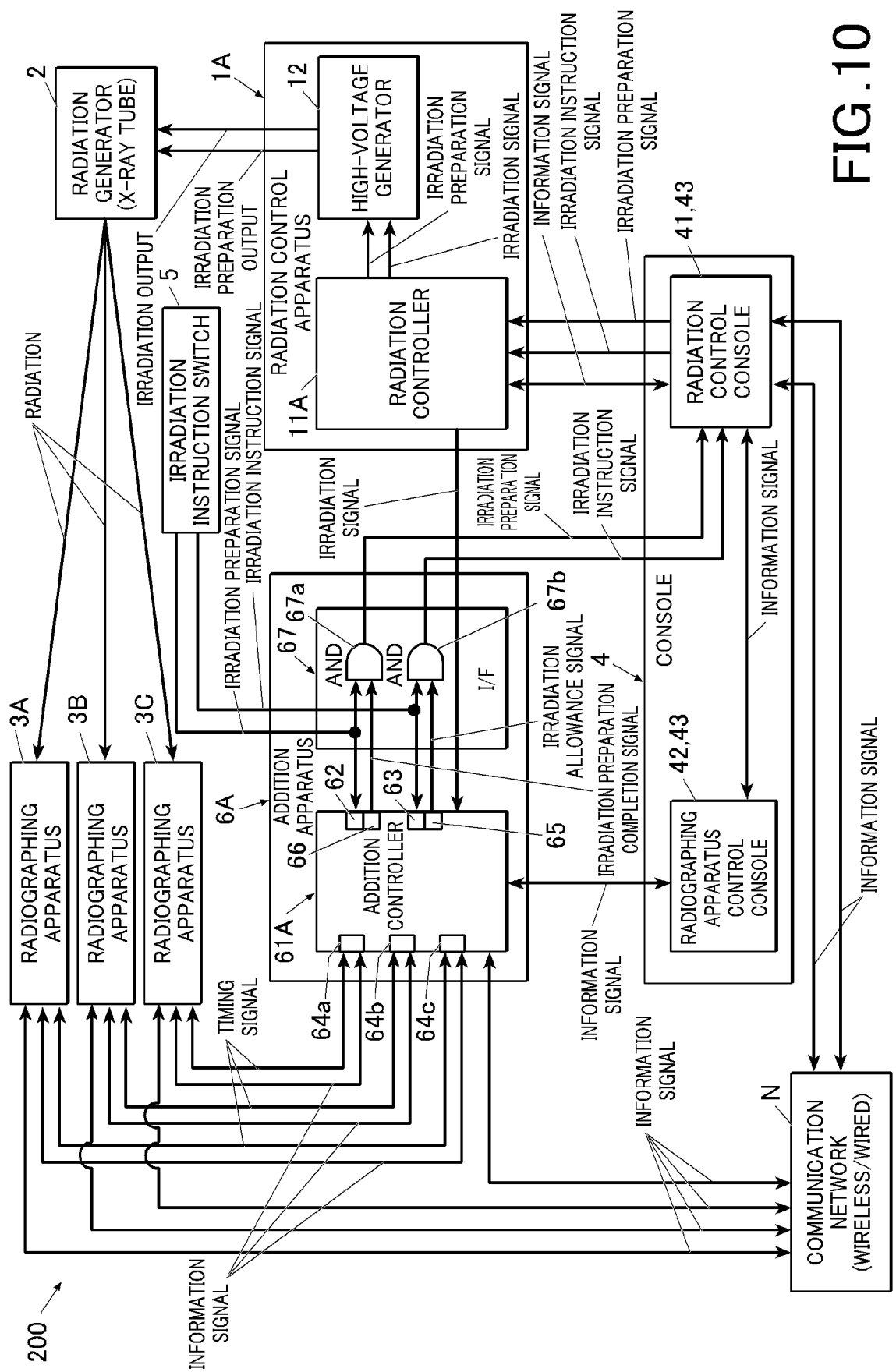
FIG. 10 is a block diagram illustrating a radiographic imaging system according to a first-B embodiment of the present invention.

For example, as illustrated in FIG. 10, the system 200 according to the present invention is a system in which the cassette 30c in the conventional system 200A illustrated in FIG. 9 is replaced with a plurality of radiographing apparatuses 3, and which further includes the radiographing apparatus control console 42 and the addition apparatus 6A in a similar manner to the above-described first-A embodiment. This system 200 is a system which can acquire a long-length dynamic image indicating a dynamic state of the object under examination by performing long-length serial radiography using the plurality of radiographing apparatuses 3 as will be described below in a similar manner to the above-described system 100. Note that, while a case will be described as an example in the following embodiment where radiographing is performed using three radiographing apparatuses 3, the number of radiographing apparatuses to be used is not particularly limited. Further, description will be provided assuming that the radiographing apparatuses 3 to be used for radiographing are the radiographing apparatuses 3A to 3C.

The addition apparatus 6A includes an addition controller 61A and an interface (hereinafter, an I/F 67).

Note that, while FIG. 10 illustrates the addition apparatus 6A in which the addition controller 61A and the I/F 67 are separately configured, these may be integrally configured.

The addition controller 61A includes a third connector 66 in addition to the first acquirer 62, the second acquirer 63, the first connector 64 and the second connector 65 which are similar to those in the above-described first-A embodiment.

Further, the I/F 67 includes a first AND circuit 67a and a second AND circuit 67b.

The first acquirer 62 is connected to one input of the first AND circuit 67a, and the third connector 66 is connected to the other input of the first AND circuit 67a.

Further, the second acquirer 63 is connected to one input of the second AND circuit 67b, and the second connector 65 is connected to the other input of the second AND circuit 67b.

Further, while, in the system 100 according to the first-A embodiment, the irradiation instruction switch 5 is connected to the console 4, and the irradiation instruction switch 5 outputs the irradiation preparation signal and the irradiation instruction signal to the addition apparatus 6 via the radiation control apparatus 1, in the system 200 according to the present embodiment, the irradiation instruction switch 5 which can output the irradiation preparation signal and the irradiation instruction signal is directly connected to the addition apparatus 6A.

Then, the addition apparatus 6A can respectively input the irradiation preparation signal and the irradiation instruction signal from the irradiation instruction switch 5 to the addition controller 61A, and one input of the first AND circuit 67a and one input of the second AND circuit 67b of the I/F 67. In other words, the first acquirer 62 can directly acquire the irradiation preparation signal, and the second acquirer 63 can directly acquire the irradiation instruction signal from the irradiation instruction switch 5.

Note that it is also possible to employ a configuration where a substrate or equipment in which the irradiation instruction switch 5 is provided or which is connected to the irradiation instruction switch 5, is connected to the I/F 67, and the first and the second acquirers 62 and 63 acquire the irradiation preparation signal and the irradiation instruction signal output from the irradiation instruction switch 5 via the substrate or the equipment.

Further, the third connector 66 according to the present embodiment outputs the radiographing preparation completion signal to the first and the second AND circuits 67a and 67b, and the second connector 65 outputs the irradiation allowance signal to the first and the second AND circuits 67a and 67b, and, in a case where AND conditions of the irradiation preparation signal and the irradiation instruction signal from the irradiation instruction switch 5 are satisfied at the first and the second AND circuits 67a and 67b, the first and the second AND circuits 67a and 67b can respectively output the irradiation preparation signal and the irradiation instruction signal to the radiation controller 11A via the radiation control console 41.

In other words, the third connector 66 and the second connector 65 according to the present embodiment can be respectively connected to the radiation control apparatus 1A via the IF 67.

Note that an example has been described in FIG. 10 where the irradiation preparation signal from the irradiation instruction switch 5 also branches so as to be input to the addition controller 61A and the first AND circuit 67a at the IF 67, and the irradiation preparation signal is output from the I/F 67 when the AND conditions with the radiographing preparation completion signal from the addition controller 61A are satisfied. However, the irradiation preparation signal does not have such a configuration, and may be configured to be directly output to the radiation control console 41 and the radiation controller 11A from the irradiation instruction switch 5.

Further, while FIG. 10 illustrates a configuration where the first connector 64 (64a, 64b, and 64c) directly transmits/receives information and signals to/from the radiographing apparatuses 3A to 3C, the first connector 64 (64a, 64b, and 64c) may be connected to other apparatuses via a relay which can relay signals and which is not illustrated.

Further, while FIG. 10 illustrates a case where the first acquirer 62, the second acquirer 63, the first connector 64 and the second connector 65 are separately provided, at least two of the first acquirer 62, the second acquirer 63, the first connector 64, the second connector 65 and the third connector 66 may be integrally configured (respective components 62 to 66 may be combined).

Further, while not illustrated, it is also possible to employ a configuration where the irradiation preparation signal and the irradiation instruction signal output from the addition apparatus 6A are directly input to the radiation controller 11A without involving the radiation control console 41.

In a case where the irradiation preparation signal and the irradiation instruction signal are input to the radiation controller 11A via the console 4, the console 4 can recognize that the radiographer gives an instruction to prepare irradiation and radiate radiation in a similar manner to the radiation controller 11A, and can make a notification of an operation, display, or the like, in accordance with the instruction to prepare irradiation and radiate radiation at the console 4.

Meanwhile, in a case where the irradiation preparation signal and the irradiation instruction signal are input to the radiation controller 11A without involving the console 4, the radiation controller 11A can receive the irradiation preparation signal and the irradiation instruction signal without being affected by other equipment, so that it is possible to realize the more stable and secure operation.

Further, while the addition controller 61A is different from the addition controller 61 according to the first-A embodiment in a program to be executed, the addition controller 61A may employ a structure similar to that of the addition controller 61 according to the first-A embodiment. (While not illustrated in FIG. 2, and, while the addition controller 61 according to the first-A embodiment also includes the third connector 66, because a command for using the third connector 66 is not included in the program, it is possible to use the addition controller similar to the addition controller 61.) Alternatively, it is also possible to use the addition controller 61A whose functions are limited to necessary functions, and which is different from the addition controller 61.

When the addition controller 61A detects that the irradiation preparation signal from the irradiation instruction switch 5 is put into an ON state, the addition controller 61A puts the radiographing preparation signal to be output to at least one of the radiographing apparatuses 3A to 3C and the console 4 into an ON state.

Further, when the addition controller 61A detects that the radiographing preparation completion signal from at least one of the console 4 and the radiographing apparatuses 3A to 3C is put into an ON state, the addition controller 61A puts the radiographing preparation completion signal to be output to the other input of the first AND circuit 67a of the I/F 67 into an ON state.

Further, when the addition controller 61A detects that the irradiation instruction signal from the irradiation instruction switch 5 is put into an ON state, the addition controller 61A puts the radiographing start signal to be output to at least one of the radiographing apparatuses 3A to 3C and the console 4 into an ON state.

Further, when the addition controller 61A detects that the irradiation start allowance signal from at least one of the console 4 and the radiographing apparatuses 3A to 3C is put into an ON state, the addition controller 61A repeatedly outputs the irradiation allowance signal (for example, a pulsed signal) which is similar to that in the first-A embodiment to the other input of the second AND circuit 67b of the I/F 67 with a predetermined period.

Further, the addition controller 61A repeatedly outputs the timing signal (for example, a pulsed signal) which is similar to that in the first-A embodiment to the radiographing apparatuses 3A to 3C with a predetermined period.

In this manner, it is possible to employ a configuration where a timer which is similar to that in the first-A embodiment is provided at the addition controller 61A to control transmission timings of the irradiation allowance signal and the timing signal.

[Operation]

An operation of the above-described system 200 will be described next. FIG. 11 and FIG. 12 are ladder charts indicating the operation of the system 200 according to the present embodiment. The operation of the radiation control apparatus 1A in the ladder charts illustrated in FIG. 11 and FIG. 12 is executed by control by the radiation controller 11A. The operations of the radiographing apparatuses 3A to 3C is executed by control by the radiographing controller 31. The operation of the addition apparatus 6A is executed by control by the addition controller 61A. The operation of the console 4 is executed through cooperation between the CPU of the console 4 and the programs stored in the ROM or the RAM.

An operation of "A: Upon installation of equipment, upon start-up of apparatus, upon change of connection equipment, and upon regular confirmation of connection equipment" (step S1 and S2) and "B: Radiographing preparation" (step S3 to S15) are similar to those in the above-described first-A embodiment as illustrated in FIG. 11.

(C: Irradiation Pre-Processing)

The addition apparatus 6A subsequently repeatedly transmits the timing signal to the radiographing apparatuses 3A to 3C, and the radiographing apparatuses 3A to 3C repeat the read-out operation of the radiographing apparatuses 3A to 3C every time the timing signal is received. Here, while the radiographing apparatuses 3A to 3C convert the read-out electric charges into an image in a case where an image such as the correction data is required, the radiographing apparatuses 3A to 3C may perform the reset operation of discarding the read-out electric charges without converting the electric charges into an image in a case where an image is not required. Alternatively, the radiographing apparatuses 3A to 3C may perform the reset operation of converting the electric charges into an image and discarding the image.

If the radiographer finishes positioning of the object under examination and puts the irradiation instruction switch 5 into the first stage (step S16), the irradiation instruction switch 5 puts the irradiation preparation signal to be output to the addition apparatus 6A into an ON state and outputs the irradiation preparation signal (step S17A).

The irradiation preparation signal is respectively input to the addition controller 61A and one input of the first AND circuit 67a of the I/F 67.

At this time, the addition controller 61A is connected to other input of the first AND circuit 67a. Therefore, even if the irradiation preparation signal to be input to one input of the first AND circuit 67a from the irradiation instruction switch 5 is put into an ON state, in a case where the radiographing preparation completion signal to be input to the other input is not in an ON state, the irradiation preparation signal to be output from the first AND circuit 67a to the radiation control console 41 remains in an OFF state.

When the addition controller 61A detects that the irradiation preparation signal from the irradiation instruction switch 5 is put into an ON state, the addition controller 61A transmits the radiographing preparation signal which gives an instruction to prepare radiographing to the console 4 (step S19).

When the console 4 receives the radiographing preparation signal, the console 4 prepares radiographing.

Radiographing preparation at the console 4 is, for example, the operation of confirming that setting of the radiographing apparatus control console 42 which constitutes the console 4 is the same as setting of the radiation control console 41 which controls irradiation of radiation, or confirming that the designated radiographing conditions, or the like, are set at the radiation control apparatus 1A and the radiographing apparatuses 3A to 3C.

Further, as described in the first-A embodiment, in this stage, the console 4 may request notification of states to the radiographing apparatuses 3A to 3C and may confirm a state of at least one of the above-described radiographing apparatuses 3A to 3C again as final confirmation.

Further, the console 4 may be configured to lock an input such as change of the radiographing conditions to the console 4 so that the radiographing conditions cannot be changed in this stage in which radiographing preparation is completed.

Note that, while FIG. 11 illustrates a case where the radiographing preparation signal is output from the addition apparatus 6A to the console 4, there is also a case where the radiographing preparation signal is not output to the console 4, but output to the radiographing apparatuses 3A to 3C, so as to cause the radiographing apparatuses 3A to 3C to prepare radiographing, and, when radiographing preparation of the radiographing apparatuses 3A to 3C is completed, the radiographing apparatuses 3A to 3C output the radiographing preparation completion signal to the addition apparatus 6A.

Further, there is also a case where the irradiation preparation signal is output to both the console 4 and the radiographing apparatuses 3A to 3C, so as to cause the both to prepare radiographing, and, when radiographing preparation of the both is completed, the console 4 and the radiographing apparatuses 3A to 3C respectively transmit the radiographing preparation completion signal to the addition apparatus 6A, and it is judged that the whole radiographing preparation is completed in a stage where the addition apparatus 6A receives the radiographing preparation completion signal from the both.

Further, while not illustrated, in a case where at least one of the console 4 and the radiographing apparatuses 3A to 3C includes a connector which inputs, from external equipment, the radiographing preparation completion signal indicating whether or not radiographing preparation is completed, at least one of the console 4 and the radiographing apparatuses 3A to 3C may be configured to put the radiographing preparation completion signal into an ON state in a case where it is detected that the radiographing preparation completion signal from the external equipment is put into an ON state.

Alternatively, while not illustrated, it is also possible to provide a connector which outputs the radiographing preparation signal to external equipment or a connector which can receive input of the radiographing preparation completion signal from external equipment at the addition apparatus 6A or the addition controller 61A.

By this means, it becomes possible to instruct external equipment to prepare radiographing from the addition apparatus 6A or the addition controller 61A, or detect that radiographing preparation of the external equipment is completed, and output the radiographing preparation completion signal to the I/F also in response to completion of radiographing preparation of the external equipment.

The addition apparatus 6A can know that radiographing preparation is completed at the console 4 and the radiographing apparatuses 3A to 3C by detecting that the radiographing preparation completion signal is put into an ON state, and, by performing control so that radiation is radiated after the radiographing preparation completion signal is put into an ON state, it becomes possible to reliably exclude a risk that the object under examination is uselessly exposed to radiation as a result of radiation being radiated in a state where at least one of the console 4 and the radiographing apparatuses 3A to 3C cannot perform radiographing.

In a case where it is detected that the radiographing preparation signal is put into an ON state or the radiographing preparation operation is started, or the radiographing preparation operation is completed, the console 4 puts a signal indicating whether or not the radiographing preparation signal is received, or a signal indicating whether or not the radiographing preparation operation is started or a radiographing preparation completion signal indicating whether or not the radiographing preparation operation is completed, into an ON state (step S20). Further, "radiographing" is displayed at the display 43 of the console 4 (step S21).

When it is detected that the radiographing preparation completion signal is put into an ON state, the addition apparatus 6A puts the radiographing preparation completion signal to be output to an input different from the input to which the irradiation preparation signal is input from the irradiation instruction switch 5 out of two types of input of the first AND circuit 67A of the I/F 67, into an ON state.

At this time, because the irradiation preparation signal from the irradiation instruction switch 5 and the radiographing preparation completion signal from the addition controller 61A, which are to be input to two types of input of the first AND circuit 67a of the I/F 67 are both put into an ON state, the first AND circuit 67a puts the irradiation preparation signal to be output to the radiation control console 41 into an ON state.

When it is detected that the irradiation preparation signal is put into an ON state, the radiation control console 41 puts the irradiation preparation signal to be output to the radiation controller 11A into an ON state. In other words, the addition apparatus 6A puts the irradiation preparation signal to be transmitted to the radiation control apparatus 1A via the radiation control console 41 into an ON state (step S18A).

When it is detected that the irradiation preparation signal is put into an ON state, the radiation control apparatus 1A (the radiation controller 11A, the high-voltage generator 12, the radiation generator 2) prepares for irradiation of radiation in a similar manner to the above-described first-A embodiment.

Note that, while a case has been described here where the addition apparatus 6A transmits the irradiation preparation signal to the radiation controller 11A after confirming that radiographing preparation of the radiographing apparatuses 3A to 3C and the console 4 is completed (receiving the radiographing preparation completion signal), it is also possible to employ a configuration where the addition apparatus 6A may transmit the irradiation preparation signal to the radiation controller 11A at the same time as transmission to the radiographing apparatuses 3A to 3C and the console 4 without confirming completion of radiographing preparation of the radiographing apparatuses 3A to 3C and the console 4.

In this case, the first AND circuit 67a of the I/F 67 is not required, and it is also possible to employ a configuration where the irradiation preparation signal received from the irradiation instruction switch 5 is distributed to each of the console 4, the radiographing apparatuses 3A to 3C, the radiation control console 41 or the radiation controller 11A.

(D: Execution of Radiographing)

Subsequently, when the radiographer puts the irradiation instruction switch 5 into the second stage (step S22), the irradiation instruction switch 5 puts the irradiation instruction signal to be output to the addition apparatus 6A into an ON state (step S23A).

At this time, the addition apparatus 6A subsequently repeatedly transmits the timing signal to the radiographing apparatuses 3A to 3C, and the radiographing apparatuses 3A to 3C repeat the read-out operation every time the timing signal is received. Here, while the read-out electric charges are converted into an image in a case where an image such as the correction data is required, it is also possible to perform the reset operation of discarding the read-out electric charges without converting the electric charges into an image in a case where an image is not required. Alternatively, it is also possible to perform the reset operation of converting the electric charges into an image and discarding the image.

The irradiation instruction signal is input to the addition controller 61A and one input of the second AND circuit 67b of the I/F 67.

At this time, the addition controller 61A is connected to the other input of the second AND circuit 67b. Therefore, even if the irradiation instruction signal to be input from the irradiation instruction switch 5 to the one input of the second AND circuit 67b is put into an ON state, in a case where the irradiation allowance signal to the other input is not in an ON state, the irradiation instruction signal to be output from the second AND circuit 67b to the radiation control console 41 remains to be an OFF state.

When the addition apparatus 6A detects that the irradiation instruction signal from the irradiation instruction switch 5 is put into an ON state, the addition apparatus 6A puts the radiographing start signal to be output to at least one of the console 4 and the radiographing apparatuses 3A to 3C into an ON state (step S25 and S26).

Figure 12:
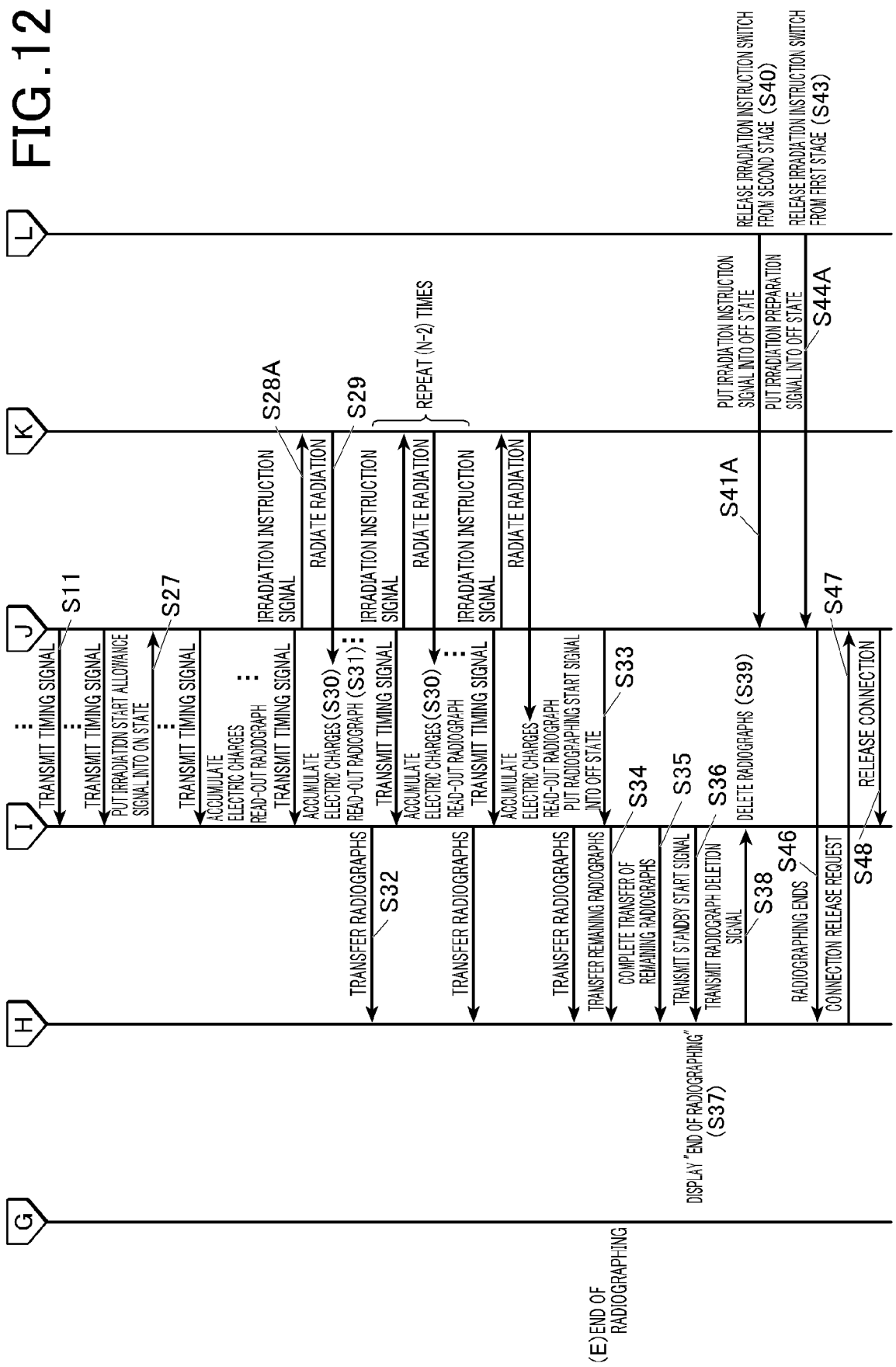
FIG. 12 is a ladder chart illustrating a last half of the operation of the radiographic imaging system in FIG. 10.

When it is detected that the radiographing start signal is put into an ON state, the radiographing apparatuses 3A to 3C put the irradiation start allowance signal to be output to the addition apparatus 6A into an ON state, for example, as illustrated in FIG. 12, by being triggered by a specific operation timing of the read-out operation performed by the own apparatuses at that time point (step S27). As the specific operation timing, for example, a timing at which read-out of the electric charges accumulated in the pixels arranged in two dimensions within the radiographing apparatus is completed over the whole two dimensions, or the like, can be used.

This is because, in the read-out operation of the radiographing apparatuses 3A to 3C, an image on the whole light receiving surface is acquired by the electric charges accumulated in the pixels arranged in two dimensions being sequentially read out, and, if the irradiation start allowance signal is put into an ON state, and radiation is radiated during read-out, a difference occurs in a signal value between the pixel in which read-out is completed and the pixel in which read-out is not completed, which may significantly degrade image quality.

Meanwhile, in the present embodiment, as will be described later, because irradiation of radiation and read-out of images of the radiographing apparatuses 3A to 3C are respectively performed based on the irradiation instruction signal and the timing signal from the addition apparatus 6A, radiation is not radiated during the read-out operation in normal routine. Therefore, it is also possible to employ a configuration where the irradiation start allowance signal is put into an ON state without a read-out timing of the radiographing apparatuses 3A to 3C described above being taken into account.

The radiographing apparatuses 3A to 3C repeat the image read-out operation also after the irradiation start allowance signal is put into an ON state. The image read out after this irradiation start allowance signal is put into an ON state is stored in the memories of the radiographing apparatuses 3A to 3C as a radiograph or transferred to the console 4. Alternatively, it is also possible to employ a configuration where part or all of the image may be stored in the memories or part or all of the image may be transmitted to the console 4 as the image obtained by reading out the electric charges of each radiation detection element 32d.

As will be described later, because radiographing is repeated in a relatively short time interval in long-length serial radiography, there is a case where the radiographs are not transmitted to the console 4 in time for radiographing intervals. Particularly, in a case where the radiographing apparatus 3A to 3C are connected to the addition controller 61A, or the radiographing apparatuses 3A to 3C are connected to the console 4 through wireless communication, because communication speed is affected by a wireless situation, by storing captured image data in the memories within the radiographing apparatuses 3A to 3C as described above, transmitting part of the image data to the console 4 during the radiographing operation and transmitting part or all of the image data to the console 4 after all radiographing is completed, it is also possible to continue radiographing without causing a radiographing error due to loss of image data or a transfer delay.

Further, the console 4 may request notification of states to the radiographing apparatuses 3A to 3C and may confirm a state of at least one of the above-described radiographing apparatuses 3A to 3C again as final confirmation in this stage as described in the first-A embodiment. Then, as a result of the state being confirmed again, in a case where it is determined that all of the radiographing apparatuses 3A to 3C are put into a state where radiographing can be continued, the console 4 may transmit a control signal to the radiographing apparatuses 3A to 3C so that the radiographing apparatuses 3A to 3C output the irradiation start allowance signal to the addition apparatus 6A.

The addition apparatus 6A can detect that the respective radiographing apparatuses 3A to 3C are put into a state where radiographing is possible by receiving the irradiation start allowance signal from the radiographing apparatuses 3A to 3C. Therefore, the addition apparatus 6A may be configured to release an interlock so as to be able to output the irradiation allowance signal for allowing irradiation of radiation to the radiation controller 11A when receiving the irradiation start allowance signal from all of the radiographing apparatuses 3A to 3C to be used for radiographing. This may be implemented as part of transition of state transition control as will be described later.

By employing a configuration where irradiation of radiation is allowed after the irradiation start allowance signal is received from all of the radiographing apparatuses 3A to 3C in this manner, it is possible to prevent the object under examination from being uselessly exposed to radiation due to radiation being radiated at a timing at which preparation of part of the radiographing apparatuses 3 to be used for radiographing is not completed or in a state where part of the radiographing apparatuses 3 cannot perform radiographing due to an error, or the like.

When the addition controller 61A receives the irradiation start allowance signal from all of the radiographing apparatuses 3A to 3C to be used for radiographing, the addition controller 61A judges that all of the radiographing apparatuses 3A to 3C to be used for radiographing are put into a state where radiographing is possible, releases an interlock so as to be able to output the irradiation allowance signal for allowing irradiation of radiation to the radiation controller 11A, and repeatedly inputs the irradiation allowance signal to the other input of the second AND circuit 67b of the I/F 67 at a timing linked with the timing at which the timing signal is transmitted to the radiographing apparatuses 3A to 3C.

At this time, because the irradiation instruction signal from the irradiation instruction switch 5 and the irradiation allowance signal from the addition controller 61A, which are to be input to the second AND circuit 67b of the I/F 67 are both put into an ON state, the second AND circuit 67b repeatedly transmits the irradiation instruction signal to the radiation controller 11A via the radiation control console 41 (step S28A). The addition controller 61A includes a timing generator for outputting the timing signal and the irradiation allowance signal at fixed intervals, and the addition controller 61A repeatedly continues output of the timing signal and the irradiation allowance signal in accordance with the timing generated by the timing generator.

Here, the timing signal and the irradiation allowance signal may be configured to be output to the radiographing apparatuses 3A to 3C at the same time, or may be configured to be respectively output in accordance with the radiographing timing of the radiographing apparatuses 3A to 3C and the radiation irradiation timing of the radiation control apparatus 1A.

In a case where the timing signal and the irradiation allowance signal are output to the radiographing apparatuses 3A to 3C at the same time, it is possible to reduce a risk that the timings may fluctuate due to an output delay upon output of signals. Further, it is also possible to branch the same signal output and use the branched signal output for the timing signal and the irradiation allowance signal.

Meanwhile, it is also possible to employ a configuration where the timing signal and the irradiation allowance signal are output at respective necessary timings while the radiographing timing on the radiographing apparatus 3 side and the radiation irradiation timing of the radiation control apparatus 1A are taken into account at the addition apparatus 6A. Because the addition apparatus 6A assumes use with various kinds of radiographing apparatuses 3A to 3C and the radiation control apparatus 1A in combination, and there is an apparatus which cannot adjust a timing for actually performing part of the radiographing sequence or irradiation of radiation after receiving the timing signal and the irradiation allowance signal, depending on the radiographing apparatuses 3A to 3C and the radiation control apparatus 1A to be combined. Therefore, by the addition apparatus 6A outputting the timing signal and the irradiation allowance signal while taking into account for the operation timing of the radiographing apparatuses 3A to 3C and the radiation control apparatus 1A, it is possible to perform radiographing while various kinds of radiographing apparatuses 3A to 3C and the radiation control apparatus 1A are combined. The addition apparatus may be configured to be able to individually adjust respective timings of signal output to match characteristics of these various kinds of radiographing apparatuses 3A to 3C and the radiation control apparatus 1A.

The last half of the operation in "D: Execution of radiographing" (step S29 to S32) and the first half of the operation in "E: End of radiographing" (step S33 to S39) are similar to those in the above-described first-A embodiment.

(E: End of Radiographing)

When the radiographer who confirms that radiographing is finished, releases the irradiation instruction switch 5 from the second stage (step S40), the irradiation instruction switch 5 puts the irradiation instruction signal into an OFF state (step S41A). Then, the radiographing apparatuses 3A to 3C also put the radiographing start signal into an OFF state.

Thereafter, when the radiographer releases the irradiation instruction switch 5 from the first stage (step S43), the irradiation instruction switch 5 puts the irradiation preparation signal into an OFF state (step S44A).

Processing from step S46 to S47 is similar to that in the above-described first-A embodiment.

A series of the radiographing operation is finished in this manner.

The system 200 according to the present embodiment operates as described above, and serial radiography in which a plurality of still images are repeatedly captured in a short period is thereby performed in a similar manner to the system 100 according to the first-A embodiment.

Note that [Modified example 1: Count the number of captured radiographs at radiographing apparatuses 3] to [Modified example 5: timing of starting coordination with synchronization source] described in the first-A embodiment can also be applied to the configuration of the first-B embodiment.

[Effects]

As described above, in the system 200 according to the present embodiment, by the addition controller 61A being connected to the radiation control apparatus 1A which can radiate radiation only once for a radiation irradiation instruction of one time in the conventional system 200A illustrated in FIG. 9, the radiation control apparatus 1A can output the irradiation signal a plurality of times for an irradiation instruction (putting the irradiation instruction switch 5 into the second stage) of one time. Therefore, it becomes possible to perform radiographing in which still images are captured a plurality of times in a short period of time, that is, serial radiography of capturing a plurality of radiographs, using a plurality of radiographing apparatuses 3.

Further, the conventional system 200A illustrated in FIG. 9 is widespread as the radiographing apparatus which captures a simple still image. Therefore, a medical institution which uses the conventional system 200A can easily convert the conventional system 200A including an existing radiation generation apparatus to a system which supports serial radiography only by adding the radiographing apparatuses 3A to 3C and the addition apparatus 6A without updating the expensive radiation generation apparatus.

Further, in the system 200, because radiographing is performed after it is confirmed at the console 4 that all of the radiographing apparatuses 3 (3A to 3C) to be used for radiographing are connected to the specific addition apparatus 6A which is the synchronization source, it is possible to minimize a risk that radiographing cannot be correctly performed at all the radiographing apparatuses 3 (3A to 3C) as a result of radiographing being performed in a state where part of the radiographing apparatuses 3 to be used for radiographing is connected to other synchronization sources, and radiographing being performed at a timing different from other radiographing apparatuses 3 to be used for radiographing. By this means, it is possible to minimize a risk that the object under examination is uselessly exposed to radiation as a result of radiographing failing.

<Sequence State Transition>

A sequence state transition operation of the systems 100 and 200 according to the above-described first-A and first-B embodiments will be described next with reference to FIG. 13 and FIG. 14.

[Assumption, Background, Problems]

The systems 100 and 200 according to the above-described first-A and first-B embodiments cannot correctly perform radiographing if each piece of connected equipment does not operate in correct order.

Further, even in a case where an error such as noise to a signal line and disconnection of a signal line, which is not intended by the radiographer occurs, it is necessary to prevent occurrence of unintended irradiation of radiation, or the like, by safely terminating radiographing.

[Operation]

First, operations of the systems 100 and 200 will be described. FIG. 13 is a state transition diagram of the systems 100 and 200, and FIG. 14 is a timing chart illustrating the operations of the systems 100 and 200.

Figure 13:
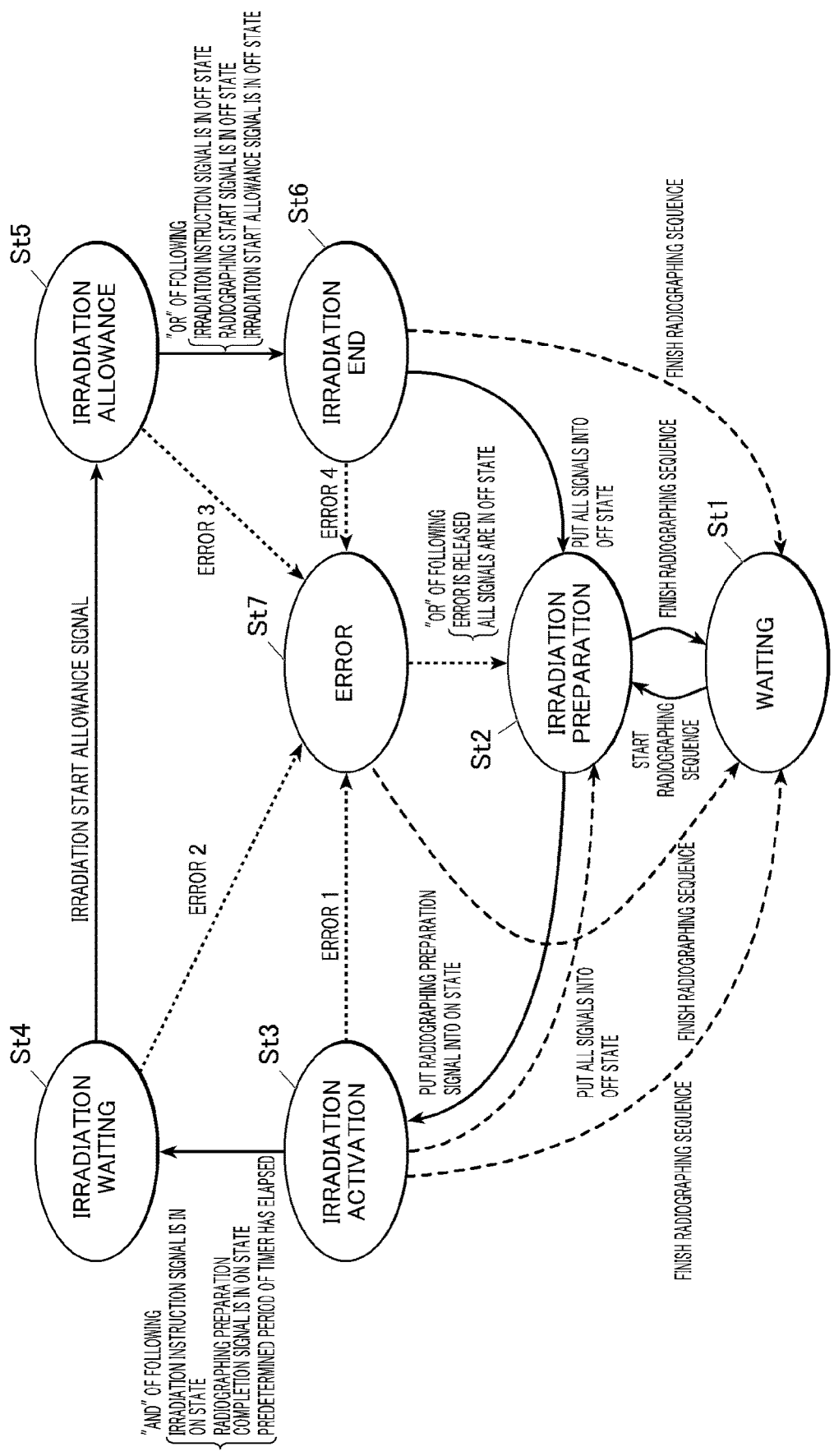
FIG. 13 is a state transition diagram for explaining transition of a state of the radiographic imaging system in FIG. 2 or FIG. 10.

As illustrated in FIG. 13, the systems 100 and 200 according to the present embodiment are first put into a waiting state St1 which is a state where a radiographing start instruction is not received from the radiographer.

Figure 14:
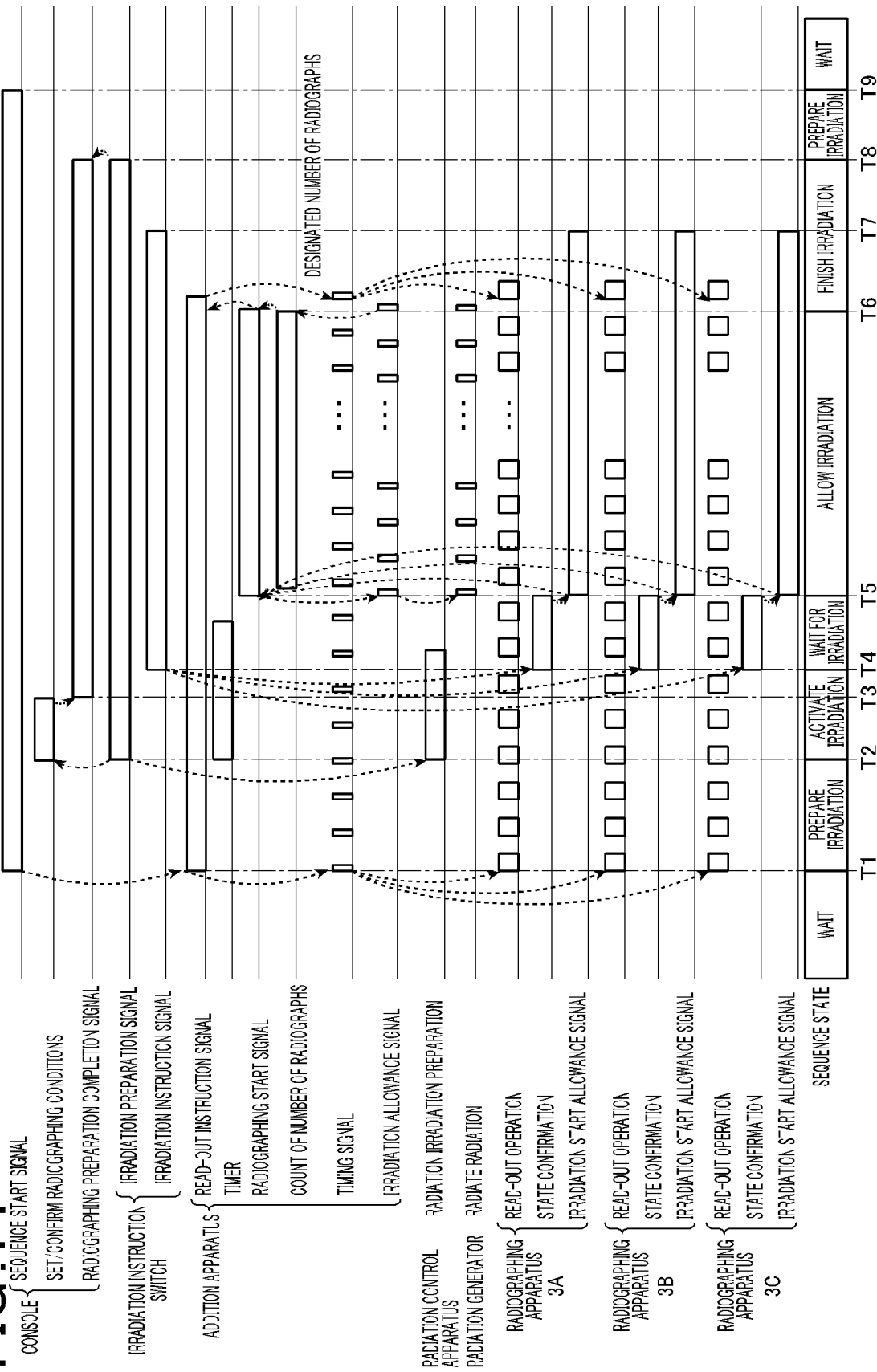
FIG. 14 is a timing chart illustrating the operation of the radiographic imaging system in FIG. 2 or FIG. 10.

Thereafter, when the console 4 receives a radiographing order from the host system 7S such as an RIS and an HIS, and the radiographer selects the radiographing order, as illustrated in FIG. 14, the console 4 puts the sequence start signal to be output to the radiographing apparatuses 3A to 3C and the addition apparatuses 6 and 6A into an ON state (T1).

Then, the radiographing apparatuses 3A to 3C and the addition apparatuses 6 and 6A start radiographing preparation. By this means, as illustrated in FIG. 13, states of the systems 100 and 200 transition to an irradiation preparation state St2.

As illustrated in FIG. 14, in the irradiation preparation state St2, the addition apparatuses 6 and 6A repeatedly transmit the timing signal to the radiographing apparatuses 3A to 3C at predetermined intervals, and the radiographing apparatuses 3A to 3C repeatedly perform the reset operation of removing electric charges accumulated in the radiographing apparatuses 3A to 3C by repeating the read-out operation every time the timing signal is received.

The read-out operation performed here is the same as the operation which is performed when the radiograph is acquired. However, because the image acquired by the reset operation is generated in the irradiation preparation state St2 during which radiation is not radiated, the image may be stored in the memories of the radiographing apparatuses 3A to 3C or may be transferred to the console 4, or may be deleted without being stored or transferred.

Meanwhile, because at least part of the image acquired through this reset operation exhibits characteristics of the individual pixels of the radiographing apparatuses 3A to 3C or characteristics of images of the radiographing apparatuses 3A to 3C, it is possible to store the image within the radiographing apparatuses 3A to 3C as, for example, the correction data (image for correction) for correcting the radiograph or transfer the image to the console 4.

At least one of a plurality of images acquired by the reset operation being repeated may be used as the correction data, or an average of signals values of the pixels corresponding to the plurality of images or an expected interpolated value in a time direction may be calculated and used as the correction data.

Examples of a method for correcting a radiograph can include a method in which signal values of the respective pixels of the correction data are respectively subtracted from the radiograph obtained by radiation being radiated.

Note that the timing signal may be configured to be able to be transmitted to the radiographing apparatuses 3A to 3C in a state other than the irradiation preparation state St2. Further, it is also possible to employ a configuration where, in a case where the state transitions to the irradiation preparation state St2, a reset operation instruction signal which instructs the radiographing apparatuses 3A to 3C to perform the reset operation is put into an ON state, and, in a case where an input indicating that the reset operation instruction signal is put into an ON state is received, the radiographing apparatuses 3A to 3C performs the reset operation.

The radiographer sets the radiographing conditions, or the like, using the radiographing apparatus control console 42 or the radiation control console 41, and starts the radiographing operation after positioning the object under examination.

Specifically, as illustrated in FIG. 14, the radiographer operates the irradiation instruction switch 5 and puts the irradiation preparation signal to be transmitted to the console 4 into an ON state (T2). Then, the states of the systems 100 and 200 transition to an irradiation activation state St3 as illustrated in FIG. 13.

In the irradiation activation state St3, the console 4 confirms states of the radiation control apparatuses 1 and 1A, the radiographing apparatuses 3A to 3C and the addition apparatuses 6 and 6A, and, in a case where it is judged that the states are states where radiographing is possible, as illustrated in FIG. 13, the console 4 puts the radiographing preparation completion signal to be transmitted to the addition apparatuses 6 and 6A into an ON state (T3).

Here, the console 4 may be configured to confirm whether the radiographing conditions set at the radiation control console 41 are the same as the radiographing conditions set at the radiographing apparatus control console 42. Further, it is also possible to employ a configuration where information indicating that the radiographing conditions are the same is displayed if the radiographing conditions set at the radiation control console 41 are the same as the radiographing conditions set at the radiographing apparatus control console 42. Alternatively, it is also possible to employ a configuration where information indicating that the radiographing conditions are different is displayed, if the radiographing conditions are different from each other.

Further, it is also possible to employ a configuration where control is performed so that the sequence cannot proceed to the subsequent radiographing sequence in a case where the radiographing conditions set at the radiation control console 41 are different from the radiographing conditions set at the radiographing apparatus control console 42.

Further, it is also possible to employ a configuration where control is performed so that, while the radiographing preparation completion signals is in an ON state, the radiographing conditions set at the radiographing apparatus control console 42 and the radiation control console 41 cannot be changed.

Meanwhile, when it is detected that the irradiation preparation signal is in an ON state, the radiation control apparatuses 1 and 1A start preparation for radiating radiation (T2). This is, for example, an operation which starts rotation of the rotating anode of the radiation generator 2, or the like.

Further, when it is detected that the irradiation preparation signal is put into an ON state, the addition apparatuses 6 and 6A start counting of the set timer (T2).

While described in detail later, by this means, it is possible to perform control so that the state cannot transition to an irradiation waiting state St4 which will be described later, until a predetermined waiting period counted by this timer has elapsed even if the radiographer puts the irradiation instruction switch 5 into the second stage (puts the irradiation instruction signal into an ON state).

Thereafter, the radiographer puts the irradiation instruction switch 5 into the second stage to put the irradiation instruction signal into an ON state (T4). While FIG. 14 illustrates a case where the irradiation instruction signal is put into an ON state after the radiographing preparation completion signal is put into an ON state, the irradiation instruction signal may be put into an ON state before the radiographing preparation completion signal is put into an ON state.

When the addition controllers 61 and 61A confirm that the irradiation instruction signal is put into an ON state, the radiographing preparation completion signal is put into an ON state, and a predetermined period counted by the timer has elapsed, the states of the systems 100 and 200 transition to the irradiation waiting state St4 as illustrated in FIG. 13.

In the irradiation waiting state St4, the addition controllers 61 and 61A confirm whether or not the radiographing apparatuses 3A to 3C are put into a state where radiographing is possible. The radiographing apparatuses 3A to 3C confirm whether or not the own apparatuses are in a state where radiographing is possible, and, in a case where the radiographing apparatuses 3A to 3C judge that the states are states where radiographing is possible, as illustrated in FIG. 14, transmit the irradiation start allowance signal to the addition controllers 61 and 61A (T5).

Confirmation as to whether or not radiographing is possible is judged by, for example, whether or not the predetermined reset operation is completed, and electric charges at the light receivers of the radiographing apparatuses 3A to 3C are removed, or whether or not the reset operation is completed in all the pixels on the light receiving surfaces (because the reset operation is performed while scanning is performed for each row on the respective pixels arranged on the light receiving surfaces in a matrix).

In a case where the addition controllers 61 and 61A detect that the irradiation start allowance signal from the radiographing apparatuses 3A to 3C is put into an ON state, states of the systems 100 and 200 transition to an irradiation allowance state St5 as illustrated in FIG. 13.

In the irradiation allowance state St5, the addition controllers 61 and 61A continue the output of the timing signal to the radiographing apparatuses 3A to 3C, and repeatedly transmit the irradiation allowance signal or the irradiation instruction signal to the radiation controllers 11 and 11A at a timing in accordance with the timing.

Further, as illustrated in FIG. 14, when the addition controllers 61 and 61A put the radiographing start signal which is an interlock inside into an ON state (T5), it becomes possible to output the irradiation allowance signal or the irradiation instruction signal to the radiation generation apparatus at a timing in accordance with the output of the timing signal. The radiation generation apparatus (the radiation controllers 11 and 11A, the high-voltage generator 12, and the radiation generator 2) generate radiation every time the irradiation allowance signal or the irradiation instruction signal is received, so that the radiation which penetrates through the object under examination can be repeatedly incident on the radiographing apparatuses 3A to 3C.

In the irradiation allowance state St5, the addition controllers 61 and 61A can be configured to perform control so as to count the number of captured radiographs every time the timing signal or the irradiation allowance signal is transmitted after the irradiation start allowance signal is put into an ON state. In this case, in a case where the counted number of captured radiographs reaches the set maximum number of radiographs to be captured, the radiographing start signal is put into an OFF state (T6), and the states of the systems 100 and 200 transition to an irradiation end state St6 as illustrated in FIG. 13.

Note that, in a case where the number of captured radiographs is counted by counting the irradiation allowance signals, because it is necessary to read out a radiograph by the last irradiation of radiation, it is also possible to employ a configuration where a timing for putting a read-out instruction signal into an OFF state is delayed, and a timing signal corresponding to one frame, which becomes a trigger of the read-out operation is further transmitted. With such a configuration, it is possible to exclude a risk that the object under examination is unnecessarily exposed to radiation as a result of radiographing being continued until the number of captured radiographs becomes equal to or larger than the set maximum number of radiographs to be captured, and the object under examination being unnecessarily irradiated with radiation.

Thereafter, when the radiographer releases the irradiation instruction switch 5 from the second stage, as illustrated in FIG. 14, the irradiation instruction signal is put into an OFF state (T7).

Thereafter, when the radiographer releases the irradiation instruction switch 5 from the first stage, the irradiation preparation signal is put into an OFF state (T8).

Then, when the addition controllers 61 and 61A confirm that all signals to be input to the addition controllers 61 and 61A are released, the states of the systems 100 and 200 transition to the irradiation preparation state St2 as illustrated in FIG. 13.

Here, "all signals" can be the irradiation preparation signal, the irradiation instruction signals, the radiographing start signal which is an interlock of the addition controllers 61 and 61A, and the irradiation start allowance signal of the radiographing apparatuses 3A to 3C.

Thereafter, in a case where the radiographer further performs radiographing, or, as a result of confirming the radiographs, judges that the acquired radiographs are not sufficient for desired purpose and it is necessary to perform radiographing again, radiographing is performed again through the above-described flow while a state of the object under examination and the radiographing conditions are changed.

Meanwhile, in a case where it is judged that it is not necessary to perform radiographing, the console 4 puts the sequence start signal into an OFF state (T9), and finishes the radiographing sequence. Then, the states of the systems 100 and 200 transition to the waiting state St1 as illustrated in FIG. 13.

Note that it is also possible to employ a configuration where the state is caused to transition to the waiting state St1 in a case where there is no input from the radiographer for a fixed period in addition to the above-described case (where judgment is performed by the radiographer).

[Operation in Case where Radiographing is not Continued]

Note that, while the above-described flow of state transition is performed in a case where radiographing is continued until the number of radiographs reaches the maximum number of radiographs to be captured, there is also a case where radiographing cannot be continued until the number of radiographs reaches the maximum number of radiographs to be captured depending on various situations.

For example, in a case where the radiographer desires to interrupt radiographing before the number of radiographs reaches the maximum number of radiographs to be captured, the radiographer releases the irradiation instruction switch 5 from the second stage to put the irradiation instruction signal into an OFF state. Then, the states of the systems 100 and 200 transition from the irradiation allowance state St5 to the irradiation end state St6. This transition occurs by one of a plurality of OR conditions for making the state transition from the irradiation allowance state St5 to the irradiation end state St6 (the irradiation instruction signal from the irradiation instruction switch 5 is put into an OFF state, the irradiation start allowance signal from the radiographing apparatuses 3A to 3C is put into an OFF state, and the radiographing start signal of the addition apparatuses 6 and 6A is put into an OFF state) being satisfied.

In the irradiation end state St6, irradiation of radiation is stopped, and, thereafter, in a similar manner to a case where radiographing is performed until the number of radiographs reaches the maximum number of radiographs to be captured, processing of transferring the remaining radiographs within the radiographing apparatuses 3A to 3C to the console 4, processing of deleting the radiographs stored within the radiographing apparatuses 3A to 3C after transferring, or the like, are performed. This is performed to, even in a case where radiographing is not performed until the number of radiographs reaches the number of radiographs to be captured designated in advance, there is a case where the radiographs can be utilized, in such a case, enable the radiographer to confirm the radiographs in a similar manner to normal radiographs.

Meanwhile, it is necessary to manage a fact that radiographing is not performed until the number of radiographs reaches the number of radiographs to be captured designated in advance, in association with the radiographs, and it is also possible to employ a configuration where a fact that radiographing is not performed until the number of radiographs reaches the number of radiographs to be captured designated in advance is noted and managed for individual radiographs or collection of the radiographs in a case where radiographing is not performed until the number of radiographs reaches the number of radiographs to be captured designated in advance.

Further, in a case where radiographing is not performed until the number of radiographs reaches the number of radiographs to be captured designated in advance, the console 4 may be configured to display that radiographing is not performed until the number of radiographs reaches the number of radiographs to be captured designated in advance through transmission of an error signal, or the like, from the addition apparatuses 6 and 6A.

[Operation Upon Occurrence of Error]

Further, there is also a case where the addition apparatuses 6 and 6A are disconnected with the radiographing apparatuses 3A to 3C during radiographing. Possible causes can be, for example, in a case where the addition apparatuses 6 and 6A are connected to the radiographing apparatuses 3A to 3C in a wired manner, removal of a cable from a connector, and, in a case where the addition apparatuses 6 and 6A are connected to the radiographing apparatuses 3A to 3C in a wireless manner, wireless crosstalk, a failure of wireless equipment, disconnection of power to wireless equipment, or the like.

Therefore, it is also possible to provide a function of monitoring whether or not an error (an error 1, an error 2, an error 3, and an error 4) occurs in respective sequence states St3 to St6 at the systems 100 and 200, and, in a case where an error is detected, cause the state to transition to an error state St7 as indicated with a dashed line in FIG. 13.

Further, it is also possible to employ a configuration where, in a case where the state transitions to the error state St7, what kind of error causes the state to transition to the error state St7 is displayed at the display 43, or the like, of the console 4.

It is also possible to employ a configuration where, in such detection of an error, for example, an error monitoring sequence for monitoring a signal in each state is performed in parallel, separately from the radiographing sequence illustrated in FIG. 13, and, in a case where an error is detected in the error monitoring sequence, a state of the radiographing sequence is caused to transition from current sequence states St3 to St6 to the error state St7.

Such monitoring of an error state can be realized by, for example, detection being continued at appropriate intervals in states of the respective states St1 to St6, and judgment being performed as to whether the states of the systems 100 and 200 are different from states which should be in the respective states St1 to St6.

For example, while FIG. 13 illustrates that, in the systems 100 and 200, in the irradiation waiting state St4, the irradiation instruction signals is required to be in an ON state, and the irradiation preparation completion signal is required to be in an ON state, and a predetermined period counted by the timer is required to elapse, in the irradiation waiting state St4, conditions other than these conditions are required to be satisfied. For example, to perform radiographing, the radiographing apparatuses 3A to 3C are required to be connected to the addition apparatuses 6 and 6A, and the radiographing apparatuses 3A to 3C are required to be powered ON.

Therefore, in monitoring of an error state, also concerning states other than these states illustrated in FIG. 13, for example, by continuously monitoring that a communication connection state signal which makes a notification that the radiographing apparatuses 3A to 3C are communicatively connected is in an ON state, that a power supply state signal which makes a notification that the radiographing apparatuses 3A to 3C are powered ON is in an ON state, and by judging whether the states are different from the states which should be in the state St1 to St6, in a case where these states become states where radiographing cannot be continued due to an unintended operation, noise, or the like, it is possible to perform processing to be performed in a case where an error occurs in the errors 1 to 4 illustrated in FIG. 13.

Alternatively, it is also possible to respectively set operation possible periods in the respective sequence states St3 to St6 illustrated in FIG. 13, and measure an operation period in each sequence state by starting timing by the timer when the state transitions to each of the sequence states St3 to St6, and perform control so that the state transitions to the error state St7 in a case where the period counted by the timer indicates that the operation possible period in that sequence state has elapsed.

Further, it is also possible to employ a configuration where, in a case where an error occurs, the addition apparatuses 6 and 6A or the radiographing apparatuses 3A to 3C which detect an error notify the console 4 of the error, and a fact that the error occurs is displayed at the console 4.

After the state transitions to the error state St7, the state is caused to transition to the irradiation preparation state St2 or the waiting state St1 by being triggered by specific conditions being satisfied (such as elimination of an error and release of all signals).

[Effects]

By using such an error detection scheme, by reliably detecting a failure of an apparatus or an operation, causing the state to transition to an error state, and returning the state to the waiting state St1 or the irradiation preparation state St2 as necessary from the middle of the radiographing sequence, it is possible to exclude a risk that the object under examination is uselessly exposed to radiation due to radiation being radiated in a state where there is a failure in an apparatus or an operation.

[Configuration Examples of Systems 100 and 200]

Specific system configuration examples when the above-described systems 100 and 200 are implemented will be described next with reference to FIG. 15 to FIG. 18. FIG. 15 to FIG. 18 illustrate simplified components illustrated in FIG. 2 and FIG. 10, and illustrates added components in a case where there are added components. Further, a connection line (a solid line, a dashed-dotted line) which connects respective apparatuses indicate wired connection, and, unless otherwise described, includes various kinds of signal lines (such as, for example, the irradiation allowance signal and the irradiation signal), a timing signal line and an information signal line illustrated in FIG. 2 and FIG. 10. Further, while FIG. 15 to FIG. 18 illustrate a system configuration example of the system 100, a system configuration example of the system 200 is a configuration in which the radiation control apparatus 1 is replaced with the radiation control apparatus 1A, the addition apparatus 6 is replaced with the addition apparatus 6A, and the irradiation instruction switch 5 is provided at the addition apparatus 6A.

System Configuration Example 1

Figure 15:
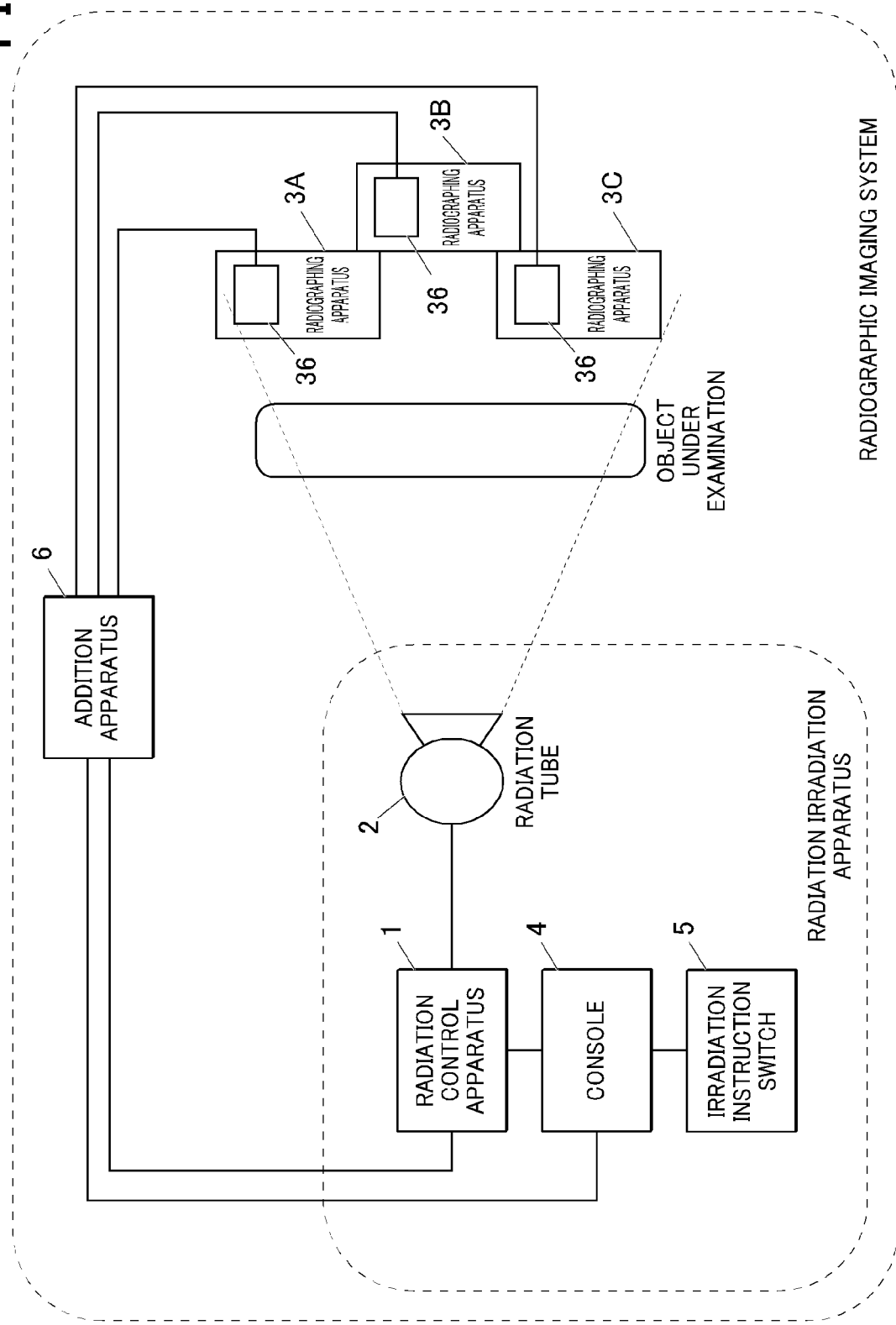
FIG. 15 is a block diagram illustrating a specific system configuration example of the radiographic imaging system in FIG. 2 or FIG. 10.

A system configuration example 1 illustrated in FIG. 15 is a basic configuration when the above-described systems 100 and 200 are implemented, and each of the radiation control apparatus 1 (1A) and the radiographing apparatuses 3A to 3C is connected to the specific addition apparatus 6 (6A) which is the synchronization source which generates the timing signal at predetermined intervals, in a wired manner (with a leased line). The addition apparatus 6 (6A) outputs the generated timing signal to the radiographing apparatuses 3A to 3C, and the radiographing apparatuses 3A to 3C perform accumulation in coordination with the input timing signal. Further, the addition apparatus 6 (6A) outputs the irradiation allowance signal to the radiation control apparatus 1 (1A) in coordination with the generated timing signal to cause the radiation control apparatus 1 (1A) to radiate radiation.

Note that, for example, in a case where a timing signal source for repeating irradiation of radiation at predetermined intervals is provided at the radiation control apparatus 1 (1A) as in the radiation control apparatus 1 (1A) for fluorography, the timing signal may be transmitted from the radiation control apparatus 1 (1A) to the addition apparatus 6 (6A), and the received timing signal may be copied at the addition apparatus 6 (6A), and transmitted to the radiographing apparatuses 3A to 3C.

System Configuration Example 2

Figure 16:
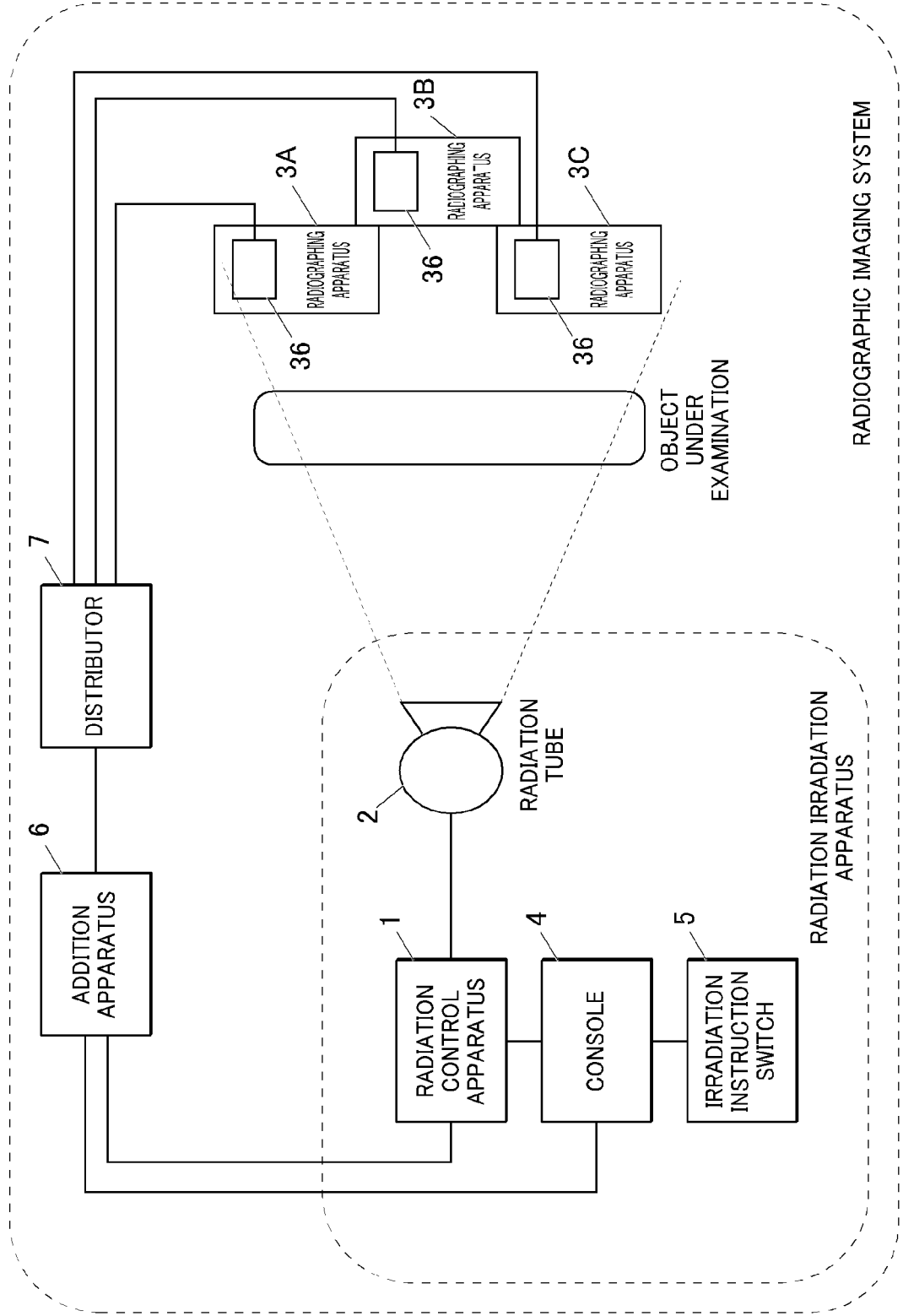
FIG. 16 is a block diagram illustrating a specific system configuration example of the radiographic imaging system in FIG. 2 or FIG. 10.

A system configuration example 2 illustrated in FIG. 16 is a configuration in which a distributor 7 is provided between the addition apparatus 6 (6A) and the radiographing apparatuses 3A to 3C in the system configuration example 1 in FIG. 15, signals (the timing signal and the information signal) from the addition apparatus 6 (6A) are distributed to the radiographing apparatuses 3A to 3C at the distributor 7, and input to the radiographing apparatuses 3A to 3C.

The distributor 7 is configured to judge with which of the radiographing apparatuses 3A to 3C, the addition apparatus 6 (6A) is to communicate each piece of communication information between the addition apparatus 6 (6A) and the radiographing apparatuses 3A to 3C, and perform communication while switching communication.

This can be realized by, for example, dividing the communication information into packets, attaching a tag for enabling identification as to which of the radiographing apparatuses 3A to 3C, information is to be communicated, for each packet, and performing switching in accordance with this tag. As such a function, for example, a communication control approach such as a switching hub may be used.

Further, the distributor 7 can be configured to distribute and communicate the timing signal from the addition apparatus 6 (6A) to the radiographing apparatuses 3A to 3C. It is also possible to employ a configuration where, for example, a pulsed signal indicating a timing is distributed so as to achieve connection to the radiographing apparatuses 3A to 3C. Upon distribution, noise may be removed from a signal, or the signal may be amplified, as necessary.

By employing the configuration illustrated in FIG. 16, it becomes possible to control the radiographing timing of a plurality of radiographing apparatuses 3A to 3C at one addition apparatus 6 (6A), so that it becomes possible to perform radiographing in which still images are repeatedly captured a plurality of times in a short period, that is, serial radiography for capturing a plurality of radiographs, using a plurality of radiographing apparatuses 3.

System Configuration Example 3

Figure 17A:
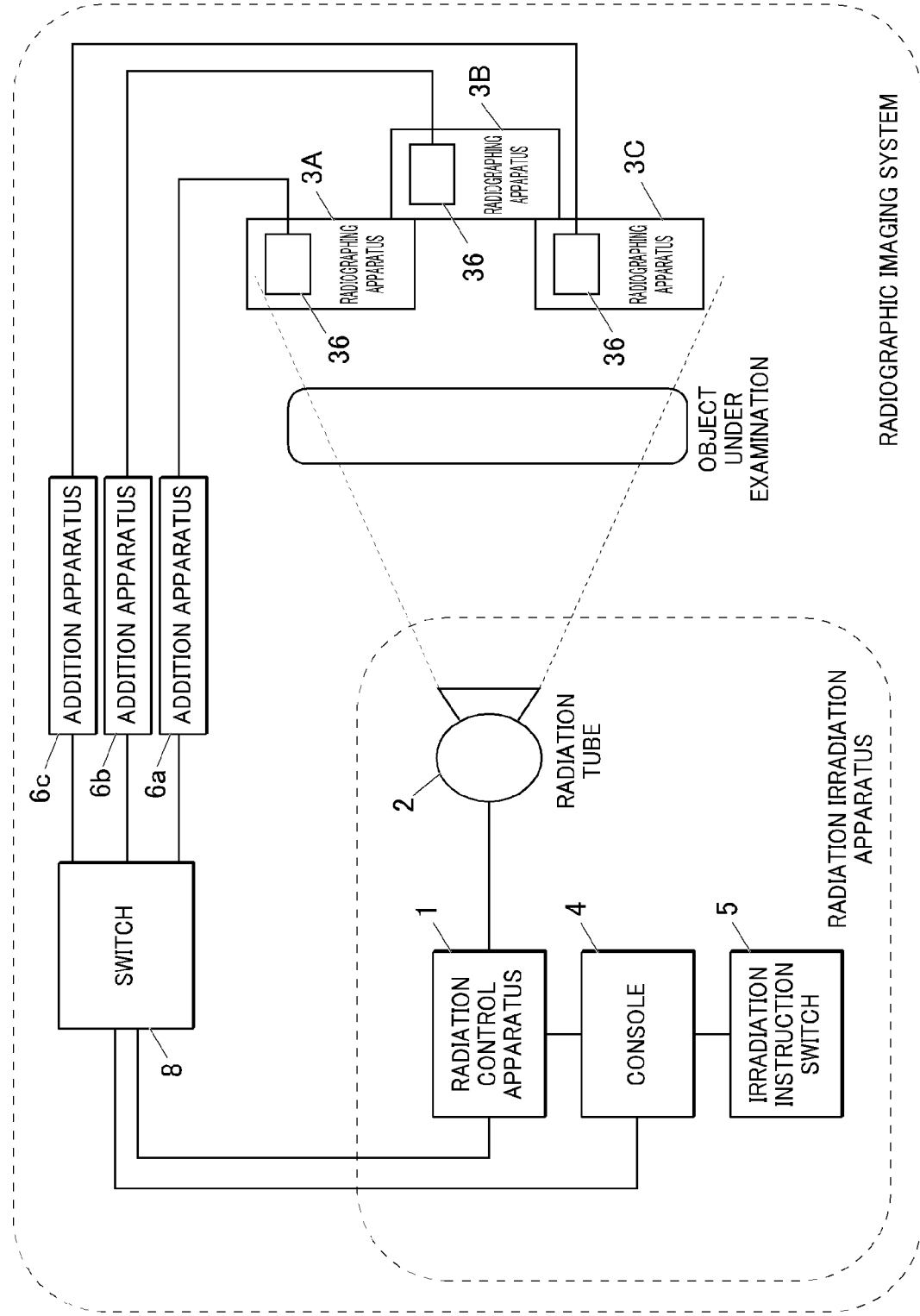
FIG. 17A is a block diagram illustrating a specific system configuration example of the radiographic imaging system in FIG. 2 or FIG. 10.

In the system configuration example 3 illustrated in FIG. 17A, the addition apparatuses 6a to 6c which are respectively connected to the radiographing apparatuses 3A to 3C in a wired manner are provided. The addition apparatuses 6a to 6c constitute the above-described addition apparatus 6 or 6A. Further, the radiation control apparatus 1 and the console 4 are connected to the addition apparatuses 6a to 6c via a switch 8 such as a hub.

In the system configuration example 3, the switch 8 has a function of generating a timing signal, and the addition apparatuses 6a to 6c copy the timing signal generated by the switch 8 and output the timing signal to the radiographing apparatuses 3A to 3C. Further, the switch 8 outputs the irradiation allowance signal to the radiation control apparatus 1 in coordination with the timing signal. The radiation control apparatus 1 causes the radiation generator 2 to radiate radiation at a timing in accordance with the irradiation allowance signal.

Alternatively, in the system configuration example 3, one of the plurality of addition apparatuses 6a to 6c may be configured to output the timing signal and the irradiation allowance signals in coordination with the timing signal.

The timing signal may be configured to be input from the above-described one of the addition apparatuses 6a to 6c which outputs the timing signal to the other addition apparatuses 6a to 6c via the switch 8 or through a wiring which is not illustrated, and input from the respective addition apparatuses 6a to 6c to the radiographing apparatuses 3A to 3C. Alternatively, the timing signal may be configured to be input to the radiographing apparatuses 3A to 3C from the above-described one of the addition apparatuses 6a to 6c which outputs the timing signal, by way of a distributor which is not illustrated.

The irradiation allowance signal may be configured to be input to the radiation control apparatuses 1 and 1A via the switch 8 or through a wiring which is not illustrated without involving the switch 8.

Here, control may be performed so that output of the radiographing preparation signal from the addition apparatuses 6 and 6A to external equipment, output of the irradiation preparation signal and the irradiation instruction signal from the irradiation instruction switch 5, and output of the irradiation allowance signal to the radiation controller 11 (11A), described in the above-described first-A embodiment and first-B embodiment, are performed at one of the plurality of addition apparatuses 6a to 6c, and the other addition apparatuses do not perform an operation relating to these signals.

Alternatively, the irradiation preparation signal and the irradiation instruction signal from one irradiation instruction switch 5 may be branched and input to the plurality of addition apparatuses 6a to 6c, and the plurality of addition apparatuses 6a to 6c may perform an operation relating to these signals.

Further, the irradiation allowance signal output from the plurality of addition apparatuses 6a to 6c may be merged and input to the radiation controller 11 (11A). When the irradiation allowance signal output is merged, by using an AND circuit, or the like, of the irradiation allowance signal from the plurality of addition apparatuses 6a to 6c, it is also possible to employ a configuration where the irradiation allowance signal is input to the radiation controller 11 (11A) in a case where the irradiation allowance signal is output from all of the plurality of addition apparatuses 6a to 6c. With such a configuration, it is possible to realize a configuration where radiation is output only in a case where all the addition apparatuses 6a to 6c output the irradiation allowance signal, and it is possible to reliably prevent the object under examination from being uselessly exposed to radiation as a result of radiation being radiated in a state where the plurality of radiographing apparatuses 3A to 3C or the addition apparatuses 6a to 6c are in a state where radiographing is not possible.

In the system configuration example 3 illustrated in FIG. 17A, connection from the individual addition apparatuses 6a to 6c to the radiographing apparatuses 3A to 3C is the same between in a case of long-length radiography and in a case of single radiography. By preparing a plurality of configurations for single radiography, providing the switch 8 which generates a timing signal in a higher stage as the synchronization source, and the individual addition apparatuses 6a to 6c synchronizing with the timing signal generated by this switch 8, it is possible to easily extend the configuration for single radiography to a configuration for multiple radiography.

Alternatively, by one of the plurality of addition apparatuses 6a to 6c generating a timing signal and a radiographing allowance signal as the synchronization source, and the individual addition apparatuses 6a to 6c synchronizing with the timing signal, it is possible to easily extend the configuration for single radiography to the configuration for multiple radiography.

System Configuration Example 4

Figure 17B:
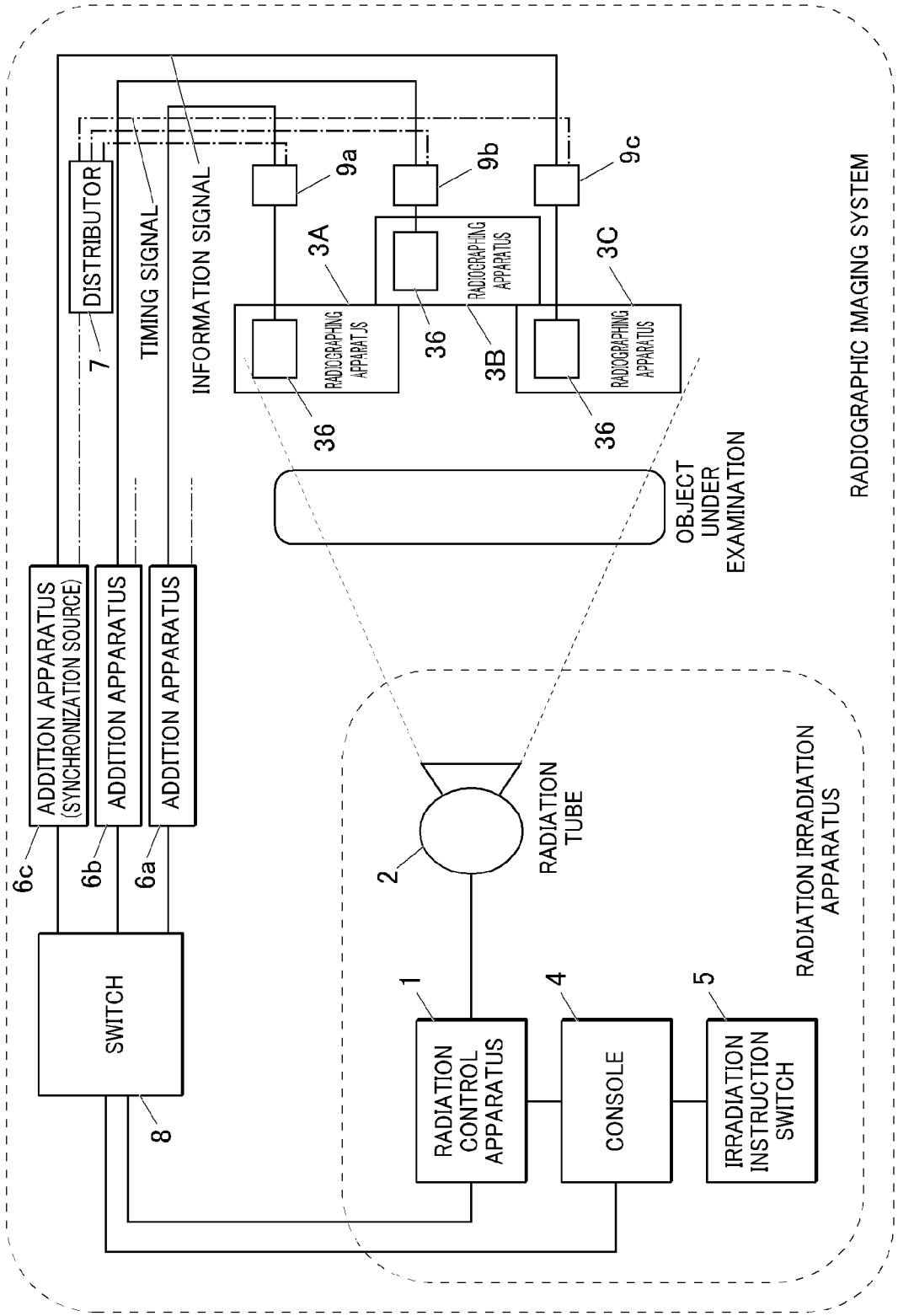
FIG. 17B is a block diagram illustrating a specific system configuration example of the radiographic imaging system in FIG. 2 or FIG. 10.

In the system configuration example 4 illustrated in FIG. 17B, the addition apparatuses 6a to 6c respectively corresponding to the radiographing apparatuses 3A to 3C are provided. The addition apparatuses 6a to 6c have a configuration of the above-described addition apparatus 6 or 6A. An information signal line and a timing signal line are out from each of the addition apparatuses 6a to 6c. The information signal lines from the addition apparatuses 6a to 6c are respectively connected to the radiographing apparatuses 3A to 3C. The timing signal line from one addition apparatus (here, the addition apparatus 6c) is distributed by the distributor 7, merged with the information signal lines at mergers 9a to 9c, and connected to the radiographing apparatuses 3A to 3C. In other words, while the radiographing apparatuses 3A to 3C perform accumulation and readout in coordination with the timing signal input from the addition apparatus 6c using the addition apparatus 6c as the synchronization source, the other information signals (including image data) are transmitted/received to/from the console 4 via the respectively corresponding addition apparatuses 6a to 6c or the addition apparatuses 6a to 6c. Further, the radiation control apparatus 1 and the console 4 are connected to the addition apparatus 6c via the switch 8 such as a hub, and the radiation control apparatus 1 causes the radiation generator 2 to radiate radiation at a timing in accordance with the irradiation allowance signal input in coordination with the timing signal from the addition apparatus 6c. Note that the mergers 9a to 9c do not have to be particularly provided.

Further, in a similar manner to the system configuration example 3 illustrated in FIG. 17A, control may be performed so that output of the radiographing preparation signal from the addition apparatuses 6 and 6A to external equipment, output of the irradiation preparation signal and the irradiation instruction signal from the irradiation instruction switch 5, and output of the irradiation allowance signal to the radiation controllers 11 and 11A, described in the above-described first-A embodiment and first-B embodiment, are performed at one of the plurality of addition apparatuses 6a to 6c, and the other addition apparatuses do not perform an operation relating to these signals.

Alternatively, the irradiation preparation signal and the irradiation instruction signal from one irradiation instruction switch 5 may be branched and input to the plurality of addition apparatuses 6a to 6c, and the plurality of addition apparatuses 6a to 6c may perform an operation relating to these signals.

Further, irradiation allowance signal output from the plurality of addition apparatuses 6a to 6c may be merged and input to the radiation controller 11 (11A). When the irradiation allowance signal output is merged, by using an AND circuit, or the like, of the irradiation allowance signal from the plurality of addition apparatuses 6A and 6, it is also possible to employ a configuration where the irradiation allowance signal is input to the radiation controller 11 (11A) in a case where the irradiation allowance signal is output from all of the plurality of addition apparatuses 6A and 6. With such a configuration, it is possible to realize a configuration where radiation is output only in a case where all the addition apparatuses 6a to 6c output the irradiation allowance signal, and it is possible to reliably prevent the object under examination from being uselessly exposed to radiation as a result of radiation being radiated in a state where the plurality of radiographing apparatuses 3A to 3C or the addition apparatuses 6a to 6c are in a state where radiographing is not possible.

Further, the irradiation allowance signal to be input from the addition apparatus 6c to the radiation control apparatus 1 may be configured to be input from the addition apparatus 6c to the radiation control apparatus 1 through a different wiring which is not illustrated without involving a hub, or the like. Because there is a case where the irradiation allowance signal is a contact signal or a pulsed signal, unlike with the information signal, there is a case where the irradiation allowance signal is required to be directly input from the addition apparatus 6c to the radiation control apparatus 1 without involving a hub, or the like. Meanwhile, there is a case where the information signal is a signal which can be communicated through a LAN, or the like, in which case, as illustrated in FIG. 17A, it is possible to connect the information signal to the radiation control apparatus 1 and the console 4 using a switch such as a hub.

In the system configuration example 4 illustrated in FIG. 17B, in a case where one radiograph is captured with one radiographing apparatus 3, or in a case where serial radiography is performed with one radiographing apparatus 3, it is possible to use the addition apparatus 6c. In a case where one radiograph is captured with one radiographing apparatus 3, only the information signal line is used, while, in a case where serial radiography is performed with one radiographing apparatus 3, it is possible to capture a plurality of radiographs at constant timings while achieving synchronization using both the information signal line and the timing signal line. In a case where one radiograph is captured with a plurality of radiographing apparatuses 3 (long-length radiography), or in a case where serial radiography in which a plurality of radiographs are captured with a plurality of radiographing apparatuses 3 is performed as described above (long-length serial radiography), it is possible to perform radiographing using the addition apparatuses 6a to 6c. In a case where one radiograph is captured with a plurality of radiographing apparatuses 3 (long-length radiography), only information signal lines of the respective addition apparatuses 6a to 6c are used. In a case where serial radiography in which a plurality of radiographs are captured with a plurality of radiographing apparatuses 3 is performed (long-length serial radiography), the information signal lines of the respective addition apparatuses 6a to 6c, and signals obtained by distributing the timing signal line of one addition apparatus 6c at the distributor 7, are used. In other words, in the system configuration example 4, it is possible to control still radiography with one radiographing apparatus 3, serial radiography using one radiographing apparatus 3, long-length radiography and long-length serial radiography, using the same addition apparatus 6c.

System Configuration Example 5

Figure 18:
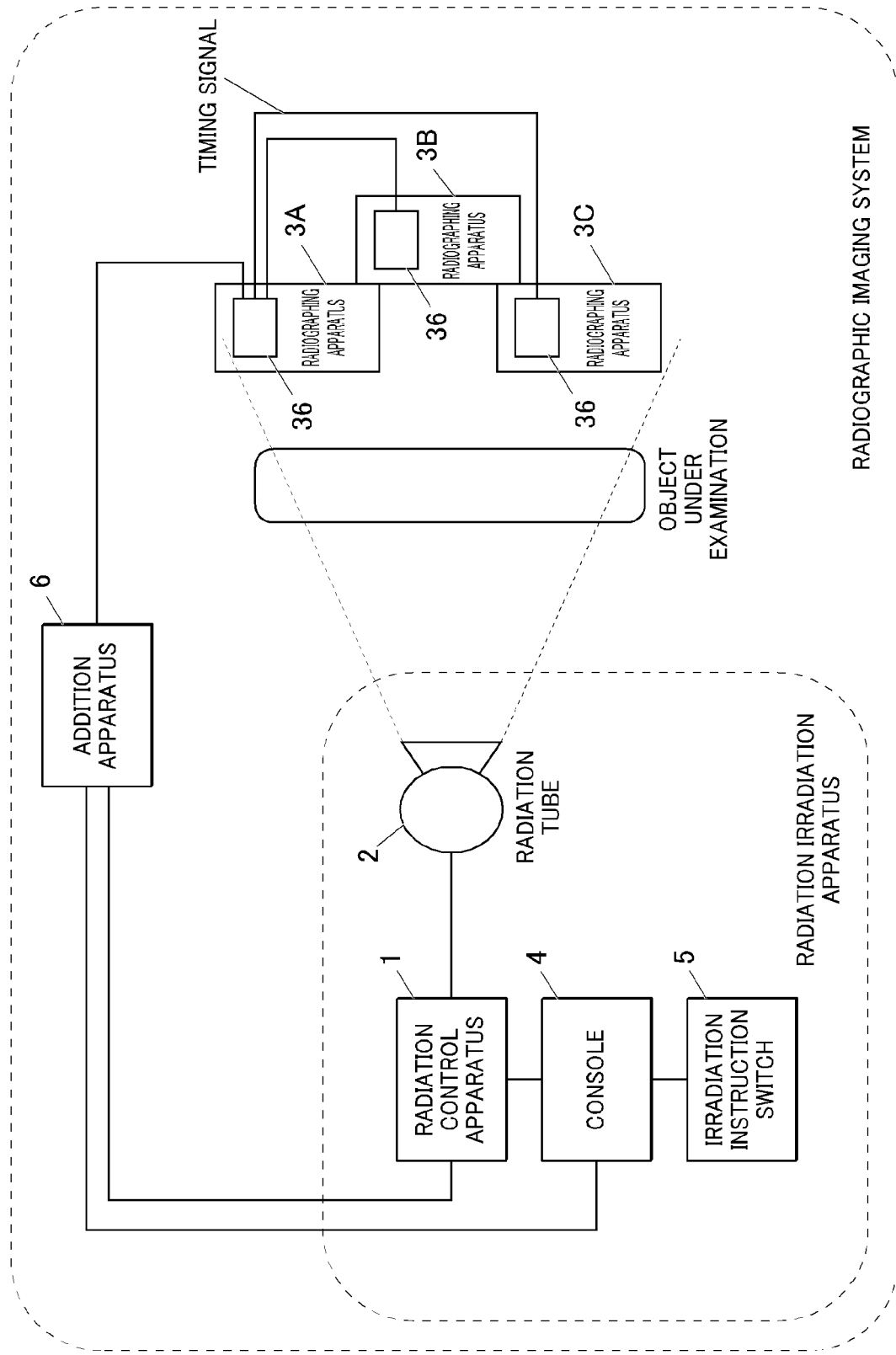
FIG. 18 is a block diagram illustrating a specific system configuration example of the radiographic imaging system in FIG. 2 or FIG. 10.

The system configuration example 5 illustrated in FIG. 18 is a configuration where the addition apparatus 6 (6A) is connected to the radiation control apparatus 1 (1A) and the console 4, and the addition apparatus 6 (6A) and the radiographing apparatuses 3B and 3C are respectively connected to the radiographing apparatus 3A. The radiographing apparatuses 3B and 3C are serially connected or cascade-connected to the radiographing apparatus 3A.

The timing signal transmitted from the addition apparatus 6 (6A) to the radiographing apparatuses 3A to 3C is input to the radiographing apparatus 3A which is a base unit, and the radiographing apparatus 3A outputs the input timing signal to the radiographing apparatuses 3B and 3C. Note that, for example, in a case where the radiation control apparatus 1 includes a timing signal source for repeating irradiation of radiation at predetermined intervals as in the radiation control apparatus 1 (1A) for fluorography, the timing signal may be transmitted from the radiation control apparatus 1 to the addition apparatus 6, and the received timing signal may be copied at the addition apparatus 6 (6A) and transmitted to the radiographing apparatuses 3A to 3C. Further, it is also possible to employ a configuration where the timing signal source is provided at the radiographing apparatus 3A, and the timing signal is output from the radiographing apparatus 3A to the addition apparatus 6 (6A), and the radiographing apparatuses 3B and 3C.

Here, information of state notifications, warm-up notification (S12), transmission of correction data (S13), notification of radiographing preparation completion (S14) and information signals for transmitting/receiving radiographs, indicated in FIG. 4, FIG. 5 and the above-described sequence description, may be configured to be output from the respective radiographing apparatuses 3A to 3C to the console 4 through the information signal lines, which are not illustrated in FIG. 18, connected to the respective radiographing apparatuses 3A to 3C.

Further, at that time, as illustrated in FIG. 15, the respective radiographing apparatuses 3A to 3C may be configured to be connected to the console 4 via the addition apparatus 6 through the information signal lines which are not illustrated in FIG. 18.

Alternatively, as illustrated in FIG. 16, the respective radiographing apparatuses 3A to 3C may be configured to be connected to the addition apparatus 6 via the information signal lines and the distributor 7 which are not illustrated in FIG. 18, and connected to the console 4 via the addition apparatus 6.

Alternatively, as illustrated in FIG. 17A, the respective radiographing apparatuses 3A to 3C may be configured to be connected to the addition apparatuses 6a to 6c which respectively correspond to the respective radiographing apparatuses 3A to 3C through the information signal lines which are not illustrated in FIG. 18. The addition apparatuses 6a to 6c may be directly connected to the console 4, or may be connected to the console 4 via the switch 8 as illustrated in FIG. 17A. Further, in this case, it is also possible to employ a configuration where the timing signal output from one of the addition apparatuses 6a to 6c is input to the radiographing apparatus 3A as a representative, and input to the other radiographing apparatuses 3B and 3C through serial connection or cascade connection as described above.

Second Embodiment

A second embodiment of the present invention will be described below.

[Configuration of System 300]

Figure 19:
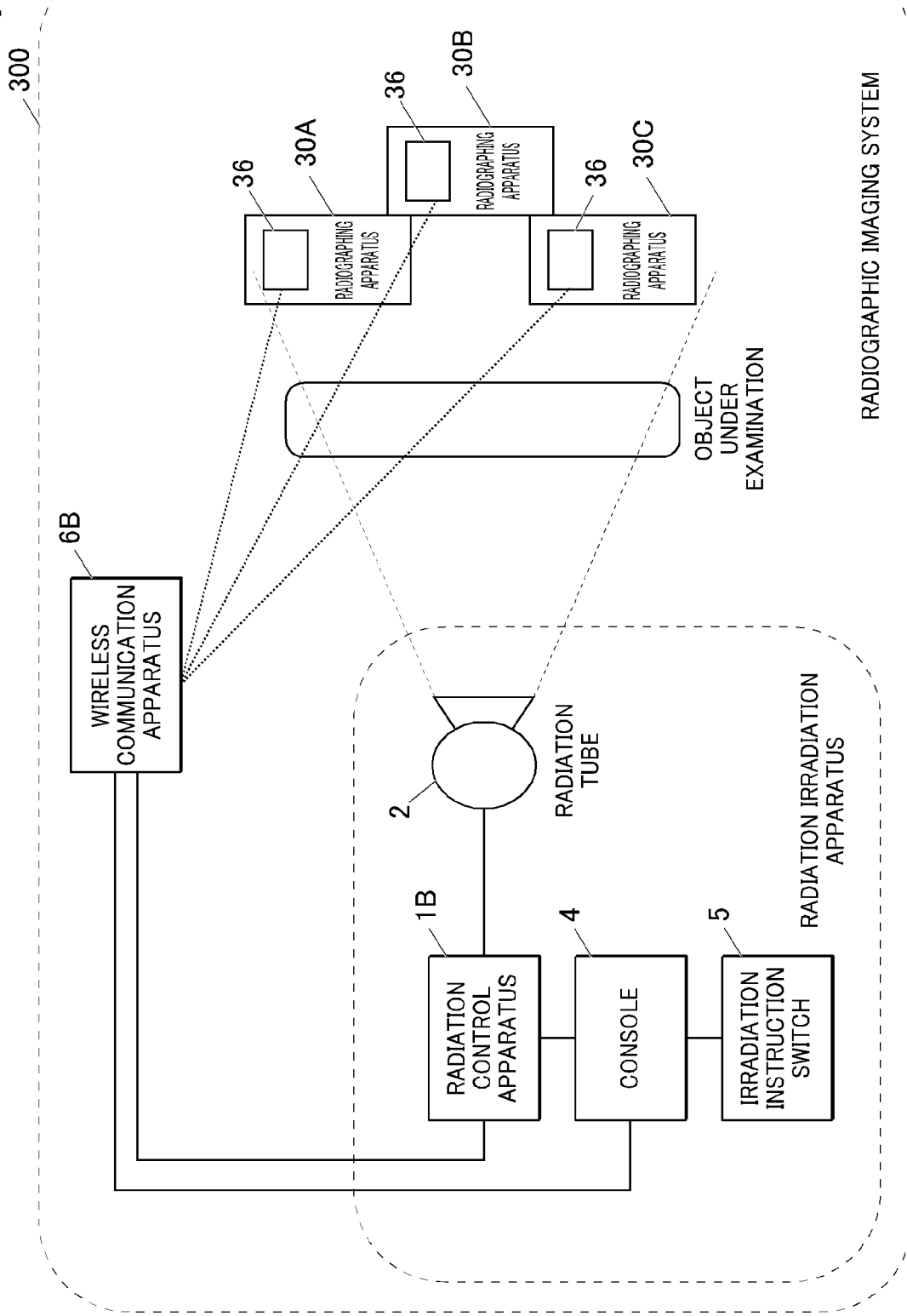
FIG. 19 is a block diagram illustrating a radiographic imaging system according to a second embodiment of the present invention.

Outline of a radiographic imaging system (hereinafter, a system 300) of the second embodiment according to the present invention will be described first. FIG. 19 is a block diagram illustrating a schematic configuration of the system 300. Note that similar reference numerals will be assigned to components which are equivalent to those in the first-A embodiment, and only different portions of the components will be described.

For example, as illustrated in FIG. 19, the system 300 of the present embodiment includes a radiation control apparatus 1B, the radiation generator 2, a radiographing apparatus 30 (30A to 30C), the console 4, the irradiation instruction switch 5, and a wireless communication apparatus 6B. The radiation control apparatus 1B is connected to the radiation generator 2, the radiation control apparatus 1B is connected to the console 4, the console 4 is connected to the irradiation instruction switch 5, the radiation control apparatus 1B is connected to the wireless communication apparatus 6B, and the console 4 is connected to the wireless communication apparatus 6B, respectively in a wired manner so as to be able to perform communication. Further, the wireless communication apparatus 6B is connected to the radiographing apparatus 30 (30A to 30C) in a wireless manner so as to be able to perform communication. Note that, in FIG. 19, connection lines connecting the respective apparatuses, indicated with solid lines indicate wired connection, and connection lines indicated with dotted lines indicate wireless connection.

Further, this system 300 can be connected to a radiography information system (RIS), a picture archiving and communication system (PACS), or the like, so as to be able to perform communication.

The system 300 is a system for performing long-length serial radiography using a plurality of radiographing apparatuses 30 in a similar manner to the first-A embodiment and the first-B embodiment. However, the system is different from the systems in the above-described embodiments in that the wireless communication apparatus 6B is used as the synchronization source for adjusting the radiographing timing of the radiographing apparatus 30 to be used for radiographing so as to match the radiation irradiation timing. Note that, while, in the following embodiment, a case will be described as an example where three radiographing apparatuses 30 are used to perform radiographing, the number of radiographing apparatuses to be used is not particularly limited. Further, description will be provided assuming that the radiographing apparatuses 30 to be used for radiographing are radiographing apparatuses 30A to 30C.

This system 300 can be used by being provided in, for example, a radiographing room, or the like, of a hospital, or can be used as a system which can move by a radiation irradiation apparatus including the radiation control apparatus 1B, the radiation generator 2, the console 4 and the irradiation instruction switch 5 being configured as a visiting car with wheels. If the system is configured to be able to move, it is possible to capture a radiograph by going off to an object under examination who has difficulty in movement.

For example, in a case where radiographing is performed using a radiographing platform provided in a radiographing room of a hospital, there is a case where it is necessary to perform radiographing in a state where the object under examination is positioned on a wheelchair or a bed, in which case, if radiographing is performed while wired cables are attached to the radiographing apparatuses 30A to 30C, there are the following problems:

cables get in the way there is a risk that communication becomes impossible as a result of cables being disconnected there is a sanitary problem because cables contact the object under examination, and there is a demand for radiographing without using wired cables.

In a case where radiographing is performed while the system is moved on the visiting car, radiographing is performed at a hospital ward where the object under examination stays. In this case, radiographing is performed at a bed where the object under examination is lying, and it is necessary to perform radiographing while placing the radiographing apparatuses 30A to 30C between the object under examination and the bed. Therefore, there are problems that cables get in the way, there is a risk that communication becomes impossible as a result of cables being disconnected, and there is a sanitary problem because cables contact the object under examination, more seriously than in the above-described case of the radiographing room, and there is a demand for radiographing without using wired cables.

In radiographing using CR before the radiographing apparatus 30 using an FPD, wired cables are not required upon radiographing, and thus, there is a demand for radiographing without using wired cables to achieve easiness so that operation becomes as easy as that in the CR.

However, by using the system 300 according to the present embodiment, it is possible to constitute a visiting car which satisfies such a demand.

[Configuration of Radiation Control Apparatus]

Figure 20:
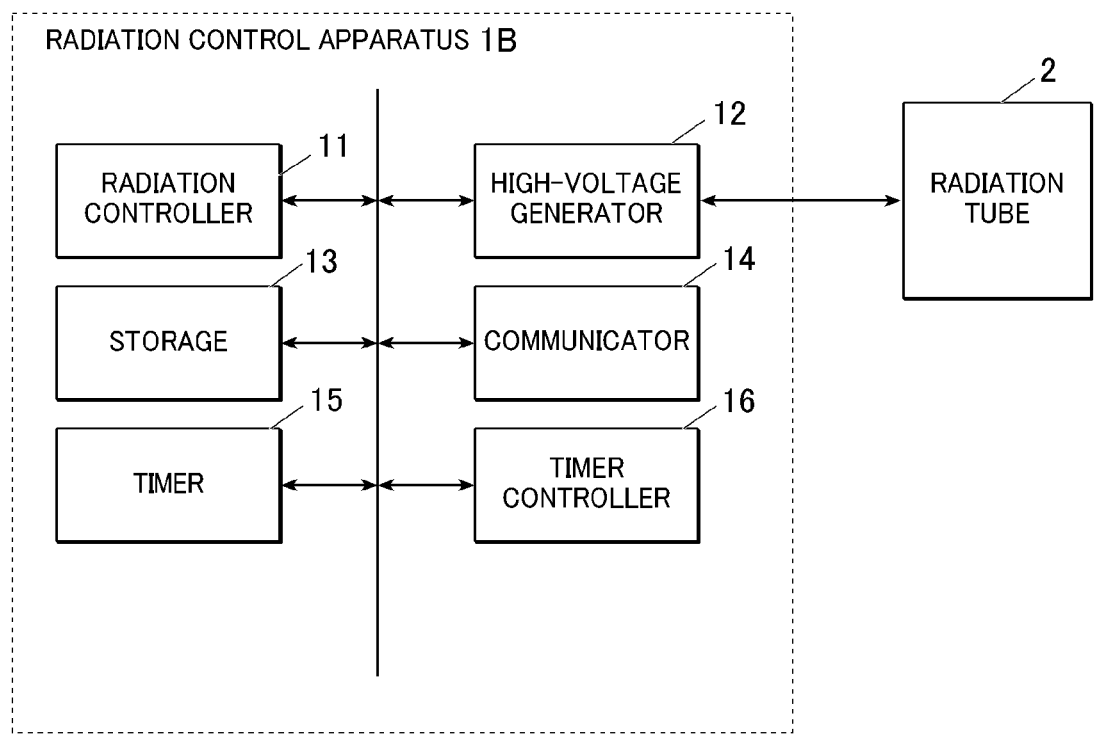
FIG. 20 is a block diagram illustrating a functional configuration of a radiation control apparatus in FIG. 19.

A configuration of the radiation control apparatus 1B in the present embodiment will be described next. FIG. 20 is a block diagram illustrating a functional configuration of the radiation control apparatus 1B. As illustrated in FIG. 20, the radiation control apparatus 1B according to the present embodiment includes a radiation controller 11B, the high-voltage generator 12, the storage 13, the communicator 14, the timer 15, the timer controller 16, or the like.

The radiation controller 11B is configured with a computer including a central processing unit (CPU), a read only memory (ROM) in which programs for causing the radiation controller 11 to operate are stored, a random access memory (RAM), an input/output interface, or the like, which are connected to a bus, an field programmable gate array (FPGA), or the like. Note that the radiation controller 11B may be configured with dedicated control circuits.

The radiation controller 11B is, for example, configured to transmit control information which instructs the high-voltage generator 12 to start application of a voltage (irradiation of radiation) based on a control signal from the console 4 and the radiographing apparatuses 30A to 30C. Further, the radiation controller 11B has a function on the radiation control apparatus 1B side relating to "determination as to whether or not the radiation controller 11B is connected to the specific wireless communication apparatus 6B" or "determination as to whether or not the radiation controller 11B coordinates with the specific wireless communication apparatus 6B", which will be described later.

The storage 13 is configured with static RAM (SRAM), a synchronous DRAM (SDRAM), a NAND flash memory, an hard disk drive (HDD), or the like.

The communicator 14 includes a connector for performing communication with external apparatuses, and controls communication with the external apparatuses. In a case where it is desired to achieve synchronization with other equipment using wired communication, the communicator 14 can achieve synchronization using, for example, protocol such as network time protocol (NTP), or a method specified in International Standards of IEEE Std. 1558-2008 (hereinafter, abbreviated as IEEE 1588).

The timer 15 is configured to start timing by being triggered by power-on, reception of a predetermined control signal from outside, or the like, and generate timer information.

Output from the timer 15 may be timing information such as a pulse at regular intervals or may be time information such as time such as year, month, date, hour, minute and second and the number of counts obtained by performing count-up from a certain time point. Note that the timer 15 may be provided outside the radiation control apparatus 1B instead of being incorporated into the radiation control apparatus 1B.

Further, in recent years, there has been a wireless LAN chip in which a timing synchronization function (TSF) specified in communication standards of IEEE 802.11 which will be described later, is mounted as standard, and which has a timer function. Therefore, it is also possible to utilize such a wireless LAN chip as the timer 15.

The timer controller 16 is connected to the communicator 14, and can acquire first timer information (time information or timing information) from the wireless communication apparatus 6B via the communicator 14. Further, the timer controller 16 is connected to the timer 15, and acquires second timer information from the timer 15. The second timer information is timer information of the timer 15 or the timer 38 at a time point at which the first timer information is received (acquired) from the specific wireless communication apparatus 6B (synchronization source). Then, the timer controller 16 corrects the timer information of the timer 15 based on the acquired first timer information and second timer information and causes the timer information of the timer 15 to coordinate with the timer information of a reference timer 602 of the wireless communication apparatus 6B.

Such a timer controller 16 may be configured to be implemented at individual semiconductors, substrates or apparatuses, or may be incorporated into part of functions of a general processor (including the radiation controller 11B) such as a CPU and an FPGA.

Further, it is possible to set setting information regarding transmission of timing information or time information of the wireless communication apparatus 6B in advance at the timer controller 16. In a case where the first timer information output from the wireless communication apparatus 6B is the timing information, and, for example, in a case where an interval at which the timing information (such as a pulse) is output from the wireless communication apparatus 6B is set at for each of x seconds, it is possible to set an interval at which the first timer information can be acquired from outside at x seconds. Meanwhile, in a case where the first timer information output from the wireless communication apparatus 6B is the time information, and, for example, in a case where an interval at which time information (such as time and the number of counts of the wireless communication apparatus 6B performing count-up from a certain time point) is output from the wireless communication apparatus 6B is set at for each of x seconds, it is possible to set an interval at which the first timer information can be acquired from outside at x seconds. Particularly, in a case where the time information is a count-up value at the wireless communication apparatus 6B, the timer controller 16 can acquire and set a count interval of the wireless communication apparatus 6B. For example, in a case where a count frequency of the wireless communication apparatus 6B is y Hz, it is possible to acquire and set a count interval of 1/y seconds.

Note that, in the present embodiment, an equipment configuration is employed where the radiation control apparatus 1B includes the high-voltage generator 12. With such a configuration, the user can deal with radiation without being conscious of the high-voltage generator 12. Therefore, for example, it is possible to deal with radiation with an equipment configuration where unintended failures, or the like, due to matching between equipment less occur. Meanwhile, it is also possible to employ a configuration where the radiation control apparatus 1B does not include the high-voltage generator 12, and the high-voltage generator 12 is independent of a body of the radiation control apparatus 1B. With such a configuration, the user can constitute equipment by selecting an arbitrary high-voltage generator 12 which is independent of the radiation control apparatus 1B, so that it is possible to improve a degree of freedom in selection of equipment.

[Configuration of Radiographing Apparatus]

Figure 21:
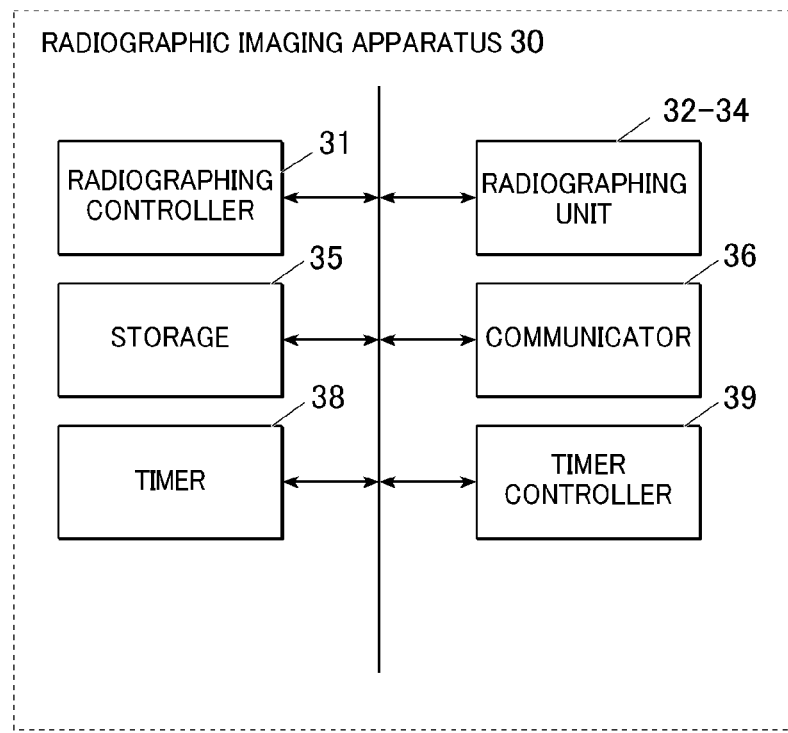
FIG. 21 is a block diagram illustrating a functional configuration of a radiographing apparatus in FIG. 19.

A configuration of the radiographing apparatuses 30A to 30C provided at the above-described system 300 will be described next. FIG. 21 is a block diagram illustrating a specific configuration of the radiographing apparatus 30

(30A to 30C). As illustrated in FIG. 21, the radiographing apparatuses 30A to 30C of the present embodiment include a radiographing controller 31, radiographing units 32 to 34, a storage 35, a communicator 36, a timer 38 and a timer controller 39. In FIG. 21, the radiation detector 32, the scanning driver 33 and the read-out unit 34 described in the first-A embodiment are collectively illustrated as the radiographing units 32 to 34. In other words, the radiographing apparatuses 30A to 30C in the present embodiment have a configuration where the timer 38 and the timer controller 39 are added to the configuration described using FIG. 3 in the first-A embodiment.

The timer 38 is configured to time by being triggered by power-on, reception of a predetermined control signal from outside, or the like, and generate the timer information.

Output from the timer 38 may be timing information such as a pulse at regular intervals or may be time information such as time such as year, month, date, hour, minute and second and the number of counts obtained by performing count-up from a certain time point. Note that the timer 38 may be provided outside the radiographing apparatus 30 instead of being incorporated into the radiographing apparatus 30. Further, in recent years, there has been a wireless LAN chip in which a timing synchronization function (TSF) specified in communication standards of IEEE 802.11 which will be described later, is mounted as standard, and which has a timer function. Therefore, it is also possible to utilize such a wireless LAN chip as the timer 38.

The timer controller 39 is connected to the communicator 36, and can acquire first timer information (time information or timing information) received from the wireless communication apparatus 6B via the communicator 36. Further, the timer controller 39 is connected to the timer 38, and acquires second timer information from the timer 38. Then, the timer controller 39 corrects the timer information of the timer 38 based on the acquired first timer information and second timer information and causes the timer information of the timer 38 to coordinate with the timer information of the reference timer 602 of the wireless communication apparatus 6B.

Further, such a timer controller 39 may be configured to be implemented at individual semiconductors, substrates or apparatuses, or may be incorporated into part of functions of a general processor (including the radiographing controller 31) such as a CPU and an FPGA.

Further, it is possible to set setting information regarding transmission of timing information or time information of the wireless communication apparatus 6B in advance at the timer controller 39 in a similar manner to the timer controller 16.

[Configuration of Wireless Communication Apparatus]

The wireless communication apparatus 6B is a base unit of the communication network, functions as an access point of wireless communication, and relays communication between the radiation control apparatus 1B and the radiographing apparatuses 30A to 30C, and communication between the console 4 and the radiographing apparatuses 30A to 30C.

Figure 22:
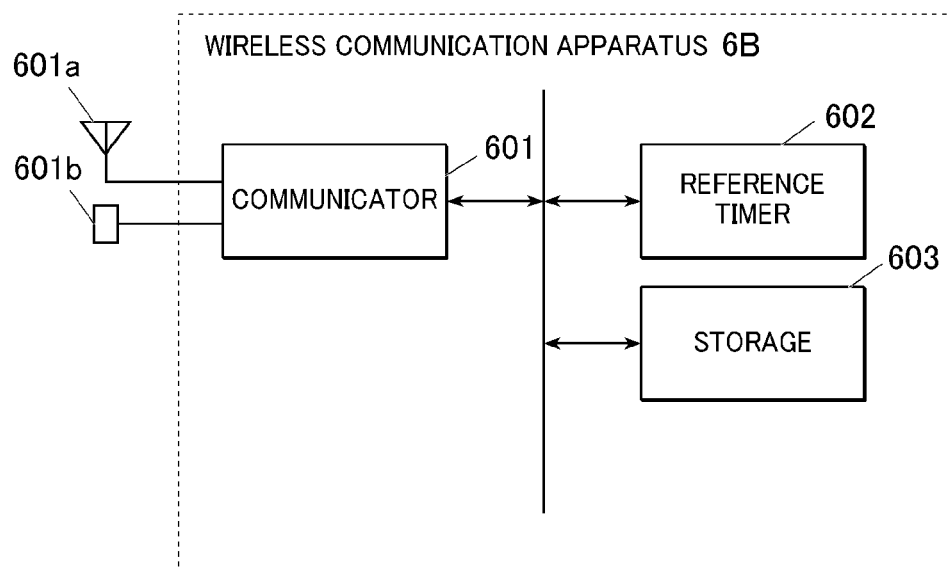
FIG. 22 is a block diagram illustrating a functional configuration of a wireless communication apparatus in FIG. 19.

FIG. 22 is a block diagram illustrating a functional configuration of the wireless communication apparatus 6B.

As illustrated in FIG. 22, the wireless communication apparatus 6B of the present embodiment includes a communicator 601, the reference timer 602, the storage 603, or the like.

The communicator 601 includes a wired communication interface and a wireless communication interface, and can perform transmission/reception of data to/from external equipment connected via a communication network such as a local area network (LAN), a wide area network (WAN) and the Internet. Further, the communicator 601 includes a connector 601b (to which a cable is to be inserted) for performing communication with the radiation control apparatus 1B in a wired manner, and an antenna 601a for performing transmission/reception of radio waves to/from the radiographing apparatuses 30A to 30C.

The reference timer 602 generates timer information which serves a reference in the radiographing operation of the system 300.

For example, the reference timer 602 is configured with a TSF timer, and generates time information to be used in a timing synchronization function (hereinafter, TSF) of communication standards of IEEE 802.11, as the timer information.

Here, the "TSF" is a function for adjusting time between an access point and equipment when equipment performs wireless communication with each other. Specifically, timer means (TSF timer) which periodically (for each 1 s) performs count-up through free-running is provided at the access point, and a beacon which is to be periodically (normally, for each 100 ms) transmitted and which includes time information upon transmission is transmitted to a terminal. Meanwhile, timer means which periodically (for each 1 s) performs count-up is also provided at the terminal, time information of a timer of the terminal is updated with the time information included in the beacon upon reception of the beacon, and count-up is continued. As a timing method, for example, counting is started from 0, and, when the time information reaches a predetermined maximum value, the count is reset to 0, and counting is repeated. The time information included in the beacon, that is, the time information of the TSF timer at a time point at which the beacon is transmitted becomes the first timer information.

Alternatively, the reference timer 602 may output other timer information different from that of the above-described TSF timer. For example, the reference timer 602 may output timing information such as a pulse at regular intervals, or may output time information such as time such as year, month, date, hour, minute and second and the number of counts obtained by performing count-up from a certain time point. Then, the timer information at a time point of transmission may be included as the first timer information, in the beacon, or the like, to be periodically (normally, for each 100 ms) transmitted by the communicator 601, and may be transmitted.

The storage 603 stores unique identification information (ID) which can uniquely identify the wireless communication apparatus 6B. Examples of the identification information can include, for example, a BSSID of the wireless communication apparatus 6B (an identifier, a MAC address of the wireless communication apparatus 6B), or the like.

Note that it is also possible to provide a unique ID to the wireless communication apparatus 6B in advance, and use the unique ID. The unique ID may be notified through radio waves (such as a beacon to be transmitted by the wireless communication apparatus 6B) or communication, or may be determined in advance in setting.

Further, in a case where an ESSID and an access key of the wireless communication apparatus 6B are unique, it is also possible to use combination of the ESSID and the access key of the wireless communication apparatus 6B as the identification information.

Whether or not the ESSID and the access key are unique can be judged by scanning surrounding wireless radio waves to confirm whether there is a wireless communication apparatus 6B.

By using combination of the ESSID and the access key, because it is possible to perform procedure of confirming the identification information through wireless connection, the procedure becomes simple.

Note that it is also possible to increase accuracy of uniqueness by specifying a wireless channel in advance, or the like.

The wireless communication apparatus 6B configured in this manner wirelessly transmits a beacon for each predetermined period (Td). The beacon includes the first timer information which is timer information of the reference timer 602 upon transmission of the beacon. Further, when the wireless communication apparatus 6B transmits the first timer information, the wireless communication apparatus 6B transmits the first timer information also to the radiation controller 11B connected in a wired manner.

Further, the wireless communication apparatus 6B can respectively transmit the identification information to the radiation control apparatus 1B and the radiographing apparatuses 30A to 30C. The identification information may be transmitted by being included in the beacon, or may be transmitted separately from the beacon.

[Radiographing Operation of System 300]

The radiographing operation in the system 300 is substantially similar to the sequence illustrated in FIG. 4 to FIG. 5 (FIG. 11 to FIG. 12) and the state transition illustrated in FIG. 13, input/output control of signals performed by the addition apparatus 6 (6A) is performed by, for example, the console 4, or the like. Further, a timing at which the radiation control apparatus 1B causes the radiation generator 2 to radiate radiation is determined based on the timer information of the timer 15. Further, timings for processing of accumulation and from read-out (transfer) to reset (initialization) at the radiographing apparatuses 30A to 30C are determined based on the timer information of the timer 38.

Figure 23:
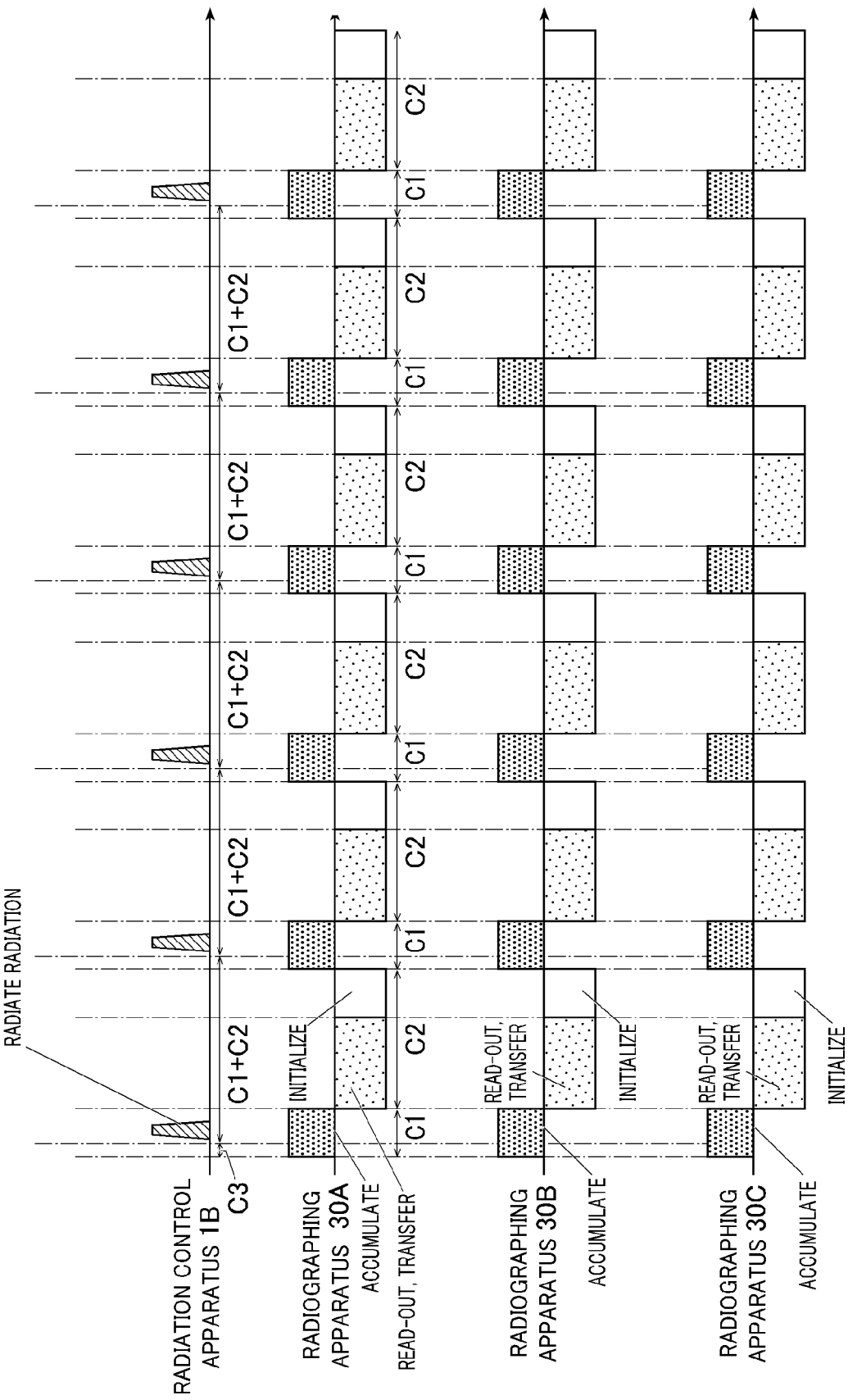
FIG. 23 is a view illustrating timings of a radiation irradiation operation and an accumulation operation of the radiographic imaging system in FIG. 19.

For example, when the radiographing controllers 31 of the radiographing apparatuses 30A to 30C receive the sequence start signal from the console 4, the radiographing controllers 31 repeat the read-out operation (including initialization) for each predetermined period from time (timing) of the timer 38 at that time point. When the irradiation instruction switch 5 is put into the second stage, and the radiographing start signal is received from the console 4, the radiographing apparatuses 30A to 30C put the irradiation start allowance signal into an ON state by being triggered by end of the read-out operation which is being performed by the own apparatuses at that time point and transmit the irradiation start allowance signal to the radiation control apparatus 1B, and, as illustrated in FIG. 23, the state transitions to the accumulation state, and the radiographing apparatuses 30A to 30C repeat accumulation for a predetermined period (C1) and read-out for a predetermined period (C2) alternately. When the radiation control apparatus 1B receives the irradiation start allowance signal, the radiation control apparatus 1B causes the radiation generator 2 to radiate radiation at intervals of a predetermined period (C1+C2) since a predetermined period (C3) has elapsed from time of the timer 15 at that time point (C1>C3). The accumulation and read-out operation, and irradiation of radiation are repeated the number of times corresponding to the number of radiographs to be captured.

[Gap of Timer]

Figure 24:
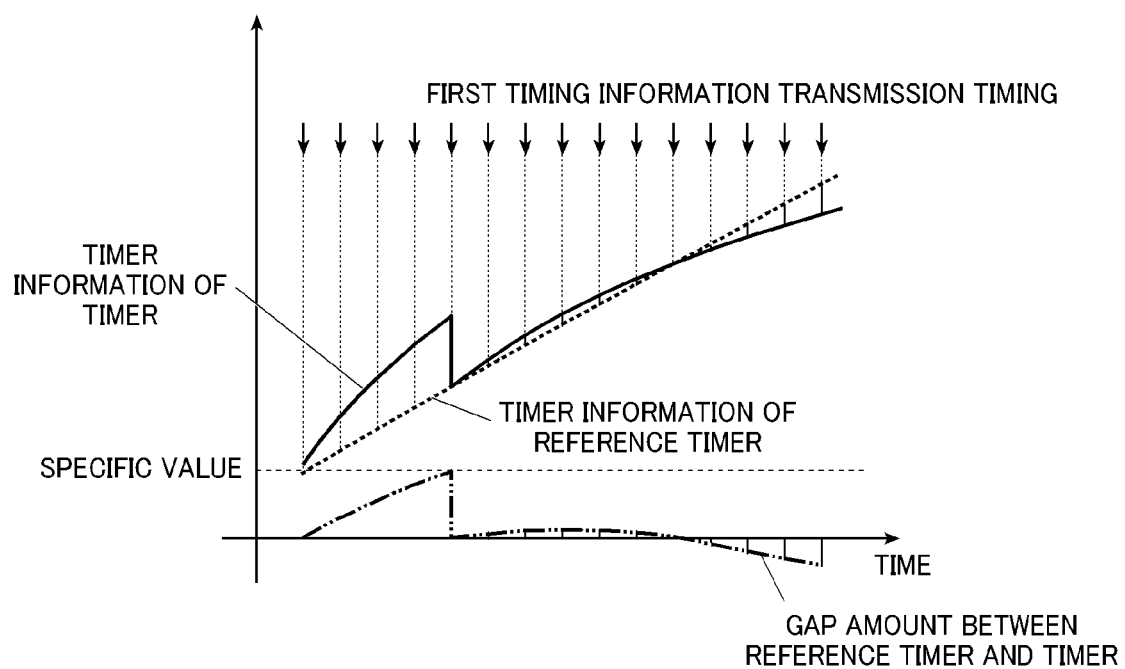
FIG. 24 is a view illustrating a gap between timer information of a reference timer of the wireless communication apparatus and timer information of a timer of the radiation control apparatus or the radiographing apparatus in the radiographic imaging system in FIG. 19.

While the system 300 is performing the operation as described above, there is a case where a slight difference occurs between timing speed of the reference timer 602 of the wireless communication apparatus 6B which is the synchronization source and timing speed of the timer 15 and the timers 38, for example, due to influence of an error, or the like, in frequencies of oscillators provided at the timer 15 of the radiation control apparatus 1B and the timers 38 of the radiographing apparatuses 30A to 30C. In such a case, if radiographing is performed for a relatively long period as in serial radiography, for example, as illustrated in FIG. 24, because a gap between the timer information of the reference timer 602 and the timer information of the respective timers 15 and 38 becomes gradually greater, and synchronization is lost, a difference occurs between the radiation irradiation timing of the radiation control apparatus 1B (radiation generator 2) and the radiographing timing of the radiographing apparatuses 30A to 30C.

Therefore, the system 300 of the present embodiment confirms and corrects a gap between the reference timer 602 which is the synchronization source and the respective timers 15 and 38 before such a gap between the radiation irradiation timing of the radiation control apparatus 1B and the radiographing timing of the radiographing apparatuses 30A to 30C becomes great to such a degree that diagnosis is affected.

A degree of a gap is confirmed based on comparison between the above-described first timer information and second timer information.

[Combination of Gap Confirmation Methods]

As described above, in the present embodiment, the first timer information generated by the wireless communication apparatus 6B may be the time information or the timing information, and also the second timer information acquired by the timer controller 16 or the timer controller 39 may be the time information or the timing information.

Therefore, comparison for confirming a gap between the first timer information and the second timer information is performed using one of the following four methods depending on a configuration of each apparatus.

1. Comparison between timing information and timing information
2. Comparison between timing information and time information
3. Comparison between time information and timing information
4. Comparison between time information and time information A method for confirming a gap amount between the first timer information and the second timer information using the respective methods will be described in detail below.

[Confirmation Method of Gap Amount in Timer Information Through Comparison Between Timing Information and Timing Information]

Figure 25:
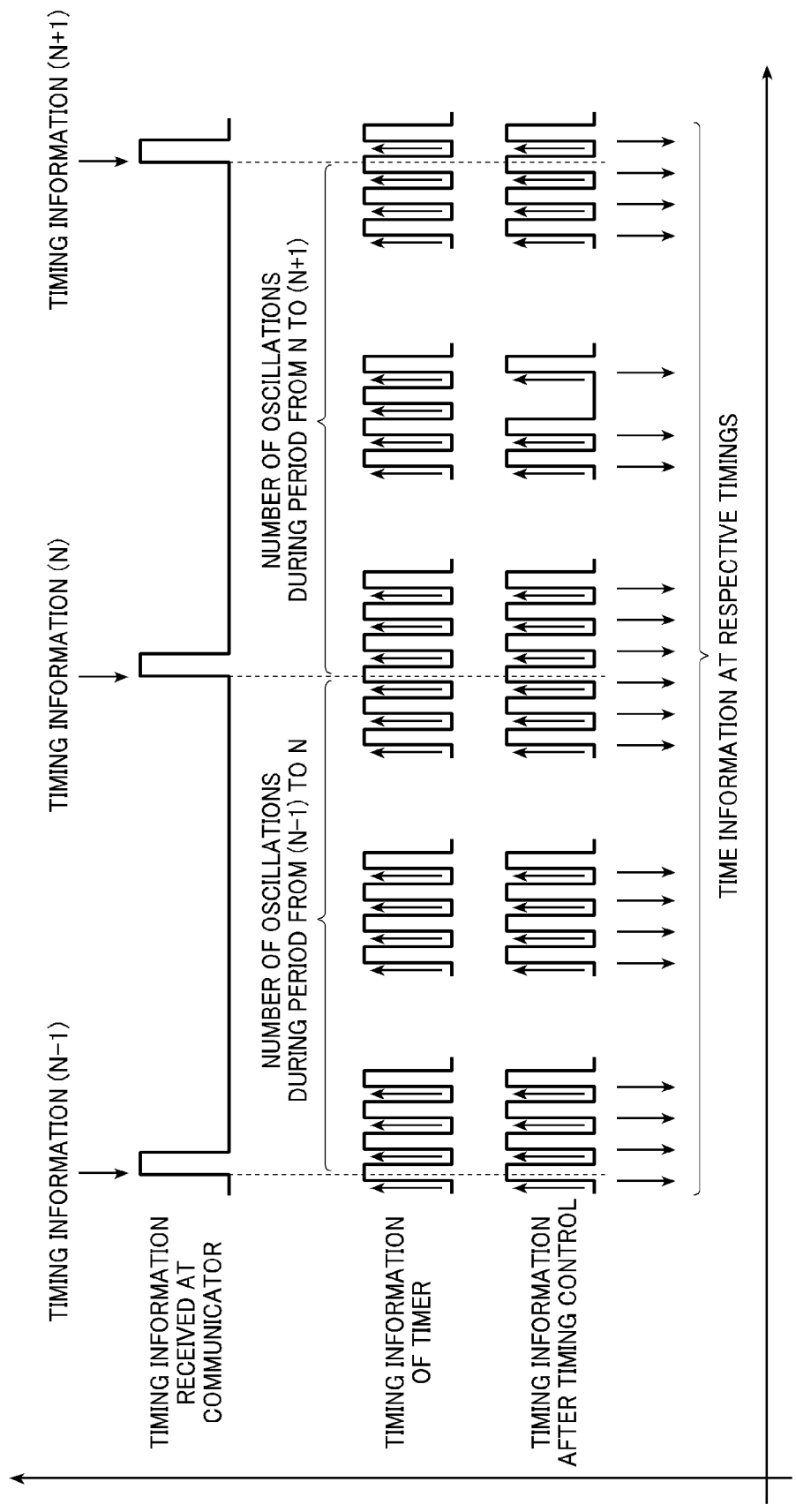
FIG. 25 is a timing chart illustrating an operation of the radiation control apparatus or the radiographing apparatus in FIG. 19.
Figure 26:
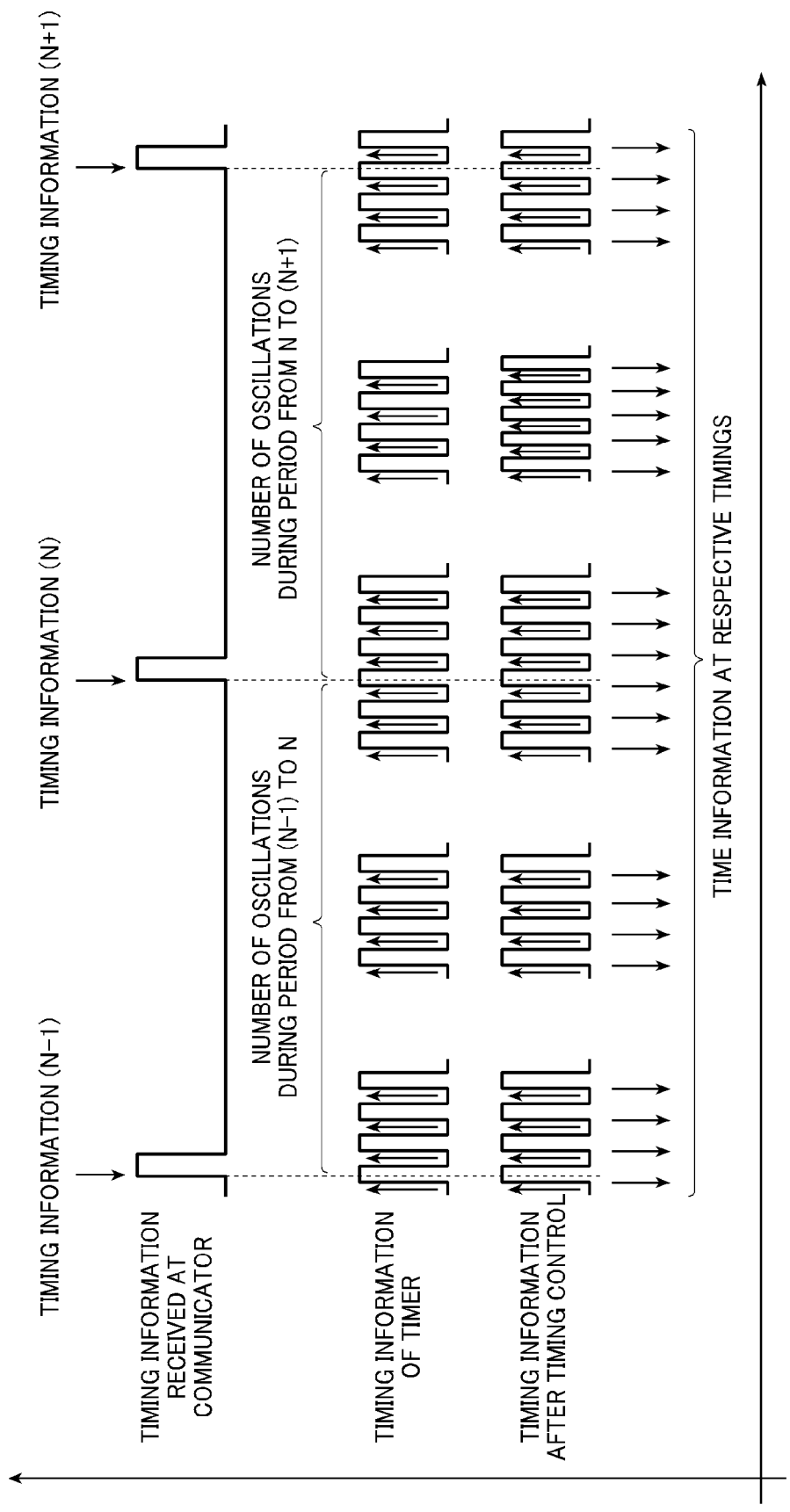
FIG. 26 is a timing chart illustrating the operation of the radiation control apparatus or the radiographing apparatus in FIG. 19.

FIG. 25 and FIG. 26 illustrate an operation of an apparatus which receives the first timer information among the radiation control apparatus 1B and the radiographing apparatuses 30A to 30C.

In a case where the wireless communication apparatus 6B is configured to output the timing information as the first timer information, and the timer controllers 16 and 39 are configured to acquire the timing information as the second timer information, for example, in the examples illustrated in FIG. 25 and FIG. 26, the timer controllers 16 and 39 count the number of pulses of the own timers 15 and 38 during a period from when the timing information is input from the wireless communication apparatus 6B until when the next timing information is input (period from when an (N−1)-th pulse is received until when an N-th pulse is received), and judges timing speed of the own timers 15 and 38 with respect to the timing speed of the wireless communication apparatus 6B.

For example, in a case where a period of output of the first timer information from the wireless communication apparatus 6B is set at 1 second, and a clock of the own timers 15 and 38 is set at 10 MHz, it is set that a pulse is counted 10,000,000 times in one second.

However, actually, as a result of pulse generation speed fluctuating by fluctuation of the reference timer 602 of the wireless communication apparatus 6B, accuracy of the timer 15 or the timer 38 itself, or change of a temperature, the number of times does not become exactly 10,000,000 times, and a difference occurs.

This difference becomes a timing difference between the reference timer 602 of the wireless communication apparatus 6B and the timers 15 and 38 of the radiation control apparatus 1B or the radiographing apparatuses 30A to 30C.

For example, in a case illustrated in FIG. 25, in a case where the number of pulses during a period from when the (N−1)-th pulse is received until when the N-th pulse is received is 10,000,010 times, which is greater than a set value by 10, it can be recognized that the own timers 15 and 38 are faster than the wireless communication apparatus 6B by 10/10,000,000.

Meanwhile, for example, in a case illustrated in FIG. 26, in a case where the number of pulses during a period from when the (N−1)-th pulse is received until when the N-th pulse is received is 9,999,990 times, which is less than the set value by 10, it can be recognized that the own timers 15 and 38 are slower than the wireless communication apparatus 6B by 10/10,000,000.

[Confirmation Method of Gap Amount of Timer Information Through Comparison Between Timing Information and Time Information]

In a case where the wireless communication apparatus 6B is configured to output the timing information as the first timer information, and the timer controllers 16 and 39 are configured to acquire time information as the second timer information, for example, in the examples illustrated in FIG. 25 and FIG. 26, the timer controllers 16 and 39 generate time information from the timing information such as pulses of the own timers 15 and 38 during a period from when the timing information is input from the wireless communication apparatus 6B until when the next timing information is input (period from when the (N−1)-th pulse is received until when the N-th pulse is received) and judges timing speed of the own timers 15 and 38 with respect to the timing speed of the wireless communication apparatus 6B from the generated time information.

For example, in a case where an period of output of the first timer information from the wireless communication apparatus 6B is set at one second, and a clock of the own timers 15 and 38 is set at 10 MHz, because a pulse is generated 10,000,000 times in one second, a pulse is generated for each 0.0000001 second. Therefore, by correcting the time information at each 0.0000001 second for each pulse, it is possible to obtain time information at each timing.

Here, while the time information may be corrected at each pulse, the time information may be collectively corrected for each of a plurality of pulses. It is also possible to employ a configuration where the time information is collectively corrected in a case where the time information is referred to.

As a result of the above-described correction of the time information being repeated over one second with the setting as described above, the time information becomes one second.

However, actually, as a result of the pulse generation speed fluctuating by fluctuation of the wireless communication apparatus 6B and the reference timer 602, accuracy of the timer 15 or the timer 38 itself, or change of a temperature, the time information does not become exactly one second, and a difference occurs.

This difference becomes a timing difference between the reference timer 602 of the wireless communication apparatus 6B and the timer 38 or the timer 15.

For example, in a case illustrated in FIG. 25, in a case where the number of pulses during a period from when the (N−1)-th pulse is received until when the N-th pulse is received is 10,000,010, which is greater than the set value by 10, a period from when the (N−1)-th pulse is received until when the N-th pulse is received becomes 1.000001 seconds, and it can be recognized that the timing speed of the own timers 15 and 38 is faster than the timing speed of the wireless communication apparatus 6B by 0,000001 seconds per one second.

Meanwhile, for example, in a case illustrated in FIG. 26, in a case where the number of pulses during a period from when the (N−1)-th pulse is received until when the N-th pulse is received is 9,999,990 times, which is less than the set value by 10, a period from when the (N−1)-th pulse is received until when the N-th pulse is received becomes 0.999999 seconds, and it can be recognized that the timing speed of the own timers 15 and 38 is slower than the timing speed of the wireless communication apparatus 6B by 0.000001 seconds per one second.

[Confirmation Method of Gap Amount of Timer Information Through Comparison Between Time Information and Timing Information]

Figure 27:
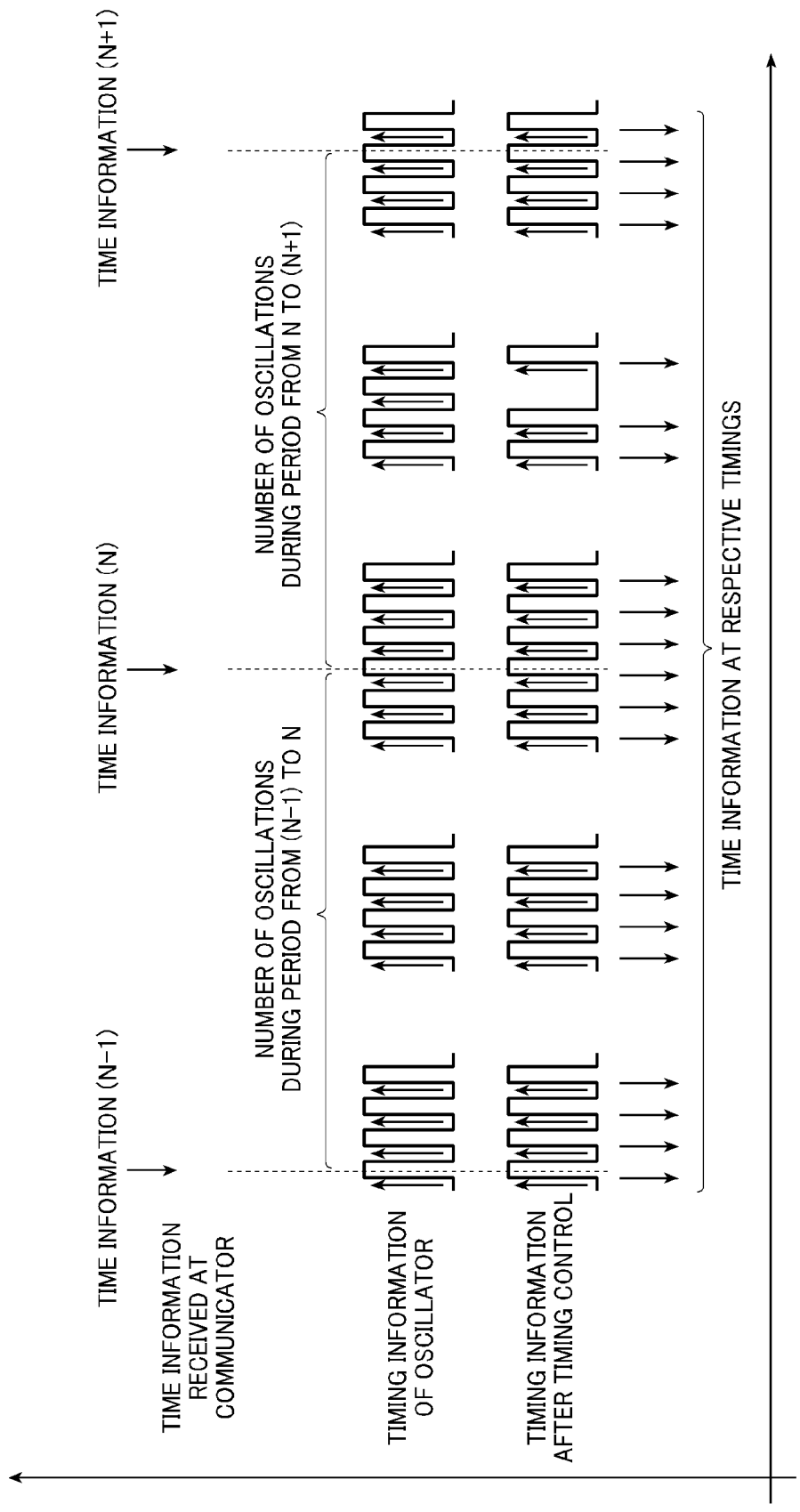
FIG. 27 is a timing chart illustrating the operation of the radiation control apparatus or the radiographing apparatus in FIG. 19.

FIG. 27 illustrates an operation of an apparatus which receives the first timer information among the radiation control apparatus 1B and the radiographing apparatuses 30A to 30C.

In a case where the wireless communication apparatus 6B is configured to output time information as the first timer information, and the timer controllers 16 and 39 are configured to acquire timing information as the second timer information, for example, in the example illustrated in FIG. 27, the timer controllers 16 and 39 count the number of pulses of the own timers 15 and 38 during a period from when the time information is input from the wireless communication apparatus 6B until when the next time information is input (period from when the (N−1)-th time information is received until when the N-th time information is received), and judges the timing speed of the own timers 15 and 38 with respect to the timing speed of the wireless communication apparatus 6B.

For example, by respectively acquiring time at a time point of (N−1) and time at a time point of N as the time information from the wireless communication apparatus 6B and calculating a difference between these, the timer controllers 16 and 39 can acquire a length (period) of a period from (N−1) to N.

Meanwhile, in a case where timer information at the time point of (N−1) and timer information at the time point of N are acquired as the time information from the own timers 15 and 38, by multiplying a difference between the timer information at the time point of (N−1) and the timer information at the time point of N by a count interval of the wireless communication apparatus 6B, the timer controllers 16 and 39 can acquire a period from the time point of (N−1) to the time point of N.

Then, the timer controllers 16 and 39 can judge the timing speed of the own timers 15 and 38 with respect to the timing speed of the wireless communication apparatus 6B by comparing the period from the time point of (N−1) to the time point of N, with a value obtained by multiplying the own pulse interval by the timer information of the pulses of the own timers 15 and 38 during this period.

[Confirmation Method of Gap Amount of Timer Information Through Comparison Between Time Information and Time Information]

In a case where the wireless communication apparatus 6B is configured to generate time information as the first timer information, and the timer controllers 16 and 39 are configured to acquire time information as the second timer information, for example, in a case illustrated in FIG. 27, by respectively acquiring time at the time point of (N−1) and time at the time point of N as the time information from the wireless communication apparatus 6B and calculating a difference between these, the timer controllers 16 and 39 can acquire a length (period) of a period from the time point of (N−1) to the time point of N.

Meanwhile, by respectively acquiring time at the time point of (N−1) and time at the time point of N as the time information from the own timers 15 and 38 and calculating a difference between these, the timer controllers 16 and 39 can acquire a period from the time point of (N−1) to the time point of N.

Then, the timer controllers 16 and 39 can judge the timing speed of the own timers 15 and 38 with respect to the timing speed of the wireless communication apparatus 6B by comparing the period from the time point of (N−1) to the time point of N based on the first timer information with a period from the time point of (N−1) to the time point of N based on the second timer information.

By comparing the first timer information and the second timer information using one of the above-described four methods, it is possible to judge the timing speed of the own timers 15 and 38 with respect to the timing speed of the wireless communication apparatus 6B.

[Judgement of Timing Accuracy]

The timer controllers 16 and 39 judge whether or not timing accuracy is sufficient based on the acquired first timer information and second timer information, and, in a case where it is judged that the timing accuracy is not sufficient, corrects the timer information of the timers 15 and 38.

(Judgment Method 1 of Timing Accuracy (Difference))

In a case where a gap amount (difference) between the first timer information and the second timer information is used to judge the timing accuracy, for example, a difference between the acquired first timer information and second timer information is calculated, and whether or not the difference exceeds a specific value is judged. Then, in a case where the difference exceeds the specific value, it is judged that the timing accuracy is not sufficient.

(Judgment Method 2 of Timing Accuracy (Change Amount))

Further, in a case where change of a gap amount (difference) is used for judgement, for example, a difference between the first timer information and the second timer information is calculated every time the first timer information and the second timer information are acquired, and the difference is stored in the storages 13 and 35. Then, a change amount between the stored difference and a difference calculated previously is calculated, and whether or not the calculated change amount exceeds a change amount calculated previously is judged. Then, in a case where the calculated change amount exceeds the previous change amount, it is judged that the timing accuracy is not sufficient.

Note that, in a case where estimation of a difference is used for judgement, for example, a difference between the acquired first timer information and second timer information and a change amount are respectively calculated and stored in the storages 13 and 35. Further, whether or not the difference and the change amount exceed the specific values may be judged in a case where similar change continues for a predetermined period (for example, a radiographing period) from the stored difference and change amount.

Note that, to judge the timing accuracy, such a difference between the first timer information and the second timer information and a value of the change amount may be used as is, or an average value of these values may be calculated, or a change state or an estimated value in the future may be calculated using an approach such as linear interpolation and spline interpolation.

In a case where an average value is calculated, for example, a difference between the acquired first timer information and second timer information is calculated and stored in the storages 13 and 35. Then, an average value is calculated from a plurality of the stored differences. Because there is a case where a change amount of the difference precipitously changes, it is possible to address such change by calculating the average value.

A parameter required for linear interpolation and spline interpolation can be obtained using, for example, a least square method, or the like. By incorporating approaches of interpolation and extrapolation which are also used in other fields in the approach for performing such judgment, it is possible to realize high-level judgment.

[Correction of Timer Information]

In a case where it is judged that the timing accuracy is not sufficient, the timer controllers 16 and 39 correct the operation of the timers 15 and 38 so that a difference between the timer information of the wireless communication apparatus 6B and the timer information of the own timers 15 and 38 becomes smaller.

Examples of a way for correction can include, for example, correction of the timing information and correction of the time information as will be described below.

(Correction of Timing Information)

For example, in the examples illustrated in FIG. 25 and FIG. 26, in a case where, as a result of confirming speed of the own timers 15 and 38 using the above-described method during a period from when the (N−1)-th first timer information is received until when the N-th first timer information is received, it is judged that the timing accuracy is not sufficient, the timer controllers 16 and 39 can be configured to correct the timing information of the own timers 15 and 38 during a period from when N-th timing information is received until when (N+1)-th timing information is received.

For example, as illustrated in FIG. 25, a method for performing correction can be realized by thinning out or adding pulses for a fixed period in accordance with the detected difference in speed.

For example, in the example illustrated in FIG. 25, in a case where the number of pulses during a period from when the (N−1)-th pulse is received until when the N-th pulse is received is 10,000,010, which is greater than the set value by 10, it is possible to employ a configuration where processing of thinning out a pulse once per 1,000,000 times is performed during a period from when the N-th pulse is received until when an (N+1)-th pulse is received. Alternatively, it is possible to employ a configuration where generation of pulses is delayed so that the number of pulses is reduced by one.

Meanwhile, for example, in the example illustrated in FIG. 26, in a case where the number of pulses during the period from when the (N−1)-th pulse is received until when the N-th pulse is received is 9,999,990 times, which is less than the set value by 10, it is possible to employ a configuration where a pulse is counted twice so that the number of pulses is increased once per 1,000,000 times during the period from when the N-th pulse is received until when the (N+1)-th pulse is received. Alternatively, it is possible to employ a configuration where generation of pulses is made quicker so that the number of pulses is increased by one.

Note that the timer controllers 16 and 39 can be configured to correct pulse intervals.

For example, in a case where a CR oscillation circuit or an LC oscillation circuit is used as a pulse source, by changing values of C (capacitor), R (resistor) and L (coil), it is possible to easily adjust the pulse intervals.

(Correction of Time Information)

In a case where it is judged that the timing accuracy is not sufficient as a result of confirming the timing speed of the own timers 15 and 38 using the above-described method during a period from when the (N−1)-th first timer information is received until when the N-th first timer information is received, the timer controllers 16 and 39 can be configured to correct the time information of the own timers 15 and 38 during a period from when the N-th time information is received until when the (N+1)-th time information is received.

As described above, both in a case where the timer information transmitted from the wireless communication apparatus 6B is timing information and in a case where the timer information is time information, or both in a case where a target to be corrected by the timer controllers 16 and 39 is timing information and in a case where the target is time information, by using the method as described above, it is possible to appropriately correct the timing speed of the timers 15 and 38 in accordance with a difference from the timing speed of the wireless communication apparatus 6B.

[Determination as to Whether or not Connected to Specific Wireless Communication Apparatus 6B]

Figure 28:
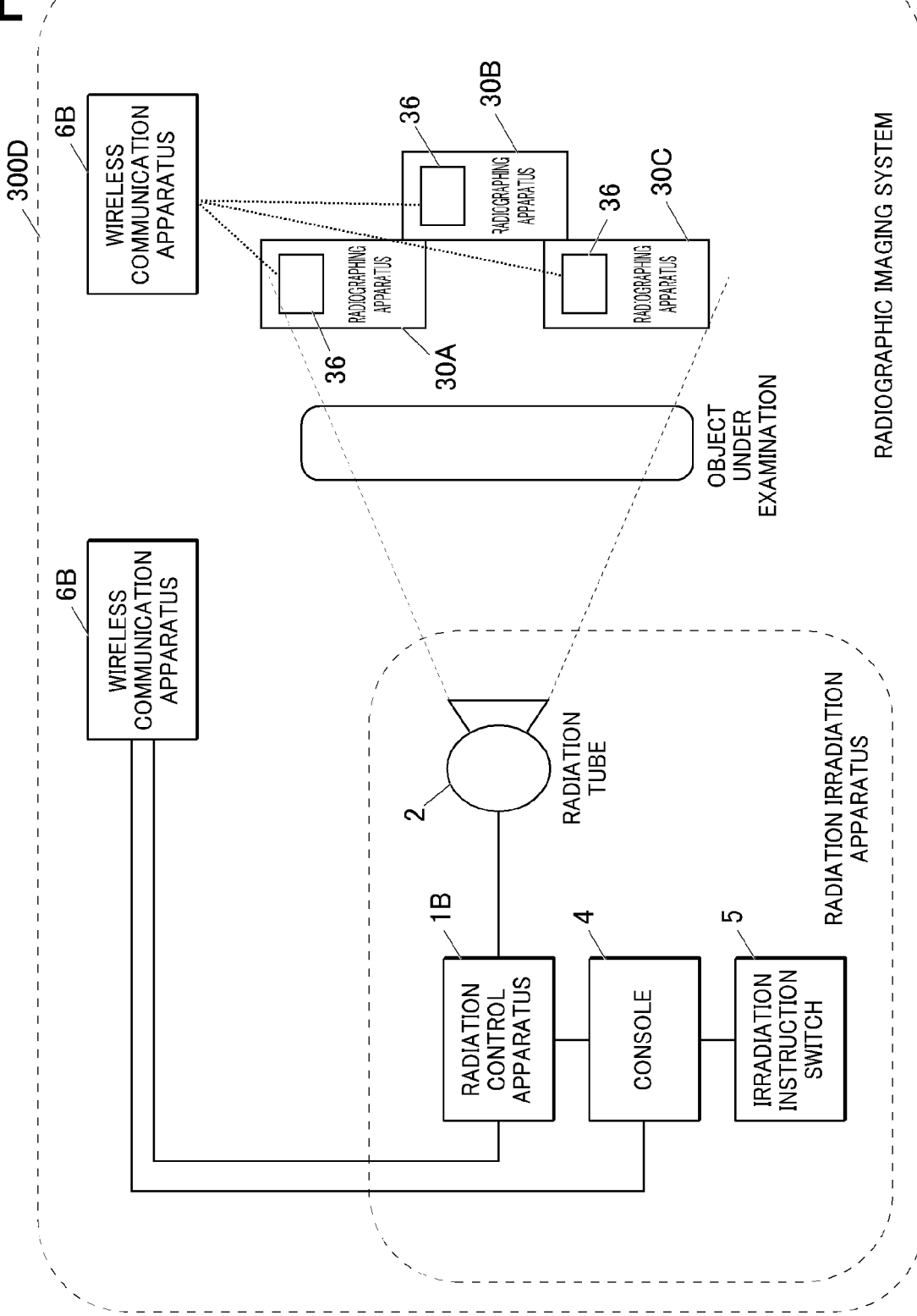
FIG. 28 is a view illustrating a wireless link of a conventional radiographing imaging system.

By the way, because the timer information of the reference timer 602 is unique for each wireless communication apparatus 6B, to adjust the radiation irradiation timing of the radiation control apparatus 1B so as to match the accumulation timing of the radiographing apparatuses 30A to 30C, the timers 15 and 38 require to acquire the first timer information from a beacon transmitted from the same wireless communication apparatus 6B. While, in a network of IEEE 802.11, means for identifying the wireless communication apparatus 6B by establishing a wireless link using an ESSID and a password for identifying the wireless communication apparatus 6B is typically used, for example, in a conventional radiographic imaging system 300D as illustrated in FIG. 28, there are problems that the radiation control apparatus 1B and the radiographing apparatuses 30A to 30C respectively establish wireless links with different access points which are located in the vicinity and for which the same settings are made, and that it is impossible to identify the wireless communication apparatus 6B without establishing a wireless link.

Therefore, in the system 300 of the present embodiment, each of the radiographing apparatuses 30A to 30C can determine whether or not the radiographing apparatus is connected to the specific wireless communication apparatus 6B to which the radiation control apparatus 1B is connected using the following (connection determination method 1) to (connection determination method 3).

(Connection Determination Method 1)

The radiographing controllers 31 of the radiographing apparatuses 30A to 30C have a function of receiving the above-described identification information from the surrounding wireless communication apparatus 6B via the communicator 36 and transferring the identification information to the radiation control apparatus 1B.

At this time, the radiographing apparatuses 30A to 30C may receive the identification information from the connected wireless communication apparatus 6B or may receive the identification information from an access point which is located around the radiographing apparatuses and which is not connected.

By this means, it is possible to use an access point which is not connected as the wireless communication apparatus 6B. Further, by this means, even if the radiographing apparatuses 30A to 30C do not have a wireless radio wave transmission function (only has a reception function), it is possible to identify the wireless communication apparatus 6B.

Meanwhile, the radiation controller 11B of the radiation control apparatus 1B has a function of acquiring identification information from the wireless communication apparatus 6B which is connected in a wired manner via the communicator 14.

Further, the radiation controller 11B has a function of receiving the identification information transferred from the radiographing apparatuses 30A to 30C, via the communicator 14.

Here, the identification information received at the radiographing apparatuses 30A to 30C from the wireless communication apparatus 6B becomes state information indicating whether the state is a first state in which the apparatuses are not connected to the specific wireless communication apparatus 6B which becomes the synchronization source or a second state in which the apparatuses are connected to the specific wireless communication apparatus 6B (the same also applies to connection determination methods 2 and 3).

Further, the radiation controller 11B has a function of determining whether or not all of the identification information received (transferred) at the radiographing apparatuses 30A to 30C matches the identification information acquired by the own apparatuses (that is, whether or not all of the radiographing apparatuses 30A to 30C are connected to the specific wireless communication apparatus 6B to which the radiation control apparatus 1B is connected), and outputting a determination result to the console 4 through the communicator 14. Further, in a case where it is determined that all the identification information acquired by the own apparatuses matches the identification information received (transferred) at the radiographing apparatuses 30A to 30C, the radiation controller 11B may release the interlock of the radiation generator 2.

When the console 4 receives the determination result from the radiation control apparatus 1B, the console 4 causes whether or not radiographing is possible using the radiographing apparatuses 30A to 30C to be displayed at the display 43 in an identifiable form based on the determination result. Further, the console 4 causes whether or not each of the radiographing apparatuses 30A to 30C upon radiographing is connected to the above-described specific wireless communication apparatus 6B to be displayed at the display 43 in an identifiable form. Here, because a display form at the display 43 is similar to that described in step S9 in the first-A embodiment, description will be incorporated (the same also applies to connection determination methods 2 to 3).

(Connection Determination Method 2)

Alternatively, a function of determining whether or not all of the radiographing apparatuses 30A to 30C are connected to the specific wireless communication apparatus 6B to which the radiation control apparatus 1B is connected may be provided at one (for example, the radiographing apparatus 30A) of the radiographing apparatuses 30A to 30C.

Specifically, the radiation controller 11B of the radiation control apparatus 1B has a function of acquiring identification information from the wireless communication apparatus 6B which is connected in a wired manner, via the communicator 14, and transferring the identification information to the radiographing apparatus 30A.

Meanwhile, the radiographing controllers 31 of the radiographing apparatuses 30A to 30C have a function of receiving identification information from the surrounding wireless communication apparatus 6B via the communicator 36.

Further, the radiographing controllers 31 of the radiographing apparatuses 30B and 30C have a function of transferring the received identification information to the radiographing apparatus 30A via the communicator 36.

Further, the radiographing controller 31 of the radiographing apparatus 30A has a function of receiving the identification information transferred from the radiation control apparatus 1B and the radiographing apparatuses 30B and 30C, via the communicator 36, determining whether or not the identification information acquired (transferred) by the radiation control apparatus 1B, the identification information transferred from the radiographing apparatuses 30B and 30C, and the identification information received by the own apparatus are all the same (that is, whether or not all of the radiographing apparatuses 30A to 30C are connected to the specific wireless communication apparatus 6B to which the radiation control apparatus 1B is connected), and outputting a determination result to the console 4 through the communicator 36.

When the console 4 receives the determination result as to whether or not all of the radiographing apparatuses 30A to 30C are connected to the specific wireless communication apparatus 6B to which the radiation control apparatus 1B is connected, the console 4 causes whether or not radiographing is possible using the radiographing apparatuses 30A to 30C to be displayed at the display 43 in an identifiable form based on the determination result. Further, the console 4 causes whether or not each of the radiographing apparatuses 30A to 30C upon radiographing is connected to the above-described specific wireless communication apparatus 6B to be displayed at the display 43 in an identifiable form. Further, the console 4 may be configured to cause the radiation control apparatus 1B to release the interlock of the radiation generator 2 in a case where the determination result indicating that all of the radiographing apparatuses 30A to 30C are connected to the specific wireless communication apparatus 6B connected to the radiation control apparatus 1B, is received.

(Connection Determination Method 3)

Alternatively, the radiation controller 11B of the radiation control apparatus 1B and the radiographing controllers 31 of the radiographing apparatuses 30A to 30C have a function of acquiring identification information from the wireless communication apparatus 6B via the communicators 14 and 36 and transferring the identification information to the console 4, and the console 4 has a function of determining and outputting whether or not all of the identification information respectively received from the radiation control apparatus 1B and the radiographing apparatuses 30A to 30C is the same (that is, whether or not all of the radiographing apparatuses 30A to 30C are connected to the specific wireless communication apparatus 6B connected to the radiation control apparatus 1B). Further, the console 4 causes whether or not radiographing is possible using the radiographing apparatuses 30A to 30C to be displayed at the display 43 in an identifiable form based on output of the determination result. Further, the console 4 causes whether or not each of the radiographing apparatuses 30A to 30C upon radiographing is connected to the above-described specific wireless communication apparatus 6B to be displayed at the display 43 in an identifiable form. Further, the console 4 may be configured to cause the radiation control apparatus 1B to release the interlock of the radiation generator 2 in a case where the output determination result indicates determination that all of the radiographing apparatuses 30A to 30C are connected to the specific wireless communication apparatus 6B connected to the radiation control apparatus 1B (second determination).

The above-described determination as to whether or not all of the radiographing apparatuses 30A to 30C are connected to the specific wireless communication apparatus 6B is performed when synchronization is achieved between the radiation control apparatus 1B and the radiographing apparatus 30, such as immediately before radiographing (irradiation of radiation) is started (for example, a timing of step S8 to S9 in the sequence illustrated in FIG. 4, FIG. 5, FIG. 11 and FIG. 12, a timing triggered by depression of the irradiation instruction switch 5) and while serial radiography is performed.

By using the radiographing imaging system 300 of the present embodiment configured in this manner, even in a case where there are a plurality of wireless communication apparatuses 6B, that is, there is a wireless network which has the same ESSID and access key around the apparatus, it is determined whether or not all of the radiographing apparatuses 30A to 30C are connected to the specific wireless communication apparatus 6B which is the synchronization source, and whether or not radiographing is possible using the radiographing apparatuses 30A to 30C is displayed at the display 43 in an identifiable manner based on the determination result. Therefore, it is possible to suppress a risk that the radiographing apparatuses 30A to 30C perform radiographing in coordination with different synchronization sources.

[Determination as to Whether or not Coordinating with Specific Wireless Communication Apparatus 6B]

Here, if the radiation control apparatus 1B and the radiographing apparatuses 30A to 30C are connected to the specific wireless communication apparatus 6B, it can be regarded as operation being performed substantially in accordance with the timing signal or the time information of the specific wireless communication apparatus 6B (that is, coordinating with the specific wireless communication apparatus 6B) by [Correction of timing information] described above. However, even if the apparatuses are connected to the specific wireless communication apparatus 6B, there is a possibility that, actually, the apparatuses do not coordinate with the wireless communication apparatus 6B for some reason (for example, failures of the timers 15 and 38, or the like). In a case where at least one of the radiographing apparatuses 30A to 30C does not coordinate with the specific (that is, the same) wireless communication apparatus 6B (synchronization source) connected to the radiation control apparatus 1B, it is impossible to perform radiographing while the accumulation timing is adjusted to match the radiation irradiation timing.

Therefore, in place of [Determination as to whether or not first timer information can be received from specific wireless communication apparatus 6B] described above, it is also possible to determine whether or not each of the radiographing apparatuses 30A to 30C is in a state where the radiographing apparatuses 30A to 30C coordinate with the specific wireless communication apparatus 6B which is the synchronization source.

For example, when the radiation control apparatus 1B is required to coordinate with the radiographing apparatuses 30A to 30C such as immediately before radiographing (irradiation of radiation) is started (for example, a timing of step S8 to S9 in the sequence illustrated in FIG. 4, FIG. 5, FIG. 11 and FIG. 12, a timing triggered by depression of the irradiation instruction switch 5) and while long-length serial radiography is performed, the console 4 requests transmission of state information indicating whether the state is a first state in which the radiographing apparatus does not coordinate with the specific wireless communication apparatus 6B to which the radiation control apparatus 1B is connected or a second state in which the radiographing apparatus coordinates with the specific wireless communication apparatus 6B, to each of the radiographing apparatuses 30A to 30C and receives the state information. Then, it is determined whether or not all of the radiographing apparatuses 30A to 30C coordinate with the specific wireless communication apparatus 6B which coordinates with the radiation control apparatus 1B based on the received state information, and causes whether or not radiographing is possible using the radiographing apparatuses 30A to 30C to be displayed at the display 43 in an identifiable form based on the determination result.

Here, examples of an approach for determining whether or not the radiographing apparatuses 30A to 30C coordinate with the wireless communication apparatus 6B connected to the radiation control apparatus 1B can include, for example, the following (coordination determination method 1) to (coordination determination method 2).

(Coordination Determination Method 1)

The radiation controller 11B of the radiation control apparatus 1B has a function of acquiring identification information from the wireless communication apparatus 6B which is connected in a wired manner, via the communicator 14 and transferring the identification information to the radiographing apparatuses 30A to 30C.

The radiographing controllers 31 of the radiographing apparatuses 30A to 30C receive the identification information from the surrounding wireless communication apparatus 6B via the communicator 36, receive the identification information transferred from the radiation control apparatus 1B via the communicator 36, and judge whether or not the identification information received from the wireless communication apparatus 6B matches the identification information received from the radiation control apparatus 1B. In a case where the identification information received from the wireless communication apparatus 6B does not match the identification information received from the radiation control apparatus 1B, it is judged that the state is the first state in which the radiographing apparatuses do not coordinate with the specific wireless communication apparatus 6B. In a case where it is judged that the identification information received from the wireless communication apparatus 6B matches the identification information received from the radiation control apparatus 1B, a difference between the first timer information received from the wireless communication apparatus 6B and the second timer information of the timer 38 is calculated, and whether or not the difference exceeds a specific value is judged. Then, in a case where the difference exceeds the specific value, it is determined that the state is the first state in which the radiographing apparatuses do not coordinate with the specific wireless communication apparatus 6B, while, in a case where the difference is equal to or less than the specific value, it is determined that the state is the second state in which the radiographing apparatuses coordinate with the specific wireless communication apparatus 6B.

(Coordination Determination Method 2)

A configuration is employed where a second timer (not illustrated) configured using, for example, an atomic clock, a GPS, NTP, or the like, is provided at each of the radiographing apparatuses 30A to 30C. In a case where an atomic clock, a GPS, or the like, is used, an antenna for receiving radio waves may be disposed.

The radiation controller 11B of the radiation control apparatus 1B has a function of acquiring identification information from the wireless communication apparatus 6B which is connected in a wired manner, via the communicator 14 and transferring the identification information to the radiographing apparatuses 30A to 30C.

Figure 29:
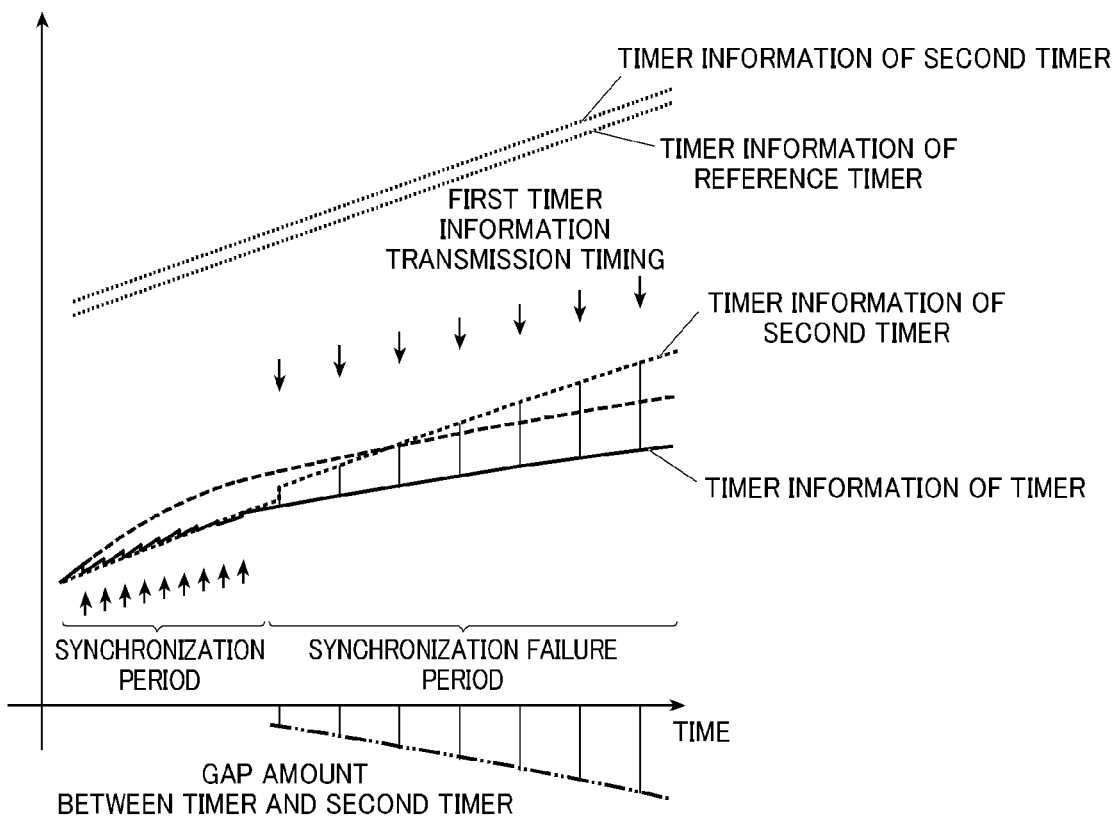
FIG. 29 is a view illustrating a gap between a second timer and the timer in the radiographic imaging system in FIG. 19.

The radiographing controllers 31 of the radiographing apparatuses 30A to 30C receive the identification information from the surrounding wireless communication apparatus 6B via the communicator 36, receive the identification information transferred from the radiation control apparatus 1B via the communicator 36, and judge whether or not the identification information received from the wireless communication apparatus 6B matches the identification information received from the radiation control apparatus 1B. In a case where the identification information received from the wireless communication apparatus 6B does not match the identification information received from the radiation control apparatus 1B, it is judged that the state is the first state in which the radiographing apparatuses do not coordinate with the specific wireless communication apparatus 6B. In a case where it is judged that the identification information received from the wireless communication apparatus 6B matches the identification information received from the radiation control apparatus 1B, the second timer information of the timer 38 is compared with the timer information of the second timer. As illustrated in FIG. 29, if coordination between the timer 38 and the reference timer 602 is lost (synchronization fails), a difference (gap amount) between the timer information of the second timer and the timer information of the timer 38 becomes greater. Therefore, the radiographing controllers 31 calculate a difference (gap amount) between the timer information of the timer 38 and the timer information of the second timer, compare the difference with a predetermined value, and, in a case where the gap amount exceeds the predetermined value, determines that the state is in the first state in which the own apparatuses do not coordinate with the wireless communication apparatus 6B, while, in a case where the gap amount is equal to or less than the predetermined value, determines that the state is the second state in which the radiographing apparatuses 30A to 30C coordinate with the wireless communication apparatus 6B.

By determining whether or not all of the radiographing apparatuses 30A to 30C coordinate with the specific wireless communication apparatus 6B connected to the radiation control apparatus 1B in this manner, even in a case where there are a plurality of wireless communication apparatuses 6B, it is possible to determine whether or not the radiographing apparatuses 30A to 30C coordinate with the specific synchronization source (wireless communication apparatus 6B) with high accuracy. Therefore, it is possible to further suppress a risk that the radiographing apparatuses 30A to 30C perform radiographing in coordination with different synchronization sources.

[Modified Examples of System 300]

Modified examples of the system configuration of the above-described system 300 will be described next with reference to FIG. 30 to FIG. 33. In FIG. 30 to FIG. 33, connection lines connecting the respective apparatuses, indicated with solid lines indicate wired connection, and connection lines indicated with dotted lines indicate wireless connection. Dashed lines indicate radiation. Further, in FIG. 30 to FIG. 33, the same reference numerals will be assigned to the apparatuses which are the same as the respective apparatuses constituting the system 300 described in the second embodiment, and, unless otherwise described, the apparatuses have functions similar to those described in the above-described second embodiment.

System Modified Example 1

Figure 30:
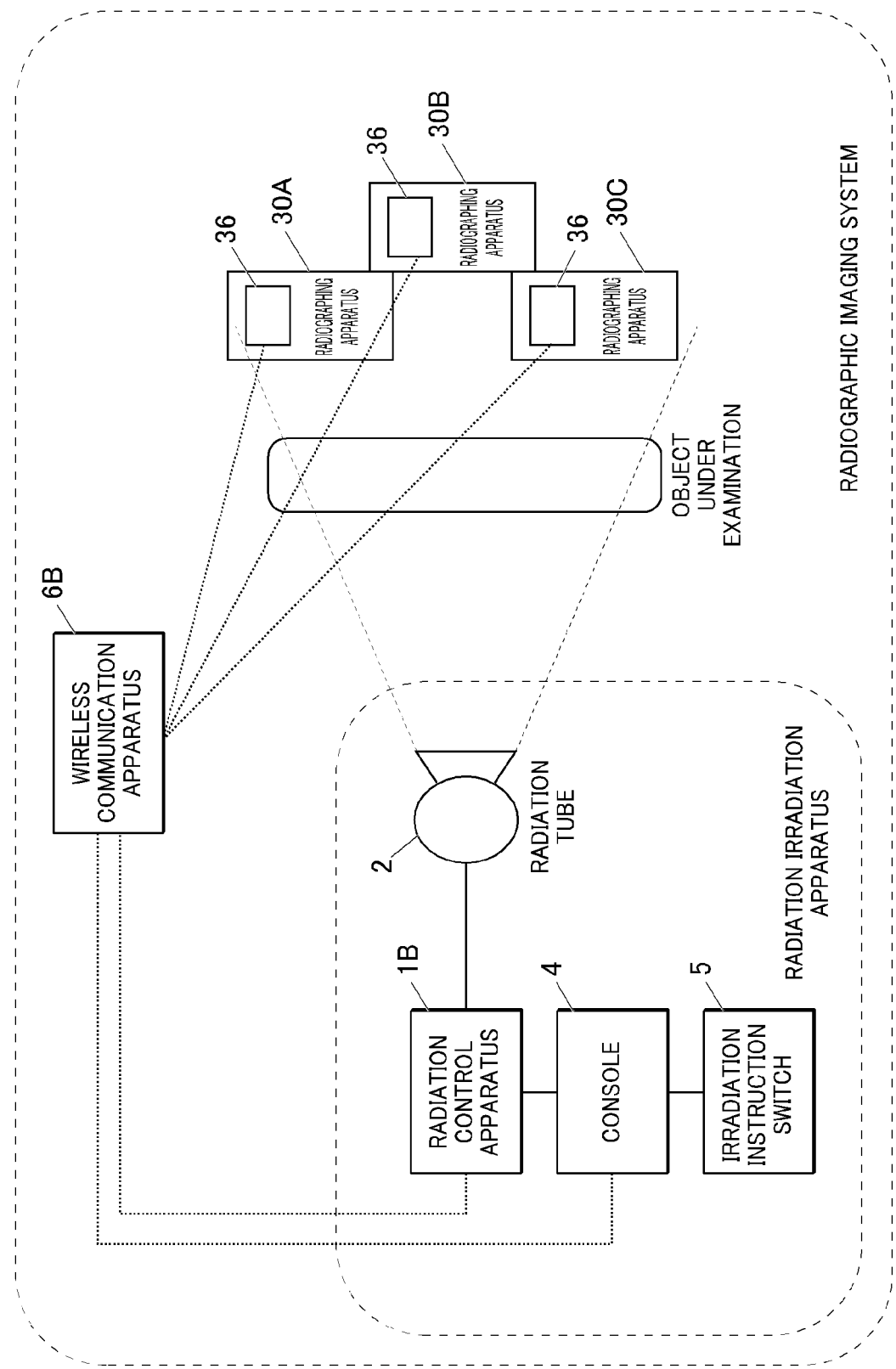
FIG. 30 is a view illustrating a modified example of the radiographic imaging system in FIG. 19.

A system modified example 1 illustrated in FIG. 30 is a configuration where, in the system 300 in FIG. 19, the radiation control apparatus 1B and the console 4 include wireless communication interfaces and are respectively connected to the wireless communication apparatus 6B in a wireless manner. With this configuration, because no cable is required to be used in radiographing using a visit car, it is possible to improve user-friendliness.

System Configuration Example 2

Figure 31:
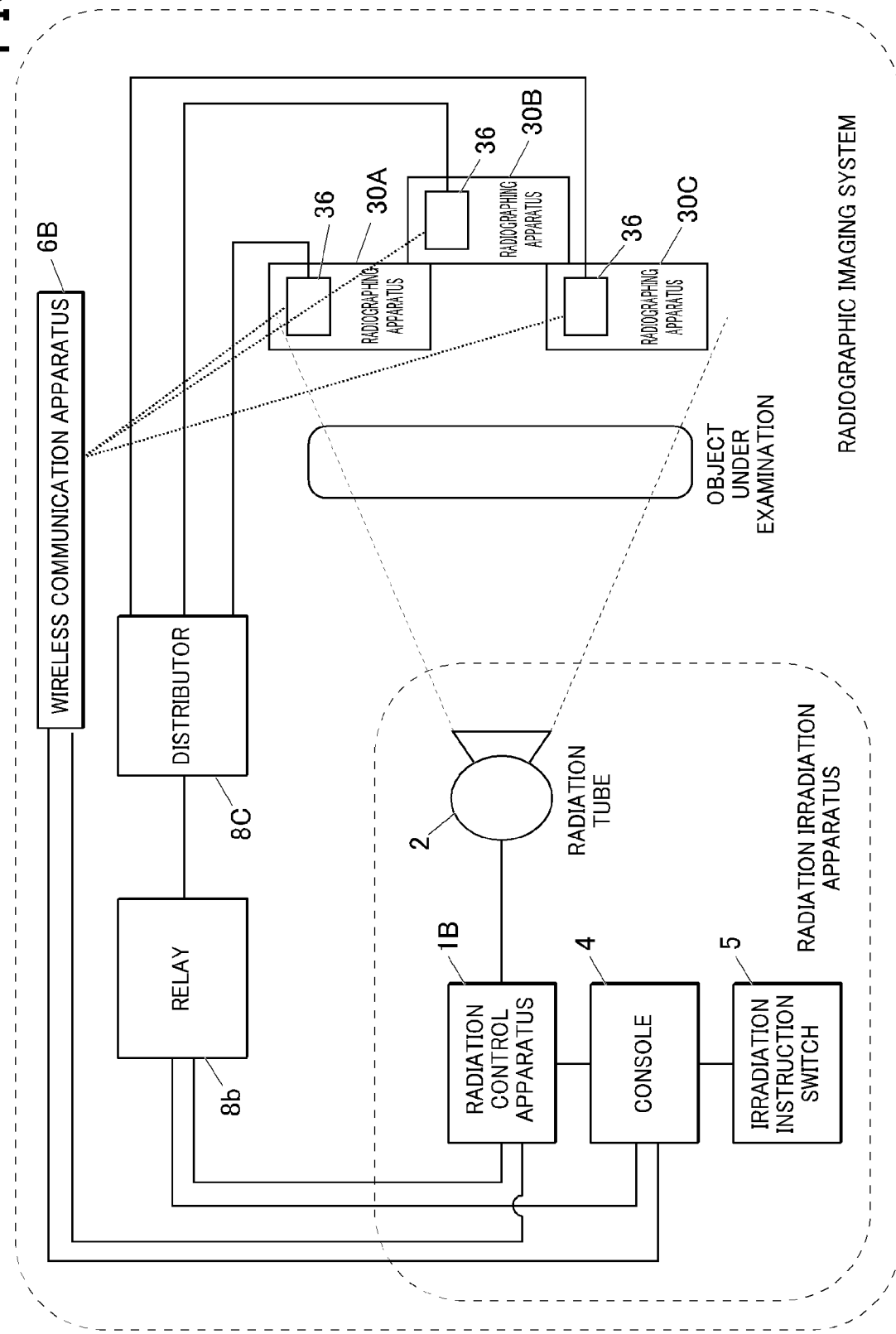
FIG. 31 is a view illustrating a modified example of the radiographic imaging system in FIG. 19.

A system modified example 2 illustrated in FIG. 31 is a configuration where, in the configuration of the system 300 in FIG. 19, further, a relay 8b and the switch 8 are newly added, and the radiation control apparatus 1B and the console 4 are connected to the radiographing apparatuses 30A to 30C via the relay 8b and the switch 8 in a wired manner. With this configuration, while the first timer information is transmitted from the wireless communication apparatus 6B to the radiographing apparatuses 30A to 30C in a wireless manner, because transfer of images and transmission and reception of other information signals are performed from the radiographing apparatuses 30A to 30C to the console 4 in a wired manner, it is possible to efficiently transfer image data, or the like.

System Modified Example 3

Figure 32:
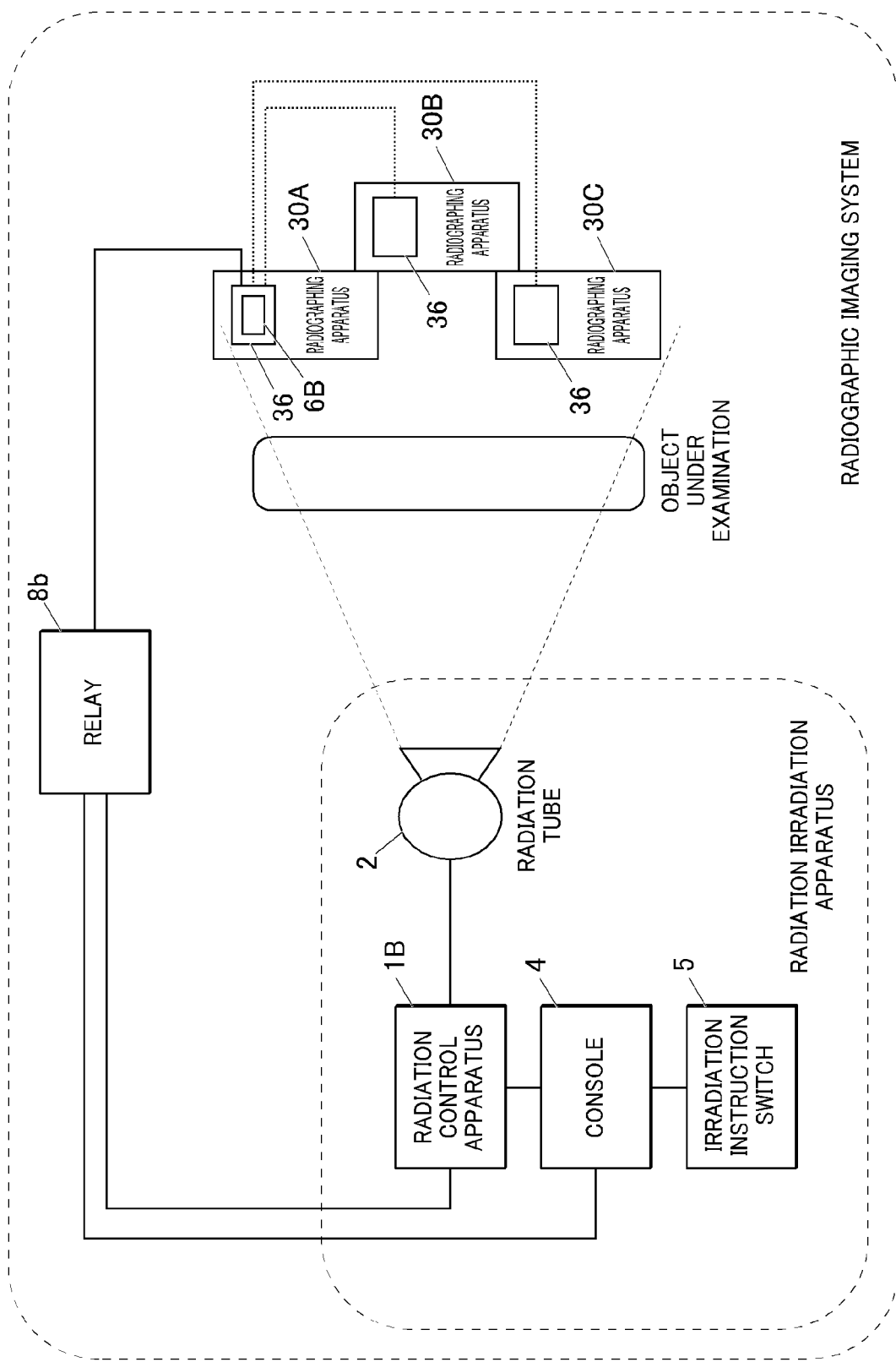
FIG. 32 is a view illustrating a modified example of the radiographic imaging system in FIG. 19.

A system modified example 3 illustrated in FIG. 32 is a configuration where the specific wireless communication apparatus 6B which becomes the synchronization source (which transmits the first timer information) is incorporated into the radiographing apparatus 30A. The wireless communication apparatus 6B within the radiographing apparatus 30A outputs timer information measured by the reference timer 602 as the first timer information, for example, on a beacon at predetermined time intervals. The communicators 36 of the radiographing apparatuses 30A to 30C receive the first timer information transmitted from the wireless communication apparatus 6B. Further, the wireless communication apparatus 6B of the radiographing apparatus 30A is connected to the radiation control apparatus 1B and the console 4 via the relay 8b in a wired manner, and transmits the first timer information to the radiation control apparatus 1B at a timing at which the beacon including the first timer information is transmitted. Further, the communicator 36 of the radiographing apparatus 30A transmits image data generated by the own apparatus and image data transmitted from the radiographing apparatuses 30B and 30C through wireless communication, to the console 4 via the relay 8b.

In the system modified example 3, in [Determination as to whether or not connected to specific wireless communication apparatus 6B] and [Determination as to whether or not coordinating with specific wireless communication apparatus 6B] described above, when identification information is acquired from equipment connected to the radiation control apparatus 1B in a wired manner, identification information of the relay 8b is acquired, and this identification information does not match the identification information of the wireless communication apparatus 6B incorporated in the radiographing apparatus 30A, acquired by the radiographing apparatuses 30A to 30C. However, by storing information of an equipment configuration of the system modified example 3 and combination of identification information of respective components when the components are connected in this equipment configuration in advance in equipment which performs determination (the radiation control apparatus 1B, the console 4 or the radiographing apparatus 30A (or the radiographing apparatus 30B or 30C)), it is possible to perform the above-described determination while recognizing that the wireless communication apparatus 6B to which the radiation control apparatus 1B is connected is the wireless communication apparatus 6B within the radiographing apparatus 30A.

Note that it is also possible to employ a configuration where the wireless communication apparatus 6B which becomes the synchronization source may be provided at the radiation control apparatus 1B or the relay 8b.

System Modified Example 4

Figure 33:
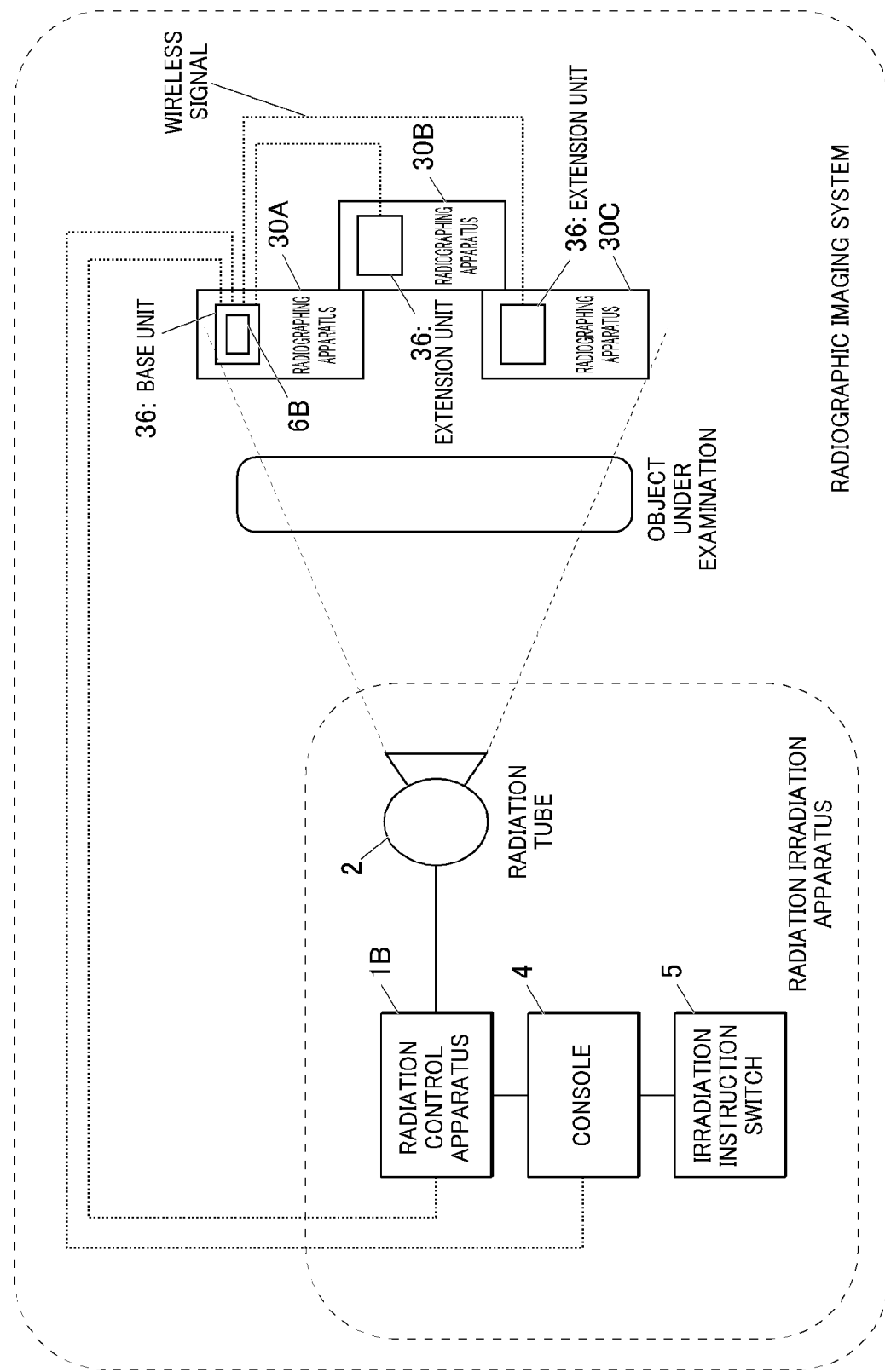
FIG. 33 is a view illustrating a modified example of the radiographic imaging system in FIG. 19.

In a system modified example 4 illustrated in FIG. 33, the radiographing apparatus 30A has a function as a wireless base unit, and includes a built-in wireless communication apparatus 6B which becomes the synchronization source. The radiographing apparatuses 30B and 30C function as wireless extension units. Further, the radiation control apparatus 1B and the console 4 include wireless communication interfaces, and are connected to the wireless communication apparatus 6B of the radiographing apparatus 30A in a wireless manner. The wireless communication apparatus 6B within the radiographing apparatus 30A outputs the timer information measured by the reference timer 602 as the first timer information, for example, on a beacon at predetermined time intervals. The communicators 14 and 36 of the radiation control apparatus 1B and the radiographing apparatuses 30A to 30C receive the first timer information transmitted from the wireless communication apparatus 6B. Further, the radiographing apparatus 30A transmits image data generated by the own apparatus and image data transmitted from the radiographing apparatuses 30B and 30C through wireless communication, to the console 4 via the wireless communication apparatus 6B through the communicator 36.

With this configuration, because no cable is required to be used, it is possible to improve user-friendliness.

<Common Functions>

Functions which are preferably commonly provided at the above-described systems 100 to 200 and the configuration examples in which these systems are applied, and the above-described system 300 and its modified examples, will be described next. Note that, in the following description, portions described as the radiographing apparatuses 3 and 3A to 3C can be replaced with the radiographing apparatuses 30 and 30A to 30C.

[Display of Supporting Serial Processing/Frame Rate]

The radiographing apparatuses 3 include apparatuses which support only still radiography, and apparatuses which support still radiography and serial radiography. Further, the radiographing apparatuses 3 which support serial radiography include apparatuses which support different radiographing intervals (frame rates). In a case of long-length serial radiography, a plurality of radiographing apparatuses 3A to 3C require to successively perform accumulation at the same time a plurality of times while the timing is adjusted to match the radiation irradiation timing. Conventionally, if radiographing is performed without confirming that a plurality of radiographic imaging apparatuses 3A to 3C to be used support serial radiography, and that the plurality of radiographic imaging apparatuses 3A to 3C can perform radiographing at a frame rate that allows radiographing to be performed at the same timing, there is a possibility that radiographing cannot be correctly performed, and it is required to perform radiographing again, which may uselessly expose the object under examination to radiation.

Therefore, for example, as described above, in step S8 in FIG. 4, FIG. 5, FIG. 11 and FIG. 12, the radiographing apparatuses 3A to 3C transmit whether or not serial radiography is possible and information of a frame rate to the console 4. As illustrated in FIG. 7, the console 4 displays information as to whether the respective radiographing apparatuses 3A to 3C support serial radiography (supporting serial processing), or do not support serial radiography (only still radiography), and frame rates (F rates) of the respective radiographing apparatuses 3A to 3C on the radiographing screen 432 (see FIG. 7). By this means, the radiographer can confirm whether long-length serial radiography can be performed using the selected radiographing apparatuses 3A to 3C. Further, in a case where long-length serial radiography is not possible, it is possible to take measures such as replacing the radiographing apparatus 3 which cannot perform long-length serial radiography with another radiographing apparatus 3 which can perform long-length serial radiography.

[Measure 1 in a Case of not Supporting Serial Processing/Mismatch of Frame Rates]

Further, for example, the console 4 judges whether or not long-length serial radiography is possible using combination of the selected radiographing apparatuses 3A to 3C based on whether or not the radiographing apparatuses 3A to 3C to be used for radiographing can perform serial radiography and/or information of the frame rates. Then, in a case where it is judged that long-length serial radiography is not possible using combination of the selected radiographing apparatuses 3A to 3C, an alarm indicating that radiographing is not possible and its reason are displayed, for example, in the display field 432b indicating whether or not radiographing is possible/a status of the radiographing screen 432 as an error message. For example, in a case where the selected radiographing apparatuses 3A to 3C include a radiographing apparatus which cannot perform serial radiography, it is judged that radiographing is not possible, and an alarm indicating that radiographing is not possible is displayed. Further, identification information of the radiographing apparatuses 3A to 3C which cannot perform serial radiography, and a position where the apparatus is loaded are displayed (for example, information of the corresponding radiographing apparatuses 3A to 3C as to whether or not serial radiography is possible is displayed in a different color).

Further, in a case where frame rates of the selected all of the radiographing apparatuses 3A to 3C are not the same, it is judged that radiographing is not possible, and an alarm indicating that radiographing is not possible and a message indicating that frame rates are not the same, are displayed at the display 43.

By this means, the radiographer can easily confirm whether or not it is possible to perform long-length serial radiography using combination of the selected radiographing apparatuses 3A to 3C. Further, in a case where long-length serial radiography is not possible with the combination, the radiographer can easily know the reason, so that the radiographer can quickly take appropriate measures (such as selecting another radiographing apparatus 3 and replacing the radiographing apparatus).

Further, in a case where the selected radiographing apparatuses 3A to 3C include the radiographing apparatus 3 which cannot perform serial radiography, the console 4 may perform control so as to make it impossible to perform radiographing by disabling depression of the irradiation instruction switch 5, or the like. By this means, it is possible to reliably prevent long-length serial radiography from being erroneously performed although the selected radiographing apparatuses 3A to 3C include the radiographing apparatus 3 which cannot perform serial radiography.

[Measure 2 in a Case of not Supporting Serial Processing/Mismatch of Frame Rates]

In a case where only the radiographing apparatuses 3 whose frame rates are different exist under a radiographing environment controlled by the console 4, the console 4 may judge whether or not, using a frame rate of one of the radiographing apparatuses 3A to 3C as a reference frame rate, radiographing is possible while frame rates of the other radiographing apparatuses 3A to 3C are adjusted at a frame rate of N times (N is an integer) of the reference frame rate. Then, in a case where it is judged that radiographing is possible, the console 4 may display a message indicating that radiographing is possible at frame rates of the radiographing apparatuses 3A to 3C, for example, on the radiographing screen 432. Further, the console 4 may judge a region of interest based on a portion to be radiographed and radiographing manipulation of the selected radiographing order information, and may display recommended arrangement of the radiographing apparatuses 3A to 3C in the display field 432b indicating whether or not radiographing is possible/a status, or the like, of the radiographing screen 432 so that the radiographing apparatuses 3A to 3C with higher frame rates are arranged in the region of interest. By this means, even in a case where only radiographing apparatuses 3A to 3C whose frame rates are different exist, it is possible to perform long-length serial radiography. Further, by displaying recommended arrangement of the radiographing apparatuses 3A to 3C so as to encourage arrangement such that a frame rate in the region of interest becomes higher, it is possible to perform radiographing without degrading image quality of the region of interest. Still further, it is also possible to make setting such that, in a case where the radiographing apparatus 3 with a high frame rate is not disposed in the region of interest, the console 4 does not allow radiographing.

In a case where, using a frame rate of one of the radiographing apparatuses 3A to 3C as a reference frame rate, radiographing is possible while frame rates of the other radiographing apparatuses 3A to 3C are adjusted at a frame rate of N times of the reference frame rate, for example, the console 4 sets radiographing conditions (irradiation conditions) at the radiation control apparatus 1 so that radiation is radiated while the frame rates are adjusted at the highest frame rate. In this case, as illustrated in FIG. 34A, while there is a possibility that radiation is radiated in the middle of read-out/initialization at the radiographing apparatuses 3 whose frame rates are low (in FIG. 34A, the radiographing apparatuses 3B and 3C), because electric charges of the radiation are accumulated as a light receiving amount for the next frame radiographing, while there is a possibility that a slight residual image is generated for an operation as a radiograph, there is a possibility that the radiograph can be sufficiently used in a case where a slow dynamic state is radiographed.

In this manner, by radiating radiation in accordance with the radiographing apparatus 3 which can perform radiographing at the highest frame rate, it is possible to radiograph a region where the radiographing apparatus 3 with the highest frame rate is disposed more precisely than in other regions. In other words, by disposing the radiographing apparatus 3 with the highest frame rate in the region of interest, it is possible to precisely radiograph the region of interest at a higher frame rate, so that it is possible to realize precise diagnosis for the region of interest.

Alternatively, in a case where, using a frame rate of one of the radiographing apparatuses 3A to 3C as a reference frame rate, it is possible to perform radiographing while frame rates of the other radiographing apparatuses 3A to 3C are adjusted at a frame rate of N times of the reference frame rate, for example, the console 4 sets irradiation conditions at the radiation control apparatus 1 so that radiation is radiated while the frame rates are adjusted at the lowest frame rate. In this case, as illustrated in FIG. 34B, while, at the radiographing apparatus 3 whose frame rate is high (in FIG. 34B, the radiographing apparatus 3A), read-out/initialization is performed in a frame for which radiation is not radiated, the radiographing controller 31 can perform control so that an image at that time is not stored within the radiographing apparatus 3, or is not transferred to the console 4, or the like, even if the image is stored. By this means, at the radiographing apparatus 3 whose frame rate is high, because read-out/initialization can be performed further again in addition to read-out/initialization of images upon irradiation of radiation, compared to a case where read-out/initialization is not performed again, a state of radiation detection element 32d is refreshed, so that it is possible to improve image quality. Alternatively, it is also possible to employ a configuration where a frame image at a timing at which radiation is not radiated is acquired as a dark image (a noise image in which radiation is not radiated), and, at the radiographing controller 31 or the console 4, the frame image is subtracted from the previous and subsequent frame images as noise components of one or both of the previous and subsequent frame images. With such a configuration, it is possible to obtain an image from which noise components are removed with the most recent dark image, so that it is possible to acquire an image with significantly improved image quality.

Here, there is a case where a dark image captured (electric charges are accumulated) at a timing at which radiation is not radiated at the radiographing apparatus 3 with a high frame rate in a case where setting is made such that radiation is radiated while the frame rates are adjusted at the lowest frame rate as described above, may be affected by a pressure received by the radiographing apparatus 3. In other words, as a result of the radiation detector 32 of the radiographing apparatus 3 being distorted by a pressure received by the radiographing apparatus 3 by the object under examination leaning against the radiographing apparatus 3, distortion occurs at a portion where a pressure is applied, of the radiation detection element 32d inside the radiation detector 32. In other words, it is possible to know distribution of a pressure received by the radiographing apparatus 3 from the dark image captured at a timing at which radiation is not radiated at the radiographing apparatus 3 whose frame rate is high. Therefore, during radiographing, at the console 4, radiographing is performed while the dark image is analyzed, and, for example, change of a pressure provided to the radiographing apparatus 3 by the object under examination, that is, body motion of the object under examination is detected. Then, in a case where body motion is large, because there is a possibility that body motion which is not appropriate for radiographing may occur, a message indicating that the body motion is large is output. For example, by displaying at the display 43 a message or outputting sound indicating that there is a possibility that body motion which is not appropriate for radiographing occurs, it is possible to issue an alarm to the radiographer that there is a possibility that the object under examination moves the body. By this means, the radiographer can regard that there is body motion which exceeds an allowable range, and can stop the radiographing. Alternatively, a monitor may be provided at a position where the object under examination can see the monitor, and the console 4 may perform control to display an alarm at the monitor so that the object under examination does not move the body.

Because it is possible to measure a pressure received by the radiographing apparatus 3 or measure distribution of the pressure by analyzing the dark image in this manner, it becomes possible to predict a state (such as body motion) of the object under examination from the measured pressure or distribution of the pressure. Further, it becomes possible to appropriately issue an alarm or stop radiographing based on the prediction.

Note that a pattern in which radiation is radiated while the frame rates are adjusted at the lowest frame rate described above, that is, a pattern in which, for the radiographing apparatus 3 whose frame rate is high, radiation is radiated at a frame rate of 1/N of the high frame rate, can also be used in radiographing by one radiographing apparatus 3 as well as in radiographing by a plurality of radiographing apparatuses 3. In other words, also in radiographing using one radiographing apparatus 3, the radiographing controller 31 or the console 4 can know a state of the object under examination by analyzing the dark image, and can issue an alarm in accordance with the state of the object under examination or can stop radiographing. Further, it is also possible to perform the above-described analysis on a dark image acquired upon positioning for adjusting a position of the object under examination before radiographing as well as on a dark image during a radiographing period. Further, it is possible to know a state of the object under examination from an analysis result of the dark image, so that it is possible to issue an alarm in accordance with the state of the object under examination or stop radiographing.

[Display of Remaining Amount of Power]

Because, in serial radiography, a plurality of frame images are successively captured, the radiographing apparatuses 3A to 3C to be used for radiographing require power for capturing a plurality of frame images. However, conventionally, in a case where serial radiography is performed using the radiographing apparatuses 3A to 3C which perform part of radiographing using at least power accumulated in batteries of the own apparatuses, as a result of radiographing being performed without confirming that whether or not an amount of power required for capturing the above-described plurality of frame images is left, a problem occurs that radiographing becomes impossible halfway, and the object under examination is uselessly exposed to radiation. Further, confirming whether the remaining battery levels of all the radiographing apparatuses 3A to 3C to be used are sufficient for capturing radiographs is troublesome work.

Therefore, for example, as described above, in step S8 of FIG. 4, FIG. 5, FIG. 11 and FIG. 12, the radiographing apparatuses 3A to 3C transmit information of the remaining amount of power of the own apparatuses to the console 4. As illustrated in FIG. 7, the console 4 displays the respective remaining amounts of power of the radiographing apparatuses 3A to 3C, for example, on the radiographing screen 432. Further, it is also possible to judge whether battery amounts sufficient for serial radiography to be performed hereafter are left at all of the radiographing apparatuses 3A to 3C and display the judgement result (for example, display in the display field 432b indicating whether or not radiographing is possible/a status in FIG. 7, display the remaining amounts of power of the corresponding radiographing apparatuses 3A to 3C in a different color, or the like). By this means, the radiographer can easily confirm the remaining amounts of power of the radiographing apparatuses 3A to 3C to be used for radiographing and can perform radiographing. In a case where a radiographing instruction to perform long-length serial radiography is issued, while it is necessary to perform confirmation for all the radiographing apparatuses 3A to 3C to be used for radiographing, because the remaining amounts of power of the respective radiographing apparatuses 3A to 3C are automatically displayed at the display 43 of the console 4, it is possible to save labor, so that it is possible to promptly perform radiographing.

[Display of Image Transfer Timing]

Further, to perform long-length serial radiography, it is necessary to appropriately designate how to process a plurality of radiographs (frame images) after radiographing. As processing to be performed on images after radiographing, for example, there is a case where the images are once stored in the memories within the radiographing apparatuses 3A to 3C during the radiographing period and transferred to an image processor such as the console 4 after radiographing is finished, and there is also a method in which the images are transferred to the image processor such as the console 4 for each time of radiographing during the radiographing period. In a case where such setting is not made at all of the radiographing apparatuses 3A to 3C using a method intended by the radiographer or the apparatus, there is a problem that, as a result of radiographing failing, the object under examination is uselessly exposed to radiation. Further, making settings at all of the individual radiographing apparatuses 3A to 3C is troublesome work, which is problematic.

Therefore, for example, as described above, in step S8 of FIG. 4, FIG. 5, FIG. 11 and FIG. 12, the radiographing apparatuses 3A to 3C transmit information of a transmission method (during radiographing/after radiographing) of radiographs set at the own apparatuses, to the console 4. For example, as illustrated in FIG. 7, the console 4 displays the transmission method (during radiographing/after radiographing) of radiographs set at the respective radiographing apparatuses 3A to 3C on the radiographing screen 432, and changes setting of the designated transmission method of radiographs of the radiographing apparatuses 3A to 3C in response to an operation by the radiographer. By this means, the radiographer can easily confirm the transmission method of radiographs of all the radiographing apparatuses 3A to 3C to be used and can appropriately set the transmission method of radiographs.

Further, while setting as to how to process a plurality of radiographs of the respective radiographing apparatuses 3A to 3C after radiographing may be designated by the radiographer from the radiographing screen 432, for example, the setting may be automatically made by the console 4 based on remaining capacity of the memories, or the like, of the selected radiographing apparatuses 3A to 3C. By this means, it is possible to save labor for individually making setting. Further, it is possible to prevent the object under examination from being uselessly exposed to radiation as a result of radiographing failing by captured radiographs being unable to be stored in the memories.

[Display of Remaining Capacity of Memory]

Further, in a case where serial radiography is performed, and images are once stored in the memories within the radiographing apparatuses 3A to 3C without being transferred while radiographing is performed, it is necessary to store a plurality of frame images. However, conventionally, in a case where capacity of memories required for storing the above-described plurality of images is not left in part of the radiographing apparatuses 3A to 3C to be used for radiographing, there is a problem that the object under examination is uselessly exposed to radiation as a result of radiographing failing by images being unable to be stored halfway. Further, individually confirming the remaining capacity of the memories of the all of the individual radiographing apparatuses 3A to 3C to be used for radiographing is troublesome work, which is problematic.

Therefore, for example, as described above, in step S8 in FIG. 4, FIG. 5, FIG. 11 and FIG. 12, the radiographing apparatuses 3A to 3C transmit information of the remaining capacity of the memories to the console 4. As illustrated in FIG. 7, the console 4 displays the remaining capacity of the memories of the respective radiographing apparatuses 3A to 3C on the radiographing screen 432. Alternatively, it is also possible to judge whether the capacity of memories sufficient for serial radiography to be performed hereafter is left in all of the radiographing apparatuses 3A to 3C and display the judgement result (for example, display in the display field 432b indicating whether or not radiographing is possible/a status, display characters, or the like, of the remaining capacity of the memories of the corresponding radiographing apparatuses 3A to 3C in a different color, or the like). By this means, the radiographer can easily confirm the remaining capacity of the memories of the radiographing apparatuses 3A to 3C to be used for radiographing before performing the radiographing. In a case where a radiographing instruction to perform long-length serial radiography is issued, while it is necessary to perform confirmation for all of the radiographing apparatuses 3A to 3C to be used for radiographing, because the remaining capacity of the memories of the respective radiographing apparatuses 3A to 3C is automatically displayed at the display 43 of the console 4, it is possible to save labor, so that it is possible to promptly perform radiographing.

[Setting of Frame Rate]

In a case where the selected radiographing apparatuses 3A to 3C can perform radiographing at a plurality of frame rates, it is necessary to set an appropriate frame rate among these frame rates. Therefore, the console 4 automatically sets the frame rates of all of the selected radiographing apparatuses 3A to 3C at a predetermined frame rate, and displays that the frame rates are set at the predetermined frame rate. For example, display of the frame rates of the radiographing apparatuses 3a to 3C on the radiographing screen 432 illustrated in FIG. 7 is displayed at the set frame rate. Alternatively, the set frame rate is displayed in a color different from a color of other frame rates. By this means, it is possible to automatically set the frame rates of the respective radiographing apparatuses 3A to 3C at an appropriate frame rate.

Alternatively, it is also possible to set a high frame rate in the region of interest without setting the frame rates of all of the radiographing apparatuses 3A to 3C at the same frame rate. In this case, recommended arrangement of the radiographing apparatuses 3A to 3C is displayed, for example, in the display field 432b indicating whether or not radiographing is possible/a status, or the like, of the radiographing screen 432 so that the radiographing apparatus 3 whose frame rate is the highest is disposed in the region of interest. Alternatively, it is also possible to set a recommended frame rate as initial setting for each type of radiographing manipulation. Alternatively, it is also possible to display recommended combination among the selected radiographing apparatuses 3 (3A to 3C), the radiographing apparatuses 3 currently recognized by the console 4, the radiographing apparatuses 3 recognized by the console 4 in a specific period such as within one week, or the radiographing apparatuses 3 set at the consoles 4 as apparatuses to be used in the radiographing environment, and a recommended frame rate are displayed for each type of radiographing manipulation, or set the recommended combination and the recommended frame rate as initial setting. By this means, it is possible to set the frame rates of the radiographing apparatuses 3 (3A to 3C) to be used for radiographing at an appropriate frame rate.

[Setting of Resolution]

In a similar manner, in a case where the selected radiographing apparatuses 3A to 3C can perform radiographing at a plurality of types of resolution, it is necessary to set appropriate resolution from them. Therefore, the console 4 sets resolution of all of the selected radiographing apparatuses 3A to 3C at predetermined resolution, and display that the resolution is set. For example, display of the resolution of the respective radiographing apparatuses 3A to 3C on the radiographing screen 432 is displayed at the set resolution. Alternatively, the set resolution is displayed in a color different from a color of other types of resolution. By this means, it is possible to automatically set the resolution of the respective radiographing apparatuses 3A to 3C at appropriate resolution. Alternatively, it is also possible to set high resolution in the region of interest without making resolution of all the radiographing apparatuses 3A to 3C the same. In this case, recommended arrangement of the radiographing apparatuses 3A to 3C is displayed, for example, on the radiographing screen 432 so that the radiographing apparatuses 3A to 3C with high resolution are disposed in the region of interest. Alternatively, it is also possible to set recommended resolution as initial setting for each type of radiographing manipulation. Alternatively, it is also possible to display recommended combination among the radiographing apparatuses 3A to 3C loaded at a long-length radiographing platform or holder which is currently used for radiographing, the radiographing apparatuses 3A to 3C currently recognized by the console 4, the radiographing apparatuses 3A to 3C recognized by the console 4 in a specific period such as within one week, or the radiographing apparatuses 3A to 3C set at the console 4 as apparatuses to be used in the radiographing environment, and recommended resolution, or set the recommended combination and the recommended resolution as initial setting. By this means, it becomes possible to set resolution of the respective radiographing apparatuses 3A to 3C to be used for radiographing at appropriate resolution.

[Automatic Mode Change 1]

To perform long-length serial radiography, it is necessary to switch a mode of all of the radiographing apparatuses 3A to 3C to be used for radiographing from a waiting mode in which power consumption is small to a radiographing mode in which power consumption is large. Manually switching the mode of the individual radiographing apparatuses 3A to 3C is troublesome work. The radiographing controllers 31 of the radiographing apparatuses 3A to 3C of the above-described embodiment automatically switch the mode to the radiographing mode when an instruction to start long-length serial radiography is issued. By this means, it is possible to save labor for switching the mode to the radiographing mode, so that it is possible to promptly perform radiographing.

[Automatic Mode Change 2]

Further, the radiographing apparatuses 3A to 3C which can perform serial radiography have two operation modes of a serial radiography mode and a still radiography mode. To perform long-length serial radiography using a plurality of radiographing apparatuses 3A to 3C, it is necessary to change the mode of all of the radiographing apparatuses 3A to 3C to be used for radiographing to the serial radiography mode. Changing the mode of all the individual radiographing apparatuses 3A to 3C is troublesome work, which is problematic. The radiographing controllers 31 of the radiographing apparatuses 3A to 3C of the above-described embodiment automatically switch the mode to the serial radiography mode when an instruction to start radiographing is issued under the radiographing conditions including serial radiography. By this means, it is possible to save labor for switching the mode to the serial radiography mode, so that it is possible to promptly perform radiographing.

[Display as to Whether or not Radiographing is Possible]

When the radiographer does not know whether or not all the radiographing preparation is completed and whether or not all of the radiographing apparatuses 3A to 3C is in a state where radiographing is possible, the radiographer does not know whether to start issuing an instruction to radiate radiation, which is problematic. Further, if radiographing is performed while all of the radiographing apparatuses 3A to 3C are not in a state where radiographing is possible, there is a problem that radiographing fails, and the object under examination is uselessly exposed to radiation.

Therefore, the console 4 displays whether or not all of the radiographing apparatuses 3A to 3C can perform radiographing (can perform long-length radiography), at the display 43. Further, in a case where radiographing is not possible, the reason thereof and the radiographing apparatus which cannot perform radiographing among the radiographing apparatuses 3A to 3C are displayed at the display 43.

Further, for example, the console 4 confirms that the above-described conditions for making it possible for the radiographing apparatuses 3A to 3C to perform radiographing are satisfied, the conditions including:

combination of radiographing apparatuses which can perform serial radiography remaining capacity of memories, remaining amount of power transition to serial radiography mode coordination with synchronization source, judges whether or not the state is a state where radiographing is possible based on a confirmation result, and displays a judgement result at the display 43. In a case where radiographing is not possible, the reason thereof, and the radiographing apparatus which cannot perform radiographing among the radiographing apparatuses 3A to 3C are displayed at the display 43. By this means, the radiographer can confirm that radiographing is possible and can reliably perform radiographing.

Further, the console 4 performs the above-described confirmation of the states of the radiographing apparatuses 3A to 3C at a halfway timing such as for each time of radiographing of each frame image in long-length serial radiography also during radiographing, and confirms whether at least one of the above-described conditions for the state where radiographing is possible is satisfied. In a case where the conditions for the state where radiographing is possible are not satisfied, a message indicating that the conditions are not satisfied is output. For example, the console 4 preferably takes measures such as displaying an alarm to the radiographer at the display 43, performing control to stop radiographing, and displaying a condition for the state where radiographing is possible, which is not satisfied. By this means, it is possible to capture each frame image in a state where radiographing can be reliably performed.

[Measure 1 Against Abnormality During Long-Length Serial Radiography]

In a case where radiographing is continued although at least one of the radiographing apparatuses 3A to 3C is put into a state where radiographing is not possible (conditions for the state where radiographing is possible are no longer satisfied) during long-length serial radiography, there is a problem that the object under examination is uselessly exposed to radiation as a result of radiographing failing. Further, if the radiographer does not know the reason why the state becomes a state where radiographing is not possible, because the radiographer does not know which state should be corrected to perform radiographing again, there is a problem that it takes a lot of trouble and time to return the state to a state where radiographing is possible again.

Therefore, the console 4 performs the above-described state confirmation of the radiographing apparatuses 3A to 3C during long-length serial radiography (for example, for each time of capturing a frame image), and, in a case where an abnormality occurs at least one of the radiographing apparatuses 3A to 3C, performs control to stop radiographing. Alternatively, identification information of the radiographing apparatus 3 at which the abnormality occurs, the reason, or the like, are displayed at the display 43.

By this means, in a case where the state becomes a state where radiographing is not possible during long-length serial radiography, it is possible to reliably deliver that the state becomes a state where radiographing is not possible to the radiographer, or stop radiographing.

[Measure 2 Against Abnormality During Long-Length Serial Radiography]

In a case where radiographing is continued although the state of the radiation control apparatus 1 becomes a state where radiographing is not possible during long-length serial radiography, there is a problem that the object under examination is uselessly exposed to radiation by radiographing failing. Further, if the radiographer does not know the reason why the state becomes a state where radiographing is not possible, because the radiographer does not know which state should be corrected to perform radiographing again, there is a problem that it takes a lot of trouble and time to return the state to a state where radiographing is possible again.

Therefore, the console 4 confirms the state of the radiation control apparatus 1 during long-length serial radiography (for example, for each time of capturing a frame image), and, in a case where an abnormality occurs at the radiation control apparatus 1, performs control to stop radiographing or display the reason why the abnormality occurs at the display 43.

By this means, in a case where the state becomes a state where radiographing is not possible during long-length serial radiography, it is possible to reliably deliver that the state becomes a state where radiographing is not possible to the radiographer, or stop radiographing.

[Radiograph Connection Processing]

To generate a long-length dynamic image, it is necessary to calculate connection positions of a plurality of radiographs acquired through the above-described long-length serial radiography for each frame and perform connection processing at the calculated connection positions (concerning calculation of connection positions, see, for example, JP 3888046B, JP 5644195B, and JP 5834971B). However, because it requires calculation time for such calculation of connection positions, it is difficult to promptly display a long-length dynamic image obtained through radiographing. For example, in a preview for allowing confirmation as to whether radiographing intended by the radiographer has been performed after radiographing, while the radiographer desires to promptly confirm the captured long-length dynamic image, it takes time to calculate connection positions for each frame, which inhibits prompt confirmation of the radiograph. Particularly, in radiographing of a patient at a medical institution, because there is a possibility that radiographing requires to be performed again, it is necessary to keep the patient at a radiographing position until confirmation of a preview is finished, and, thus, it is desired to promptly confirm the radiograph to judge whether or not an abnormality occurs during radiographing.

Because most of abnormalities which require re-radiographing are abnormalities such that, as a result of a patient making an unintended move (body motion) during the radiographing period, a portion (portion of interest) which is important upon diagnosis goes out from an image region, or the radiograph is not appropriate for use in diagnosis, it is often the case that whether it is necessary to perform radiographing again can be judged without performing connection processing. Further, the region of interest is typically not disposed in a connection region across a plurality of radiographing apparatuses 3 and, in most cases, the region of interest is disposed near the center of the specific radiographing apparatus 3. Therefore, in most cases, it is not necessary to connect radiographs also in a case where it is judged whether radiographing quality of the radiographs is sufficient for diagnosis.

Therefore, the consoles 4 of the systems 100 to 300 preferably have a simple display mode in which radiographs are displayed without performing connection processing or while thinning out connection processing (using frame images at part of timings) as one of image display modes after radiographing.

Figure 35:
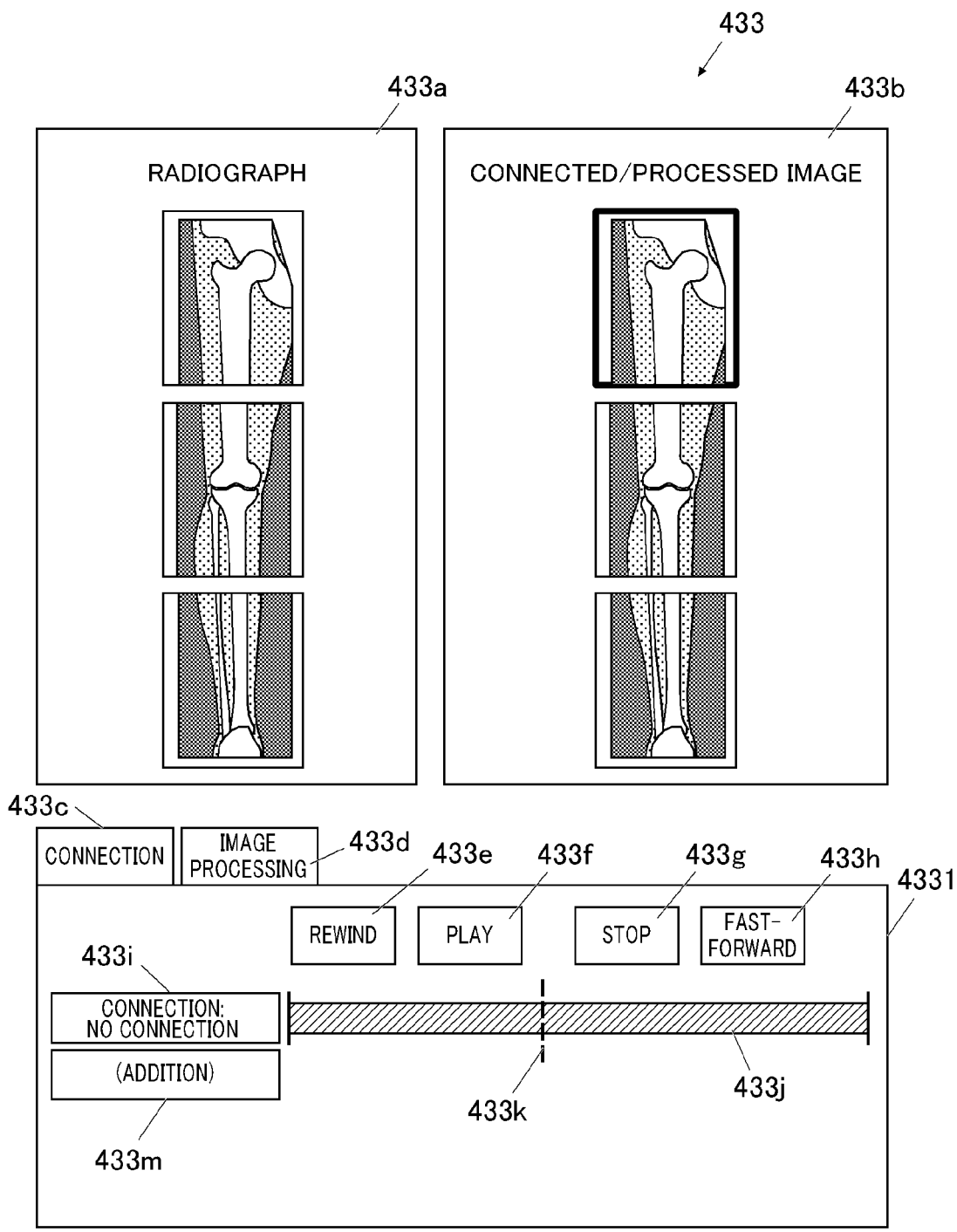
FIG. 35 is a view illustrating an example of a preview screen.

FIG. 35 is a view illustrating an example of a preview screen 433 to be displayed by the console 4 at the display 43 after radiographing is completed in a case where the simple display mode is set. As illustrated in FIG. 35, in the preview screen 433, a radiograph display region 433a, a processed image display region 433b, a connection tab 433c, an image processing tab 433d, or the like, are provided. The console 4 performs processing on the radiographs (frame images) obtained through long-length serial radiography or displays (reproduces) a preview in accordance with an operation from the preview screen 433.

The radiograph display region 433a is a region where the radiographs respectively acquired from the radiographing apparatuses 3A to 3C are arranged and displayed. For example, a representative frame image (for example, a first frame image) among the radiographs respectively acquired from the radiographing apparatuses 3A to 3C is displayed. The processed image display region 433b is a region where a preview of processed images obtained by performing connection processing and/or image processing on radiographs is displayed. The connection tab 433c is a tab indicating display of an operation screen to which a connection position calculation method for radiographs can be input. As the connection position calculation method, for example, "no connection" is set by default. The image processing tab 433d is a tab indicating an operation screen to which processing conditions of image processing for radiographs can be input. FIG. 35 illustrates an example where the connection tab 433c is depressed.

In an operation screen 4331 displayed by the connection tab 433c being depressed by an operator, a rewind button 433e, a play button 433f, a stop button 433g and a fast-forward button 433h are provided, and through an operation of these buttons by the radiographer, the console 4 reproduces and displays part, a plurality of, or all of radiographs captured at the same timing in long-length serial radiography, in the processed image display region 433b, or performs fast-forwarding, rewinding, skipping to a specific position and reproduction, or the like. Part, a plurality of or all of the images to be reproduced can be actively switched by images which are desired to be reproduced among images displayed in the processed image display region 433b being clicked with a mouse, or the like, of the operator.

Further, in the operation screen 4331, a connection position calculation button 433i on which the connection position calculation method is displayed (for example, "no connection" indicating that the connection position is not calculated is displayed by default), a time axis 433j, a dotted line 433k indicating a reproduction position, or the like, are displayed. When the dotted line 433k is moved along the time axis 433j using the mouse, or the like, the console 4 changes images to be displayed in the processed image display region 433b.

As described above, because "no connection" is set as the connection position calculation method by default, and the console 4 displays a preview without performing connection processing of frame images captured at the same timing in long-length serial radiography, the console 4 can promptly provide a preview of a long-length dynamic image. Further, by operating part of the displayed radiographs, it is also possible to display (reproduce) a preview of only part of radiographs among radiographs (frame images) captured at the same timing.

Note that, when images are displayed in the processed image display region 433b, the console 4 arranges and displays the images in a radiographing direction or in radiographing order instead of simply arranging the images. For example, in a case where radiographing is performed while the radiographing apparatuses 3A to 3C are arranged from above in this order, images are arranged and displayed in the radiographing order while respective relative positions are reflected, such that an image obtained from the radiographing apparatus 3A is displayed in an upper part, an image obtained from the radiographing apparatus 3B is displayed in a middle part, and an image obtained from the radiographing apparatus 3C is displayed in a lower part.

Further, images may be displayed as a moving image in which the images are connected in a pseudo manner by bringing images arranged in a radiographing direction or in radiographing order close to each other or displaying the images while part of the images are made to overlap with each other.

Here, by the connection position calculation button 433i of the operation screen 4331 being selected with the mouse, or the like, it is possible to display a pull-down menu of the connection position calculation method, and if another connection position calculation method is selected from the pull-down menu, the console 4 performs connection processing on radiographs using the selected connection position calculation method and displays the processed images in the processed image display region 433b. Examples of the connection position calculation method which can be selected from the pull-down menu, can include a method in which connection processing is performed after connection positions are calculated using frame images at part of timings of the captured long-length dynamic image, and a method in which connection processing is performed after connection positions (individual positions) of frame images at all timings are individually calculated. Examples of the method in which connection positions are calculates using frame images at part of timings can include, for example, processing of the following (1) to (4).

Figure 36:
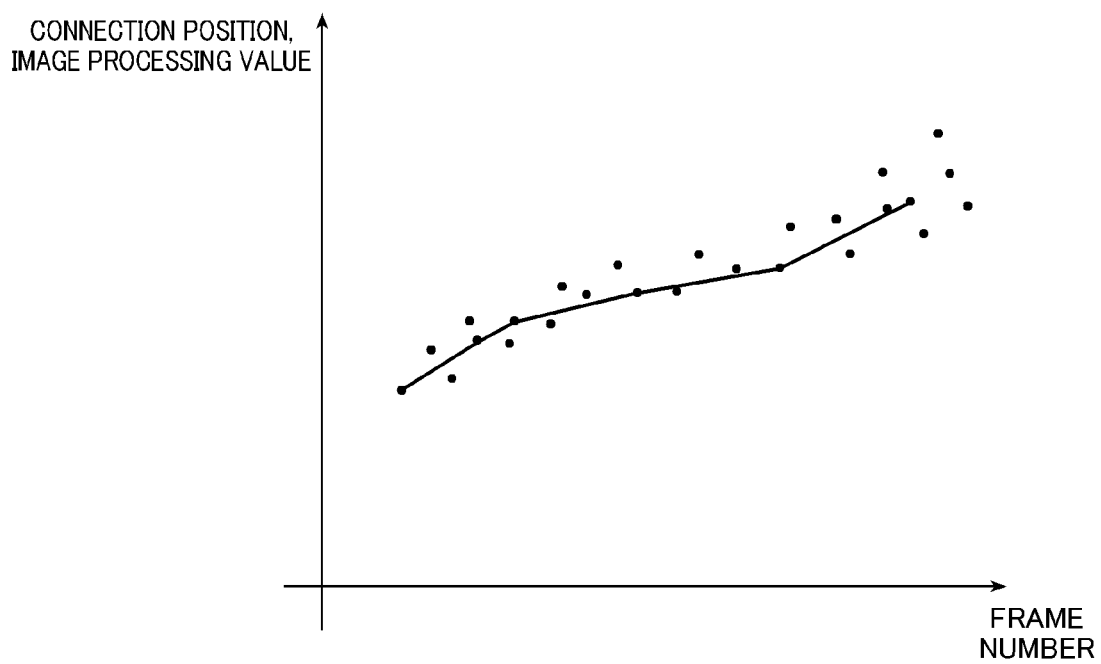
FIG. 36 is a view for explaining an approach for calculating a connection position (image processing value) of frame images at a same timing obtained in a long-length image.

(1) Connection positions are calculated for each fixed interval of a series of frame images, and connection positions are obtained through interpolation processing for frame images for which the connection positions are not calculated (see FIG. 36).

Figure 37:
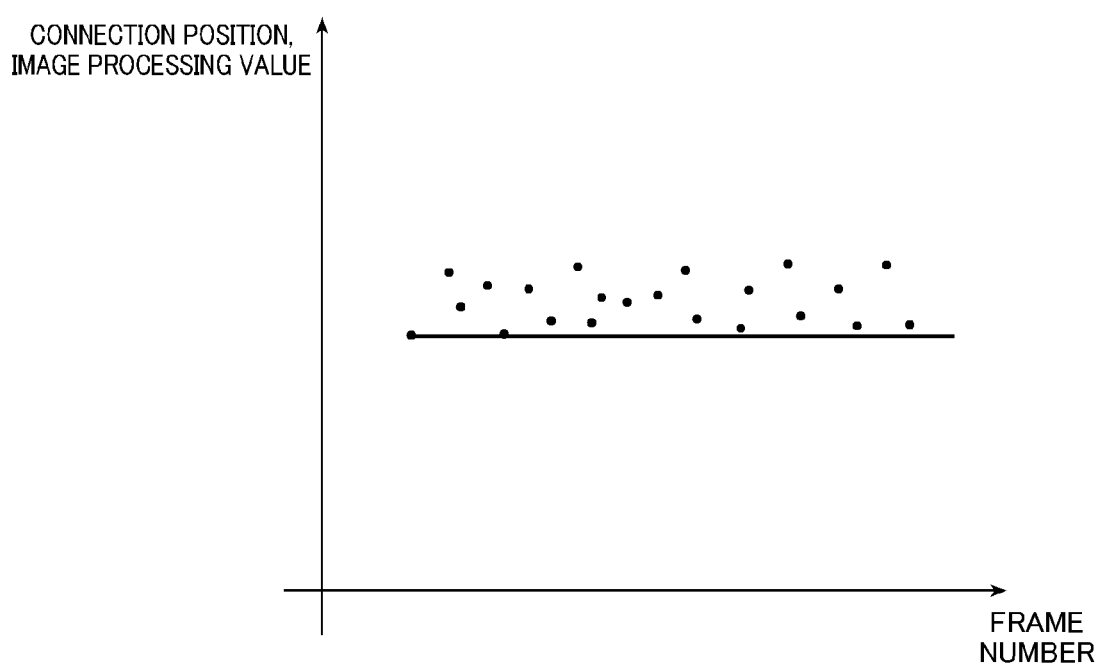
FIG. 37 is a view for explaining an approach for calculating a connection position (image processing value) of frame images at a same timing obtained in a long-length image.

(2) A connection position is calculated using the first frame image, and the connection position for the first frame image is set as connection positions for the other frame images (see FIG. 37).

Because the positions of the radiographing apparatuses 3A to 3C are fixed during long-length serial radiography, it can be considered that the connection positions do not move so much. Therefore, by calculating a connection position using only the first and the last frame images and obtaining connection positions for the other frame images through interpolation as in (2), it is possible to promptly provide a preview of a long-length dynamic image.

Figure 38:
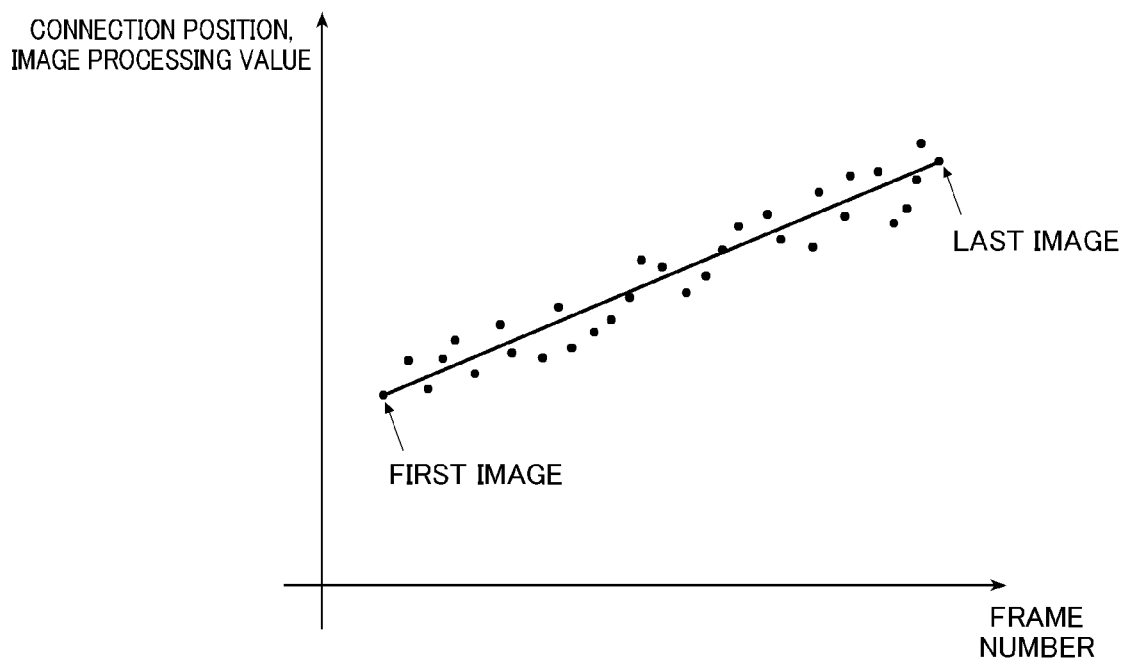
FIG. 38 is a view for explaining an approach for calculating a connection position (image processing value) of frame images at a same timing obtained in a long-length image.

(3) A connection position is calculated using the first frame image and the last frame image, and the other frame images are connected at positions obtained through linear interpolation of the connection positions (it is also possible to use an interpolation method other than linear interpolation) (see FIG. 38).

Typically, as one type of fluctuation, an offset component which monotonously fluctuates the position of the radiograph over elapsed time is included. By using positions of the first and the last radiographs in calculation of the connection position, it is possible to remove this offset component.

Figure 39:
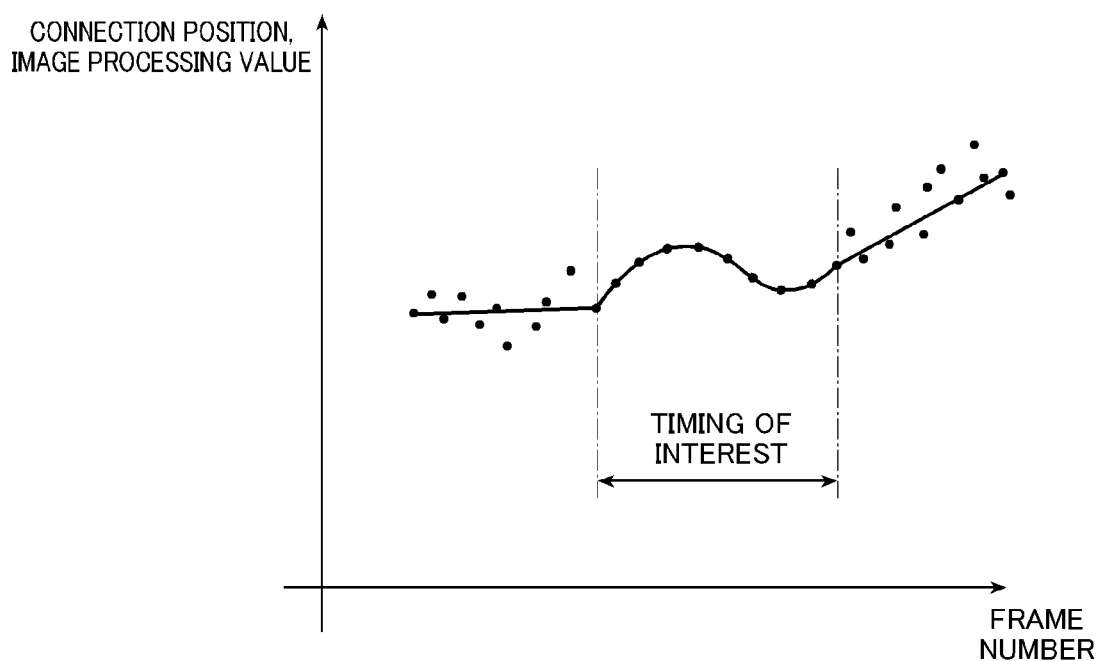
FIG. 39 is a view for explaining an approach for calculating a connection position (image processing value) of frame images at a same timing obtained in a long-length image.

(4) Connection positions are individually calculated for frame images in a specific period, and values of interpolants obtained by interpolating the connection positions are used as connection positions for frame images in other periods (see FIG. 39).

It takes time for processing if processing of calculating connection positions for frame images constituting a long-length dynamic image, at individual timings, is performed. Meanwhile, concerning a period during which confirmation is performed particularly carefully in diagnosis, it is desired to perform more detailed processing than that in other periods, so as to make a diagnosis with improved radiograph quality. Therefore, for example, for frame images in a timing period of interest, which includes a dynamic state which is important for diagnosis, connection positions are calculated for the individual frame images instead of interpolation being performed. For frame images in a period other than the timing period of interest, connection processing is performed using values obtained by extrapolating interpolants created with the value in the timing period of interest as the connection positions. It is also possible to use an interpolation method other than linear interpolation as interpolation. For example, it is possible to use multi-order function interpolation or spline interpolation.

As the timing period of interest, for example, in a case where a dynamic state of the breast is serially radiographed, because breathing is not controlled in the beginning, at least a period of one breathing cycle after a predetermined period has elapsed can be set as the timing period of interest.

By performing processing which takes time while narrowing down timings at which it is desired to improve image quality, it is possible to improve image quality of a required portion and shorten a processing period.

Here, in graphs illustrated in FIG. 36 to FIG. 39, FIG. 41 and FIG. 42, values obtained in a case where the values are calculated at individual frame images are indicated with dots, and values calculated using frame image at part of timings which have been described above or which will be described below are indicated with lines.

Figure 40:
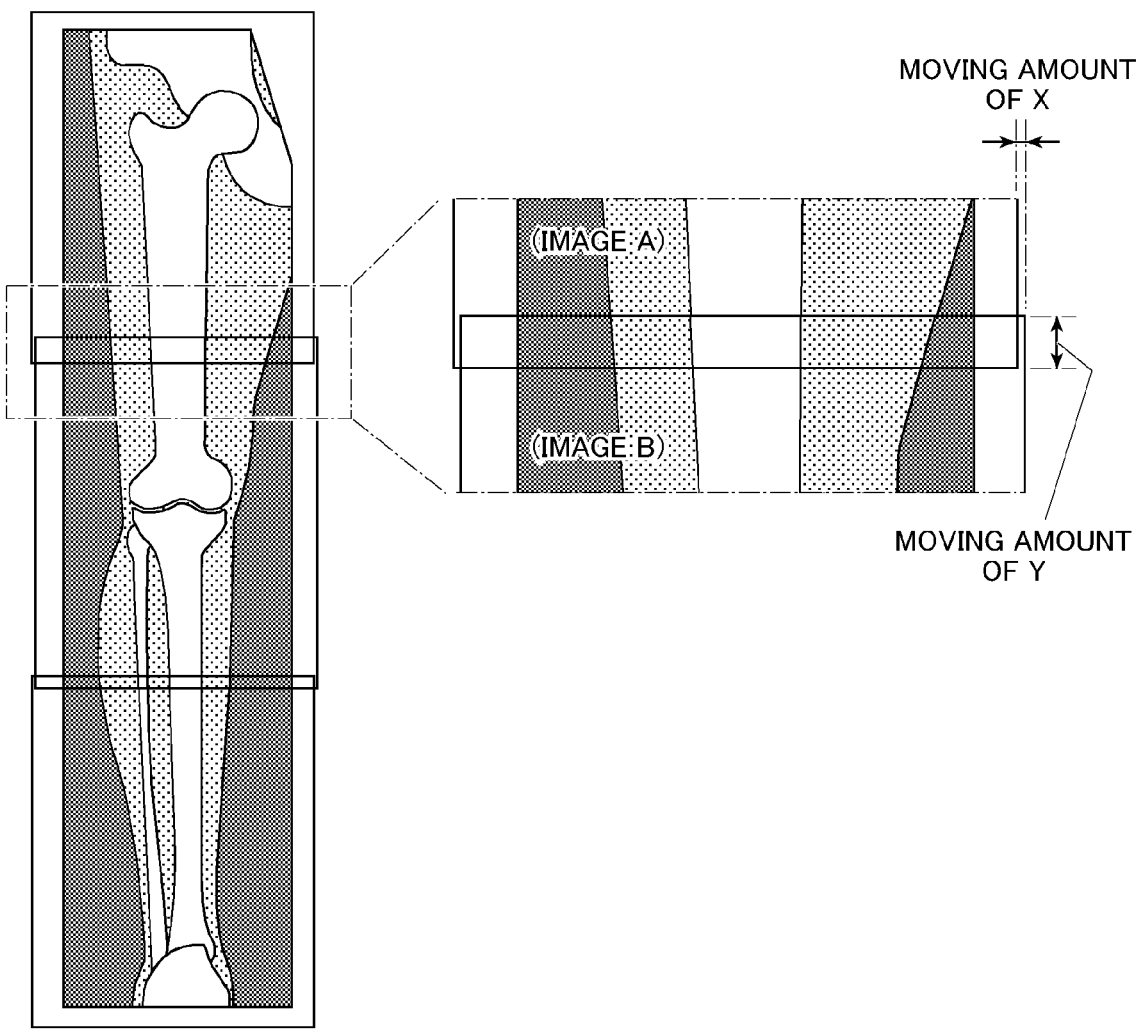
FIG. 40 is a view for explaining connection processing.

Note that, in connection processing, while connection is performed by calculating a moving amount of X and a moving amount of Y of each image as a connection position and moving each radiograph by X and Y as illustrated in FIG. 40, it is also possible to perform connection by rotating each image or changing magnifying power. Also concerning these rotating angle and magnifying power, connection processing may be performed by obtaining the rotating angle and the magnifying power when the frame images at respective timings are connected through interpolation processing, from the rotating angle and the magnifying power obtained with the frame images at part of timings in a similar manner to the connection position.

Further, in a case where frame images are connected after connection positions are calculated for each of the frame images (or while frame images are tinned out) captured at individual timings, there is a case where connection positions are different between adjacent frame images, and, in a case where such frame images are reproduced as a moving image, the moving image may be such that the connection positions are misaligned, which is an unfavorable moving image, and quality of the moving image may significantly degrade.

Figure 41:
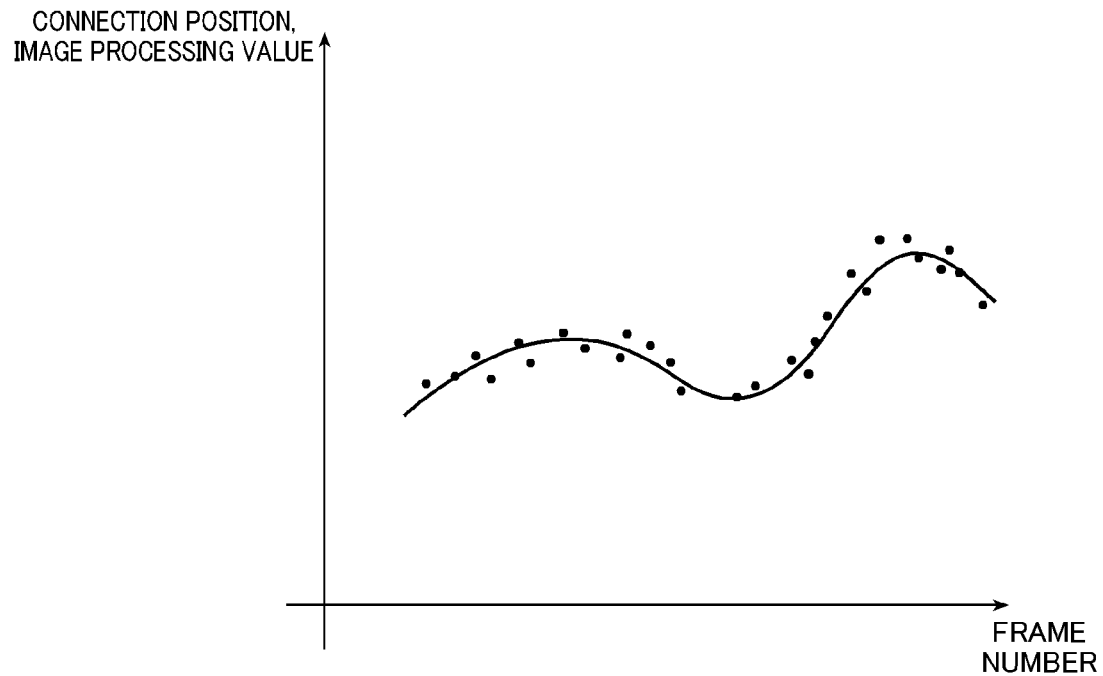
FIG. 41 is a view for explaining an approach for calculating a connection position (image processing value) of frame images at a same timing obtained in a long-length image.

Therefore, as illustrated in FIG. 41, in a case where connection positions are calculated with the respective frame images, it is preferable to connect the frame images after smoothing these connection positions. Particularly, in a case where a dynamic state such as, for example, breathing and blood flow, which fluctuates with a constant period, is radiographed, it is preferable to perform smoothing while approximating the connection position with a periodic function which suits the constant period. By this means, the connection positions between adjacent frame images do not become clumsy, so that a smooth dynamic image can be obtained, which makes it easier to make a diagnosis.

Further, it is also possible to make connection processing to be performed in a specific period, different from connection processing to be performed in other periods.

For example, in a case where a ventilatory function of the lung is serially radiographed, because there is less body motion during a period while the patient holds his/her breath, there is less fluctuation in the connection positions, and it is less necessary to determine the connection positions while taking into account the images for each frame. Meanwhile, during a period while the patient performs an operation of taking a breath in or out, because there is a high possibility that the connection positions change in association with the operation of taking a breath in or out, it is necessary to determine the connection positions while taking into account the respective images.

Figure 42:
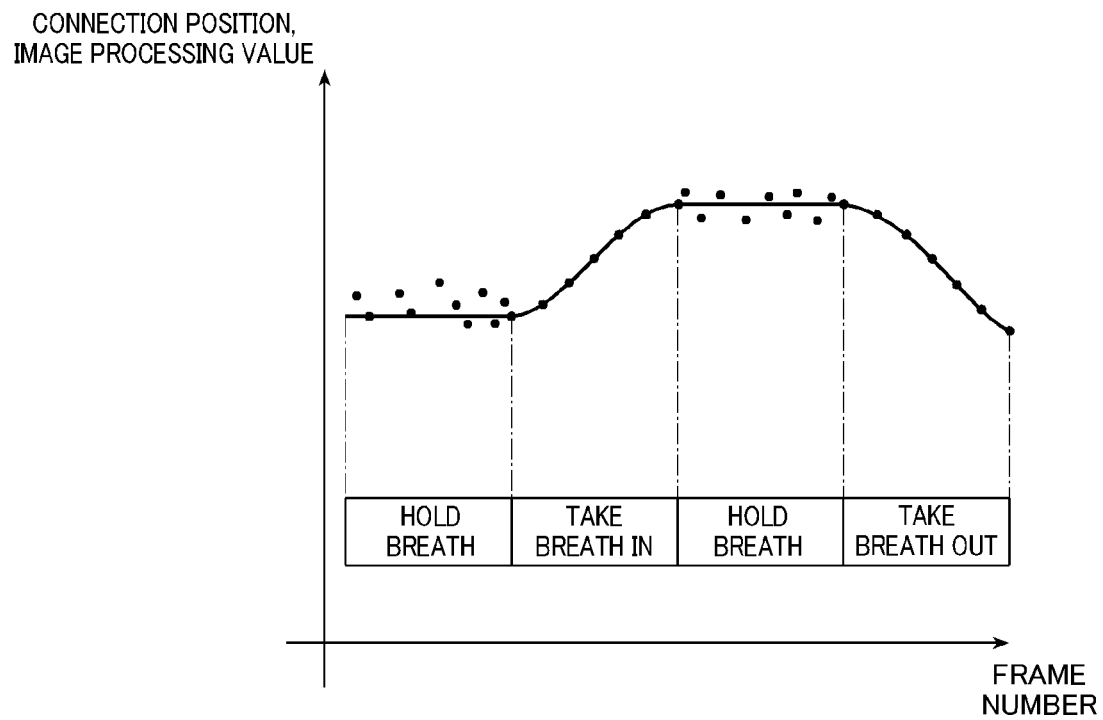
FIG. 42 is a view for explaining an approach for calculating a connection position (image processing value) of frame images at a same timing obtained in a long-length image.

Therefore, in a case where the ventilatory function of the lung is radiographed in long-length serial radiography, as illustrated in FIG. 42, by performing connection processing while calculating the connection positions for each frame for frame images at timings (period) of taking a breath in and frame images at timings (period) of taking a breath out, and calculating positions, the rotating angle, the magnifying power, or the like, which are parameters of connection, through the above-described interpolation processing, from values obtained with part of the frame images without calculating the connection positions for each frame during a period while the patient holds his/her breath, it is possible to speed up the processing. Alternatively, it is also possible to calculate connection positions for each frame for frame images at timings (period) of taking a breath in and for frame images at timings (period) of taking a breath out, while reducing frame images for which connection positions are to be calculated and determining connection positions through interpolation for frame images for which the connection positions are not calculated during a period while the patient holds his/her breath.

Alternatively, it is also possible to calculate connection positions at timings of interest (period of high interest) and not to calculate connection positions during other periods (not to perform connection processing or to perform interpolation).

The timings of interest (at which timings, a degree of interest is relatively high or low) are different in accordance with radiographing manipulation and types of targets to be diagnosed. For example, in a case where the ventilatory function of the lung is to be diagnosed in an image of a dynamic state of the breast, timings at which the patient holds his/her breath is less interested, and timings of taking a breath in or out at which fluctuation is large are the timings of interest. In a case where a blood flow function is the target to be diagnosed, timings at which the heart beats are the timings of interest. Therefore, it is also possible to store initial setting of processing in the console 4 for each type of radiographing manipulation (for each type of targets to be diagnosed) and use the initial setting. Further, it is also possible to use timings determined for each type of radiographing manipulation (for each type of targets to be diagnosed) as the timings of interest, and give an instruction of timings using instruction equipment such as, for example, auto voice.

By this means, by improving image quality by performing connection processing which requires a processing period with higher accuracy in a period of relatively high interest in accordance with radiographing manipulation (types of targets to be diagnosed) and omitting the connection processing in other periods, it is possible to shorten an overall processing period.

Further, as described above, the calculation method of the connection positions includes a method (individual positions) which relatively requires a processing period, but which is capable of calculating values close to values calculated from individual images, a method (interpolation), with which a processing period can be relatively reduced, and which uses interpolated values instead of using values calculated from the individual images, and a method (fixed positions) which diverts the connection positions calculated from other frame images.

Figure 43:
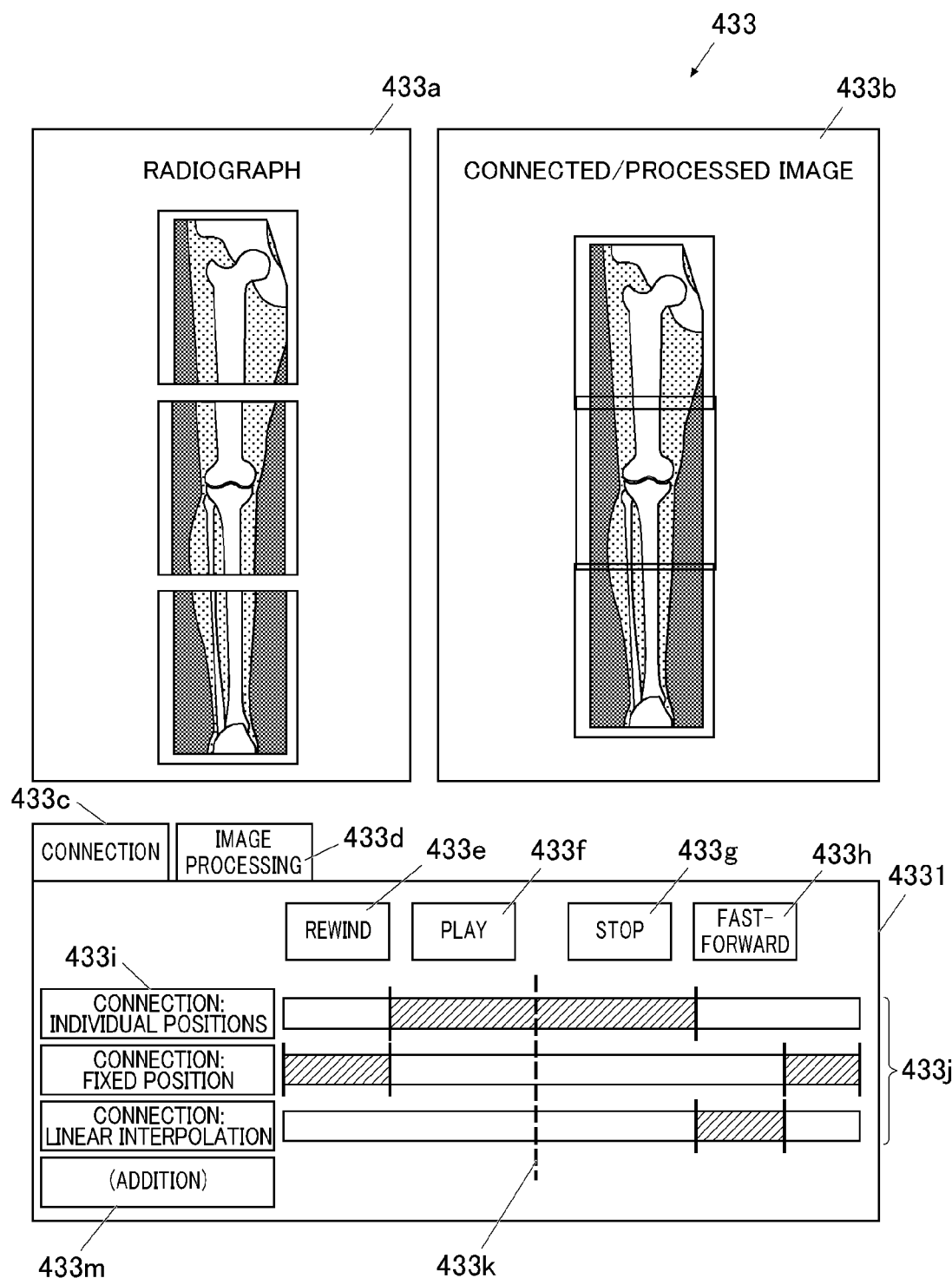
FIG. 43 is a view illustrating a user interface for setting a calculation approach of a connection position for each period of a long-length dynamic image.

Therefore, for example, as illustrated in FIG. 43, the calculation method of the connection positions may be set for each period of a long-length dynamic image by adding the calculation method of connection positions by depressing an addition button 433*m* on the preview screen 433 illustrated in FIG. 35, or the like, and designating a period in which the calculation method of the respective connection positions is to be applied on a time axis. By this means, it is possible to obtain a long-length dynamic image intended by the radiographer.

Further, while various methods as disclosed in, for example, JP 3888046B, JP 5644195B, JP 5834971B, or the like, have been proposed for calculation of connection positions, if a region to be searched is large when connection positions are searched for, most of the methods require a longer processing period. Meanwhile, there is a less possibility that connection positions become largely different between temporally adjacent frame images in calculation of connection positions for a long-length dynamic image obtained by successively performing radiographing in a relatively short period. Therefore, as illustrated in FIG. 44, it is preferable to narrow down a region for which connection positions are to be searched for to the vicinity of the connection positions of the previous frame images. Then, in a case where the connection positions have not been calculated or the connection positions are largely different from those of the previous images or surrounding images in search after the search range is narrowed down, it is preferable to perform search again while extending the search range. By this means, it is possible to shorten a period required for calculation of the connection positions, so that it is possible to promptly obtain a long-length dynamic image.

By the way, in a case where a problem occurs upon image processing which is performed in a post-process of the connection processing, there is a risk that the images may disappear. Further, the processing may include irreversible processing which makes it impossible to return the images to original images again, and there is a problem in a case where it is desired to undo the processing. Further, also in a case where it is possible to undo the processing, because a plurality of images exert influence in the connection region, there is a case where the images become unsharp, which is problematic in a case where it is desired to confirm images before connection.

Therefore, the console 4 stores and holds frame images acquired from the respective radiographing apparatuses 3A to 3C before connection in RAM, or the like. Further, in a case where there are a plurality of types of image processing, images before processing are stored and held in RAM, or the like, for each type of processing. Note that whether to store images before processing may be able to be selected by the user through an operation of the operator.

By this means, in a case where a problem occurs upon image processing, or in a case where it is desired to undo image processing, it is possible to confirm images before processing.

[Calculation of Image Processing Values]

In a case where captured images are used for a diagnosis, by performing various kinds of image processing such as contrast adjustment processing and emphasis processing of images on the radiographs, it is possible to obtain images which are more user-friendly for a person who makes a diagnosis, so that it is possible to help the person make a correct diagnosis. However, such image processing requires calculation, and there is a problem that it requires a calculation period. Further, because it is necessary to perform image processing on a plurality of frame images to make a diagnosis using a long-length dynamic image, it requires an extremely longer processing period than that for still images, and the processing period becomes problematic.

Here, the image processing is divided into processing of analyzing density information of an image and calculating an image processing value (adjustment value for adjusting the strength and level of image processing), and processing of performing correction processing on the density information of the image using the calculated image processing value. It requires a number of kinds of calculation processing to calculate the image processing value, and it takes time for processing depending on types of image processing.

Further, in another perspective, in a diagnosis using a long-length dynamic image, there is a case where change between frame images adjacent in a time direction is used for a diagnosis. For example, in analysis of ventilation of the lung, by analyzing a region of the lung from the density information of the image and analyzing a change amount, that is, increase and decrease of the region of the lung in a time direction, it is possible to analyze an amount of ventilation. However, in a case where an adjustment amount of the contrast adjustment processing on which such density information is assumed is largely different between frame images adjacent in a time direction, because the region of the lung is analyzed differently in a time direction from the density information subjected to contrast processing with the adjustment amount, it becomes impossible to correctly analyze the ventilation amount.

Further, in a case where image quality such as contrast or the adjustment amount for adjusting image quality such as contrast is largely different between frame images adjacent in a time direction even if the region of the lung is not analyzed as described above, in a case where, for example, density is largely different between the respective frame images, there is a problem that a moving image becomes clumsy in a case where the frame images are sequentially displayed, and image quality significantly degrades.

Therefore, as illustrated in FIG. 36, the console 4 calculates the image processing value using part of frame images (frame images at part of timings) instead of calculating the image processing value using all of the frame images of the long-length dynamic image, and performs image processing on the individual images with the image processing value obtained by interpolating the calculated image processing value.

By this means, it is possible to shorten a processing period required for calculation of the image processing value, so that it is possible to promptly provide a long-length dynamic image subjected to image processing.

Examples of a method for calculating the image processing value using part of the frame images can include, for example, processing of the following (1) to (4).

(1) The image processing value is calculated using the first frame image, and image processing is performed on the other frame images with the image processing value for the first frame image (see FIG. 37).

(2) The image processing value is calculated using the first and the last frames, and image processing is performed on the other frame images with the image processing value obtained by performing linear interpolation on the image processing value (see FIG. 38).

(3) The image processing value is calculated with frame images at specific intervals, and image processing is performed with the image processing value obtained by performing linear interpolation on the image processing value (see FIG. 39).

By performing calculation of the image processing value which takes time while narrowing down the timing to a timing at which it is desired to improve image quality, it is possible to improve image quality at a necessary portion and shorten a processing period.

Further, if processing is performed with the image processing values which are respectively calculated for individual frame images which constitute a long-length dynamic image, there is a case where the image processing values are considerably different between frame images adjacent in a time direction, and there is a problem that, in a case where the images are reproduced as a moving image, the moving image becomes clumsy, and image quality drastically degrades.

Therefore, as illustrated in FIG. 41, in a case where the image processing values are calculated at the respective frame images, it is preferable to perform image processing with the image processing values obtained by smoothing these image processing values. Particularly, in a case where a dynamic state which fluctuates with a constant period such as, for example, breathing and blood flow is radiographed, it is preferable to approximate and smooth the image processing values with a periodic function which suits the constant period. By this means, the moving image does not become clumsy as a result of the image processing values being considerably different between adjacent frame images, and becomes a smooth moving image, so that it is possible to make it easier to make a diagnosis.

Further, image processing to be performed in a specific period may be made different from image processing to be performed in other periods.

For example, in a case where a ventilatory function of the lung is serially radiographed, as illustrated in FIG. 42, by performing high-accuracy image processing which requires a long processing period on frame images at timings (period) of taking a breath in and frame images at timings (period) of taking a breath out, and performing image processing which requires a short processing period during a period while the patient holds his/her breath, the processing is speeded up.

By this means, it is possible to improve image quality by performing processing which requires a long processing period with higher accuracy in a period of relatively high interest in accordance with radiographing manipulation and types of targets to be diagnosed, and shorten an overall processing period.

Figure 45:
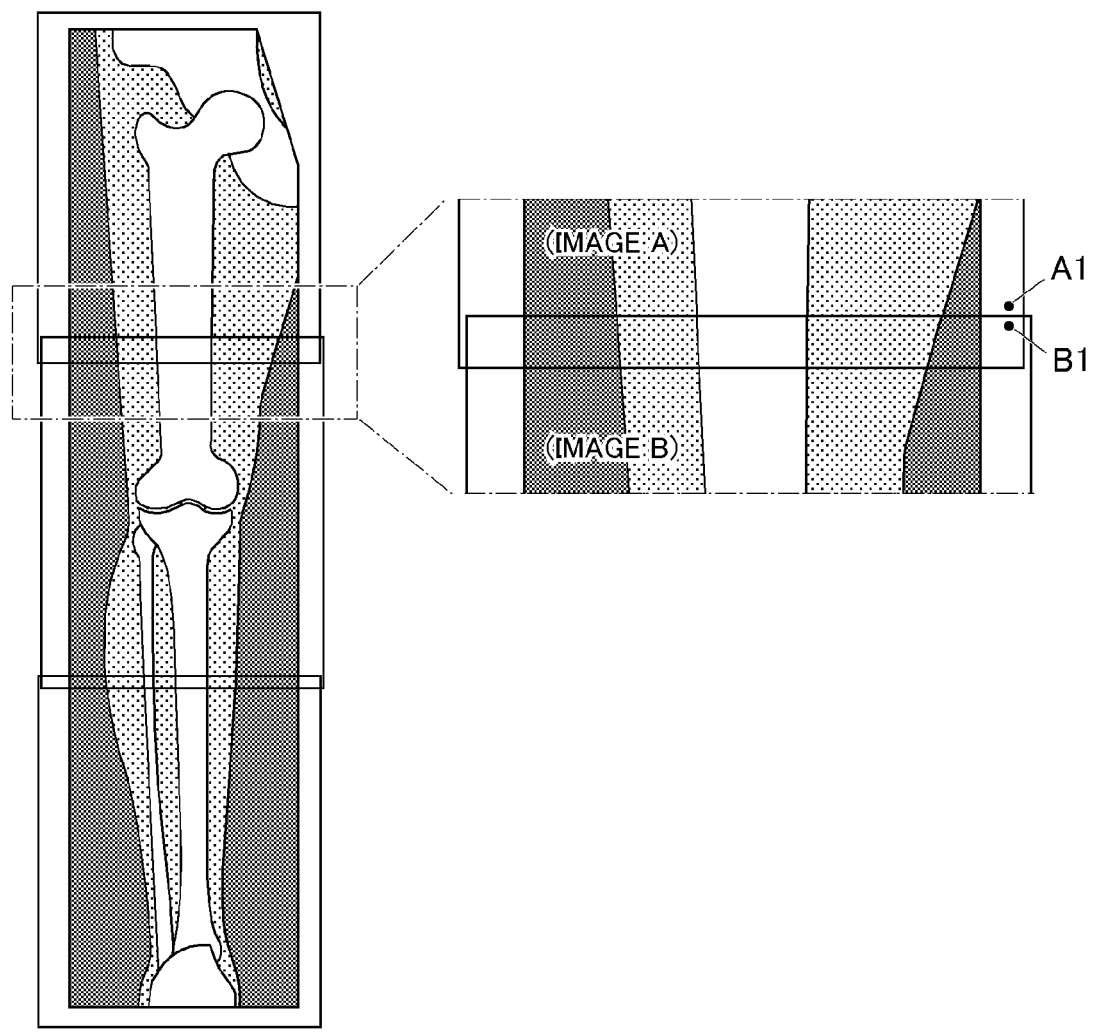
FIG. 45 is a view for explaining density in a spatial direction around the connection position.
Figure 46:
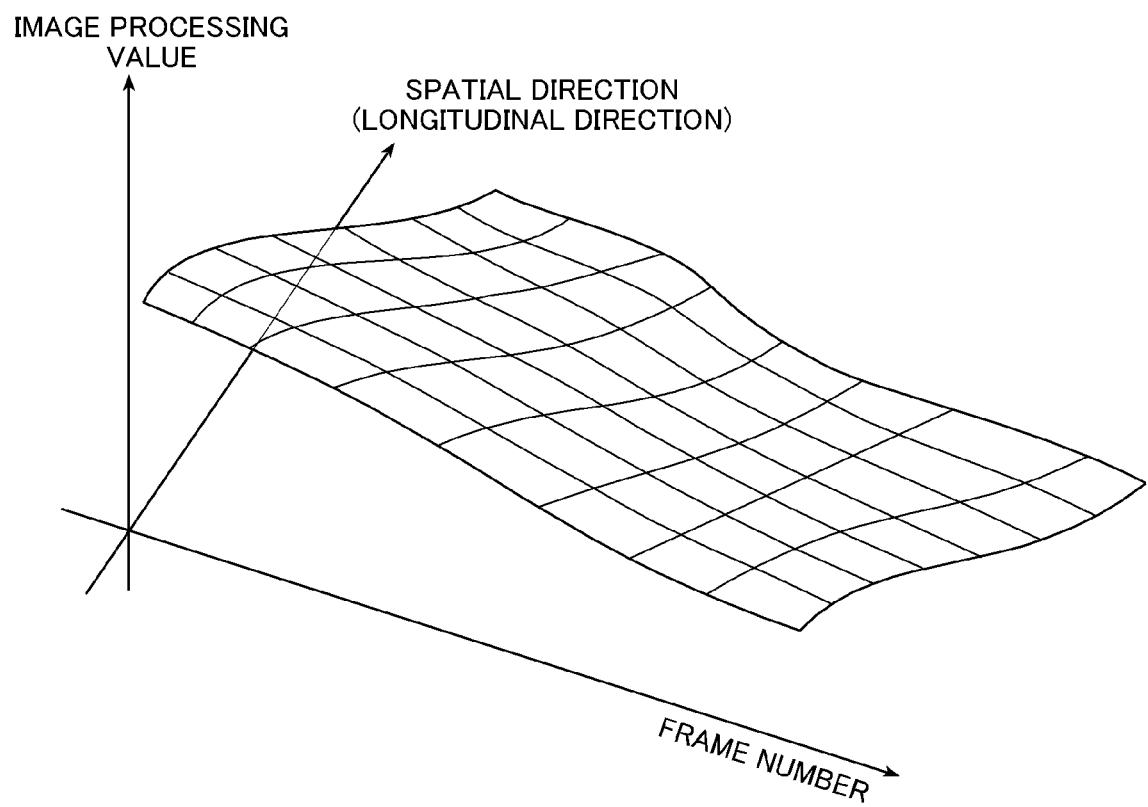
FIG. 46 is a view illustrating an image processing value in which information in a time direction and in the spatial direction is taken into account.

Further, it is preferable to perform processing with the image processing values calculated so that the images are smoothly connected in a spatial direction after connection as well as in a time direction of radiographing. For example, in a case where contrast after contrast adjustment processing on which the density information is assumed or the adjustment value for processing is largely different between images adjacent in a spatial direction, for example, in a case where an image A and an image B illustrated in FIG. 45 are connected so that the image B is connected on the image A, if density largely changes at portions of A1 and B1, an unnatural long-length image is obtained. Therefore, as illustrated in FIG. 46, the contrast after the contrast adjustment processing or the adjustment value for processing is calculated while information in the time direction and in the spatial direction is taken into account so that density becomes as close as possible in the spatial direction after connection as well as in the time direction of radiographing.

By this means, a long-length dynamic image which is smooth also in the spatial direction can be obtained, so that it makes it easier to make a diagnosis.

While description has been described above using an example where images are connected smoothly in the time direction and in the spatial direction in terms of contrast, such image processing for performing processing so that images are smoothly connected in the time direction and in the spatial direction is not limited to contrast. For example, processing may be performed so that images are smoothly connected in the time direction and in the spatial direction in a similar manner, for other image processing such as noise suppression processing, image sharpening processing, dynamic range compression processing, and grid removal processing.

Figure 47:
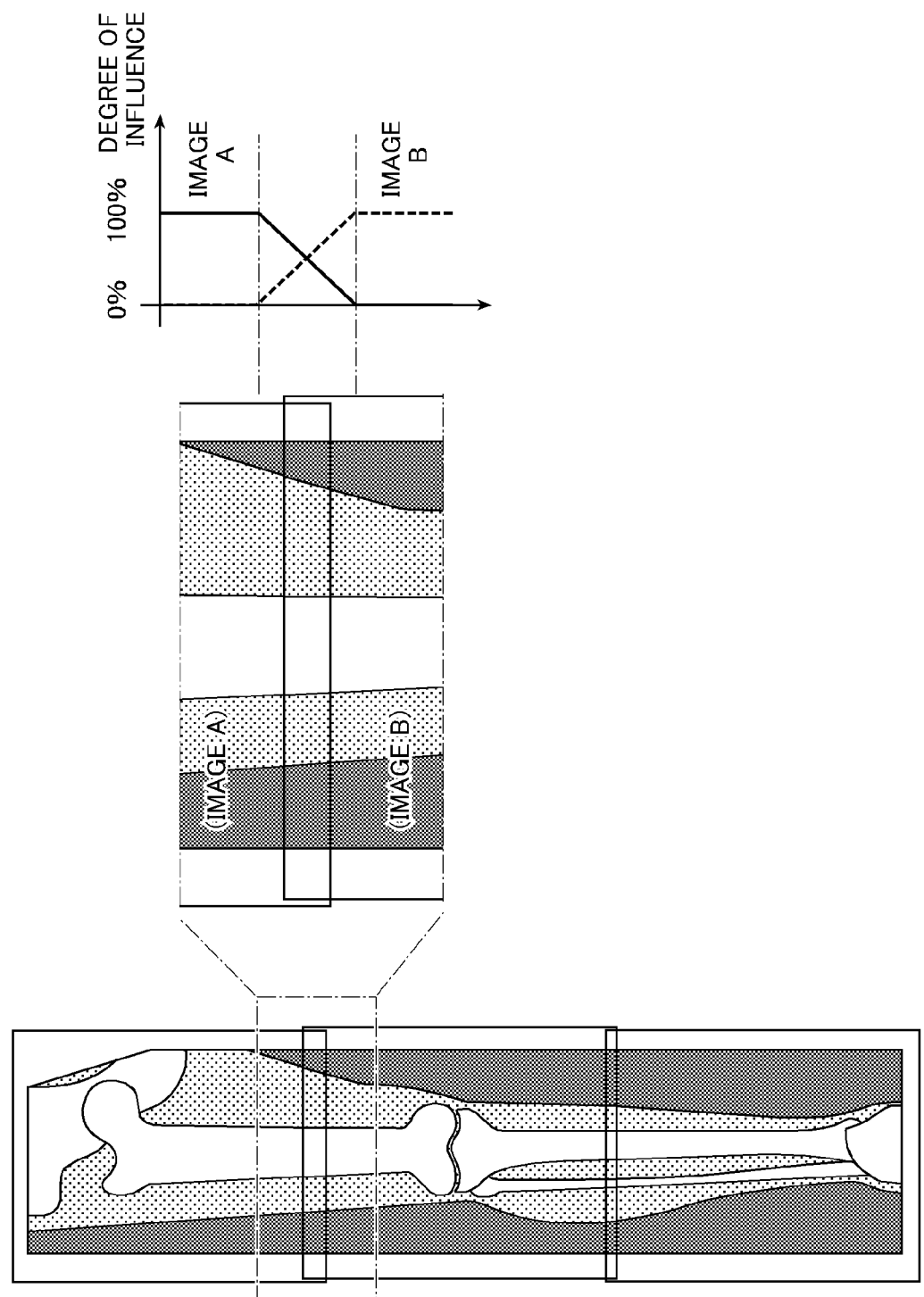
FIG. 47 is a view illustrating a level of influence of each image at a connection portion where two images overlap with each other by connection.

Alternatively, the images may be connected so that a degree of influence becomes respectively smaller toward the other image in a connection portion of two images. For example, as illustrated in FIG. 47, by changing a degree of influence of the image A from 100% to 0% toward the image B and, inversely, changing a degree of influence of the image B from 0% to 100% toward the image A in a region of the connection portion, the images are smoothly connected at the connection portion.

Further, a long-length dynamic image may be constituted so that a degree of influence of the past image becomes gradually smaller in a time direction not in a spatial direction. By this means, images are not clumsily misaligned between adjacent frame images, and constitute a smooth moving image, so that it makes it easier to make a diagnosis.

Further, while, in a case of image processing which requires not only one image processing value, but requires a plurality of image processing values, the above-described processing cannot be performed, by performing processing while interpolating vectors, matrixes, and tensors as well as values with idea similar to the above idea, it is possible to apply the above-described processing to processing which requires a plurality of image processing values.

Further, in a case where a plurality of kinds of image processing are performed, because a long-length dynamic image cannot be confirmed until all kinds of the image processing are finished for the respective frame images of the long-length dynamic image, so that it takes time to confirm the long-length dynamic image, there is a problem in prompt confirmation of images and judgment as to whether or not it is necessary to perform radiographing again.

Figure 48:
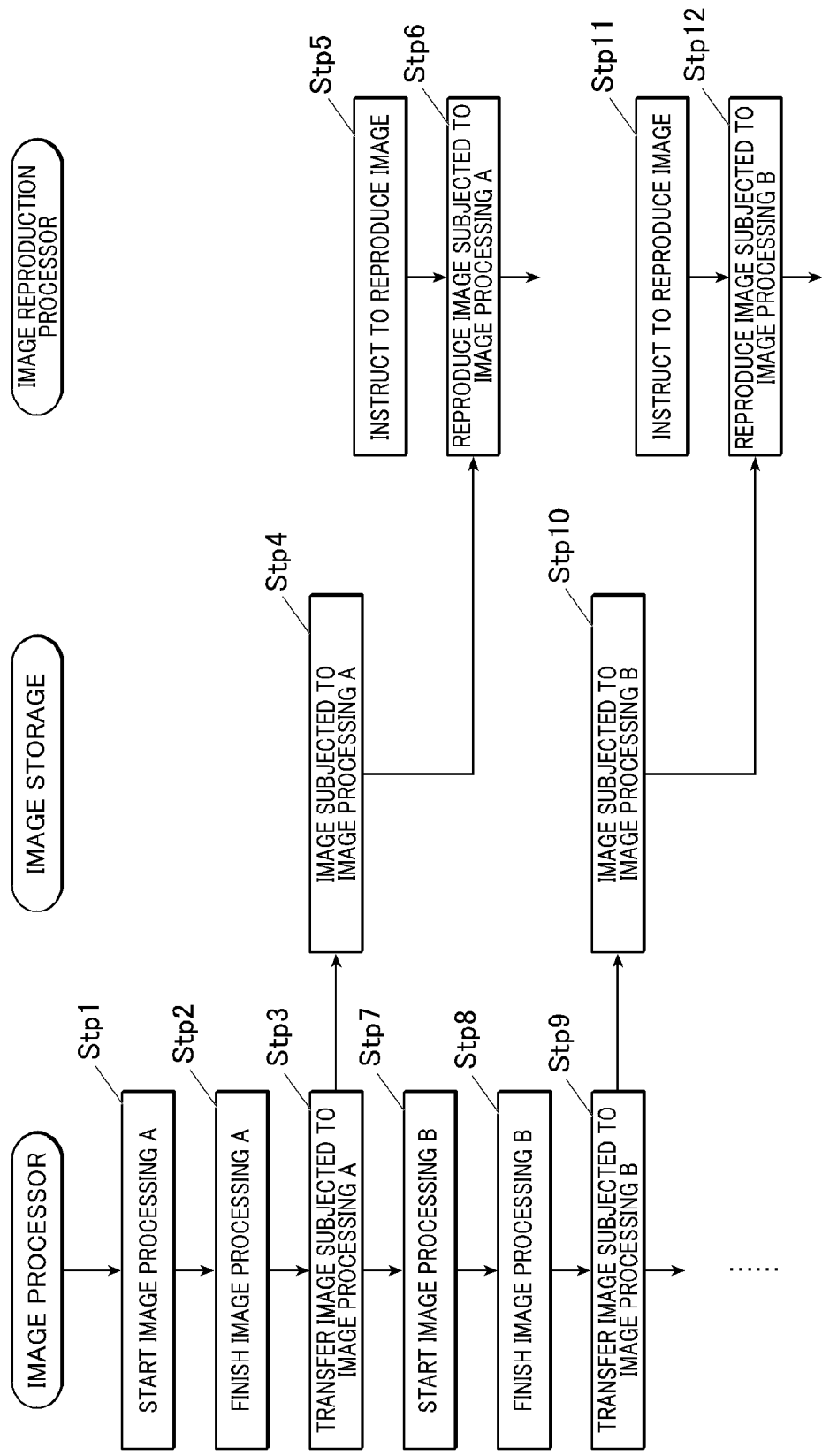
FIG. 48 is a flowchart illustrating flow of image processing, storage and image reproduction at a console in FIG. 19.

Therefore, the console 4 performs specific image processing first and displays the image at the display 43, and displays the image again after performing another image processing afterward. For example, as illustrated in FIG. 48, for example, after image processing A is started and finished on the respective frame images of a long-length dynamic image at the image processor of the console 4 (step Stp1 and Stp2), the image subjected to the image processing A is transferred to an image storage (such as RAM) (Stp3). The image storage stores the transferred image subjected to the image processing A (step Stp4). Then, when an instruction to reproduce the image is given from the operator (Stp5), the image subjected to the image processing A stored in the image storage is reproduced at the image reproduction processor (Stp6). Further, when transfer of the image subjected to the image processing A is finished, at the image processor, image processing B is started on the respective frame images subjected to the image processing A (Stp7), and, when the image processing B is finished (Stp8), the image subjected to the image processing B (radiograph subjected to the image processing A and B) is transferred to the image storage (Stp9). The image storage stores the transferred image subjected to the image processing B (step Stp10). Then, when an instruction to reproduce the image is given from the operator (Stp11), at the image reproduction processor, the image subjected to the image processing B stored in the image storage is reproduced (Stp12). This processing is repeated the number of times corresponding to the number of kinds of image processing. Note that the image processor and the image reproduction processor are functional parts which are to be executed in coordination with the CPU of the console 4 and the program.

In other words, the image processor performs processing such that one kind of processing is performed on all of the frame images which are successive in a time direction, and after the one kind of processing is completed, the next processing is performed on all of the frame images which are successive in a time direction, instead of the processing transitioning to processing of the next frame image after all kinds of the processing are performed on one frame image. The image subjected to processing is stored in the image storage in a stage at which one kind of processing is completed, and, in a case where an instruction to reproduce the image is given, it is possible to display a long-length dynamic image of the images which have been processed by then.

Alternatively, instead of image processing being performed on all of the frame images in the time direction, image processing is performed while picking frame images at fixed intervals or in a specific time slot, and display is performed only with the picked images.

By this means, it is possible to promptly display a long-length dynamic image, so that it is possible to promptly confirm the images and judge whether to perform radiographing again.

By the way, in a case where a problem occurs upon image processing, there is a risk that the images may disappear. Further, the processing may include irreversible processing which makes it impossible to return the images to original images again, and there is a problem in a case where it is desired to undo the processing.

Therefore, in a case where there are a plurality of kinds of image processing to be performed, the console 4 stores and holds frame images before processing in RAM, or the like, for each kind of processing. Note that whether to hold images before processing may be able to be selected by the user through an operation of the operator.

By this means, in a case where a problem occurs upon image processing, or in a case where it is desired to undo the image processing, it is possible to confirm the images before processing.

Although embodiments of the present invention have been described and illustrated in detail, the disclosed embodiments are made for purposes of illustration and example only and not limitation. The scope of the present invention should be interpreted by terms of the appended claims. Detailed configurations and detailed operations of the respective apparatuses which constitute the system described in the above-described embodiment can be changed as appropriate within a scope not deviating from the gist of the present invention.

What is claimed is:

1. A radiographic imaging system that performs radiographing, comprising:
    a radiographic imaging apparatus; and
    a control apparatus,
    wherein the radiographic imaging apparatus includes:
        a radiation detector that detects radiation and generates an electrical signal; and
        a radiographing controller that performs a reading operation of the electrical signal before capturing a radiograph, and
    wherein whether or not the radiographing controller performs the reading operation of the electrical signal is switchable before successive radiographing by the radiographic imaging apparatus.

2. The radiographic imaging system according to claim 1, wherein the control apparatus includes an operator that receives an operation input by a radiographer, and
    wherein, in response to the operation input, whether or not the radiographing controller performs the reading operation of the electrical signal is switched.

3. The radiographic imaging system according to claim 1, wherein the radiographic imaging apparatus includes a temperature gauge that measures a temperature of the radiographic imaging apparatus, and
    wherein, based on at least one of the temperature measured by the temperature gauge and a state of change in the temperature, whether or not the radiographing controller performs the reading operation of the electrical signal is switched.

4. The radiographic imaging system according to claim 1, wherein, based on at least one of a number of radiographs captured in a past specific period, a radiographing mode, and an interval of past radiographing, the control apparatus switches whether or not the radiographing controller performs the reading operation of the electrical signal.

5. The radiographic imaging system according to claim 4, wherein, upon the radiographing mode being a serial radiography mode, the radiographic imaging apparatus repeats the reading operation of the electrical signal by the radiographing controller.

6. The radiographic imaging system according to claim 1, wherein the radiographic imaging apparatus switches whether or not the radiographing controller performs the reading operation of the electrical signal based on a control signal from the control apparatus.

7. The radiographic imaging system according to claim 1, wherein at least one of a number of times of the reading operation and a time in which the reading operation is performed is changeable.

8. The radiographic imaging system according to claim 1, wherein the radiographic imaging apparatus includes a plurality of radiographic imaging apparatuses, and
    wherein the plurality of radiographic imaging apparatuses switch whether or not the radiographing controller performs the reading operation of the electrical signal under different conditions from each other.

9. The radiographic imaging system according to claim 1, wherein the radiographic imaging apparatus includes a plurality of radiographic imaging apparatuses, and
    wherein, in all of the plurality of radiographic imaging apparatuses, whether or not the radiographing controller performs the reading operation of the electrical signal is switched under a condition for a radiographic imaging apparatus that requires the reading operation of the electrical signal by the radiographing controller most among the plurality of radiographic imaging apparatuses.

10. The radiographic imaging system according to claim 1, wherein the electrical signal read by the radiographing controller is correction data of a captured radiograph.

11. The radiographic imaging system according to claim 1, wherein the radiographic imaging apparatus notifies the control apparatus of completion of the reading operation of the electrical signal by the radiographing controller.

12. The radiographic imaging system according to claim 1, wherein, in continuously performed radiographing in response to a plurality of similar radiographing orders, the radiographing controller does not perform the reading operation of the electrical signal in second and subsequent radiographing.

\* \* \* \* \*